US009862750B2

(12) United States Patent
Lakey

(10) Patent No.: US 9,862,750 B2
(45) Date of Patent: Jan. 9, 2018

(54) RECOMBINANT POLYPEPTIDE

(71) Applicant: University of Newcastle Upon Tyne, Tyne and Wear (GB)

(72) Inventor: Jeremy Lakey, Tyne and Wear (GB)

(73) Assignee: University of Newcastle Upon Tyne (GB)

( * ) Notice: Subject to any disclaimer, the term of this patent is extended or adjusted under 35 U.S.C. 154(b) by 23 days.

(21) Appl. No.: 14/407,424

(22) PCT Filed: Jun. 11, 2013

(86) PCT No.: PCT/GB2013/051524
§ 371 (c)(1),
(2) Date: Dec. 11, 2014

(87) PCT Pub. No.: WO2013/186545
PCT Pub. Date: Dec. 19, 2013

(65) Prior Publication Data

US 2015/0299272 A1 Oct. 22, 2015

(30) Foreign Application Priority Data

Jun. 11, 2012 (GB) .................................. 1210286.9
Jan. 11, 2013 (GB) .................................. 1300529.3

(51) Int. Cl.
| | |
|---|---|
| *C07K 14/00* | (2006.01) |
| *C07K 14/24* | (2006.01) |
| *A61L 27/22* | (2006.01) |
| *A61L 27/52* | (2006.01) |
| *A61L 15/32* | (2006.01) |
| *A61L 15/60* | (2006.01) |
| *C12N 15/70* | (2006.01) |

(52) U.S. Cl.
CPC .............. *C07K 14/24* (2013.01); *A61L 15/32* (2013.01); *A61L 15/60* (2013.01); *A61L 27/227* (2013.01); *A61L 27/52* (2013.01); *C12N 15/70* (2013.01); *A61L 2300/424* (2013.01); *C07K 2319/00* (2013.01)

(58) Field of Classification Search
None
See application file for complete search history.

(56) References Cited

U.S. PATENT DOCUMENTS

2003/0180315 A1* 9/2003 Nataro ................ C07K 14/245
424/190.1

FOREIGN PATENT DOCUMENTS

| | | | |
|---|---|---|---|
| EP | 2455104 | A1 | 5/2012 |
| WO | 9842834 | A1 | 10/1998 |
| WO | 9957276 | A1 | 11/1999 |
| WO | 0055206 | A1 | 9/2000 |
| WO | 0066756 | A1 | 11/2000 |
| WO | 02059156 | A2 | 8/2002 |
| WO | 2009009759 | A2 | 1/2009 |
| WO | 2012065751 | A1 | 5/2012 |
| WO | 2013186545 | A2 | 12/2013 |

OTHER PUBLICATIONS

Klemm, Per et al., “Fimbrial surface display systems in bacteria: from vaccines to random libraries”, Microbiology, 2000, vol. 146, pp. 3025-3032.
P.A. Parment et al., “Hemagglutination (Fimbriae) and Hydrophobicity in Adherence of Serratia marcescens to Urinary Tract Epithelium and Contact Lenses”, Current Microbiology, vol. 25, 1992, pp. 113-118.
Clarissa Cowan et al., “Invasion of Epithelial Cells by Yersinia pestis: Evidence for a Y. pestis-Specific Invasin”, Infection and Immunity, vol. 68, No. 8, Aug. 2000, pp. 4523-4530.
Anton V. Zavialov et al., “Secretion of Recombinant Proteins via the Chaperone/Usher Pathway in *Escherichia coli*”, Applied and Environmental Microbiology, vol. 67, No. 4, Apr. 2001, pp. 1805-1814.
William R. Schwan et al., “Osmolarity and pH Growth Conditions Regulate fim Gene Transcription and Type 1 Pilus Expression in Uropathogenic *Escherichia coli*”, Infection and Immunity, vol. 7, No. 3, Mar. 2002, pp. 1391-1402.
Ulrich Hersel et al., “RGD modified polymers: biomaterials for stimulated cell adhesion and beyond”, Biomaterials vol. 24, 2003, pp. 4385-4415.
Wen-Tssann Liu et al., “Enhanced immune response by amphotericin B following NS1 protein prime-oral recombinant *Salmonella* vaccine boost vaccination protects mice from dengue virus challenge”, Vaccine vol. 24, May 16, 2006, pp. 5852-5861.
Fengzhi Liu et al., “Effects of Psa and F1 on the Adhesive and Invasive Interactions of Yersinia pestis with Human Respiratory Tract Epithelial Cells”, Infection and Immunity, vol. 74, No. 10, Oct. 2006, pp. 5636-5644.
Marta Kur et al., “A two-plasmid *Escherichia coli* system for expression of Dr adhesins”, Protein Expression & Purification vol. 55, Apr. 27, 2007, pp. 361-367.
Beata Zalewska et al., “DAF- and collagen-binding properties of chimeric Dr fimbriae”, Microbiology vol. 153, Apr. 3, 2007, pp. 2733-2742.
Jangwook Lee et al., “Controlled delivery of heat shock protein using an injectable microsphere/hydrogel combination system for the treatment of myocardial infarction”, Journal of Controlled Release vol. 137, Apr. 14, 2009, pp. 196-202.
Andrei Soliakov et al., “The structure of Yersinia pestis Caf1 polymer in free and adjuvant bound states”, Vaccine vol. 28, Jun. 18, 2010, pp. 5746-5754.
Xiao Di Yu et al., “Allosteric Mechanism Controls Traffic in the Chaperone/Usher Pathway”, Structure, vol. 20, Nov. 7, 2012, pp. 1861-1871.
UK Intellectual Property Office, “Patents Act 1977: Search Report under Section 17(5)”, in connection with related Patent Application No. GB1210286.9, dated Oct. 2, 2012, 5 pages.
UK Intellectual Property Office, “Patents Act 1977: Search Report under Section 17(6)”, in connection with related Patent Application No. GB1210286.9, dated Feb. 18, 2013, 3 pages.

(Continued)

*Primary Examiner* — Jim Ketter
(74) *Attorney, Agent, or Firm* — Kolisch Hartwell, P.C.

(57) ABSTRACT

The invention provides a chaperone/usher family polymer comprising at least one chaperone/usher family polypeptide monomer, wherein said at least one chaperone/usher family polypeptide monomer comprises an exogenous bioactive sequence.

28 Claims, 81 Drawing Sheets

(56) References Cited

OTHER PUBLICATIONS

UK Intellectual Property Office, "Patents Act 1977: Search Report under 17(5)", in connection with related Patent Application No. GB1300529.3, May 30, 2013, 5 pages.
Jacqueline Van Ekelenburg, Authorized Officer, European Patent Office, "International Search Report" in connection with related PCT Patent Application No. PCT/GB2013/051524, dated Dec. 5, 2013, 10 pages.
Didier Gurdjian, Authorized Officer, European Patent Office, "Written Opinion of the International Searching Authority" in connection with related PCT Patent Application No. PCT/GB2013/051524, dated Dec. 5, 2013, 15 pages.
Karlyshev, A.V. et al., "Caf1 R gene and its role in the regulation of capsule formation of Y. pestis", FEBS Letters, vol. 305, No. 1, Jun. 1992, pp. 37-40.
Rolfs, A., et al., "Yersinia pestis KIM ORF Project", Synthetic construct Yersinia pestis cl Figure 3
a)
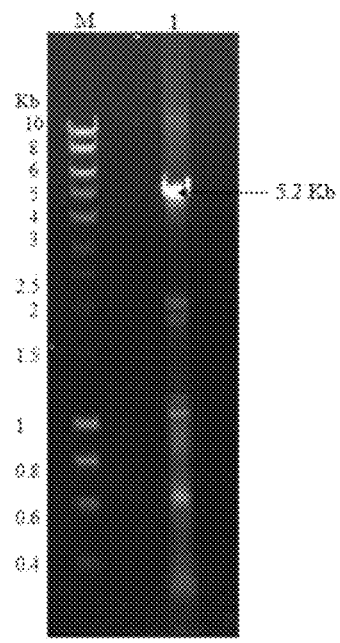
b)
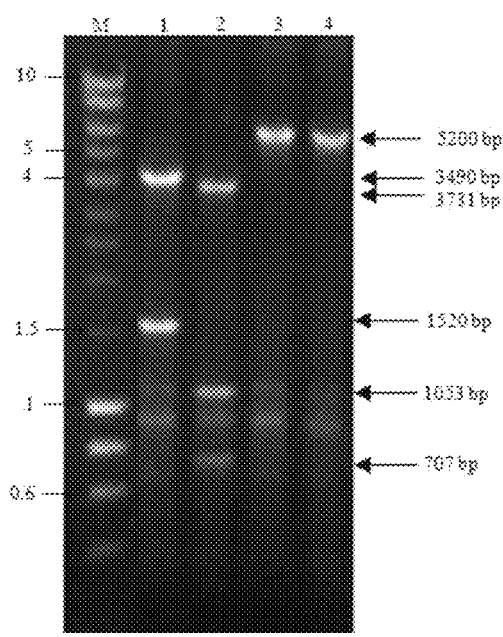

Figure 4
a)
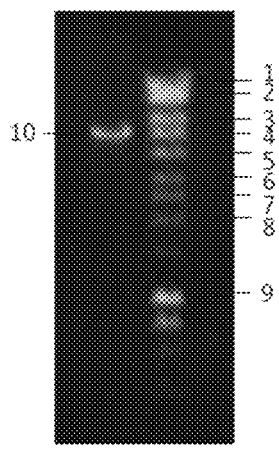
| # | Bands | Molecular weight (bp) |
|---|---|---|
| 1 | Molecular standard 1 (Std1) | 100.0000000000 |
| 2 | Molecular standard 2 (Std2) | 80.0000000000 |
| 3 | Molecular standard 3 (Std3) | 60.0000000000 |
| 4 | Molecular standard 1 (Std1) | 50.0000000000 |
| 5 | Molecular standard 1 (Std1) | 40.0000000000 |
| 6 | Molecular standard 1 (Std1) | 30.0000000000 |
| 7 | Molecular standard 1 (Std1) | 25.0000000000 |
| 8 | Molecular standard 1 (Std1) | 20.0000000000 |
| 9 | Molecular standard 1 (Std1) | 10.0000000000 |
| 10 | Unknown band (U1) | 64.32499551138 |
b)
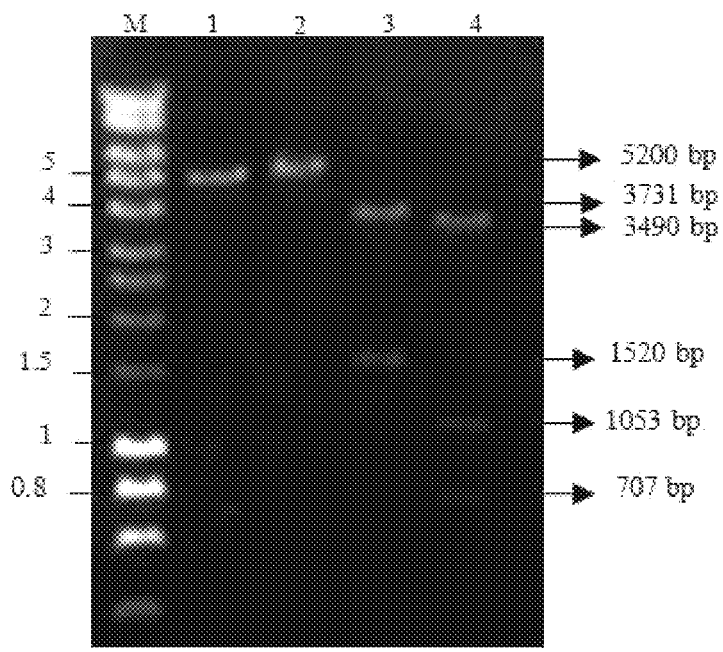

Figure 9
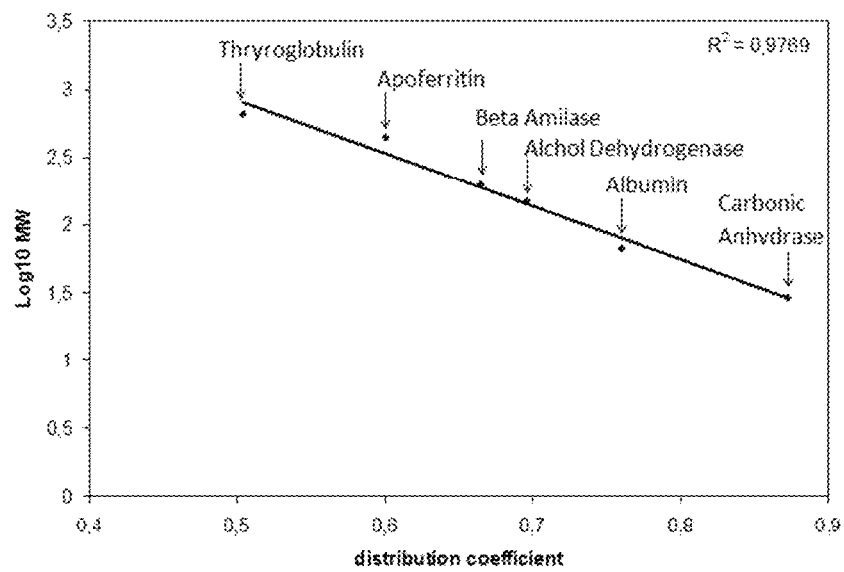
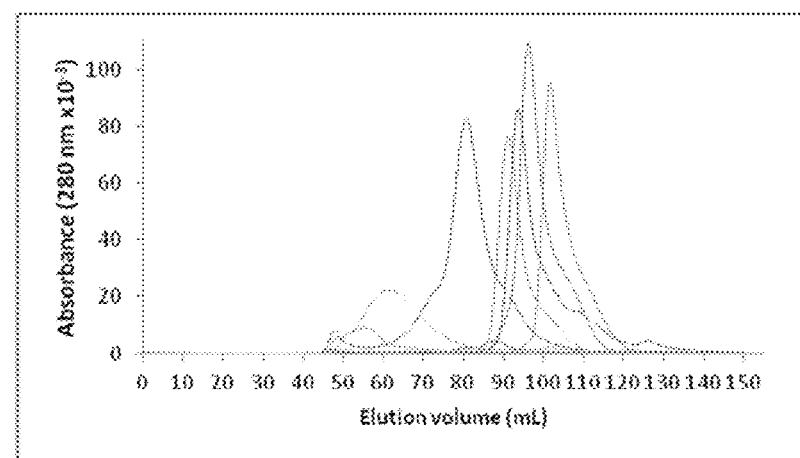

Figure 16
pGEM-TF1
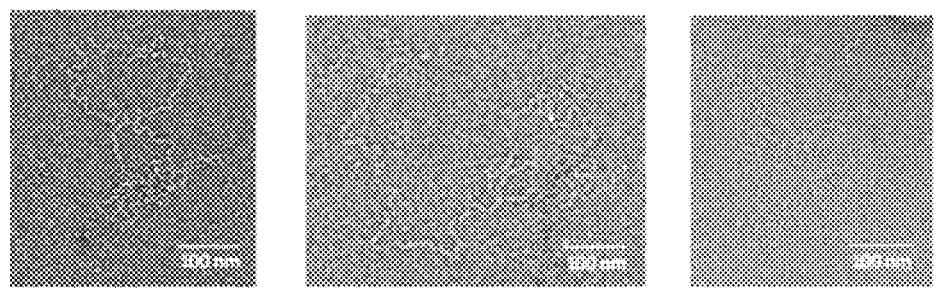
pGEM-TF1 Mutant Caf1QDGN76RGDS
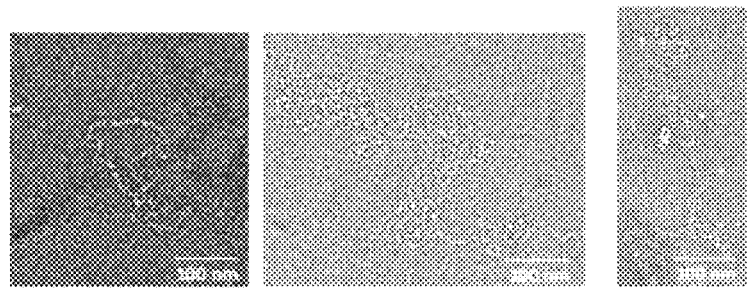

Figure 20
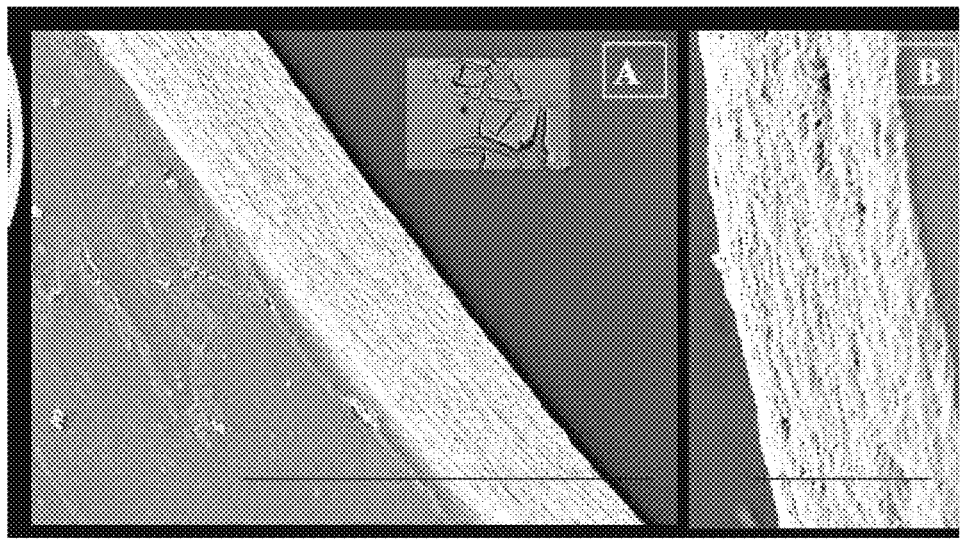
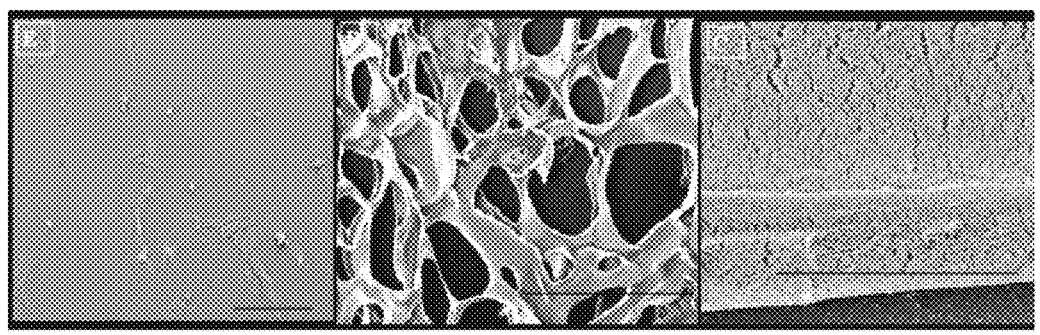

Figure 21
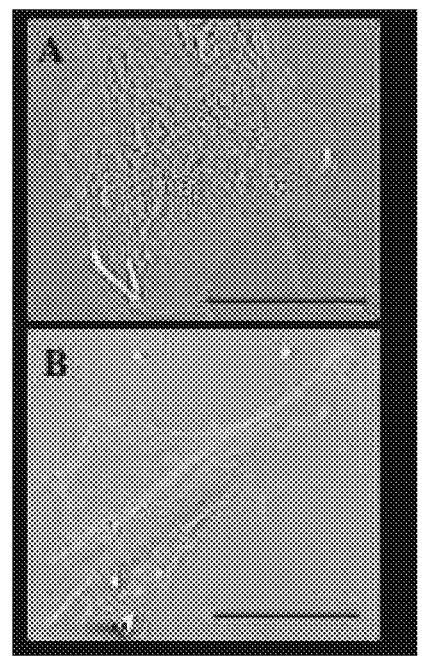
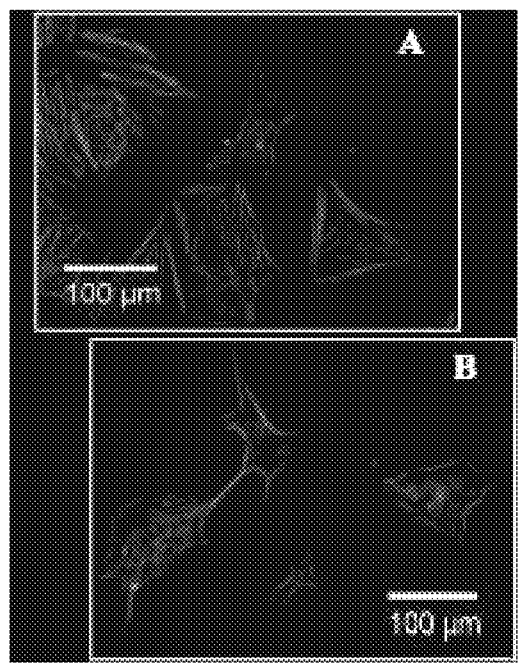

Figure 22

SEQ ID NO:1

CAF1

>ENA|CAA43966|CAA43966.1 Yersinia pestis F1 capsule antigen : Location:1..513

```
ATGAAAAAAATCAGTTCCGTTATCGCCATTGCATTATTTGGAACTATTGCAACTGCTAAT
GCGGCAGATTTAACTGCAAGCACCACTGCAACGGCAACTCTTGTTGAACCAGCCCGCATC
ACTCTTACATATAAGGAAGGCGCTCCAATTACAATTATGGACAATGGAAACATCGATACA
GAATTACTTGTTGGTACGCTTACTCTTGGCGGCTATAAAACAGGAACCACTAGCACATCT
GTTAACTTTACAGATGCCGCGGGTGATCCCATGTACTTAACATTTACTTCTCAGGATGGA
AATAACCACCAATTCACTACAAAAGTGATTGGCAAGGATTCTAGAGATTTTGATATCTCT
CCTAAGGTAAACGGTGAGAACCTTGTGGGGATGACGTCGTCTTGGCTACGGGCAGCCAG
GATTTCTTTGTTCGCTCAATTGGTTCCAAAGGCGGTAAACTTGCAGCAGGTAAATACACT
GATGCTGTAACCGTAACCGTATCTAACCAATAA
```

Figure 23

SEQ ID NO:2

Caf1M

>ENA|CAA43967|CAA43967.1 Yersinia pestis hypothetical protein : Location:1..777

ATGATTTTAAATAGATTAAGTACGTTAGGAATTATTACTTTCGGCATGCTTAGTTTTGCT
GCGAACTCTGCTCAACCAGATATCAAATTCGCAAGCAAAGAGTATGGCGTGACTATAGGT
GAGAGTAGGATCATATACCCGTTAGATGCTGCTGGCGTTATGGTCTCGGTGAAAAACACC
CAAGATTATCCGGTTCTCATTCAGTCTAGGATCTACGACGAGAATAAAGAAAAAGAATCA
GAGGATCCTTTCGTGGTCACTCCGCCATTGTTTCGATTGGATGCTAAGCAACAAAATTCT
TTGCGTATAGCTCAGGCTGGAGGTGTTTTCCCGCGAGATAAAGAGAGCCTAAAGTGGTTA
TGCGTAAAAGGGATTCCACCAAAGGATGAAGATATATGGGTTGATGATGCGACAAATAAG
CAAAAATTCAATCCAGACAAAGATGTGGGAGTGTTCGTGCAATTCGCAATTAATAATTGC
ATTAAGCTTTTGGTTCGACCGAATGAATTAAAAGGAACCCCTATACAGTTTGCTGAAAAG
TTAAGCTGGAAAGTTGATGGGGGGAAGCTAATTGCTGAAAACCCCTCACCTTTCTACATG
AACATAGGTGAATTAACATTTGGAGGGAAAAGTATTCCTTCTCACTATATTCCACCTAAA
TCGACGTGGGCTTTTGATTTGCCAAAAGGACTAGCGGGAGCACGTAATGTTTCGTGGAGA
ATAATTAATGATCAGGGAGGGTTGGATCGTTTGTATTCCAAAAATGTGACTTTATGA

Figure 24

SEQ ID NO:3

Caf1A

>ENA|CAA43968|CAA43968.1 Yersinia pestis hypothetical protein : Location:1..1000

```
ATGAGGTATTCAAAGCTGTTCCTGTGTGCAGGGTTAACTTTGGCAACATTGCCTTGTTGG
GGACGCGCATATACTTTTGACTCTACTATGCTTGATACGAATAGTGGAGAGAGTATAGAT
GTATCTCTTTTTAATCAAGGACTTCAACTTCCAGGTAATTATTTTGTTAATGTTTTTGTA
AATGGTCGAAAGGTAGACTCTGGAAATATCGACTTCCGTCTAGAAAAACATAATGGAAAA
GAACTTCTTTGGCCATGCCTATCATCCTTACAATTGACAAAGTATGGCATTGATATAGAT
AAATATCCTGATTTAATAAAATCTGGTACAGAGCAATGTGTTGATTTATTAGCAATACCA
CATTCAGATGTGCAGTTTTATTTTAATCAGCAGAAATTATCGTTAATTGTGCCACCACAG
GCACTTTTACCTAGATTTGATGGCATTATGCCAATGCAATTGTGGATGACGGCATTCCT
GCTCTGTTCATGAATTATAATACGAACATGCAGACAAGAAAATTCAGAGAAGGAGGCAAG
TCTCTGGACTCTTATTATGCTCAGTTGCAACCGGGATTAAACATAGGGGCTTGGCGCTTT
CGTAGTTCAACCTCATGGTGGAAACAACAAGGATGGCAGCGTTCGTATATTTATGCCGAG
CGAGGATTGAATACAATTAAGAGCCGTTTGACATTGGGGAAACCTATTCTGATAGCAGT
ATCTTTGACAGTATCCCGATTAAGGGGATAAAAATTGCTTCAGATGAATCGATGGTTCCT
TATTACCAATGGAATTTTGCTCCAGTTGTTCGCGGTATCGCACGTACACAAGCCAGGGTA
GAGGTTTTAAGAGATGGCTACACTGTAAGTAATGAGTTGGTGCCCTCGGGACCATTTGAG
TTAGCAAATCTTCCTCTGGGTGGGGGGAGTGGTGAGCTGAAAGTCATCATTCATGAAAGT
GATGGAACAAAGCAAGTTTTTACAGTTCCATATGACACAC
```

Figure 25

SEQ ID NO:4

Caf1R

ENA|CAA43969|CAA43969.1 Yersinia pestis hypothetical protein : Location:1..906

```
ATGCTAAAACAGATGACTGTAAATTCAATTATTCAATATATAGAAGAGAATCTCGAGTCG
AAATTCATTAACATTGACTGTTTGGTTTTGTATTCAGGATTCAGCAGAAGGTATTTGCAA
ATTTCCTTTAAGGAATATGTCGGAATGCCTATTGGAACATATATTAGAGTTAGAAGGGCT
AGTAGAGCTGCTGCACTATTACGGCTTACAAGGCTGACAATAATAGAGATATCAGCAAAG
CTTTTTTATGATTCGCAACAGACATTCACCAGAGAATTTAAGAAAATATTTGGTTATACC
CCACGGCAGTATAGGATGATCCCTTTTTGGTCCTTTAAAGGTTTGTTGGGTAGAAGGGAA
ATTAACTGTGAATACCTTCAACCACGAATCTGTTACCTTAAAGAGAGAAATATAATTGGT
CAATGCTTTAATTTTAGGGATTTAGTGTTCTACTCTGGGATAGATTCAAAATGTAGATTG
GGTAAGTTATATGATTCGTTGAAGAAAAATACAGCTATAACAGTATCAAACAGAATCCCC
TTTCATGATAAAACGAATGACATTATTGCAAGAACGGTTGTTTGGGATAGGAATAAGCAT
TTCAGCGATAGTGAAATAAAGGTAGATAAAGGCCTGTATGCTTATTTTTTCTTCAATGAT
ACATATGATCAGTATGTTCATCACATGTACAACATATATTATAACTCTTTGCCTATTTAT
AATTTAAATAAGCGGGATGGTTACGATGTGGAGGTCATAAAAAGACGAAATGACAATACT
ATTGATTGTCATTATTTTCTCCCGATTTATTGTGATGACATGGAGTTTTACAATGAAATG
CAGGTATATCACAATAATATTGTGAAGCCGGAAATGTCAGTAACATTAGGATTACCAAAG
AGTTAA
```

Figure 26

SEQ ID NO:5

Caf1

```
         10         20         30         40         50         60
MKKISSVIAI ALFGTIATAN AADLTASTTA TATLVEPARI TLTYKEGAPI TIMDNGNIDT 70         80         90        100        110        120
ELLVGTLTLG GYKTGTTSTS VNFTDAAGDP MYLTFTSQDG NNHQFTTKVI GKDSRDFDIS 130        140        150        160        170
PKVNGENLVG DDVVLATGSQ DFFVRSIGSK GGKLAAGKYT DAVTVTVSNQ
```

Figure 27

SEQ ID NO:6

Caf1M

```
              10         20         30         40         50         60
      MILNRLSTLG IITFGMLSFA ANSAQPDIKF ASKEYGVTIG ESRIIYPLDA AGVMVSVKNT 70         80         90        100        110        120
      QDYPVLIQSR IYDENKEKES EDPFVVTPPL FRLDAKQQNS LRIAQAGGVF PRDKESLKWL 130        140        150        160        170        180
      CVKGIPPKDE DIWVDDATNK QKFNPDKDVG VFVQFAINNC IKLLVRPNEL KGTPIQFAEN 190        200        210        220        230        240
      LSWKVDGGKL IAENPSPFYM NIGELTFGGK SIPSHYIPPK STWAFDLPKG LAGARNVSWR

250
      IINDQGGLDR LYSKNVTL
```

Figure 28A

Caf1A

SEQ ID NO: 7

```
          10         20         30         40         50         60
   MRYSKLFLCA GLTIATLPCW GRAYTFDSTM LDTNSGESID VSLFNQGLQL PGNYFVNVFV 70         80         90        100        110        120
   NGRKVDSGNI DFRLEKHNGK ELLWPCLSSL QLTKYGIDID KYPDLIKSGT EQCVDLLAIP 130        140        150        160        170        180
   HSDVQFYFNQ QKLSLIVPPQ ALLPRFDGIM PMQLWDDGIP ALFMNYNTNM QTRKFREGGK 190        200        210        220        230        240
   SLDSYYAQLQ PGLNIGAWRF RSSTSWWKQQ GWQRSYIYAE RGLNTIKSRL TLGETYSDSS 250        260        270        280        290        300
   IFDSIPIKGI KIASDESMVP YYQWNFAPVV RGIARTQARV EVLRDGYTVS NELVPSGPFE 310        320        330        340        350        360
   LANLPLGGGS GELKVIIRES DGTKQVFTVP YDTPAVALRK GYFEYSMMGG EYRPANDLTQ 370        380        390        400        410        420
   TSYVGALGMK YGLPRNLTLY GGLQGSQNYH AAALGIGAML GDFGAISTDV TQADSQKNKQ 430        440        450        460        470        480
   KKESGQRWRV RYNKYLQSGT SLNIASEEYA TEGFNKLADT LNTYCKPNTR NDCRFDYAKP 490        500        510        520        530        540
   KNKVQFNLSQ SIPGSGTLNF SGYRKNYWRD SRSTTSFSVG YNHFFRNGMS LTLNLSKTQN 550        560        570        580        590        600
   INKYGEKTSE LLSNIWLSFP LSRWLGNNSI NSNYQMTSDS HGNTTHEVGV YGEAFDRQLY 610        620        630        640        650        660
   WDVRERFNEK GRKYTSNALN LNYRGTYGEI SGNYSYDQTQ SQLGIGVNGN MVITQYGITA
```

Figure 28B

```
       670        680        690        700        710        720
GQKTGDTIAL VQAPDISGAS VGYWPGMKTD FRGYTNYGYL TPYRENKVEI NPVTLPNDAE 730        740        750        760        770        780
ITNNIVSVIP TKGAVVLAKF NARIGGRLFL HLKRSDNKPV PFGSIVTIEG QSSSSGIVGD 790        800        810        820        830
NSGVYLTGLP KKSKILVKWG RDKNQSCSSN VVLPEKTDIS GAYRLSTTCI LNN
```

Figure 29

Caf1R

SEQ ID NO:8

```
         10         20         30         40         50         60
  MLKQMTVNSI IQYIEENLES KFINIDCLVL YSGFSRRYLQ ISFKEYVGMP IGTYIRVRRA 70         80         90        100        110        120
  SRAAALLRLT RLTIIEISAK LFYDSQQTFT REFKKIFGYT PRQYRMIPFW SFKGLLGRRE 130        140        150        160        170        180
  INCEYLQFRI CYLKERNIIG QCFNFRDLVF YSGIDSKCRL GKLYDSLKKN TAITVSNRIP 190        200        210        220        230        240
  FHDKTNDIIA RTVVWDRNKH FSDSEIKVDK GLYAYFFFND TYDQYVHHMY NIYYNSLPIY 250        260        270        280        290        300
  NLNKRDGYDV EVIKRRNDNT IDCHYFLPIY CDDMEFYNEM QVYHNNIVKP EMSVTLGLPK

SafA

SEQ ID NO:9

```
          10         20         30         40         50         60
MKSIKKLIIA SALSMMAASC YAGSFLPNSE QQKSVDIVFS SPQDLTVSLI PVSGLKAGKN 70         80         90        100        110        120
APSAKIAKLV VNSTTLKEFG VRGISNNVVD STGTAWRVAG KNTGKEIGVG LSSDSLRRSD 130        140        150        160
STEKWNGVNW MTFNSNDTLD IVLTGPAQNV TADTYPITLD VVGYQP
```

Figure 31

SafA

SEQ ID NO:10

ENA|CAC44268|CAC44268.1 Salmonella enterica subsp. enterica serovar Typhimurium salmonella atypical fimbria subunit A : Location:1..501

ATGAAAAGCATAAAAAAATTGATTATCGCAAGTGCGTTGAGCATGATGGCTGCTAGTTGT
TATGCTGGCTCATTTTTGCCGAACTCAGAGCAACAAAAATCAGTGGATATTGTGTTTTCC
TCTCCCCAAGATTTAACCGTATCGCTTATTCCAGTGTCGGGCTTAAAGGCTGGGAAAAAT
GCTCCTAGCGCGAAAATTGCGAAGCTTGTAGTTAATTCTACTACTCTTAAAGAATTCGGG
GTCAGGGGGATTTCTAACAACGTGGTAGACAGTACTGGCACTGCATGGCGTGTAGCTGGT
AAAAATACTGGTAAAGAGATCGGTGTGGGCTTATCAAGTGACAGTCTTAGAAGATCTGAT
AGCACGGAAAAATGGAATGGGGTGAACTGGATGACCTTTAATAGCAATGACACACTTGAT
ATTGTCCTGACAGGACCGGCGCAGAATGTCACAGCTGACACGTACCCAATAACTTTAGAC
GTAGTGGGATATCAACCTTAA

Figure 32

Afa1 (AfaE1)

SEQ ID NO:11

```
        10         20         30         40         50         60
MKKLAIIGAT SVMMMTGTAQ ANFTSSGTNG KVDLTITEEC RVTVESKSES FLRSGLVANR 70         80         90        100        110        120
HITNLGIQST GCGTGQRVAL KLGAGSYDDT NGAHMTHENG TDKLLVSMGS ATGDGTQDGG 130        140        150        160
VYYINRDGNW NGQMVFIVRN DQQHLPTGKY TLNLEGGFWT K
```

Figure 33

Afa1

SEQ ID NO:12

ENA|AAA23981|AAA23981.1 Escherichia coli hypothetical protein : Location:1..456

ATGAAAAAATTAGCGATCATAGGCGCAACCAGCGTAATGATGATGACCGGCACCGCTCAA
GCCAATTTTACCAGCAGCGGCACCAACGGGAAGGTCGACCTGACTATAACCGAAGAATGC
CGCGTGACAGTCGAGAGCAAAAGCGAGTCGTTCTTGCGAAGCGGCCTGGTCGCCAACAGG
CACATCACTAACCTCGGGATCCAATCCACGGGGTGTGGGACAGGACAACGTGTCGCGCTC
AAGCTTGGCGCGGGCTCGTACGACGACACGAACGGGGCGCACATGACGCACGAAAACGGC
ACTGACAAGCTTCTGGTGAGTATGGGCTCTGCGACGGGCGATGGGACCCAAGACGGCGGT
GTATATTATATCAACCGGGACGGAACTGGAACGGGCAGATGGTGTTCATCGTACGAAATG
ACCAACAGCACCTACCAACCGGCAAGTACACCCTGA

Figure 34

FimA

SEQ ID NO:13

```
          10         20         30         40         50         60
MKIKTLAIVV LSALSLSSTA ALAAATTVNG GTVHFKGEVV NAACAVDAGS VDQTVQLGQV 70         80         90        100        110        120
RTASLAQEGA TSSAVGFNIQ LNDCDTNVAS KAAVAFLGTA IDAGHTNVLA LQSSAAGSAT 130        140        150        160        170        180
NVGVQILDRT GAALALDGAT FSSETTLNNG TNTIPFQARY FATGAATSGA ANADATFKVQ

FimA

SEQ ID NO:14

>ENA|AF490872|AF490872.1 Escherichia coli isolate APEC 133 FimA (fimA) gene, complete cds. : Location:1..549

```
ATGAAAATTAAAACTCTGGCAATCGTTGTTCTGTCGGCTCTGTCCCTCAGTTCTACAGCG
GCTCTGGCCGCTGCCACGACGGTAAATGGTGGGACCGTTCACTTTAAAGGGGAAGTTGTT
AACGCCGCTTGCGCAGTTGATGCAGGCTCTGTTGATCAAACCGTTCAGTTAGGACAGGTT
CGTACCGCATCGCTGGCACAGGAAGGAGCGACCAGTTCTGCTGTCGGTTTTAACATTCAG
CTGAATGATTGCGATACCAATGTTGCATCTAAAGCCGCTGTTGCCTTTTTAGGTACGGCG
ATTGATGCGGGTCATACCAACGTTCTGGCTCTGCAGAGTTCAGCTGCGGGTAGCGCAACA
AACGTTGGTGTGCAGATCCTGGACAGAACGGGTGCTGCGCTGGCGCTGGACGGTGCGACA
TTTAGTTCAGAAACAACCCTGAATAACGGAACCAACACCATTCCGTTCCAGGCGCGTTAT
TTTGCAACCGGTGCCGCAACCTCGGGTGCTGCTAATGCGGATGCGACCTTCAAGGTTCAG
TATCAATAA
```

Figure 36

PapA

SEQ ID NO:15

```
            10         20         30         40         50         60
    MIKSVIAGAV AMAVVSFGVN NAAPTIPQGQ GKVTFNGTVV DAPCSISQKS ADQSIDFGQL 70         80         90        100        110        120
    SKSFLEAGGV SKPMDLDIEL VNCDITAFKG GNGAKKGTVK LAFTGPIVNG HSDELDTNGG 130        140        150        160        170        180
    TGTAIVVQGA GKNVVFDGSE GDANTLKDGE NVLHYTAVVK KSSAVGAAVT EGAFSAVANF

NLTYQ
```

Figure 37

PapA

SEQ ID NO:16 tgccggtgcg gtagctatgg cagtggtgtc ttttggtgta aataatgctg ctccaactat
tccacagggg cagggtaaag taacttttaa cggaactgtt gttgatgctc catgcagcat
ttctcagaaa tcagctgatc agtctattga ttttggacag ctttcaaaaa gcttccttga
ggcaggaggt gtatccaaac caatggactt agatattgaa ttggttaatt gtgatattac
tgcctttaaa ggtggtaatg gcgccaaaaa agggactgtt aagctggctt ttactggccc
gatagttaat ggacattctg atgagctaga tacaaatggt ggtacgggca cagctatcgt
agttcagggg gcaggtaaaa acgttgtctt cgatggctcc gaaggtgatg ctaataccct
gaaagatggt gaaaacgtgc tgcattatac tgctgttgtt aagaagtcgt cagccgttgg
tgccgctgtt actgaaggtg ccttctcagc agttgcgaat ttcaacctga cttatcagta
atactgataa

Figure 38

SafB

SEQ ID NO:17

```
          10         20         30         40         50         60
    MKIISFGVMA AVLFVSNSIT PPVYAAEQKL SLNTKSFSVK LGATRVIYHA GTVGATLSVS 70         80         90        100        110        120
    NPQNYPILVQ SSVKAADKSS PAPFLVMPPL FRLEANQQSQ LRIVRTGGDM PTDRETLQWV 130        140        150        160        170        180
    CVKAVPPENE PSDTQAKGAT LDLNLSINVC DKLIFRPDAV KGTPEDVAGN LRWVEAGNKL 190        200        210        220        230        240
    KVENPTPFYM NLASVTVGGK PITGLEYIPP FADKTLNMPG SAHGDVEWRV ITDFGGESHP

FHYVLK
```

Figure 39

SafB

SEQ ID NO:18

```
  1 atgaaaatta ttagttttgg tgtaatggcg gctgttttat tcgtctctaa ttctataact
 61 cctccagtgt atgccgctga gcagaaatta agtttaaaca ctaaatcatt cagcgtgaag
121 ctgggggcta cacgggtgat ttatcacgct ggtacagttg gagccacgct ctcggtgagc
181 aacccgcaga attaccctat tttggttcag tcttcagtca aagcagcaga caaaagttcg
241 cctgctcctt ttttggtgat gccgcctcta tttcgtttag aagcgaacca gcagagtcaa
301 ctgcgtattg tccgtactgg tggtgacatg ccaacggatc gtgagacttt acagtgggtc
361 tgtgtaaagg cggtaccacc cgaaaatgaa ccgtcggata cacaggctaa gggcgcgacc
421 cttgacctca atttgtccat caacgtctgt gataagctga ttttccgccc ggatgccgtg
481 aaggggacgc cggaagatgt tgcaggaaat ttaagatggg tggaggcggg caacaaactt
541 aaggtggaga accccacccc gttttacatg aatttagcct ccgtcacagt aggggaaag
601 cccattacag ggcttgagta tatccccct tttgctgaca aaacactaaa tatgccaggt
661 agtgcccatg gtgatgtcga gtggagagtt attactgact ttggtggtga aagtcatccg
721 ttccactacg tccttaaata a
```

Figure 40

DraB

SEQ ID NO:19

```
         10         20         30         40         50         60
MKMRAVAVFT GMLTGVLSVA GLLSAGAYAA GGEGNMSASA TETNARVFSL HLGATRVVYN 70         80         90        100        110        120
PASSGETLTV INDQDYPMLV QSEVLSEDQK SPAPFVVTPP LFRLDGQQSS RLRIVRTGGE 130        140        150        160        170        180
FPPDRESLQW ICVKGIPPKE GDRWAEGKDG EKKADKVSLN VQLSVSSCIK LFVRPPAVKG 190        200        210        220        230        240
RPDDVAGKVE WQRAGNRLKG VNPTPFYINL STLTVGGKEV KEREYIAPFS SREYPLPAGH

RVRFSGR
```

Figure 41

DraB

SEQ ID NO:20

```
  1 atgaaaatgc gggctgtggc tgtgttcacc ggcatgctga cgggagtgtt atcagtggca
 61 ggtttgctgt cagcggggge atatgccgcc gggggagaag ggaatatgtc tgcatccgcg
121 acggagacaa acgccagagt attctcgctg catctggggg ccacgcgggt ggtttacaac
181 ccggcctcgt cgggggagac gctgacggtg attaatgacc aggactatcc gatgctggtg
241 cagtcggagg tgctgagtga ggaccagaag agtccggcgc cttttgtggt gacaccgccg
301 ttgttccgtc ttgatggtca gcagtcgagt cgtctgcgta ttgtcaggac gggcggggag
361 tttccgccag accgtgagag tctgcagtgg atttgcgtga aaggcattcc gccgaaggaa
421 ggtgacaggt gggcggaagg gaaggacggg gagaagaagg ctgacaaagt ctccctgaat
481 gtacagcttt cagtgagcag ctgcatcaag ctgtttgttc gtccgccggc ggtgaagggg
541 cgaccggatg atgtggccgg caaggtggag tggcagaggg ccggcaacag gctgaagggg
601 gttaacccga cgccgtttta catcaacctg tccacgctga cggtgggggg taaggaagtg
661 aaggagcgtg aatatattgc gccgttttcc tcccgtgaat atccgctgcc tgcggggcat
721 cgggtaaggt tcagtggaag gtga
```

Figure 42A

SafC

SEQ ID NO:21

```
         10         20         30         40         50         60
  MKFKQPALLL FIAGVVHCAN AHTYTFDASM LGDAAKGVDM SLFNQGLQQP GTYRVDVMVN 70         80         90        100        110        120
  GKRVDTRDVV FKLEKDGQGT PVLAPCLTVS QLSRYGVKTE DYPQLWKAAK PPDECADLTA 130        140        150        160        170        180
  IPQAKAVLDI NNQQLQLSIP QLALRPEFKG IAPEDLWDDG IPAFLMNYSA RTTQTDYKMD 190        200        210        220        230        240
  MVGRDNSSWV QLQPGINIGA WRVRNATSWQ RSSQLSGKWQ AAYTYAERGL YSLKSRLTLG 250        260        270        280        290        300
  QKTSQGEIFD SVPFTGVMLA SDDNMVPYSE RQFAPVVRGI ARTQARVEVK QNGYTIYNTT 310        320        330        340        350        360
  VAPGPFALRD LSVTDSSGDL HVTVWEADGS TQMFVVPYQT PAIALHQGYL KYSLLAGRYR 370        380        390        400        410        420
  SSDSATDKRQ IAQATLMYGL PWNLTAYGGI QSATHNQAAL LGLGGSLGRW GSLSVDGSDT 430        440        450        460        470        480
  HSQRQGEAVQ QGASWRLRYS NQLTATGTNF FLTRWQYASQ GYNTLSDVLD SYRHNGNRLW 490        500        510        520        530        540
  SWRENLQPSS RTTLMLSQSW GRHLGNLSLT GSRTDWRNRP GHDDSYGLSW GTSIGGGSLS 550        560        570        580        590        600
  LNWNQNRTLW RNGAHRKENI TSLWFSMPLS RWTGNNVSAS WQMTSPSHGG QTQQVGVNGE 610        620        630        640        650        660
  AFSQQLDWEV RQSYRADAPP GGGNNSALHL AWNGDYGLLG GDYSYSRAMR QMGVNIAGGI
```

Figure 42B

```
           670        680        690        700        710        720
    VIHHHGVTLG QPLQGSVALV EAPGASGVPV GGWPGVKTDF RGDTTVGNLN VYQENTVSLD 730        740        750        760        770        780
    PSRLPDDAEV TQTDVRVVPT EGAVVEAKFH TRIGARALMT LKREDGSAIP FGAQVTVNGQ 790        800        810        820        830
    DGSAALVDTD SQVYLTGLAD KGELTVKWGA QQCRVNYRLP AHKGIAGLYQ MSGLCR
```

Figure 43A

SafC

SEQ ID NO:22 atgaag ttcaaacaac ctgccttgct actgttcatc gcgggagtgg
ttcattgcgc aaatgcgcac acttacacat tcgatgcatc aatgttgggc gatgcagcga
aagggttga tatgtcgctc tttaaccagg ggttacaaca gccagggact tatcgcgtgg
acgtgatggt gaatggtaaa cgtgtcgaca cccgtgatgt ggtgttcaaa ttggaaaagg
atgggcaagg aacgcctgtt ctggctcctt gtttgacggt cagtcagctt tcacgctacg
gcgtaaaaac ggaagattac cctcagttgt ggaaagcagc aaagccccca gatgagtgtg
cggatctgac cgccattcca caggctaaag cggtactgga tatcaataat cagcaactgc
aactgagtat tccgcagttg gcgttgcgtc cggaatttaa ggggatcgct ccagaagatc
tttgggatga tggtattccg gcgtttctga tgaactacag tgcgaggaca acgcagacgg
attacaaaat ggatatggtg gggcgtgaca actcttcctg ggtacaactg caaccgggaa
tcaatatagg tgcgtggcgt gtccgcaatg cgaccagctg gcagcggagt agtcaactgt
cggggaagtg gcaggcagca tatacctatg ctgagcgtgg actgtactca ctaaaaagtc
gtctgactct ggggcaaaag acttcgcagg gggagatatt tgatagtgtg ccatttaccg
gtgtgatgtt ggcatcggat gacaacatgg tgccctacag tgagcggcag tttgctccgg
tagtgcgtgg gattgcccgc acgcaggctc gggtggaggt caaacagaat ggttacacca
tttacaacac cactgtggcg cccggaccgt ttgcactgcg ggatctgtcg gtaacagaca
gtagtggtga tctgcatgtc accgtgtggg aggccgatgg cagtacacaa atgtttgtgg
tgccgtatca gaccccggcg atagcactgc accagggata tttgaagtac agcctgttgg
cgggccgata ccgatcgtca gactctgcaa cggataagcg gcagatcgcg caggctacgt
tgatgtatgg tctgccgtgg aatctcactg catacggcgg tatacagagt gcaacgcata
atcaagctgc attgcttggt ttgggggggat ctctcgggcg gtgggggagt ttatctgtcg
atggaagcga cacacacagt cagcgtcagg gggaggcggt acagcaagga gcctcctggc
gactgcgtta cagcaaccag ctgactgcga cggggacaaa tttttttctg acgagatggc
agtatgcctc gcagggctat aacaccctat ccgatgtgct cgacagttat cgacataatg
gcaaccgtct atggtcgtgg cgggaaaatt tgcagccgag ctcgcgtact accctgatgt
tgagtcagtc atgggggagg catttgggca atctgagttt aaccggttcc cgtaccgact
ggcgtaatcg ccccggtcat gatgacagct acggactgag ttggggaacc tctatcggag
ggggctcgct gtcattgaac tggaatcaaa acagaacgct gtggcgcaat ggcgcgcacc
gtaaagagaa cataaccagc ctgtggttca gtatgccatt aagccgctgg acggggaata
atgtaagtgc tagttggcag atgacttcac catcacacgg tggtcagacg caacaagtgg
gggtcaacgg agaggcattc agtcagcaac tggattggga ggtgcgtcag agttaccgtg
ccgatgcccc gccaggtggt ggtaataaca gcgcattgca cttggcatgg aatggggatt
acggcctgtt aggtggtgac tatagctaca gccgggcgat gcgccagatg ggagtcaata
tcgcgggagg tatagttatc caccatcatg gtgtgacgct ggggcaacct ttgcaaggct
cagtggcgct ggttgaagcg ccaggggcct cggggtgcc agttggcggc tggcctggcg
ttaagacgga ttttcgtggc gacaccacag tgggcaacct gaacgtctat caggagaata
cagtcagcct cgatccgtcg cgactaccgg atgacgcaga ggtcacacaa accgatgtgc
gcgtggtgcc aaccgaaggg gcggtggtgg aagcgaagtt tcacactcgc atcggggcca

Figure 43B gggcactgat gacgctgaaa cgggaagatg gtagcgccat tcctttcggg gcgcaggtta
cagtcaatgg gcaggatggc agtgctgctc tggtggatac tgatagccag gtttatctca
ctggtttggc ggataagggc gaactgacgg tgaaatgggg agcacagcaa tgtcgggtta
actaccgcct acctgcccac aagggaatcg cgggcttgta tcaaatgagc ggtctctgca
gatag

Figure 44A

DraC

SEQ ID NO:23

```
         10         20         30         40         50         60
  MRDTSSGRMR TGVTGLALAV MVACVMFRAE SGIARTYSFD AAMLKGGGKG VDLTLFEEGG 70         80         90        100        110        120
  QLPGIYPVDI ILNGSRVDSQ EMAFHAERDA EGRPYLKTCL TREMLARYGV RIEEYPALFR 130        140        150        160        170        180
  ASGEGRGASV AEEACADLTA IPQATESYQF AAQQLVLGIP QVAPSAAEGD WPEALWDDGI 190        200        210        220        230        240
  PAFLLNWQAN AGRSEYRGYG KRVTDSYWVS LQPGINIGPW RVRNLTTWNR SSGQSGKWES 250        260        270        280        290        300
  SYIRAERGLN GIKSRLTLGE DYTPSDIFDS VPFRGAMMSS DESMVPYNLR EFAPVVRGIA 310        320        330        340        350        360
  RTQARIEVRQ NGYLIQSQTV APGAFALTDL PVTGSGSDLQ VTVLESDGTA QVFTVPFTTP 370        380        390        400        410        420
  AIALREGYLK YNVTAGQYRS SDDAVEHTSL GQVTAMYGLP WGLTVYGGLQ GADDYQSAAL 430        440        450        460        470        480
  GLGWSLGRLG AVSLDTTHSR GQQKGHDYET GDTWRIRYNK SFELTGTSFT AASYQYSSDG 490        500        510        520        530        540
  YHTLPDVLDT WRDDRYAYRH TENRSRRTTL SLSQSLGQWG YVGLNGSRDE YRDRPHRDYF 550        560        570        580        590        600
  GASYSTSWNN ISLSVNWSRN RNSGGYYGGW SRTEDSVSMW MSVPLGRWFG GADNDISTTA 610        620        630        640        650        660
  QMQRSTGQDT RYEAGLNGRA FDRRLYWDVR EQMVPGSESH ADTSRLNLTW YGTYGELTGM
```

Figure 44B

```
            670        680        690        700        710        720
       YSYSSTMRQL NAGMSGSMVA HSEGVTFGQR TGDTVALIAA PGVSGASVGG WPGVRTDFRG 730        740        750        760        770        780
       YTLAGYASPY QENVLTLDPT TFPEDAEVPQ TDSRVVPTKG AVVRAGFRTR VGGRALVSLA 790        800        810        820        830        840
       RQDGTPLPFG AVVTVEGEAG QAAGSAGVVG DRGEVYLSGL KESGKLKAQW GENSLCHADY

850

RLPEEKGPAG IFLTRTVCM
```

Figure 45A

DraC

SEQ ID NO:24

```
   1 atgcgtgata cttcttcagg gcggatgaga acggggggtga cagggctggc gctggctgtg
  61 atggtggcct gtgtgatgtt tcgtgcggag agtggtattg cgcgcaccta ctcctttgat
 121 gcggccatgc tgaaaggtgg cgggaagggg gtgacctga ccctgtttga ggaaggtggg
 181 cagttacccg gcatttatcc ggttgacatt atcctgaatg gttcccgtgt ggattcacag
 241 gagatggcct ttcacgcgga gagggacgcg gagggcaggc cttatctgaa gacctgtctg
 301 acccgtgaga tgctggcgcg ttacggggtc aggattgagg aatatccggc gttgttccgt
 361 gcatccggag agggtcgtgg tgcctccgtg gcggaggagg cctgtgctga cctgacggcg
 421 ataccgcagg ccacggagag ttatcagttt gctgcccagc aactggttct gggtatccct
 481 caggtggcac cgtccgcagc tgagggggat tggccggagg cgttatggga tgatggcatt
 541 ccggcttttc tgctgaactg gcaggcgaat gcggggcgca gtgagtaccg gggttacggg
 601 aagcgtgtca cggacagtta ctgggtcagt ctgcagccgg gaatcaacat tggaccctgg
 661 cgtgtgagga acctgaccac ctggaacagg tcatccggtc agtcgggaaa atgggagagt
 721 tcatacatac gtgctgagcg ggggctgaac gggataaaga gtcgcctgac gctgggtgag
 781 gattacacgc cgtcagacat ttttgacagt gtgcctttcc gggggggcgat gatgagttct
 841 gatgagagta tggtgcctta aacctgcgt gaatttgcgc cggttgtacg tggcattgcc
 901 cgcacgcagg ccaggataga ggtgcgtcag aacggctatc tgatacaaag tcagacggtg
 961 gcgccgggggg catttgccct gacggacctg ccggtgacgg ggtccggcag tgacctgcag
1021 gtgacggtgc tggaatcaga cgggacggcg caggttttca cggtgccgtt caccacgccg
1081 gccattgcgc tgcgtgaggg gtacctgaag tacaacgtca cggcgggtca gtaccgttca
1141 tcggatgatg cggttgagca cacgtcgctg ggacaggtga cggccatgta cggtctgccg
1201 tgggggctga cggtgtacgg gggggcttcag ggagcggacg attaccagtc tgcggctctg
1261 gggcttggct ggtcactggg gcgtctgggg gcggtgtcgc tggacacgac gcactcccgg
1321 gggcagcaga agggacatga ttatgagacc ggtgacacct ggcgtatccg ttataacaag
1381 tcgtttgagc tgacggggac gagttttacg gcagcgagtt atcagtactc atcggatggt
1441 taccatacgc tgccggacgt gctggacacc tggcgtgatg accggtacgc ataccgtcac
1501 acggagaacc ggagtcgccg taccacgctg agtctgagtc agtccctggg tcagtggggc
1561 tatgtgggac tgaacggcag ccgggatgag taccgtgaca gaccgcaccg tgattatttt
1621 ggcgcgtcat acagtacgtc ctggaacaat atctcgctgt cggttaactg gtcacgcaac
1681 cgcaacagcg gcggctatta ccgtggctgg tcgcgtacgg aagacagtgt cagtatgtgg
1741 atgagtgtgc cgctgggacg ctggtttggg ggggcggata acgatatcag taccacggcg
1801 cagatgcagc gttccacggg acaggatacc cggtatgagg ccgggctgaa cggacgggca
1861 tttgaccgcc ggctgtactg ggatgtccgt gagcagatgg tgccgggcag tgagagccat
1921 gctgacacca gtcgtctgaa cctgacgtgg tacgggacat atggtgaact gacgggggatg
1981 tacagttaca gcagcacgat gcgccagctg aacgccggga tgtccggcag catggttgcc
2041 cacagtgagg gggtcacctt tggtcagcgg accgggggata cggtggcact gattgcggca
2101 ccgggcgtga gtggtgcgtc tgtgggtggc tggccgggtg tgagaacgga tttccggggg
2161 tatacgctgg ccggttatgc gtcaccgtac caggagaacg tgctgacact ggacccgacg
2221 acgtttccgg aggatgcgga agtgccgcag acggacagtc gtgtggtgcc gacgaagggg
```

Figure 45B 2281 gcagtggtcc gggccggatt caggacccgt gtgggtggtc gtgcgctggt gagtctggcc
2341 cgtcaggacg gaacgccgct gccgtttggt gcggtggtga cagttgaggg cgaagcgggt
2401 caggctgcgg gatcagccgg tgtggtggga gaccgtggtg aggtgtacct gagcgggctg
2461 aaggaaagcg gtaagctgaa ggcgcagtgg ggagagaaca gtctgtgcca tgcggattac
2521 cgtcttccgg aagagaaggg tcctgcgggg atatttctga cccgtacggt gtgtatgtga

Figure 46

FimH

SEQ ID NO:25

```
         10         20         30         40         50         60
MKRVITLFAV LLMGWSVNDW SFACKTANGT AIPIGGGSAN VYVNLAPVVN VGQNLVVDLS 70         80         90        100        110        120
TQIFCHNDYP ETITDYVTLQ RGSAYGGVLS NFSGTVKYSG SSYPFPTTSE TPRVVYNSRT 130        140        150        160        170        180
DKPWPVALYL TPVSSAGGVA IKAGSLIAVL ILRQTNNYNS DDFQFVWNIY ANNDVVVPTG 190        200        210        220        230        240
GCDVSARDVT VTLPDYPGSV PIPLTVYCAK SQNLGYYLSG TTADAGNSIF TNTASFSPAQ 250        260        270        280        290        300
GVGVQLTRNG TIIPANNTVS LGAVGTSAVS LGLTANYART GGQVTAGNVQ SIIGVTFVYQ
```

Figure 47

FimH

SEQ ID NO:26

```
   1 taagagtcag cctataccta cagctgaacc cgaagagatg attgtaatga aacgagttat
  61 taccctgttt gctgtactgc tgatgggctg gtcggtaaat gactggtcat tcgcctgtaa
 121 aaccgccaat ggtaccgcta tccctattgg cggtggcagc gccaatgttt atgtaaacct
 181 tgcgcccgtc gtgaatgtgg ggcaaaacct ggtcgtggat ctttcgacgc aaatctttg
 241 ccataacgat tatccggaaa ccattacaga ctatgtcaca ctgcaacgag gctcggctta
 301 tggcggcgtg ttatctaatt tttccgggac cgtaaaatat agtggcagta gctatccatt
 361 tcctaccacc agcgaaacgc cgcgcgttgt ttataattcg agaacggata agccgtggcc
 421 ggtggcgctt tatttgacgc ctgtgagcag tgcgggcggg gtggcgatta agctggctc
 481 attaattgcc gtgcttattt tgcgacagac caacaactat aacagcgatg atttccagtt
 541 tgtgtggaat atttacgcca ataatgatgt ggtggtgcct actggcggct gcgatgtttc
 601 tgctcgtgat gtcaccgtta ctctgccgga ctaccctggt tcagtgccaa ttcctcttac
 661 cgtttattgt gcgaaaagcc aaaacctggg gtattacctc tccggcacaa ccgcagatgc
 721 gggcaactcg attttcacca ataccgcgtc gttttcacct gcacagggcg tcggcgtaca
 781 gttgacgcgc aacggtacga ttattccagc gaataacacg gtatcgttag gagcagtagg
 841 gacttcggcg gtgagtctgg gattaacggc aaattatgca cgtaccggag ggcaggtgac
 901 tgcagggaat gtgcaatcga ttattggcgt gactttgtt tatcaataaa gaaatcacag
 961 gacattgcta atgctggtac gcaatattac ctgaagctaa aaacctgcac gttagccctt
1021 tgtaggccag ataagacgcg
```

Figure 48

FimG

SEQ ID NO:27

```
          10         20         30         40         50         60
  MKWCKRGYVL AAILALASAT IQAADVTITV NGKVVAKPCT VSTTNATVDL GDLYSFSLMS 70         80         90        100        110        120
  AGAASAWHDV ALELTNCPVG TSRVTASFSG AADSTGYYKN QGTAQNIQLE LQDDSGNTLN 130        140        150        160
  TGATKTVQVD DSSQSAHFPL QVRALTVNGG ATQGTIQAVI SITYTYS
```

Figure 49

FimG

SEQ ID NO:28

```
  1 atgaaatggt gcaaacgtgg gtatgtattg gcggcaatat tggcgctcgc aagtgcgacg
 61 atacaggcag ccgatgtcac catcacggtg aacggtaagg tcgtcgccaa accgtgtacg
121 gtttccacca ccaatgccac ggttgatctc ggcgatcttt attctttcag tcttatgtct
181 gccggggcgg catcggcctg gcatgatgtt gcgcttgagt tgactaattg tccggtggga
241 acgtcgaggg tcactgccag cttcagcggg gcagccgaca gtaccggata ttataaaaac
301 caggggaccg cgcaaaacat ccagttagag ctacaggatg acagtggcaa cacattgaat
361 actggcgcaa ccaaaacagt tcaggtggat gattcctcac aatcagcgca cttcccgtta
421 caggtcagag cattgacagt aaatggcgga gccactcagg gaaccattca ggcagtgatt
481 agcatcacct atacctacag ctga
```

Figure 50

FimF

SEQ ID NO:29

```
         10         20         30         40         50         60
MRNKPFYLLC AFLWLAVSHA LAADSTITIR GYVRDNGCSV AAESTNFTVD LMENAAKQFN 70         80         90        100        110        120
NIGATTPVVP FRILLSPCGN AVSAVKVGFT GVADSHNANL LALENTVSAA SGLGIQLLNE 130        140        150        160        170
QQNQIPLNAP SSALSWTTLT PGKPNTLNFY ARLMATQVPV TAGHINATAT FTLEYQ
```

Figure 51

FimF

SEQ ID NO:30

```
  1 atgagaaaca aaccttttta tcttctgtgc gcttttttgt ggctggcggt gagtcacgct
 61 ttggctgcgg atagcacgat tactatccgc ggctatgtca gggataacgg ctgtagtgtg
121 gccgctgaat caaccaattt tactgttgat ctgatggaaa acgcggcgaa gcaatttaac
181 aacattggcg cgacgactcc tgttgttcca tttcgtattt tgctgtcacc ctgtggtaat
241 gccgtttctg ccgtaaaggt tgggtttact ggcgttgcag atagccacaa tgccaacctg
301 cttgcacttg aaaatacggt gtcagcggct tcgggactgg gaatacagct tctgaatgag
361 cagcaaaatc aaatacccct taatgctcca tcgtccgcgc tttcgtggac gaccctgacg
421 ccgggtaaac caaatacgct gaatttttac gcccggctaa tggcgacaca ggtgcctgtc
481 actgcggggc atatcaatgc cacggctacc ttcactcttg aatatcagta a
```

Figure 52

PapG

SEQ ID NO:31

```
          10         20         30         40         50         60
  MKKWFPAFLF LSLSGGNDAL AGWHNVMFYA FNDYLTTNAG NVKVIDQPQL YIPWNTGSAT 70         80         90        100        110        120
  ATYYSCSGPE FASGVYFQEY LAWMVVPKHV YTNEGFNIFL DVQSKYGWSM ENENDKDFYF 130        140        150        160        170        180
  FVNGYEWDTW TNNGARICFY PGNMKQLNNK FNDLVFRVLL PVDLPKGHYN FPVRYIRGIQ 190        200        210        220        230        240
  HHYYDLWQDH YKMPYDQIKQ LPATNTLMLS FDNVGGCQPS TQVLNIDHGS IVIDRANGNI 250        260        270        280        290        300
  ASQTLSIYCD VPVSVKISLL RNTPPIYNNN KFSVGLGNGW DSIISLDGVE QSEEILRWYT 310        320        330
  AGSKTVKIES RLYGEEGKRK PGELSGSMTM VLSFP
```

Figure 53

PAP G

SEQ ID NO:32

```
1 ggccagtatg agcatgattt ataactgagt catacctaaa tgaataactg taattacgga
61 agtgatttct gatgaaaaaa tggttccctg cttttttatt tttatccctg tcaggcggta
121 atgatgcttt agctggatgg cacaatgtca tgttttatgc ttttaacgac tatttaacta
181 caaatgctgg taatgttaag gttattgacc aacctcagct atatataccc tggaatacag
241 gctctgctac agcaacttat tattcgtgct caggtccgga atttgcgagt ggagtgtatt
301 ttcaggagta tctggcctgg atggttgttc ctaaacatgt ctatactaat gaggggttta
361 atatatttct tgatgttcag agcaaatatg gttggtctat ggagaatgaa aatgacaaag
421 atttttactt ctttgttaat ggttatgaat gggatacatg gacaaataat ggtgcccgta
481 tatgtttcta tcctggaaat atgaagcagt tgaacaataa atttaatgat ttagtattca
541 gggttctttt gccagtagat ctccccaagg gacattataa ttttcctgtg agatatatac
601 gtggaataca gcaccattac tatgatctct ggcaggatca ttataaaatg ccttacgatc
661 agattaagca gctacctgcc actaatacat tgatgttatc attcgataat gttgggggat
721 gccagccgtc aacacaagta cttaatatag accatgggag tattgtgatt gatcgtgcta
781 acggaaatat tgcaagtcag acgctttcaa tttattgcga tgtaccagtt agtgtaaaaa
841 tatctctgct cagaaataca ccaccaatat acaataataa taaattttcg gttgggttag
901 gtaatggctg ggattcgata atatctcttg atggggttga acagagtgag gaaatattac
961 gctggtacac agccggctca aaaacagtaa agattgagag caggttgtat ggtgaagagg
1021 gaaagagaaa acccggggag ctatctggtt ctatgactat ggttctgagt ttcccctgaa
1081 taagatgatg gattatctga ctggctgttc atcagtcgga taatgatgaa aactgatgag
1141 caacaggttg tcgggcaatg tcaggatcc
```

Figure 54

PapF

SEQ ID NO:33

```
         10         20         30         40         50         60
MIRLSLFISL LLTSVAVLAD VQINIRGNVY IPPCTINNGQ NIVVDFGNIN PEHVDNSRGE 70         80         90        100        110        120
VTKTISISCP YKSGSLWIKV TGNTMGGGQN NVLATNITHF GIALYQGKGM STPLILGNGS 130        140        150        160
GNGYGVTAGL DTARSTFTFT SVPFRNGSGI LNGGDFQTTA SMSMIYN
```

Figure 55

PapF

SEQ ID NO:34 atgatt cgtttatcat tatttatatc gttgcttctg acatcggtcg
ctgtactggc tgatgtgcag attaacatca gggggaatgt ttatatcccc ccatgcacca
ttaataacgg gcagaatatt gttgttgatt ttgggaatat taatcctgag cacgtggaca
actcacgtgg tgaagtcaca aaaaccataa gcatatcctg tccgtataag agtggctctc
tctggataaa agttacggga aatactatgg gaggaggtca gaataatgta ctggcaacaa
atataactca ttttggtata gcgctgtatc agggaaaagg aatgtcaaca cctcttatat
taggtaatgg ttcaggaaat ggttacggag tgacagcagg tctggacaca gcacgttcaa
cgttcaccttt tacttcagtg ccctttcgta atggcagcgg gatactgaat ggcggggatt
tccagaccac ggccagtatg agcatgattt ataactga

Figure 56

PapE

SEQ ID NO:35

```
         10         20         30         40         50         60
MKKIRGLCLP VMLGAVLMSQ HVHAVDNLTF RGKLIIPACT VSNTTVDWQD VEIQTLSQNG 70         80         90        100        110        120
NHEKEFTVNM RCPYNLGTMK VTITATNTYN NAILVQNTSN TSSDGLLVYL YNSNAGNIGT 130        140        150        160        170
AITLGTPFTP GKITGNNADK TISLHAKLGY KGNMQNLIAG PFSATATLVA SYS
```

Figure 57

PapE

SEQ ID NO:36 at gaaaaagata agaggtttgt gtcttccggt aatgctgggg
gcagtgttaa tgtctcagca tgtacatgca gttgataatc tgaccttcag aggaaaactg
attattcctg cctgtactgt aagcaacaca actgttgact ggcaggatgt agagattcag
accctgagtc aaaatggaaa tcacgaaaaa gagtttactg tgaatatgcg gtgtccctat
aatctgggaa caatgaaggt tacgataacg gcaacaaaca cttataacaa tgctatttta
gttcagaata catcaaacac atcttctgat gggttactcg tttatcttta taacagtaat
gcaggaaata ttgggactgc gataacttta gggactccat ttacgcccgg aaaaatcaca
ggtaataatg cagataaaac tatatcactt catgccaaac ttggatataa agggaatatg
cagaatttga tagccggtcc tttctctgca

Figure 58

PapK

SEQ ID NO:37

```
         10         20         30         40         50         60
  MIKSTGALLL FAALSAGQAI ASDVAFRGNL LDRPCHVSGD SLNKHVVFKT RASRDFWYPP 70         80         90        100        110        120
  GRSPTESFVI RLENCHATAV GKIVTLTFKG TEEAALPGHL KVTGVNAGRL GIALLDTDGS 130        140        150        160        170
  SLLKPGTSHN KGQGEKVTGN SLELPFGAYV VATPEALRTK SVVPGDYEAT ATFELTYR
```

Figure 59

PapK

SEQ ID NO:38 atgataaa aagcacaggc gctcttttac tgtttgccgc actgtctgcc
ggacaggcaa tagcctcaga tgtggcattc aggggtaatc tgcttgacag accctgccat
gtgtccggtg acagtctgaa taaacatgtc gtcttcaaaa cccgggcgtc cagggatttc
tggtatccgc ccggacgttc gccgacagag tcgtttgtca tcaggctgga aaactgccat
gcaacagcag ttggcaaaat tgtgaccctg acctttaagg ggacggaaga ggcggccctc
ccgggccatc tgaaggtaac cggagtgaat gctggccggt taggcattgc actgctggac
accgatggca gcagtctgct gaaacccggc acctcccata acaaaggcca gggggaaaag
gttaccggaa acagtcttga gcttcctttc ggcgcgtatg ttgtggcaac gccggaagcc
ctgcggacga agagtgtggt acccggtgat tatgaagcaa cagccacgtt tgaattgaca
tatcgttag Figure 60
Falcon tubes containing 0.2% L-arabinose and no D-glucose
E. coli TOP10/ pAH34L     E. coli TOP10/pBAD33_SD_Caf1 + pAH34L     E. coli TOP10/pBAD33_SD_Caf1
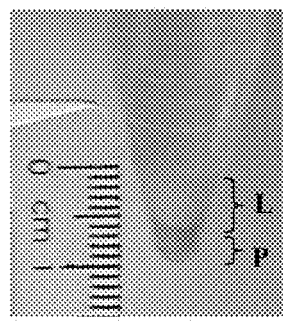 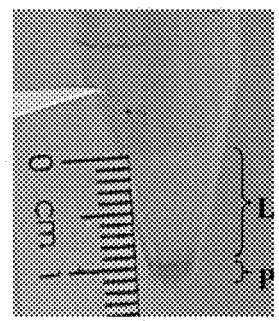 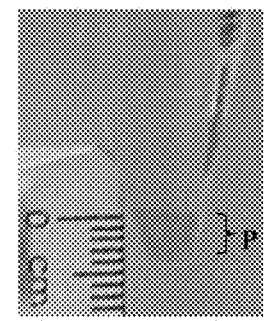
Falcon tubes containing 0.2% of L-arabinose and 0.2% of D-glucose
E. coli TOP10/ pAH34L     E. coli TOP10/pBAD33_SD_Caf1 + pAH34L     E. coli TOP10/pBAD33_SD_Caf1
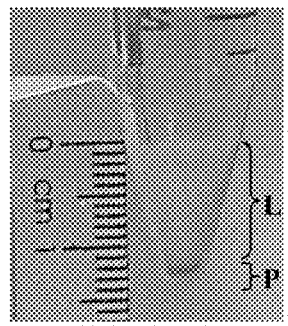 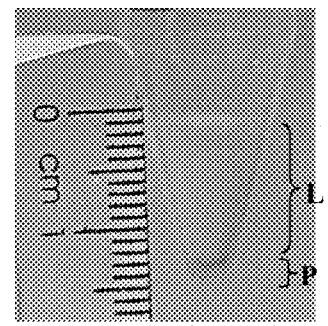 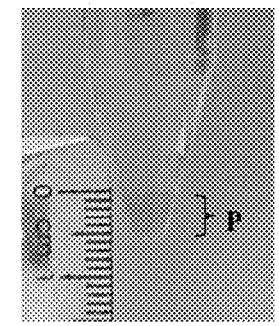

Plasmids and percentage of L-arabinose used

Figure 66
(a)
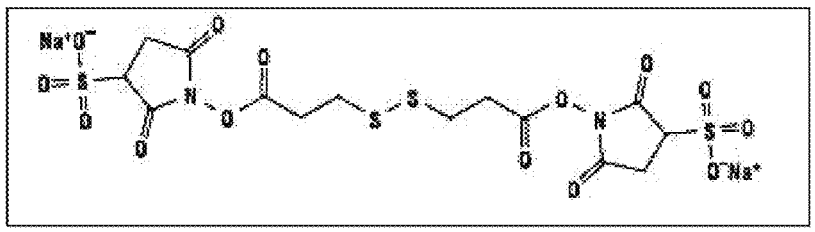
DTSSP cross-linker structure.
(b)
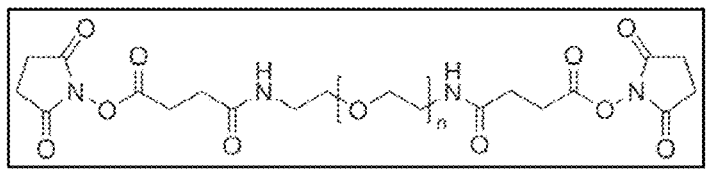
NHS-PEG-NHS cross-linker structure.
(c)
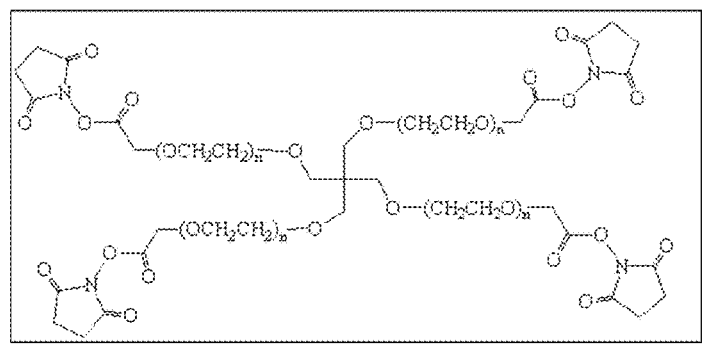
4-Arm NHS-PEG cross-linker structure.

Figure 69
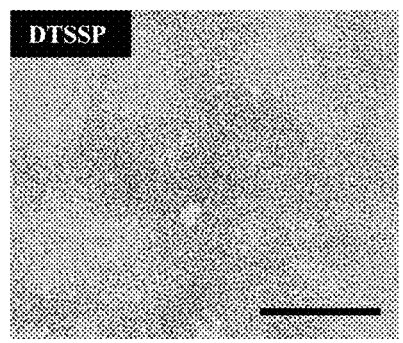
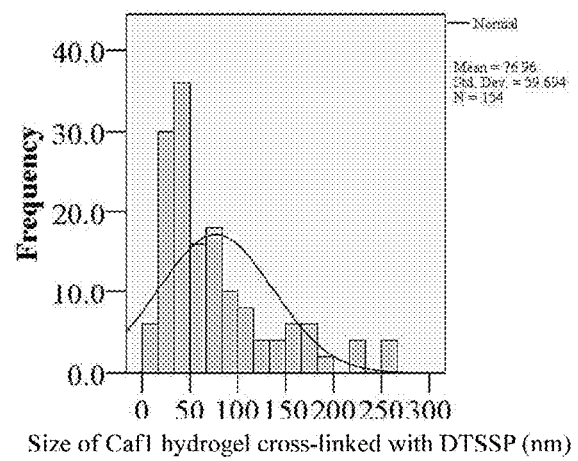
Size of Caf1 hydrogel cross-linked with DTSSP (nm)
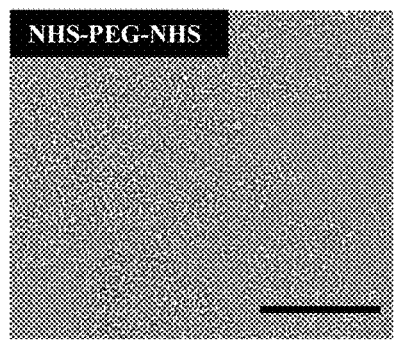
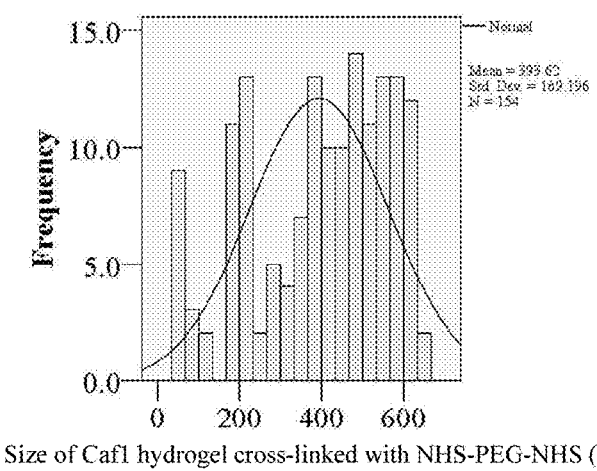
Size of Caf1 hydrogel cross-linked with NHS-PEG-NHS (nm)
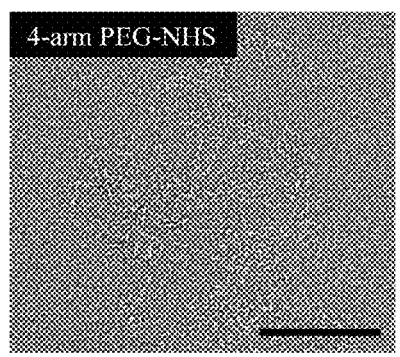
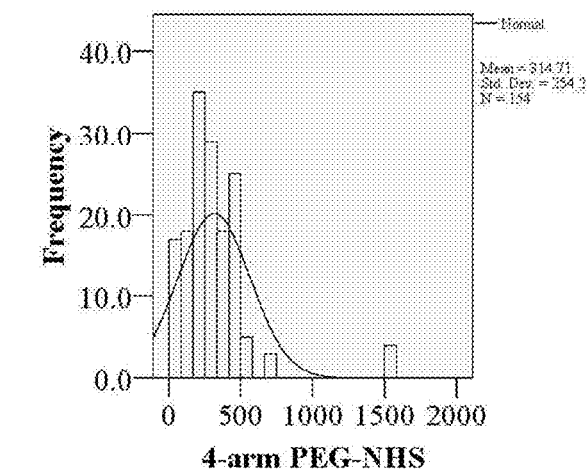
Size of Caf1 hydrogel cross-linked with 4-arm PEG-NHS

RECOMBINANT POLYPEPTIDE

This invention relates to a protein polymer comprising a recombinant protein monomer with an exogenous bioactive sequence. More particularly the invention relates to chaperone/usher family polymers comprising at least one chaperone/usher family polypeptide monomer, wherein said at least one chaperone/usher family polypeptide monomer comprises an exogenous bioactive sequence.

BACKGROUND

In vivo proteins and other extracellular matrix (ECM) components form an interlinking mesh in which cells integrate and interact. One way to mimic this natural architecture is through crosslinking artificial polymers to create 3 dimensional cell culture systems.

The cell culture and tissue engineering fields are well developed and a variety of ECM equivalents have been developed. These equivalents vary in the material that is used for a scaffold and consequently in the type cells that are capable of propagating therein.

Fibronectin (FN) is a predominant ECM protein that mediates cell attachment and growth. FN contains several ligands, including the tripeptide RGD and the peptide PHSRN (SEQ ID NO:40), which mediate cell adhesion. Naturally derived proteins such as fibronectin can be useful as scaffolds for in vitro cell attachment. However, a potential problem with any animal derived protein is the possibility of disease transmission.

Accordingly a range of engineered 3 dimensional scaffolds, which recreate the native 3 dimensional tissue, have been suggested. Current 3 dimensional scaffolds are not ideal (7). For instance, it is difficult to produce a scaffold which is specific for a particular cell line or tissue type; there is also among these scaffolds a high batch-to-batch variability; it is complicated to change a single property of these scaffolds without interfering with others. For example, if one would like to alter the viscosity of a particular scaffold one can eventually modify simultaneously the adhesion ligand density and mode of presentation or the porosity of the scaffold which could influence the diffusion properties of nutrients through the scaffold (11).

Accordingly, there remains the need for the provision of an improved cell culture environment.

BRIEF SUMMARY OF THE DISCLOSURE

In one aspect, the invention provides a chaperone/usher family polymer comprising at least one chaperone/usher family polypeptide monomer, wherein said at least one chaperone/usher family polypeptide monomer comprises an exogenous bioactive sequence.

Preferably, the bioactive sequence is substantially non-immunogenic.

Preferably, the monomer is substantially free from naturally occurring adhesion motifs.

Preferably, said monomer is a FG loop long family polypeptide monomer, for example a FG loop long family polypeptide monomer selected from the group consisting of Caf1, Saf1 and Afa/Dr. More preferably, said monomer is a Caf1 polypeptide. Still more preferably, said monomer is at least 70% identical to the polypeptide of SEQ ID NO:5.

Alternatively, said monomer is a FG loop short family polypeptide monomer, for example a FG loop short family polypeptide monomer selected from the group consisting of Fim and Pap.

Preferably, said bioactive sequence is selected from the group consisting of a cell adhesion recognition motif, a growth factor sequence motif and a protease site. More preferably, said bioactive sequence is a cell adhesion recognition motif. Still more preferably, said cell adhesion recognition motif is an extracellular matrix cell adhesion recognition motif. Still more preferably, said cell adhesion recognition motif is selected from collagen, elastin, fibronectin, laminin or tenascin. Preferably, said cell adhesion recognition motif comprises the amino acid sequence RGD. Alternatively, or additionally, said cell adhesion recognition motif comprises the amino acid sequence PHSRN.

Preferably, said bioactive sequence is comprised within said monomer at a site which is comprised within a loop structure upon folding of said polypeptide.

Preferably, said polymer is a fraction 1 antigen polymer, and said at least one chaperone/usher family polypeptide monomer is a CAF1 polypeptide monomer.

Preferably, said polymer comprises at least one further chaperone/usher family polypeptide monomer, wherein said further chaperone/usher family polypeptide monomer differs from said at least one chaperone/usher family polypeptide monomer comprising an exogenous bioactive sequence by at least one amino acid. More preferably, the further chaperone/usher family polypeptide monomer is the chaperone/usher family polypeptide monomer described herein without said exogenous bioactive sequence.

Preferably, the further chaperone/usher family polypeptide monomer is a naturally occurring CAF1 polypeptide monomer. More preferably, said at least one naturally occurring CAF1 polypeptide monomer is a *Yersinia pestis* CAF1 polypeptide. Still more preferably, said *Yersinia pestis* CAF1 polypeptide has the polypeptide sequence of SEQ ID NO:5.

Preferably, said further chaperone/usher family polypeptide monomer comprises an exogenous bioactive sequence that is distinct from said exogenous bioactive sequence of said at least one chaperone/usher family polypeptide monomer. More preferably, said exogenous bioactive sequence of said at least one chaperone/usher family polypeptide monomer is a cell adhesion recognition motif comprising the amino acid sequence RGD and wherein said exogenous bioactive sequence of said at least one further chaperone/usher family polypeptide monomer is a cell adhesion recognition motif comprising the amino acid sequence PHSRN.

In a further aspect, the invention provides a hydrogel comprising the chaperone/usher family polymer according to the invention.

Preferably, the hydrogel further comprises a cross linking agent. More preferably, said cross linking agent is a biodegradable cross linking agent. Alternatively, said cross linking agent is a non-degradable cross linking agent.

Preferably, said cross linking agent comprises polyethylene glycol.

In a further aspect, the invention provides use of a hydrogel according to the invention as a cell support scaffold.

Preferably, said scaffold is a 2D cell support scaffold. Alternatively, said scaffold is a 3D cell support scaffold.

In a further aspect, the invention provides a wound dressing comprising the hydrogel according to the invention.

In a further aspect, the invention provides a hydrogel according to the invention for use in the treatment of a wound.

Preferably, said wound is a chronic wound or wherein said wound is an acute wound.

In a further aspect, the invention provides an ocular implant comprising the hydrogel according to the invention.

In a further aspect, the invention provides a hydrogel according to the invention for use in the treatment of an ocular injury.

In a further aspect, the invention provides a method for producing a chaperone/usher family polymer comprising at least one chaperone/usher family polypeptide monomer comprising an exogenous bioactive sequence, said method comprising:
  i) incorporating a nucleic acid molecule that encodes a chaperone/usher family polypeptide monomer comprising an exogenous bioactive sequence into an expression vector for expression in a host cell; and
  ii) transfecting a host cell with the expression vector;
wherein said host cell is provided with a nucleic acid molecule that encodes a periplasmic chaperone specific for the chaperone/usher family polypeptide monomer and a nucleic acid molecule that encodes an outer membrane usher protein specific for the chaperone/usher family polypeptide monomer and wherein the resulting transfected host cell produces a chaperone/usher family polymer.

Preferably, the bioactive sequence is substantially non-immunogenic.

Preferably, the monomer is substantially free from naturally occurring adhesion motifs.

Preferably, said chaperone/usher family polymer is a fraction 1 antigen polymer and said at least one chaperone/usher family polypeptide monomer comprising an exogenous bioactive sequence is a CAF1 polypeptide monomer. More preferably, said nucleic acid molecule that encodes the CAF1 polypeptide monomer comprising an exogenous bioactive sequence has at least 70% identity to the nucleotide sequence of SEQ ID NO: 1.

Preferably, said nucleic acid molecule that encodes a periplasmic chaperone specific for the chaperone/usher family polypeptide monomer encodes a periplasmic chaperone specific for CAF1 and wherein said nucleic acid molecule that encodes an outer membrane usher protein specific for the chaperone/usher family polypeptide monomer encodes an outer membrane usher protein specific for CAF1. More preferably, said nucleic acid molecule that encodes the periplasmic chaperone specific for CAF1 has at least 70% identity to the nucleotide sequence of SEQ ID NO: 2.

Preferably, said nucleic acid molecule that encodes the outer membrane usher protein specific for CAF1 has at least 70% identity to the nucleotide sequence of SEQ ID NO: 3.

Preferably, said host cell is provided with the nucleic acid molecule that encodes a periplasmic chaperone specific for CAF1 by:

i) incorporating the nucleic acid molecule that encodes a periplasmic chaperone specific for CAF1 into an expression vector for expression in the host cell; and ii) transfecting the host cell with the expression vector.

Preferably, said expression vector further comprises the nucleic acid molecule that encodes a CAF1 polypeptide monomer comprising a cell adhesion recognition motif.

Preferably, said host cell is provided with the nucleic acid molecule that encodes the outer membrane usher protein specific for CAF1 by:

i) incorporating the nucleic acid molecule that encodes the outer membrane usher protein specific for CAF1 into an expression vector for expression in the host cell; and ii) transfecting the host cell with the expression vector.

More preferably, said expression vector further comprises the nucleic acid molecule that encodes a CAF1 polypeptide monomer comprising a cell adhesion recognition motif and/or the nucleic acid molecule that encodes a periplasmic chaperone specific for CAF1.

Preferably, said host cell is further provided with a nucleic acid molecule that encodes an expression regulator specific for the chaperone/usher family polypeptide monomer. More preferably, said nucleic acid molecule that encodes an expression regulator specific for the chaperone/usher family polypeptide monomer encodes an expression regulator specific for CAF1.

Preferably, said nucleic acid molecule that encodes the expression regulator specific for CAF1 has at least 70% identity to the nucleotide sequence of SEQ ID NO: 4.

Preferably, said bioactive sequence is a cell adhesion recognition motif.

Preferably, said host cell is a bacterial cell. More preferably, said bacterial cell is a gram negative bacterial cell. Still more preferably, said bacterial cell is *Escherichia coli.*

In a further aspect, the invention provides use of a fraction 1 antigen polymer as an antifouling agent.

In a further aspect, the invention provides an antifouling composition comprising a fraction 1 antigen polymer.

BRIEF DESCRIPTION OF THE DRAWINGS

Embodiments of the invention are further described hereinafter with reference to the accompanying drawings, in which:

FIG. 1 is a schematic diagram of Kanamycin-resistant plasmid pAH34L which contains the thermoregulated caf operon that includes the gene encoding F1 antigen and other genes involved in the export and assembly of F1 antigen on the bacterial cell surface in *Y. pestis* (3, 12).

FIG. 2 is a schematic diagram of F1 fibre assembly and export to the surface of the bacteria cell. Caf1M is in blue; Caf1 is in red or green; Caf1A is in golden yellow. At stage 1 the F1 subunit is secreted to the periplasm; At stage 2 the Caf1M-Caf1 complex is formed in the periplasm; At stage 3 F1 fibre starts to form long polymers (elongation process). The polymerization step releases one molecule of Caf1M (M). Zaviolov and Knight reported that excessive Caf1M molecules are packed into tetramers (T) (15). Donor sequences are indicated by arrows: A1 and G1 strand-forming sequences in Caf1M are in blue, Gd strand-forming sequence in Caf1 is either in red or green. In the Caf1M-Caf1 complex, the first domain of Caf1M, and Caf1, form a fused hetero-barrel.

FIG. 3 shows the results of PCR amplification of caf operon using pAH34L vector as a template and restriction digest of PCR product a) PCR amplification. M, molecular size markers (sizes, left margin); lane 1, caf operon. Right margins, size of PCR product. b) Restriction digestion of PCR product. M, molecular size markers (sizes, left margin); lane 1, caf operon digested with BamHI restriction enzyme showed two bands of 3731 bp and 1520 bp; lane 2, caf operon digested with HindIII showed three bands of 3490 bp and 1053 bp and 707 bp; lane 3, caf operon digested with EcoRI showed a single band of 5200 bp due to the absence of the specific EcoRI restriction site; lane 4, caf operon non-digested showed a single band of 5200 bp. Right margins, size of DNA fragments in kb.

FIG. 4 shows characterisation of purified caf operon PCR product and its restriction digest a) Quantification of the PCR product. M, molecular size markers (sizes, in table); Lane U1, caf operon purified. b) Restriction digestion of PCR product. M, molecular size markers (sizes, left margin); lane 1, caf operon non-digested; lane 2, caf operon digested with EcoRI showed a single band of 5200 bp due to the absence of the specific EcoRI restriction site; lane 3, caf operon digested with BamHI restriction enzyme showed two bands of 3731 bp and 1520 bp; lane 4, caf operon digested with HindIII showed three bands of 3490 bp, 1053 bp and 707 bp. Right margins, size of DNA fragments (kb).

FIG. 5 shows representative sequencing results of the Caf1 operon cloned into plasmid pGEM-T EASY—caf operon (pGEM-TF1), showing the start of the caf operon with cafR gene sequence and the end of the caf operon with caf1 gene sequence. a) cafR gene sequence (SEQ ID NO:75) and amino acid sequences (SEQ ID NOs:76-86) using the Expasy tool (http://expasy.org/tools/dna.html). b) caf1 gene sequence (SEQ ID NO:87) and amino acid sequences (SEQ ID NOs:88-91) using the Expasy tool (http://expasy.org/tools/dna.html). Universal primers such as T7 Promoter Primer (5'-AAT TCT AAT ACG ACT CAC TAT AGG-3') (SEQ ID NO:73) or the pUC/M13 Forward Primer (5'-GTA AAA CGA CGG CCA GTG-3') (SEQ ID NO:74) were used to sequence ssDNA produced by the pGEM-T EASY vector.

FIG. 6 shows restriction digestion of pGEM-TF1. Gel electrophoresis shows M, molecular size markers (sizes, left margin); lane 1, pGEM-TF1 digested with EcoRI showed a two bands of 5.2 Kb and 3 Kb; lane 2, pGEM-TF1 non-digested showed a single band of 8.2 Kb. (a) Diagram shows caf operon insert (5.2 Kb), pGEM-T EASY vector (3 Kb) and EcoRI cut sites; (b) Diagram shows caf operon insert (5.2 Kb), pGEM-T EASY vector (3 Kb) and after ligation the resulting plasmid of 8.2 Kb.

FIG. 7 shows SDS-PAGE (on the left) and western blotting using a anti Caf1 antibody (on the right). lane 1 contained molecular mass marker proteins (molecular mass×10$^3$ kda arrowed). Sample analyzed (10 µl) was prepared from overnight bacterial cell culture Escherichia coli (pgem-tf1) grown at 37° C. The protein sample was heated at 95° C. for 5 minutes and an equal volume of SDS-PAGE buffer was added to each sample before loading the samples on 12% SDS-PAGE gels. One of the gels was stained with Coomassie Blue r250 (lane 3) and the other gel was blotted. The resulting blot was probed with anti-Caf1 antibody (lane 2 of the western blot) and then developed with HRP goat anti-mouse antibody (Sigma-Aldrich) colour development solution with 4cn (4-chloro-1-naphthol).

FIG. 8 shows mass spectrometry of a peptide digest of purified caf1 protein showing the gene product to be mature Caf1 minus the leader peptide.

FIG. 9 shows calibration curve using Superdex 200 gel filtration column. Top panel shows the expected linear relationship between the distribution coefficient and log molecular mass. Lower panel shows actual elution profiles of calibrating proteins indicating a void volume of approximately 48 ml. FIG. 9 shows the calibration of the gel filtration column with the proteins in the upper panel and their elution profiles in the bottom panel.

FIG. 10 shows Caf1 protein purification. a) Gel filtration column chromatography on Superdex 200 FPLC. The caf1 fractions were applied to a Superdex 200 gel filtration FPLC column. The main peak of Caf1 was near the void volume indicating that long polymers have formed. b) SDS-Page gel. Lane 1 contained molecular mass marker proteins (molecular mass×10$^3$ kDa arrowed). Sample analyzed (10 µL) was prepared after purification Superdex 200. Fractions were collected from the main peak and confirm the presence of Caf1 in this peak. Each fraction of protein was heated at 95° C. for 5 minutes and an equal volume of SDS-PAGE buffer was added to each sample before loading the samples on 12% SDS-PAGE gel.

FIG. 11 shows measurement of purified Caf1 protein concentration using a spectrophotometer.

FIG. 12 shows formation of caf1 oligomers. The leading Caf1 purified fractions (FIG. 8) were heated at 95° C. for 45 seconds to induce partial fragmentation of the non-covalent polymer. Lanes 1-5 showed the oligomerization of Caf1 (expressed using the new plasmid pGEMTF1). Lane 6 shows commercial purified recombinant F1 (rF1) used as a control in this study and also heated at 85° C.

FIG. 13 shows Caf1M:Caf1 complex. Caf1M, the chaperone (in green) and Caf1, F1 fibre (in blue). Figure was generated using Pymol software (http://www.pymol.org) using the published PDB file 1P5U. A) F1 amino acid sequence (SEQ ID NO:5) shows the loops of F1 fibre (highlighted in salmon, pink, orange, dark blue and yellow) which were used to incorporate the RGDS peptide (SEQ ID NO:39).

Figure 14A:
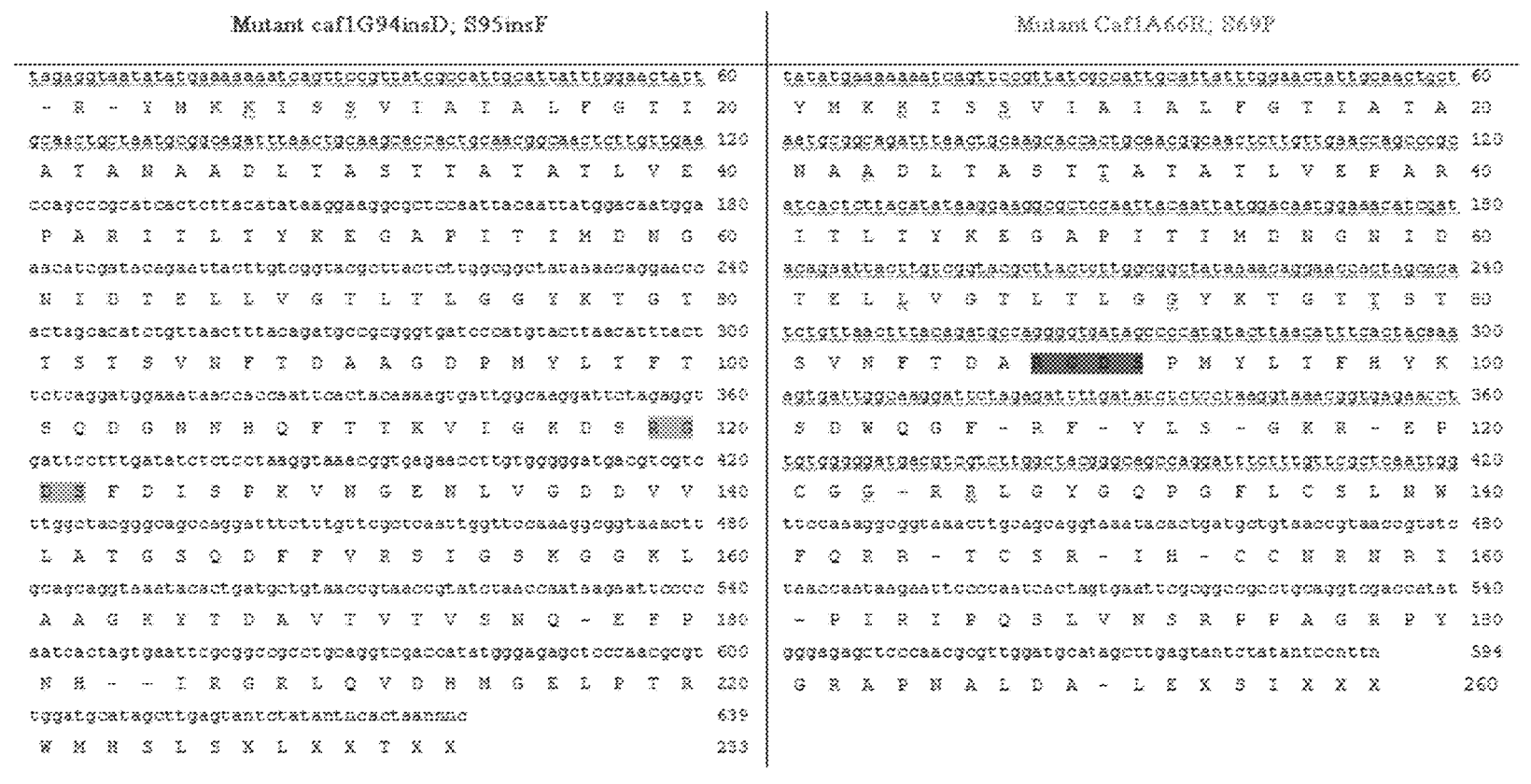
Figure 14B:
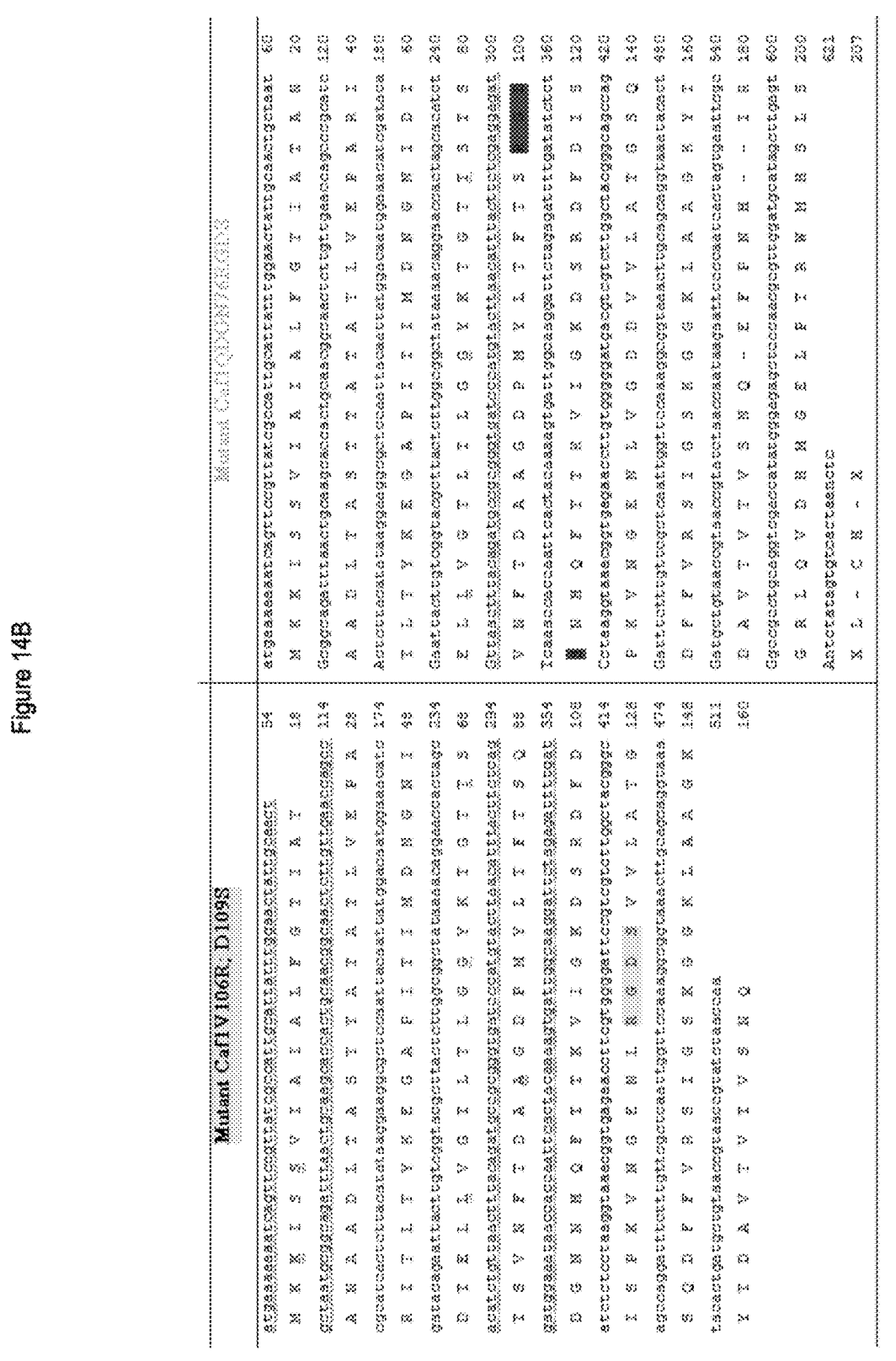

FIGS. 14A and 14B show results from sequencing showing the successful insertion of RGDS peptide (SEQ ID NO:39) into F1 loops. Nucleotide sequences (SEQ ID NOs: 92, 96, 104, and 106) and amino acid sequences (SEQ ID NOs:93-95, 97-103, 105, 107, and 108) are presented. Upper panel: chromatogram from reverse sequencing and blast of the caf1 gene sequence (GenBank, accession number AY450847) using the Expasy tool (http://expasy.org/tools/dna.html). Lower panel: chromatogram from reverse sequencing and blast of the caf1 gene sequence (GenBank, accession number AY450847) Expasy tool (http://expasy.org/tools/dna.html). Universal primer T7 Promoter Primer (5'-AAT TCT AAT ACG ACT CAC TAT AGG-3') (SEQ ID NO:73) was used to sequence ssDNA produced by the pGEM-TF1 vector.

FIG. 15 shows fractions of purified Caf1QDGN76RGDS mutant after Size exclusion chromatography. Lane 2-9 showed Caf1QDGN76RGDS mutant oligomers when samples were heated at 95° C. for differing times.

FIG. 16 shows transmission electron microscopy images of fibres of Caf1. Images were obtained using Phillips CM100 transmission electron microscope. Caf1 and Caf1-RGDS protein samples were stained with 2% (w/v) uranyl acetate. The image magnification used was 130000×.

FIG. 17 shows PC12 cell adhesion assay using glass coverslips coated with Caf1 and Caf1-RGDS protein. Images were obtained using Zeiss Fluorescence microscope. The image magnification used was 400× and 200× as indicated next to each set of images. Scale bar=20 µm. Stains are DAPI (blue) and rhodamine phalloidin (orange).

FIG. 18 compares the structures of RGDS peptides in a modified CAF1 polymer of the invention and fibronectin.

FIG. 19 is a schematic representation of a preferred cross linking method of the invention. Spheres represent sites of lysine residues suitable for crosslinking.

FIG. 20 shows scanning electron microscopy images of A, B, D—CAF1:4NHS-PEG (1:5); C—CAF1:4NHS-PEG (1:2); A, B, C—2% Glutaraldehyde fixation; D—freeze drier process; E—Rat osteoblasts attached on CAF1:4NHS-PEG (1:5) hydrogel. Scale bar: 50 µm (A, B, C and D) and 200 µm (E).

FIG. 21 shows SEM and fluorescence microscopy images of rat primary osteoblasts grown on surfaces coated with A) fibronectin and B) CAF1 comprising RDGS. Scale bar: 10 µm.

FIG. 22 is the nucleic acid sequence of SEQ ID NO:1.
FIG. 23 is the nucleic acid sequence of SEQ ID NO:2.
FIG. 24 is the nucleic acid sequence of SEQ ID NO:3.
FIG. 25 is the nucleic acid sequence of SEQ ID NO:4.
FIG. 26 is the amino acid sequence of SEQ ID NO:5.
FIG. 27 is the amino acid sequence of SEQ ID NO:6.

FIGS. 28A and 28B are the amino acid sequence of SEQ ID NO:7.
FIG. 29 is the amino acid sequence of SEQ ID NO:8.
FIG. 30 is the amino acid sequence of SEQ ID NO:9.
FIG. 31 is the nucleic acid sequence of SEQ ID NO:10.
FIG. 32 is the amino acid sequence of SEQ ID NO:11.
FIG. 33 is the nucleic acid sequence of SEQ ID NO:12.
FIG. 34 is the amino acid sequence of SEQ ID NO:13.
FIG. 35 is the amino acid sequence of SEQ ID NO:14.
FIG. 36 is the amino acid sequence of SEQ ID NO:15.
FIG. 37 is the amino acid sequence of SEQ ID NO:16.
FIG. 38 is the amino acid sequence of SEQ ID NO:17.
FIG. 39 is the amino acid sequence of SEQ ID NO:18.
FIG. 40 is the amino acid sequence of SEQ ID NO:19.
FIG. 41 is the amino acid sequence of SEQ ID NO:20.
FIGS. 42A and 42B are the amino acid sequence of SEQ ID NO:21.
FIGS. 43A and 43B are the nucleic acid sequence of SEQ ID NO:22.
FIGS. 44A and 44B are the amino acid sequence of SEQ ID NO:23.
FIGS. 45A and 45B are the nucleic acid sequence of SEQ ID NO:24.
FIG. 46 is the amino acid sequence of SEQ ID NO:25.
FIG. 47 is the nucleic acid sequence of SEQ ID NO:26.
FIG. 48 is the amino acid sequence of SEQ ID NO:27.
FIG. 49 is the nucleic acid sequence of SEQ ID NO:28.
FIG. 50 is the amino acid sequence of SEQ ID NO:29.
FIG. 51 is the amino acid sequence of SEQ ID NO:30.
FIG. 52 is the amino acid sequence of SEQ ID NO:31.
FIG. 53 is the amino acid sequence of SEQ ID NO:32.
FIG. 54 is the amino acid sequence of SEQ ID NO:33.
FIG. 55 is the amino acid sequence of SEQ ID NO:34.
FIG. 56 is the amino acid sequence of SEQ ID NO:35.
FIG. 57 is the amino acid sequence of SEQ ID NO:36.
FIG. 58 is the amino acid sequence of SEQ ID NO:37.
FIG. 59 is the nucleic acid sequence of SEQ ID NO:38.
FIG. 60 shows co-expression of Caf1 WT using the plasmids pAH34L and pBAD33. Represented are the images of the Falcon tubes containing E. coli TOP10/pBAD33_SD_Caf1, E. coli TOP10/pAH34L and E. coli TOP10/pBAD33_SD_Caf1+pAH34L in the presence of 0.2% of L-arabinose and in the presence or absence of D-glucose. Legend: L—Flocculent layer; P—cell pellet.
FIG. 61 shows the relationship between the size of flocculent layer of Caf1 and the relative density of Caf1 for each preparation. The level of protein secreted through the Caf1 system increases as the arabinose percentage is increased such that Caf1 expression is enhanced at high arabinose concentrations. The addition of glucose unexpectedly enhances rather than decreases the protein production probably because it acts as an additional carbon source and its repression is lost over the 16 h fermentation run.
FIG. 62 shows Western blots of Caf1-FLAG epitope NT protein expression. Heterologous Caf1 protein samples from the supernatant were heated in 2×SDS-sample buffer, at 100° C. for 45 seconds or 5 minutes. Non-heated samples in 2×SDS-sample buffer were also loaded onto SDS-PAGE gel (A) pBAD33_SD_caf1 NT-FLAG+pAH34L probed for Caf1 with the monoclonal anti-Caf1 antibody. (B) pBAD33_SD_caf1 NT-FLAG+pAH34L probed for FLAG epitope with anti-flag epitope antibody. M, molecular weight marker proteins (molecular mass×$10^3$ kDa); lane 1, pBAD33_SD_caf1 NT-FLAG+pAH34L sample non-heated; lane 2, pBAD33_SD_caf1 NT-FLAG+pAH34L sample heated at 95° C. for 45 seconds; lane 3, pBAD33_SD_caf1 NT-FLAG+pAH34L sample heated at 95° C. for 5 minutes; lane 4, pBAD33_SD_caf1 NT-FLAG sample non heated; lane 5, pBAD33_SD_caf1 NT-FLAG sample heated at 95° C. for 45 seconds; lane 6, pBAD33_SD_caf1 NT-FLAG sample heated at 95° C. for 5 minutes; lane 7, pAH34L sample non-heated; lane 8, pAH34L sample heated at 95° C. for 45 seconds; lane 9, pAH34L sample heated at 95° C. for 5 minutes.

FIG. 63 shows Western blots of Caf1-6His-NT protein expression. Heterologous Caf1 protein samples from the supernatant were heated in 2×SDS-sample buffer, at 100° C. for 45 seconds and 5 minutes. Non-heated samples in 2×SDS-sample buffer were also loaded onto SDS-PAGE gel (A) pBAD33_SD_caf1-6His-NT+pAH34L probed for Caf1 with the monoclonal anti-Caf1 antibody. (B) pBAD33_SD_caf1 6His-NT+pAH34L probed for polyhistidine with anti-polyhistidine antibody. M, molecular weight marker proteins (molecular mass×$10^3$ kDa); lane 1, pBAD33_SD_caf1-6His-NT+pAH34L sample non-heated; lane 2, pBAD33_SD_caf1-6His-NT+pAH34L sample heated at 95° C. for 45 seconds; lane 3, pBAD33_SD_caf1-6His-NT+pAH34L sample heated at 95° C. for 5 minutes; lane 4, pBAD33_SD_caf1-6His-NT sample non heated; lane 5, pBAD33_SD_caf1-6His-NT sample heated at 95° C. for 45 seconds; lane 6, pBAD33_SD_caf1-6His-NT sample heated at 95° C. for 5 minutes; lane 7, pAH34L sample non-heated; lane 8, pAH34L sample heated at 95° C. for 45 seconds; lane 9, pAH34L sample heated at 95° C. for 5 minutes.

FIG. 64 shows Western blots of Caf1-6His-NT spacer protein expression. Heterologous Caf1 protein samples from the supernatant were heated in 2×SDS-sample buffer, at 100° C. for 45 seconds and 5 minutes. Non-heated samples in 2×SDS-sample buffer were also loaded onto SDS-PAGE gel (A) pBAD33_SD_caf1 6His-NT spacer+pAH34L probed for Caf1 with the monoclonal anti-Caf1 antibody. (B) pBAD33_SD_caf1-6His-NT spacer+pAH34L probed for polyhistidine with anti-polyhistidine antibody. M, molecular weight marker proteins (molecular mass×$10^3$ kDa); lane 1, pBAD33_SD_ caf1-6His-NT spacer+pAH34L sample non-heated; lane 2, pBAD33_SD_caf1-6His-NT spacer+pAH34L sample heated at 95° C. for 45 seconds; lane 3, pBAD33_SD_caf1-6His-NT spacer+pAH34L sample heated at 95° C. for 5 minutes; lane 4, pBAD33_SD_caf1 6His-NT spacer sample non heated; lane 5, pBAD33_SD_caf1-6His-NT spacer sample heated at 95° C. for 45 seconds; lane 6, pBAD33_SD_caf1-6His_NT_Spacer sample heated at 95° C. for 5 minutes; lane 7, pAH34L sample non-heated; lane 8, pAH34L sample heated at 95° C. for 45 seconds; lane 9, pAH34L sample heated at 95° C. for 5 minutes.

FIG. 65 shows Western blots of heterogeneous Caf1 protein expression. Heterogeneous Caf1 protein samples from the supernatant were heated in 2×SDS-sample buffer, at 100° C. for 45 seconds. M, molecular weight marker proteins (molecular mass×$10^3$ kDa); lane 1, pBAD33_SD_caf1-PHSRN Loop1+pAH34L; lane 2, pBAD33_SD_caf1-Cys-NT+pAH34L; lane 3, pBAD33_SD_caf1-G350 Loop 4+pAH34L; lane 4, pBAD33_SD_caf1-Q1060 Loop2+pAH34L; lane 5, pBAD33_SD_caf1-PENFF-NT+pAH34L; lane 6, pBAD33_SD_caf1-PHSRN Loop 3+pAH34L; lane 7, Caf1.

FIG. 66 shows exemplary crosslinkers; (a) DTSSP crosslinker structure; (b) NHS-PEG-NHS crosslinker structure; (c) 4-arm NHS-PEG crosslinker structure.

FIG. 67 shows an image of the Caf1 hydrogel cross-linked with 4-arm PEG-NHS. (A) Caf1 hydrogel formed after 2 minutes of reaction (Caf1:4 arm PEG-NHS, ratio of crosslinking of 1:2). (B) Swelling of Caf1 hydrogels in polypropylene micro-centrifuge tubes after addition of PBS. Caf1: 4-arm PEG-NHS, ratios of cross-linking (w/w): Tube 1—1:10; Tube 2—1:5; Tube 3—1:3; Tube 4—1:2.

FIG. 68 shows analysis of Caf1 protein cross-linking using different cross-linkers by 4-20% gradient polyacrylamide gel electrophoresis. Legend: M, molecular weight marker proteins (molecular mass×$10^3$ kDa); lanes 1-4, Caf1 hydrogel cross-linked with DTSSP; lanes 5-8, Caf1 hydrogel cross-linked with NHS-PEG-NHS; lanes 9-12, Caf1 hydrogel cross-linked with 4-arm PEG-NHS. The ratios of cross-linking used in this study were: lane 1—1:10; lane 2—1:5; lane 3—1:3; lane 4—1:2; lane 5—1:10; lane 6—1:5; lane 7—1:3; lane 8—1:2; lane 9—1:10; lane 10—1:5; lane 11—1:3; lane 12—1:2. The gradient polyacrylamide gel was stained with Coomassie Brilliant Blue G-250 stain. Precision Plus Protein standard was used.

FIG. 69 shows a TEM image of Caf1 hydrogel cross-linked with different cross-linkers (w/w ratio of 1:10). The scale bar represents 100 nm. The size distribution of cross-linked Caf1 hydrogel meshes is also shown FIG. 70 shows transmission electron microscopy images of Caf1 hydrogels and controls: cpCaf1, 4-arm PEG-NHS and Caf1 polymer. All specimens were negatively stained. The scale bar indicates 100 nm.

FIG. 71 shows transmission electron microscopy (TEM) images of Caf1 polymers cross-linked with 4-arm PEG-NHS at various ratios of cross-linking (w/w, cross-linker; Caf1). All specimens were negatively stained. The scale bar indicates 100 nm.

FIG. 72 shows scanning electron microscopy images of Caf1 hydrogel cross-linked with 4-arm PEG-NHS (w/w ratio 1:3).

FIG. 73 shows scanning electron microscopy images of Caf1 hydrogel cross-linked with 4-arm PEG-NHS after freeze-drying (w/w ratio 1:3). A—Fragments of Caf1 hydrogel after freeze-dried process. B—Original image of Caf1 hydrogel. C—Image of the Caf1 hydrogel pore. D—Image processed by Jmicrovision version 1.2.5 (Roduit, 2007). Measurements of pore diameter were conducted by drawing lines, as the red lines represented on the image across the pore of the hydrogel. The size of the pore was calculated. This equation was obtained from Soliakov et al., 2010.

FIG. 74 shows environmental scanning electron microscopy images of Caf1 hydrogel cross-linked with 4-arm PEG-NHS after (w/w ratio 1:3). A—Caf1 hydrogel. B—Original image of Caf1 hydrogel. C—Caf1 hydrogel. D—Image processed by Jmicrovision version 1.2.5. Measurements of pore diameter were conducted by drawing lines, as the red lines represented on the image, across the pore of the hydrogel.

FIG. 75 shows scanning electron microscopy images of (A) Mouse 3T3 Fibroblasts. (B) Rat primary osteoblasts. The white arrows show the cells. Cell adhesion on Caf1 hydrogel cross-linked with 4-arm PEG-NHS (ratio of 1:3).

DETAILED DESCRIPTION

The inventors have surprisingly identified that flexible protein nanofibres made from engineered chaperone/usher protein monomers can be used to create realistic cell microenvironments. The flexible protein nanofibres can be crosslinked with a non-toxic and non-immunogenic cross-linker to produce hydrogels in accordance with the invention. In one embodiment, the nanofibre hydrogel is composed of monomeric folding units which incorporate bioactive protein sequences. Preferably, the hydrogels are robust and protease resistant.

Figure 18:
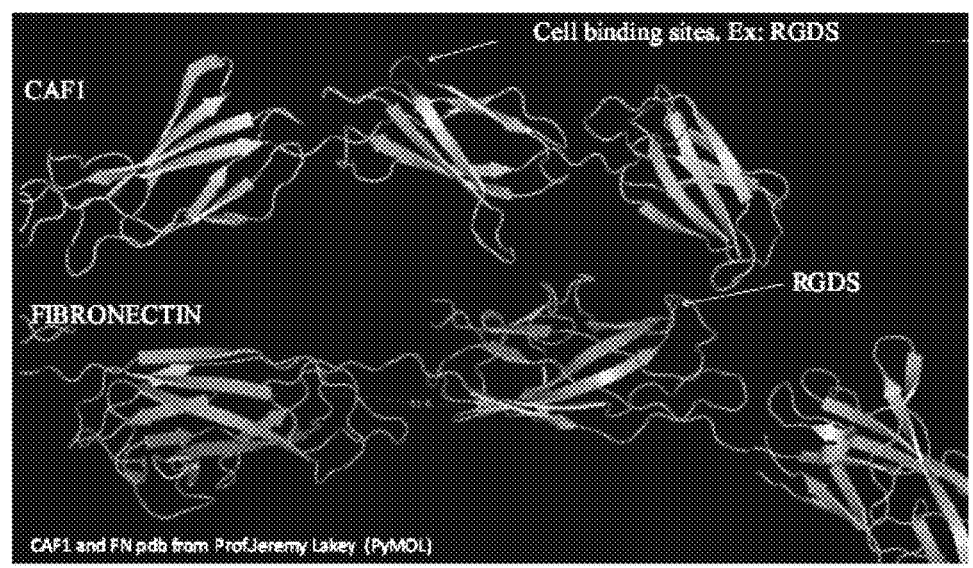

Specifically, the inventors have identified that the chaperone/usher family of polymers, and in particular the FG loop long (FGL) family members, which comprise a single or mixed monomer subunit type(s), such as *Yersinia pestis* Caf1, *Salmonella* Saf1 and *E coli* Afa/Dr, show unexpected structural similarity to fibronectin, as illustrated in FIG. 18.

Using the Caf1 monomer fraction 1 antigen polymer as a model, the inventors have shown that the chaperone/usher family of polymers, and in particular the FG loop long (FGL) family members, exhibit cell attachment inhibition behaviour when formed into a hydrogel comprising naturally occurring chaperone/usher polymers such as fraction 1 antigen polymer (without any evidence of cell toxicity). This unexpected property of chaperone/usher polymers makes them particularly useful as antifouling agents, which can be used in antifouling compositions.

However, unexpectedly, the inventors have found that incorporation of commonly used bioactive sequences, such as the cell adhesion motif RGDS (SEQ ID NO:39) from fibronectin, into chaperone/usher monomers such as CAF1, is enough to reverse the attachment inhibition which results in the production of chaperone/usher polymers, such as fraction 1 antigen polymer, which when formed into a hydrogel promote cell attachment, survival and proliferation (see FIGS. 20 and 21).

The naturally occurring regions of the polymer of the invention therefore provide a surface into which specific bioactive sequences can be introduced, wherein the resultant polymer behaviour with regard to promoting cell attachment, survival and/or proliferation is determined by the specific bioactive sequence(s) incorporated therein. These properties provide significant advantages when the polymer of the invention is used, for example, in the fields of cell culture and regenerative medicine as there is complete freedom on which cell interactions may be promoted or inhibited (by way of incorporating different bioactive sequences into the polymer). Advantageously, the polymer of the invention can therefore be used to promote selective cell adhesion and/or selective interaction between the polymer and target components (e.g. peptides, proteins, cross-linking units, enzymes, antibodies, cells, reagents etc) with low or no background interaction between target components and the naturally occurring regions of the polymer.

The inventors have surprisingly found that a chaperone/usher family polypeptide monomer comprising an exogenous bioactive sequence can retain its polymeric form. The inventors have exemplified this using mutated FG loop long family polypeptide monomers, specifically caf1 monomers (e.g. caf1 monomers comprising an exogenous (bioactive) sequence such as RGDS (SEQ ID NO:39), a FLAG tag, a His tag etc.). Chaperone/usher family polypeptide monomers were produced containing a range of different experimental exogenous sequences. In each case, these experimental monomers were shown to retain their ability to assume polymeric form and be surprisingly stable. This indicates that this feature of chaperone/usher family polypeptide monomers is not limited to a specific exogenous sequence but is more generally applicable.

Advantageously, the chaperone/usher family polypeptide monomers of the invention can be used to generate a homogeneous or heterogeneous (i.e. mixed) polymer. By way for example, a mixed polymer may comprise naturally occurring and mutant monomers. Alternatively, a mixed polymer may comprise two distinct mutant monomers, optionally in the presence of naturally occurring monomers. The inventors have demonstrated the successful production of a mixed polymer comprising wildtype caf1 monomers and caf1 mutant forms (see for example FIGS. 62 to 65 and corresponding text). Such polymers have a wide range of advantages as discussed in more detail herein.

The chaperone-usher (CU) proteins form long polymeric pili on the cell surface. The chaperone stabilizes monomers secreted into the periplasm and transfers them to the end of the growing polymeric pilus situated within the outer-membrane usher protein, which translocates the nascent polymers to the cell surface. The polymerization mechanism is termed "donor strand exchange" and was first described for the FimC-FimH chaperone-adhesin complex from uropathogenic *Escherichia coli*. The subunits are composed of a β-sandwich immunoglobulin domain, in which, what would be the C-terminal β-strand is displaced to the N terminus where it cannot complete the native fold. In vivo the subunit is first partially stabilized after secretion by insertion of a β-strand from the chaperone. The final stable fold is achieved by the replacement of the chaperone parallel β-strand by the "spare" anti-parallel β-strand from the N terminus of the subsequent subunit, thus linking them to form a chain.

Caf 1 (also known as fraction 1 antigen polymer) is a CU protein from the plague bacterium, *Yersinia pestis*, where it serves as a polymeric virulence factor and vaccine component. It is formed from monomers by a donor-strand exchange (DSE) mechanism as described above. Caf1 atypical polymers form a gelatinous capsule that is thought to protect the pathogen against phagocytosis.

In vivo, expression, assembly and secretion of fraction 1 antigen polymer is performed via the classical chaperone-usher pathway (5) and is mediated by a group of four genes, which are organized in the caf operon. The fraction 1 antigen polymer (CAF1 monomer) is encoded by the caf1 gene which is temperature regulated by a transcriptional activator caf1R gene. A periplasmic chaperone, caf1M, is used for the assembly of F1 capsule produced by the plague pathogen *Y. pestis* and an outer membrane protein, the caf1A usher, works as an assembly platform/secretion machinery (see FIG. 1) (12, 14, 15).

Caf1 was cloned and expressed by Miller and co-workers (8) from *E. coli* containing the recombinant low-copy plasmid pAH34L, which contains caf operon (FIG. 3). This plasmid pAH34L has been shown to be a good system for Caf1 protein expression. However it was difficult to mutate F1 in this plasmid, due to its total size (around 11 Kbp) and the lack of convenient restriction sites.

Monomers

In a first aspect the invention provides a chaperone/usher family polypeptide monomer comprising an exogenous bioactive sequence.

Preferably the polypeptide is recombinant or synthetic, i.e. produced by recombinant or synthetic production techniques well known in the art.

As used herein, the phrase "a chaperone/usher family polypeptide monomer" refers to a polypeptide subunit, preferably a major subunit, of a long polymeric protein fibre typically found on the surface of gram-negative bacteria, the biogenesis of which is controlled by the chaperone/usher pathway.

Chaperone/usher family polypeptides can be separated into two groups based upon their higher order structure. The chaperone/usher family polypeptides of the invention may be FG loop long family members (also known as the atypical adhesion family). The FG loop long (FGL) family members comprise a single monomer subunit type. *Yersinia pestis* Caf1, *Salmonella* Saf1 and *E coli* Afa/Dr adhesion are examples FGL or atypical adhesion family monomer subunits, which form thin, difficult-to-image polymeric fibres. The FG loop short (FGS) family members (also known as the typical adhesion family), named after a structural feature of their chaperones, can be made up of up to six different monomeric subunits. The *E coli* Fim (Type 1 pilus) and Pap (P pilli) proteins are examples of FGS or typical adhesion family monomer subunits, which present a rod-like linear structure based upon a tightly wound helix of subunits. The chaperone/usher family polypeptide monomer of the invention may be a FG loop long (FGL) family member or a FG loop short (FGS) family member.

The chaperone usher protein families share a basic immunoglobulin domain fold and thus can be seen to have structural homology. This is also reflected in their sequence homology. The level of homology is high amongst similarly structured proteins eg Pap and Fim families but across the wider family this homology decreases to levels that may be considered insignificant unless the 3D structural homology is also considered. A good description of the similarities and differences within the disparate chaperone usher protein family is provided in FIG. 2 of reference (18).

Preferably the chaperone/usher family polypeptide monomer subunit is a Caf1 polypeptide monomer, a Saf1 polypeptide monomer, an Afa/Dr polypeptide monomer, a Fim A, H, G or F polypeptide monomer, or a Pap A, G, F, E or K polypeptide monomer.

The amino acid sequence of a naturally occurring Caf1 polypeptide monomer, from *Yersinia pestis*, is shown in SEQ ID NO: 5. The sequence is approximately 150 amino acid residues in length. The polypeptide monomer is encoded by a Caf1 nucleic acid molecule having the nucleotide sequence as shown in SEQ ID NO: 1. Caf1 is synthesised with a 21 amino acid cleavable signal peptide, which is cleaved during translocation of the monomer across the inner membrane.

The amino acid sequence of a naturally occurring Saf1 polypeptide monomer, from *Salmonella*, is shown in SEQ ID NO: 9. The sequence is approximately 145 amino acids in length. The polypeptide monomer is encoded by a Saf1 nucleic acid molecule having the nucleotide sequence as shown in SEQ ID NO: 10.

The amino acid sequence of a naturally occurring Afa/Dr polypeptide monomer, from *Escherichia coli*, is shown in SEQ ID NO: 11. The sequence is approximately 140 amino acids in length. The polypeptide monomer is encoded by an Afa/Dr nucleic acid molecule having the nucleotide sequence as shown in SEQ ID NO: 12.

The amino acid sequence of a naturally occurring Fim A polypeptide monomer, from *Escherichia coli*, is shown in SEQ ID NO: 13. The sequence is approximately 150 amino acids in length. The polypeptide monomer is encoded by a Fim A nucleic acid molecule having the nucleotide sequence as shown in SEQ ID NO: 14.

The amino acid sequence of a naturally occurring Fim H polypeptide monomer, from *Escherichia coli*, is shown in SEQ ID NO: 25. The sequence is approximately between 150 and 200 amino acids in length. The polypeptide monomer is encoded by a Fim H nucleic acid molecule having the nucleotide sequence as shown in SEQ ID NO: 26.

The amino acid sequence of a naturally occurring Fim G polypeptide monomer, from *Escherichia coli*, is shown in SEQ ID NO: 27. The sequence is approximately between 150 and 200 amino acids in length. The polypeptide monomer is encoded by a Fim G nucleic acid molecule having the nucleotide sequence as shown in SEQ ID NO: 28.

The amino acid sequence of a naturally occurring Fim F polypeptide monomer, from *Escherichia coli*, is shown in SEQ ID NO: 29. The sequence is approximately between 150 and 200 amino acids in length. The polypeptide monomer is encoded by a Fim F nucleic acid molecule having the nucleotide sequence as shown in SEQ ID NO: 30.

The amino acid sequence of a naturally occurring Pap A polypeptide monomer, from *Escherichia coli*, is shown in SEQ ID NO: 15. The sequence is approximately between 150 and 200 amino acids in length. The polypeptide monomer is encoded by a Pap A nucleic acid molecule having the nucleotide sequence as shown in SEQ ID NO: 16.

The amino acid sequence of a naturally occurring Pap G polypeptide monomer, from *Escherichia coli*, is shown in SEQ ID NO: 31. The sequence is approximately 300 amino acids in length. The polypeptide monomer is encoded by a Pap G nucleic acid molecule having the nucleotide sequence as shown in SEQ ID NO: 32.

The amino acid sequence of a naturally occurring Pap F polypeptide monomer, from *Escherichia coli*, is shown in SEQ ID NO: 33. The sequence is approximately between 150 and 200 amino acids in length. The polypeptide monomer is encoded by a Pap F nucleic acid molecule having the nucleotide sequence as shown in SEQ ID NO: 34.

The amino acid sequence of a naturally occurring Pap E polypeptide monomer, from *Escherichia coli*, is shown in SEQ ID NO: 35. The sequence is approximately between 150 and 200 amino acids in length. The polypeptide monomer is encoded by a Pap E nucleic acid molecule having the nucleotide sequence as shown in SEQ ID NO: 36.

The amino acid sequence of a naturally occurring Pap K polypeptide monomer, from *Escherichia coli*, is shown in SEQ ID NO: 37. The sequence is approximately between 150 and 200 amino acids in length. The polypeptide monomer is encoded by a Pap K nucleic acid molecule having the nucleotide sequence as shown in SEQ ID NO: 38.

As used herein, the term "nucleic acid molecule" includes DNA molecules (e.g., a cDNA or genomic DNA) and RNA molecules (e.g., a mRNA) and analogs of the DNA or RNA generated, e.g., by the use of nucleotide analogs. The nucleic acid molecule can be single-stranded or double-stranded, but preferably is double-stranded DNA.

As used herein, "naturally-occurring" refers to a polypeptide sequence that occurs in nature or to a nucleic acid molecule, e.g. a RNA or DNA molecule having a nucleotide sequence that occurs in nature (e.g., encodes a natural protein). Said nucleic acid molecules include an open reading frame encoding protein, and can further include non-coding regulatory sequences and introns. The terms "naturally-occurring" and "wildtype" are used interchangeably herein.

As used herein, the term "exogenous" refers to a heterologous polypeptide or nucleic acid sequence which is not present or naturally occurring within a chaperone/usher family polypeptide monomer sequence. It should be noted that the exogenous polypeptide or nucleic acid sequence may comprise a polypeptide or nucleic acid sequence which is identical or partially homologous to an endogenous polypeptide sequence or nucleic acid sequence of the cell. The term "endogenous" as used herein refers to any polypeptide or nucleic acid sequence which is present and/or naturally occurring in a chaperone/usher family polypeptide monomer sequence.

Within one aspect of the invention, the chaperone/usher family polypeptide monomer comprises an exogenous sequence. The exogenous sequence may be a bioactive sequence or any other desired exogenous sequence.

As used herein, "bioactive sequence" refers to a peptide sequence which has a specific biological function. Bioactive sequences are well known in the art and may be derived from any naturally occurring polypeptide including ECM components, cell adhesion molecules, cell surface receptors, growth factors, cytokines, chemokines, etc. For example, the bioactive sequence may mediate cell adhesion (or cell attachment), cell growth and/or cell differentiation (or induction of a cellular phenotype).

In a preferred embodiment the bioactive sequence is a cell adhesion recognition motif, a growth factor sequence motif or a protease site.

Preferably, the cell adhesion recognition motif is an extracellular matrix cell adhesion recognition motif, for example a motif derived from an extracellular matrix component such as collagen, elastin, fibronectin, laminin, osteopontin vitronectin or tenascin. Preferably, the cell adhesion recognition motif is derived from fibronenctin and comprises the amino acid sequence RGD (Arg-Gly-Asp), more preferably RGDS (Arg-Gly-Asp-Ser) (SEQ ID NO:39). Alternatively, the cell adhesion recognition motif is derived from fibronenctin and comprises the amino acid sequence PHSRN (Pro-His-Ser-Arg-Asn) (SEQ ID NO:40).

Alternatively, the cell adhesion recognition motif is derived from Collagen I and comprises the amino acid sequence GTPGPQGIAGQRGVV (SEQ ID NO:41). Alternatively, the cell adhesion recognition motif is derived from Collagen IV and comprises the amino acid sequence MNYYSNS (SEQ ID NO:42). Alternatively, the cell adhesion recognition motif is derived from Laminin and comprises the amino acid sequence YIGSR (SEQ ID NO:43). Alternatively, the cell adhesion recognition motif is derived from Laminin and comprises the amino acid sequence IKVAV (SEQ ID NO:44). Alternatively, the cell adhesion recognition motif is derived from Fibronectin and comprises the amino acid sequence FHRRIKA (SEQ ID NO:45). Alternatively, the cell adhesion recognition motif is derived from Fibronectin and comprises the amino acid sequence LDVP (SEQ ID NO:46). Alternatively, the cell adhesion recognition motif is derived from Fibronectin and comprises the amino acid sequence IDAP (SEQ ID NO:47).

Alternatively, the bioactive sequence is a growth factor sequence motif derived from Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), Tumor_necrosis_factor-alpha (TNF-α), Vascular endothelial growth factor (VEGF), Wnt Signaling Pathway, placental growth factor (PIGF), Foetal Bovine Somatotrophin (FBS), IL-1—Cofactor for IL-3 and IL-6 (activates T cells), IL-2—T-cell growth factor (stimulates IL-1 synthesis, activates B-cells and NK cells), IL-3 (stimulates production of all non-lymphoid cells); IL-4—Growth factor (for activated B cells, resting T cells, and mast cells), IL-5 (induces differentiation of activated B cells and eosinophils), IL-6 (stimulates Ig synthesis, growth factor for plasma cells), IL-7 (growth factor for pre-B cells), Neurone growth factor (NGF), Fibroblast growth factor (FGF) or Bone morphogenic protein 2 (BMP), e.g. a bioactive sequence comprising KIPKASSVPTELSAISTLYL (SEQ ID NO:48).

Alternatively, the bioactive sequence is a protease site derived from known matrix metalloproteinase cleavage sites.

In a preferred embodiment, the chaperone/usher family peptide monomer comprising the bioactive sequence is at least 70%, 75%, 80%, 85%, 90%, 95%, 96%, 97%, 98%, 99% or 100% identical (e.g., identical to the entire length) to the polypeptide of any one of SEQ ID NO's: 5, 9, 11, 13, 15, 25, 27, 29, 31, 33, 35 and 37.

The chaperone/usher family peptide monomer comprising the bioactive sequence of the invention exhibits the biological activity of the bioactive sequence whilst retaining chaperone/usher family monomer activity, e.g. the ability to form a polymeric protein fibre.

Calculations of sequence homology or identity (the terms are used interchangeably herein) between sequences are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 75%, 80%, 82%, 84%, 85%, 86%, 87%, 88%, 89%, 90%, 91%, 92%, 93%, 94%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman et al. (1970) *J. Mol. Biol.* 48:444-453) algorithm which has been incorporated into the GAP program in the GCG software package (available at http://www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a BLOSUM 62 scoring matrix with a gap penalty of 12, a gap extend penalty of 4, and a frameshift gap penalty of 5.

The percent identity between two amino acid or nucleotide sequences can be determined using the algorithm of Meyers et al. (1989) *CABIOS* 4:11-17) which has been incorporated into the ALIGN program (version 2.0), using a PAM120 weight residue table, a gap length penalty of 12 and a gap penalty of 4.

Preferably, the bioactive sequence is comprised within the chaperone/usher family polypeptide at a site which is comprised within a loop structure upon folding of said polypeptide. Loop regions suitable for insertion of amino acids occur adjacent to amino acid residues 1, 15, 27-40, 51-58, 64-69, 77-82, 92-117, 127-135 of the naturally occurring Caf1 polypeptide. Examples of suitable insertion sites for Caf1 are shown in FIG. 26 (insertion sites are underlined). More preferably, the chaperone/usher family polypeptide is a CAF1 polypeptide and the bioactive sequence is comprised within loop 5 of the folded CAF1 polypeptide (QDGNN). Alternatively, the bioactive sequence can be added at the N or C termini of the polypeptide. Alternatively, the bioactive sequence can be added synthetically for example by attaching a synthetic peptide molecule to a cysteine residue engineered into the Caf1 monomer.

Preferably the chaperone/usher polypeptide monomer further comprises an affinity tag, inserted in any one of the aforementioned loop sites, but preferably at the N-terminus (or C-terminus) of the polypeptide.

Preferably, the chaperone/usher family polypeptide monomer comprises two or more bioactive sequences, as hereinbefore described.

Polymers

In one aspect the invention relates to a chaperone/usher family polymer comprising at least one chaperone family polypeptide monomer according to the invention.

As used herein "chaperone/usher family polymer" refers to a long polymeric protein fibre, typically found on the surface of gram-negative bacteria comprising monomeric polypeptide subunits, the biogenesis of which is controlled by the chaperone/usher pathway.

The polymer may be a mixed polymer (i.e. a polymer comprising two or more distinct monomer units; e.g. a naturally occurring Caf1 monomer and a caf1 monomer comprising an exogenous bioactive sequence).

Preferably, the chaperone/usher family polymer according to the invention comprises at least one further chaperone/usher family polypeptide monomer, wherein said further chaperone/usher family polypeptide monomer differs from said at least one chaperone/usher family polypeptide monomer comprising an exogenous bioactive sequence by at least one amino acid. More preferably, the further chaperone/usher family polypeptide monomer is the chaperone/usher family polypeptide monomer as described above without said exogenous bioactive sequence.

Mixed polymers have a number of advantages. For example, a mixed polymer may only include a low density of active motifs (e.g. monomers comprising exogenous bioactive sequences), interspersed with inactive monomers (e.g. naturally occurring monomers or monomers lacking exogenous bioactive sequences). The low density of active motifs in the polymer may be sufficient to promote the desired biological activity (e.g. promote cell adhesion to the polymer). Using mixed monomer subunits to generate the polymer can improve expression levels of the polymer if the monomer comprising the active motif (e.g. the exaogenous bioactive sequence) is slow to assemble in the secretion pathway.

In certain applications it may be preferred that the monomer and/or polymers of the invention are substantially non-immunogenic. Many of the uses to which polymers may be put, for example as scaffolds for cell growth in vivo, such as in wound healing or ocular implant applications, will benefit from employing polymers that do not elicit an immune response.

The polymers of the invention may comprise substantially non-immunogenic chaperone/usher family polypeptide monomers. Alternatively, or additionally, the polymers of the invention may comprise exogenous bioactive sequences that are substantially non-immunogenic.

In particular, polymers of the invention may comprise exogenous bioactive sequences that are derived from non-immunogenic sources. It will be appreciated that in this context a "non-immunogenic" source should be considered to be a source (such as a polypeptide from which the exogenous sequence is derived) that does not elicit an immune response in a subject to whom the polymer comprising the exogenous sequence may subsequently be administered. For example, in the case of a polymer to be administered to a human subject, a human polypeptide may be expected to provide a suitable non-immunogenic source of an exogenous polypeptide that is in turn substantially non-immunogenic. Accordingly, suitable examples of the polymers of the invention may comprise exogenous bioactive sequences that are derived from mammalian sources, such as human sources.

Various assays by which immunogenicity (or otherwise) of polymers of the invention, or exogenous bioactive sequences or sources of such sequences, can be investigated will be well known to those skilled in the art, and it will be a simple matter for the skilled person to apply such assays.

Suitable polymers of the invention may comprise chaperone/usher family polypeptide monomers that are free from, or substantially free from, naturally occurring adhesion motifs, such as cell adhesion motifs. In particular, such monomers may be free from, or substantially free from, sites that allow the adhesion of human cells.

Alternatively polymers of the invention may comprise chaperone/usher family polypeptide monomers in which exogenous bioactive sequences provide the only cell adhesion (in particular human cell adhesion) motifs/sites. As discussed elsewhere in the present disclosure, the finding that certain chaperone/usher family polypeptides (such as Caf1) inhibit adhesion of human cells is both new and unexpected. It is also surprising that exogenous bioactive sequences comprising cell adhesion motifs can be incorporated in such otherwise non-adhesive monomers without adversely influencing the ability of these monomers to form polymers.

Preferably, the chaperone/usher family polymer is a fraction 1 antigen polymer, comprising or consisting of naturally occurring CAF1 polypeptide monomers and/or a CAF1 polypeptide monomer comprising an exogenous (bioactive) sequence in accordance with the invention.

Figure 1:
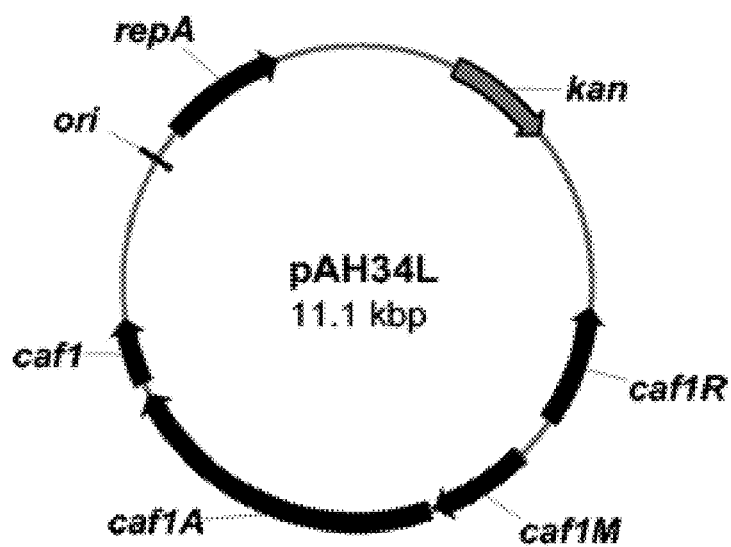
Figure 2:
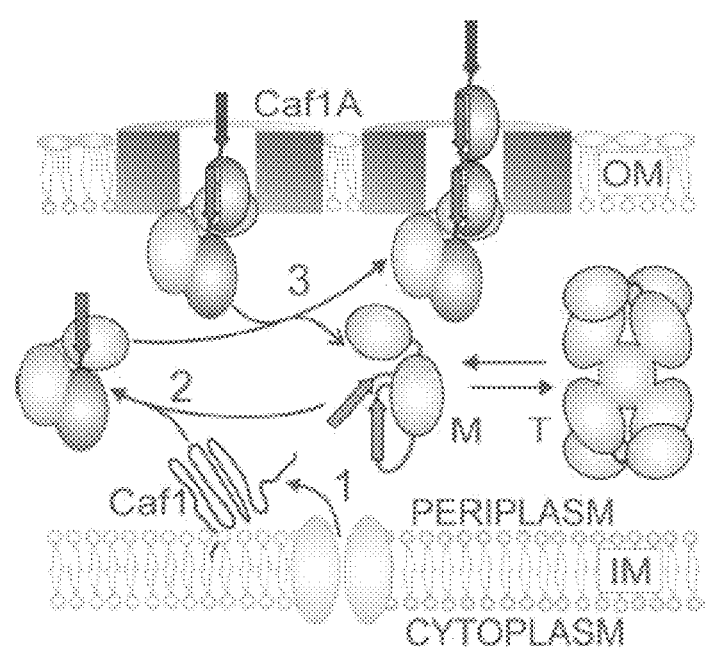

As used herein "fraction 1 antigen polymer" or "F1 polymer" are used interchangeably to refer to a polymer of CAF1 monomer subunits. The polymer is typically expressed by Yersinia pestis. The polymers may be up to 1.5 micron in length and comprise in excess of 250 CAF1 monomers. Expression, assembly and secretion of the F1 polymer is performed via the classical chaperone usher pathway and is mediated by a group of four genes, which are organized in the caf operon. The F1 capsule structural subunit, the CAF1 monomer, is encoded by the caf1 gene, which is temperature regulated by a transcriptor activator caf1R gene. A periplasmic chaperone, caf1M, is used for the assembly of F1 capsule produced Y. Pestis and an outer membrane protein, the caf1A usher, serves as a assembly platform/secretion machinery, gene products (see FIG. 2).

Preferably, the fraction 1 antigen polymer of the invention contains at least one CAF1 polypeptide monomer comprising an exogenous bioactive sequence in accordance with the invention and at least one naturally occurring CAF1 polypeptide monomer (i.e. the polymer is a mixed polymer.)

Alternatively, the chaperone/usher family polymer is a fraction 1 antigen polymer, comprising or consisting of naturally occurring CAF1 polypeptide monomers and/or a CAF1 polypeptide monomer comprising an exogenous bioactive sequence in accordance with the invention. Still more preferably the fraction 1 antigen polymer comprises or consists of a CAF1 polypeptide monomer comprising a cell adhesion recognition motif, such as RGD or PHSRN.

Alternatively, the chaperone/usher family polymer is SAF1 polymer, comprising or consisting of naturally occurring SAF1 polypeptide monomers and/or a SAF1 polypeptide monomer comprising an exogenous bioactive sequence in accordance with the invention.

Preferably, the SAF1 polymer of the invention contains at least one SAF1 polypeptide monomer comprising an exogenous bioactive sequence in accordance with the invention and at least one naturally occurring SAF1 polypeptide monomer.

Alternatively, the chaperone/usher family polymer is a SAF1 polymer, comprising or consisting of naturally occurring SAF1 polypeptide monomers and/or a SAF1 polypeptide monomer comprising an exogenous bioactive sequence in accordance with the invention. Still more preferably the SAF1 comprises or consists of a SAF1 polypeptide monomer comprising cell adhesion recognition motif, such as RGD or PHSRN.

Alternatively, the chaperone/usher family polymer is an Afa or Dr adhesion polymer, comprising or consisting of naturally occurring Afa/Dr polypeptide monomers and/or a Afa/Dr polypeptide monomer comprising an exogenous bioactive sequence in accordance with the invention.

Preferably, the Afa/Dr polymer of the invention contains at least one Afa/Dr polypeptide monomer comprising an exogenous bioactive sequence in accordance with the invention and at least one naturally occurring Afa/Dr polypeptide monomer.

Alternatively, the chaperone/usher family polymer is an Afa/Dr 1 polymer, comprising or consisting of naturally occurring Afa/Dr polypeptide monomers and/or an Afa/Dr polypeptide monomer comprising an exogenous bioactive sequence in accordance with the invention. Still more preferably the Afa/Dr comprises or consists of an Afa/Dr polypeptide monomer comprising cell adhesion recognition motif, such as RGD or PHSRN.

Preferably the chaperone/usher family polymer comprises or consists of a chaperone/usher family polypeptide monomer comprising cell adhesion recognition motif, such as RGD or PHSRN. Alternatively said polymer comprises a polypeptide monomer comprising a growth factor sequence motif or a protease site.

Still more preferably, the chaperone/usher family polymer comprises a first chaperone/usher family polypeptide monomer comprising an exogenous bioactive sequence in accordance with the invention and a second chaperone/usher family polypeptide monomer comprising an exogenous bioactive sequence in accordance with the invention, wherein said first and second monomers comprise distinct exogenous bioactive sequences. The bioactive sequence is preferably selected from a cell adhesion recognition motif, a growth factor sequence motif or a protease site. Still more preferably, the chaperone/usher family polymer further comprises a naturally occurring chaperone/usher family polypeptide monomer.

Preferably, where the chaperone/usher family polymer has properties which affect cell growth, such as the Afa type polymer, then it may be useful to modify the wild type polymer to remove this activity prior to incorporation of the exogenous bioactive sequence.

Hydrogels

In one aspect the invention provides a hydrogel comprising or consisting of a chaperone/usher family polypeptide monomer according to the invention or a chaperone/usher family polymer according to the invention.

As used herein, the term "hydrogel" refers to a water-swellable polymeric matrix, consisting of a network of macromolecules held together by covalent crosslinks. The matrix can absorb a substantial amount of water to form an elastic gel. The hydrogel swelling can be affected by conditions in which the hydrogel is placed, such as by pH, temperature, and the local ion concentration and type. Preferably, the hydrogel is insoluble.

The swollen state of a hydrogel may be characterized by several parameters, including the swelling ratio under changing conditions, the permeability coefficient of certain solutes, and the mechanical behavior of the hydrogel under conditions of its intended use.

Preferably, the monomers and/or polymers of the hydrogel are crosslinked so as to provide structure and physical integrity to the matrix. The cross linking may be due to chemical, physical, or radiation crosslinking.

In the case of physical crosslinking, the linking may result from hydrogen bonding, Van der Waals interactions, ionic bonding, or combinations thereof. Physical cross linking may be initiated by mixing two precursors that are physically separated until combined in situ or as a consequence of a prevalent condition in the physiological environment, including temperature, pH, ionic strength, combinations thereof.

Chemical (covalent) crosslinking may be accomplished by any of a number of mechanisms including, but not limited to, free radical polymerization, condensation polymerization, anionic or cationic polymerization, step growth polymerization, electrophile-nucleophile reactions or combinations thereof.

Radiation crosslinking may be achieved by any number of mechanisms including, but not limited to, exposing the hydrogel article to at least one of visible light radiation, infrared radiation, ultraviolet radiation, electron beam radiation, gamma radiation, or x-ray radiation.

Typically, the polymer constituents are cross-linked via chemical or physical processes such that they form a "mesh-like" insoluble polymer network.

Preferably, the hydrogel comprises a cross linking agent. These crosslinking agents may comprise for example monoaldehydes, dialdehydes, sodium hypochlorite, diisocyanates, dicarboxylic acid halides and chlorinated epoxides.

Preferably, the crosslinking agent comprises Poly(ethylene glycol) (PEG). PEG is a chemical compound composed of repeating ethylene glycol units and has been explored as a cell scaffold as well as in drug delivery devices and establishing therapeutic proteins. However, PEG by itself is non-reactive, non-toxic, non-immunogenic, soluble and highly flexible to create insoluble networks, it requires end-functionalization with cross-linking groups. A number of chemistries have been developed for the functionalization of PEG including the addition of acrylate, thiol, amine, maleimide or vinyl sulfone reactive groups. As cross-linked networks, these materials are non-degradable under physiological conditions. Polyethylene glycol spacer arms have a defined structure and molecular weight which ensures reproducible protein-modification effects. Moreover, it provides high stability, reduced tendency toward aggregation and immunogenicity even at high molecular weights.

Figure 19:
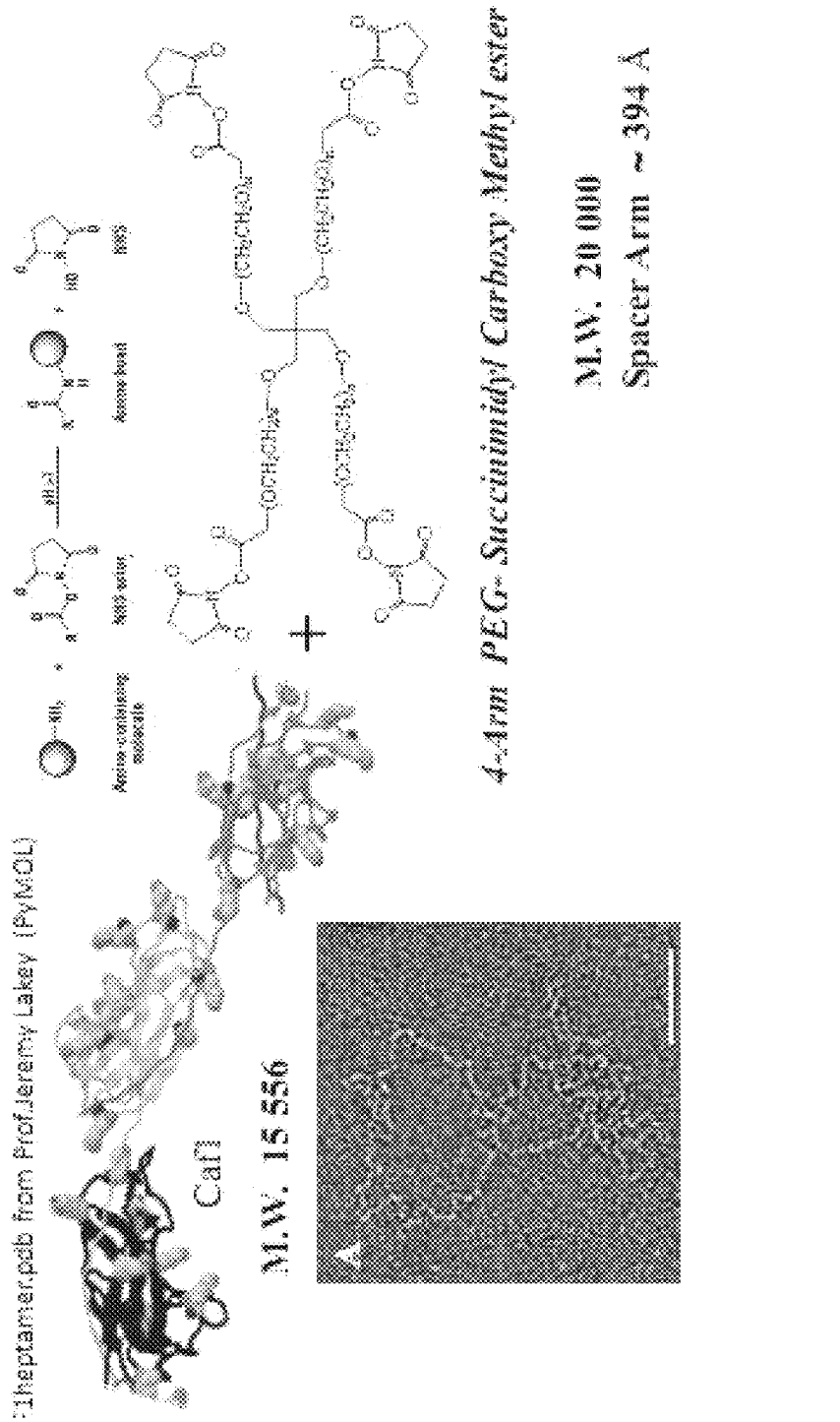

More preferably the crosslinking agent is a 4-arm PEG succinimidyl carboxy methyl ester, as illustrated in FIG. 19, (Creative PEG works product PSB-465 4-Arm PEG-NHS (SG), MW 20 k Da, spacer arm length of approximately 2×197 Å—see FIG. 66($c$)). A preferred crosslinking method of the invention is also illustrated in FIG. 19.

Other possible crosslinkers include but are not limited to:
(i) the linear homobifunctional, short spacer arm, DTSSP (Sulfo-DSP) (3,3'-Dithiobis[sulfosuccinimidylpropionate]) with molecular weight of 608.51 and a spacer arm with approximately of 12.0 Å. DTSSP is water-soluble and thiol-cleavable (see FIG. 66($a$)).
(ii) the linear homobifunctional, long spacer arm, NHS-PEG-NHS (O,O'-Bis[2-(N-Succinimidyl-succinylamino)ethyl]polyethylene glycol) with a molecular weight of 10000 and a spacer arm of approximately 197 Å (see FIG. 66($b$)).

Preferably the crosslinking agent is a biodegradable crosslinking agent. Advantageously such crosslinking agents make the hydrogel biodegradable or absorbable. As used herein, the term "biodegradable" refers to material or polymer that can be degraded, preferably adsorbed and degraded in a patient's body. Alternatively, the cross linking agent is a non-degradable cross linking agent.

The skilled person would readily identify crosslinker to monomer/polymer ratios that are suitable in accordance with the present invention. By way of example, but not by way of limitation, ratios of 1:120, 1:5, 1:3, or 1:2 (monomer:crosslinker (w/w)) may be used.

Uses

The hydrogels and/or polymers of the invention can be used in cell culture. The inventors have surprisingly found that the presence of a chaperone/usher family polypeptide monomer of the invention (or the polymer of the invention) in hydrogels increases cell viability and reduces cell cytotoxicity.

In one aspect the invention provides use of a hydrogel of the invention as a cell support scaffold.

The term "scaffold", as used herein, refers to any material that allows attachment of cells and subsequent proliferation and differentiation. "Attachment", "attach" or "attaches" as used herein, refers to cells that adhere directly or indirectly to a substrate as well as to cells that adhere to other cells.

The scaffolds of the invention may be fibres (i.e. 1 dimensional), cell culture plates (i.e. 2 dimensional), or matrices (i.e. 3 dimensional). 2 dimensional cell culture systems can provide the base for investigating cell and tissue morphogenesis, can also be used to examine how epigenetic factors affect physiological phenomena and to investigate the dynamic relationship between cell function and interactions with cellular microenvironment outside of the organism. 3 dimensional scaffolds can be used to recreate the native 3 dimensional structure of a tissue.

The scaffolds of the invention are of particular use in cell-based assays and tissue culture systems.

The scaffold may be unseeded and otherwise free of cells. Alternatively, the scaffold may be seeded with cells.

The polymers and/or hydrogels of the invention have numerous biomedical applications. For example, the polymers and/or hydrogels of the invention may be used as material for the treatment of wounds, as vehicles for the release of drugs, or as coatings on the surface of medical devices.

Accordingly, the polymers and/or hydrogels of the invention are of particular use in various therapeutic settings. In particular, the hydrogels of the invention may be used to deliver cells to a tissue in need thereof. In one embodiment, the scaffolds are used to deliver cells to the eye of a mammalian subject. Alternatively, the scaffolds of the invention may be used to deliver cells to a wound bed of a mammalian subject in need thereof.

Accordingly, the invention provides the use of a hydrogel of the invention as a medicament.

The invention also provides the use of a polymer of the invention as a medicament. The polymer of the invention may be used in a method of treating a wound, for example in wound healing, in an equivalent manner as described below for the hydrogel of the invention. Accordingly, the invention provides a polymer of the invention for use in treating a wound, e.g. a skin wound.

Also provided is a method of treating a skin wound comprising implanting a hydrogel of the invention into the skin, skin wound or skin wound bed of a mammalian subject in need thereof. The method is of particular use in re-epithelialisation and of particular use in skin re-epithelialisation. The term "re-epithelialisation" relates to the repair, replacement, functional recovery and ultimate regeneration of damaged epithelium inside the body (including skin), or outside the body.

There is also provided hydrogel of the invention for use in treating a skin wound.

As used herein the term "wound" relates to damaged tissues, preferably damaged skin, where the integrity of the skin or tissue is disrupted as a result from i.e. external force, bad health status, aging, exposure to sunlight, heat or chemical reaction or as a result from damage by internal physiological processes. Wounds where the epithelium such as the epidermis is damaged are considered to be an open wound. Wound healing is the process of regenerating the covering cell layers of a tissue, preferably by re-epithelialisation or reconstruction.

The introduction of a hydrogel capable of supporting normal skin cell attachment and migration and proliferation will help to accelerate wound healing by providing an immediate alternative substrate for unaffected skin cells at the wound margins to migrate across.

The invention provides a method of treating an ocular injury comprising implanting a hydrogel of the invention into the eye of a mammalian subject in need thereof.

There is also provided a hydrogel of the invention for use in treating an ocular injury.

As used herein, the term "ocular injury" refers to conditions resulting in an insufficient stromal micro-environment to support stem cell function, for example aniridia, keratitis, neurotrophic keratopathy, Keratoconus, Meesman's dystrophy, Epithelial Basement Membrane Dystrophy and chronic limbitis; or conditions that destroy limbal stem cells such as Partial limbal stem cell deficiency, Total stem cell deficiency, Ocular herpes, chemical or thermal injuries, Stevens-Johnson syndrome, ocular cicatricial pemphigoid, contact lens wear, or microbial infection.

There is also provided an ocular implant comprising a hydrogel of the invention.

In one embodiment the hydrogel is seeded with cells, such as corneal cells or stem cells prior to implantation. Alternatively, the hydrogels may be seeded with cells after implantation. Preferably, said cells are autologous, i.e. said cells are derived from the individual to be treated or alternatively the cells may be non-autologous.

The invention also provides a pharmaceutical composition comprising a hydrogel in accordance with the invention together with a pharmaceutically acceptable excipient, diluent or carrier. In one embodiment the composition further comprises one or more of the following: growth factors, lipids, genes, etc., or compounds for altering the acidity/alkalinity (pH) of the wound, or compounds for altering the growth and performance of the transplanted cells and those at the margins of the wound/injury.

The term "pharmaceutically-acceptable carrier" as used herein means one or more compatible solid or liquid fillers, diluents or encapsulating substances that are suitable for administration into a human. When administered, the pharmaceutical compositions of the present invention are administered in pharmaceutically acceptable preparations. Such preparations may routinely contain pharmaceutically acceptable concentrations of salt, buffering agents, preservatives, compatible carriers, cytokines and optionally other therapeutic agents, preferably agents for use in wound healing such as growth factors, peptides, proteolytic inhibitors, extracellular matrix components, steroids and cytokines. The term "carrier" denotes an organic or inorganic ingredient, natural or synthetic, with which the active ingredient is combined to facilitate the application. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. As used herein, a pharmaceutically acceptable carrier includes any conventional carrier, such as those described in Remington's Pharmaceutical Sciences, by E. W. Martin, Mack Publishing Co, Easton, Pa., 15$^{th}$ Edition (1975).

In a further aspect there is provided a pharmaceutical composition in accordance with the invention for use as a medicament, for example, for use in treating ocular injury, corneal replacement or wound healing.

The compositions or hydrogels of the invention are administered/for administration in effective amounts. An "effective amount" is the amount of a composition or hydrogel that alone, or together with further doses, produces the desired response. The compositions or hydrogels used in the foregoing methods preferably are sterile and contain an effective amount of the active ingredient for producing the desired response in a unit of weight or volume suitable for administration to a patient. The response can, for example, be measured by measuring the physiological effects of the composition or micro-organ cell composites upon the rate of or extent of wound healing or corneal repair.

In a further aspect, the monomer and/or polymer of the invention may be used in or on cell culture apparatus (for example to promote cell adhesion to a surface of the cell culture apparatus). Accordingly, in one aspect, the invention provides cell culture apparatus (e.g. a cell culture vessel such as a petri-dish, multi-well plate or cell culture flask; or a coverslip used for cell culture) comprising a monomer and/or polymer according to the invention. Preferably, the monomer and/or polymer is comprised within a hydrogel according to the invention.

Vectors

The invention includes expression vectors for producing a recombinant chaperone/usher family polypeptide monomer. Preferably the expression vector comprises those genetic elements which are necessary for expression of the recombinant chaperone/usher family polypeptide monomer in a bacterial cell. The elements required for transcription and translation in the bacterial cell include a promoter, a coding region for a chaperone/usher family polypeptide monomer, and a transcriptional terminator.

As used herein, the term "expression vector" refers to a nucleic acid molecule capable of transporting another nucleic acid to which it has been linked. The vector can be capable of autonomous replication or it can integrate into a host DNA. The vector may include restriction enzyme sites for insertion of recombinant DNA and may include one or more selectable markers. The vector can be a nucleic acid in the form of a plasmid, a bacteriophage or a cosmid.

"Operably linked" as used herein, refers to a single or a combination of the below-described control sequences together with a coding sequence in a functional relationship with one another, for example, in a linked relationship so as to direct expression of the coding sequence.

"Control elements" as used herein, refers to, DNA or RNA elements that are capable of controlling gene expression. Examples of expression control sequences include promoters, enhancers, silencers, Shine Dalgarno sequences, TATA-boxes, internal ribosomal entry sites (IRES), attachment sites for transcription factors, transcriptional terminators, polyadenylation sites, RNA transporting signals or sequences important for UV-light mediated gene response. Preferably the expression vector includes one or more control elements operatively linked to the nucleic acid sequence to be expressed. Preferably, the control element is a transcription promoter element.

"Promoter" and "transcription promoter element", are used herein interchangeably to refer to the nucleotide sequences in DNA or RNA to which RNA polymerase binds to begin transcription. The promoter may be inducible or constitutively expressed. Alternatively, the promoter is under the control of a repressor or stimulatory protein. Preferably the promoter is a T7, T3, lac, lac UV5, tac, trc, [lambda]PL, Sp6 or a UV-inducible promoter. More preferably the promoter is a T7 or T3 promoter, known to be functional in bacteria, for example E. coli. In the wild type Caf operon the promoter is temperature sensitive allowing inexpensive induction of protein production. Coupling this with extra plasmids with other promoters will allow the different combinations of monomers to be controlled.

"Transcriptional terminator" as used herein, refers to a DNA element, which terminates the function of RNA polymerases responsible for transcribing DNA into RNA. Preferred transcriptional terminators are characterized by a run of T residues preceded by a GC rich dyad symmetrical region. More preferably transcriptional terminators are terminator sequences from the T7 phage.

The design of the expression vector depends on such factors as the choice of the host cell to be transformed, the level of expression of protein desired, and the like. The expression vectors of the invention can be introduced into host cells to thereby produce proteins or polypeptides.

Expression vectors of the invention can be bacterial expression vectors, for example recombinant bacteriophage DNA, plasmid DNA or cosmid DNA, yeast expression vectors e.g. recombinant yeast expression vectors, vectors for expression in insect cells, e.g., recombinant virus expression vectors, for example baculovirus, or vectors for expression in plant cells, e.g. recombinant virus expression vectors such as cauliflower mosaic virus, CaMV, tobacco mosaic virus, TMV, or recombinant plasmid expression vectors such as Ti plasmids.

Most preferably the vector is suitable for bacterial expression, e.g. for expression in *Escherichia coli, Bacillus subtilis, Salmonella, Staphylocoocus, Streptococcus*, etc.

Preferably the vector is capable of propagation in the bacterial cell and is stably transmitted to future generations.

Preferably, the vector is a bacterial expression vector. Preferably, the expression vector is a high-copy-number expression vector; alternatively, the expression vector is a low-copy-number expression vector, for example, a Mini-F plasmid.

Preferably, the vector is a bacterial expression vector comprising a T7 promoter system. Alternatively, the vector is bacterial expression vector comprising a tac promoter system.

More preferably, the vector is a pGem expression vector.

In a preferred embodiment an expression vector of the invention comprises a nucleic acid molecule that encodes a recombinant chaperone/usher family polypeptide monomer, wherein said chaperone/usher family polypeptide monomer is a CAF1 polypeptide monomer, preferably a recombinant polypeptide monomer of the invention comprising a exogenous bioactive sequence, as hereinbefore described. Most preferably, the vector comprises a nucleic acid molecule that encodes a recombinant CAF1 polypeptide monomer, wherein said exogenous bioactive sequence is a cell adhesion recognition motif, as hereinbefore described.

Alternatively, the vector of the invention comprises a nucleic acid molecule that encodes a recombinant chaperone/usher family polypeptide monomer, wherein said chaperone/usher family polypeptide monomer is a SAF1 polypeptide monomer, preferably a recombinant polypeptide monomer of the invention comprising an exogenous bioactive sequence, as hereinbefore described. Most preferably, the vector comprises a nucleic acid molecule that encodes a recombinant SAF1 polypeptide monomer, wherein said exogenous bioactive sequence is a cell adhesion recognition motif, as hereinbefore described.

Alternatively, the vector of the invention comprises a nucleic acid molecule that encodes a recombinant chaperone/usher family polypeptide monomer, wherein said chaperone/usher family polypeptide monomer is an Afa/Dr polypeptide monomer, preferably a recombinant polypeptide monomer of the invention comprising an exogenous bioactive sequence, as hereinbefore described. Most preferably, the vector comprises a nucleic acid molecule that encodes a recombinant Afa/Dr polypeptide monomer, wherein said exogenous bioactive sequence is a cell adhesion recognition motif, as hereinbefore described.

In a further embodiment, the expression vector further comprises a nucleic acid molecule that encodes a periplasmic chaperone specific for the recombinant chaperone/usher family polypeptide monomer.

As used herein "periplasmic chaperone specific for the recombinant chaperone/usher family polypeptide monomer" refers to a periplasmic chaperone which is specific for the secretion of the recombinant chaperone/usher family polypeptide monomer. Preferably, within a cell, the periplasmic chaperone interacts with the recombinant chaperone/usher family polypeptide monomer, forming a stable chaperone-monomer complex, and facilitating release of the monomer from the cytoplasmic membrane. More preferably, the periplasmic chaperone interacts with the monomer by blocking an active site thereby preventing premature monomer-monomer interactions.

Preferably, the vector comprises a nucleic acid molecule that encodes a recombinant CAF1 polypeptide monomer and a nucleic acid molecule that encodes a periplasmic chaperone specific for CAF1, e.g. CAF1M.

Preferably said nucleic acid molecule that encodes a periplasmic chaperone specific for CAF1 encodes a polypeptide comprising or consisting of an amino acid sequence that is at least 70%, 75%, 80%, 85%, 90%, 95%, 96%, 97%, 98%, 99% or 100% identical (e.g., identical to the entire length) to the polypeptide of SEQ ID NO:6.

Alternatively, said nucleic acid molecule that encodes a periplasmic chaperone specific for CAF1 comprises or consists of a nucleotide sequence that is at least 70%, 75%, 80%, 85%, 90%, 95%, 96%, 97%, 98%, 99% or 100% identical (e.g., identical to the entire length) to the nucleic acid molecule of SEQ ID NO:2.

Alternatively, the vector comprises a nucleic acid molecule that encodes a recombinant SAF1 polypeptide monomer and a nucleic acid molecule that encodes a periplasmic chaperone specific for SAF1, e.g. SAFB.

Preferably said nucleic acid molecule that encodes a periplasmic chaperone specific for SAF1 encodes a polypeptide comprising or consisting of an amino acid sequence that is at least 70%, 75%, 80%, 85%, 90%, 95%, 96%, 97%, 98%, 99% or 100% identical (e.g., identical to the entire length) to the polypeptide of SEQ ID NO:17.

Alternatively, said nucleic acid molecule that encodes a periplasmic chaperone specific for SAF1 comprises or consists of a nucleotide sequence that is at least 70%, 75%, 80%, 85%, 90%, 95%, 96%, 97%, 98%, 99% or 100% identical (e.g., identical to the entire length) to the nucleic acid molecule of SEQ ID NO:18.

Alternatively, the vector comprises a nucleic acid molecule that encodes a recombinant Afa/Dr polypeptide monomer and a nucleic acid molecule that encodes a periplasmic chaperone specific for Afa/Dr, e.g. DraB.

Preferably said nucleic acid molecule that encodes a periplasmic chaperone specific for Afa/Dr encodes a polypeptide comprising or consisting of an amino acid sequence that is at least 70%, 75%, 80%, 85%, 90%, 95%, 96%, 97%, 98%, 99% or 100% identical (e.g., identical to the entire length) to the polypeptide of SEQ ID NO:19.

Alternatively, said nucleic acid molecule that encodes a periplasmic chaperone specific for Afa/Dr comprises or consists of a nucleotide sequence that is at least 70%, 75%, 80%, 85%, 90%, 95%, 96%, 97%, 98%, 99% or 100% identical (e.g., identical to the entire length) to the nucleic acid molecule of SEQ ID NO:20.

In a further embodiment, the expression vector further comprises a nucleic acid molecule that encodes an outer membrane usher protein specific for the recombinant chaperone/usher family polypeptide monomer.

As used herein "outer membrane usher protein specific for the recombinant chaperone/usher family polypeptide monomer" refers to an outer membrane usher protein which is specific for the secretion of the recombinant chaperone/usher family polypeptide monomer. Preferably, the usher protein is capable of binding to a chaperone/monomer complex and initiating polymer assembly. Upon binding of the chaperone/monomer complex, the usher facilitates the dissociation of the monomer from the chaperone, thereby exposing an active site for monomer-monomer interaction. In this way the monomer grows through the usher as a linear fibre which is translocated to the cell surface.

Preferably, the vector comprises a nucleic acid molecule that encodes a recombinant CAF1 polypeptide monomer and a nucleic acid molecule that encodes an outer membrane usher protein specific for CAF1, e.g. CAF1A.

Preferably said nucleic acid molecule that encodes an outer membrane usher protein specific for CAF1 encodes a polypeptide comprising or consisting of an amino acid sequence that is at least 70%, 75%, 80%, 85%, 90%, 95%, 96%, 97%, 98%, 99% or 100% identical (e.g., identical to the entire length) to the polypeptide of SEQ ID NO:7.

Alternatively, said nucleic acid molecule that encodes an outer membrane usher protein specific for CAF1 comprises or consists of a nucleotide sequence that is at least 70%, 75%, 80%, 85%, 90%, 95%, 96%, 97%, 98%, 99% or 100% identical (e.g., identical to the entire length) to the nucleic acid molecule of SEQ ID NO:3.

Preferably, the vector comprises a nucleic acid molecule that encodes a recombinant SAF1 polypeptide monomer and a nucleic acid molecule that encodes an outer membrane usher protein specific for SAF1, e.g. SAFC.

Preferably said nucleic acid molecule that encodes an outer membrane usher protein specific for SAF1 encodes a polypeptide comprising or consisting of an amino acid sequence that is at least 70%, 75%, 80%, 85%, 90%, 95%, 96%, 97%, 98%, 99% or 100% identical (e.g., identical to the entire length) to the polypeptide of SEQ ID NO:21.

Alternatively, said nucleic acid molecule that encodes an outer membrane usher protein specific for SAF1 comprises or consists of a nucleotide sequence that is at least 70%, 75%, 80%, 85%, 90%, 95%, 96%, 97%, 98%, 99% or 100% identical (e.g., identical to the entire length) to the nucleic acid molecule of SEQ ID NO:22.

Preferably, the vector comprises a nucleic acid molecule that encodes a recombinant Afa/Dr polypeptide monomer and a nucleic acid molecule that encodes an outer membrane usher protein specific for Afa/Dr e.g. DraC.

Preferably said nucleic acid molecule that encodes an outer membrane usher protein specific for Afa/Dr encodes a polypeptide comprising or consisting of an amino acid sequence that is at least 70%, 75%, 80%, 85%, 90%, 95%, 96%, 97%, 98%, 99% or 100% identical (e.g., identical to the entire length) to the polypeptide of SEQ ID NO:23.

Alternatively, said nucleic acid molecule that encodes an outer membrane usher protein specific for Afa/Dr comprises or consists of a nucleotide sequence that is at least 70%, 75%, 80%, 85%, 90%, 95%, 96%, 97%, 98%, 99% or 100% identical (e.g., identical to the entire length) to the nucleic acid molecule of SEQ ID NO:24.

In a further embodiment, the expression vector further comprises a nucleic acid molecule that encodes an expression regulator protein specific for the recombinant chaperone/usher family polypeptide monomer.

As used herein "an expression regulator protein specific for the recombinant chaperone/usher family polypeptide monomer" refers to an expression regulator protein which is specific for the transcriptional regulation of the recombinant chaperone/usher family polypeptide monomer.

Preferably, the vector comprises a nucleic acid molecule that encodes a recombinant CAF1 polypeptide monomer and a nucleic acid molecule that encodes an expression regulator protein specific for CAF1, e.g. CAF1R.

Preferably said nucleic acid molecule that encodes an expression regulator protein specific for CAF1 encodes a polypeptide comprising or consisting of an amino acid sequence that is at least 70%, 75%, 80%, 85%, 90%, 95%, 96%, 97%, 98%, 99% or 100% identical (e.g., identical to the entire length) to the polypeptide of SEQ ID NO:8.

Alternatively, said nucleic acid molecule that encodes an expression regulator protein specific for CAF1 comprises or consists of a nucleotide sequence that is at least 70%, 75%, 80%, 85%, 90%, 95%, 96%, 97%, 98%, 99% or 100% identical (e.g., identical to the entire length) to the nucleic acid molecule of SEQ ID NO:4.

Preferably, the vector comprises a nucleic acid molecule that encodes a recombinant SAF1 polypeptide monomer and a nucleic acid molecule that encodes an expression regulator protein specific for SAF1.

Still more preferably, the vector comprises two or more nucleic acid molecules selected from the group consisting of: i) a nucleic acid molecule that encodes a periplasmic chaperone specific for the recombinant chaperone/usher family polypeptide monomer; ii) a nucleic acid molecule that encodes an outer membrane usher protein specific for the recombinant chaperone/usher family polypeptide monomer; and iii) a nucleic acid molecule that encodes an expression regulator protein specific for the recombinant chaperone/usher family polypeptide monomer.

More preferably said nucleic acid molecule that encodes a recombinant CAF1 polypeptide monomer encodes a polypeptide comprising or consisting of an amino acid sequence that is at least 70%, 75%, 80%, 85%, 90%, 95%, 96%, 97%, 98%, 99% or 100% identical (e.g., identical to the entire length) to the polypeptide of SEQ ID NO:5. Alternatively, said nucleic acid molecule that encodes a recombinant CAF1 polypeptide monomer comprises or consists of a nucleotide sequence that is at least 70%, 75%, 80%, 85%, 90%, 95%, 96%, 97%, 98%, 99% or 100% identical (e.g., identical to the entire length) to the nucleic acid molecule of SEQ ID NO:1.

In another embodiment the expression vector comprises a nucleic acid molecule as described previously, comprising specific changes in the nucleotide sequence so as to optimize codons and mRNA secondary structure for translation in the host cell. Preferably, the codon usage of the nucleic acid is adapted for expression in the host cell, for example codon optimisation can be achieved using Calcgene, Hale, R S and Thomas G. *Protein Exper. Purif.* 12, 185-188 (1998), UpGene, Gao, W et al. *Biotechnol. Prog.* 20, 443-448 (2004), or Codon Optimizer, Fuglsang, A. *Protein Exper. Purif.* 31, 247-249 (2003). Amending the nucleic acid according to the preferred codon optimization can be achieved by a number of different experimental protocols, including, modification of a small number of codons, Vervoort et al. *Nucleic Acids Res.* 25: 2069-2074 (2000), or rewriting a large section of the nucleic acid sequence, for example, up to 1000 bp of DNA, Hale, R S and Thomas G. *Protein Exper. Purif.* 12, 185-188 (1998). Rewriting of the nucleic acid sequence can be achieved by recursive PCR, where the desired sequence is produced by the extension of overlapping oligonucleotide primers, Prodromou and Pearl, *Protein Eng.* 5: 827-829 (1992). Rewriting of larger stretches of DNA may require up to three consecutive rounds of recursive PCR, Hale, R S and Thomas G. *Protein Exper. Purif.* 12, 185-188 (1998), Te'o et al, *FEMS Microbiol. Lett.* 190: 13-19, (2000).

Alternatively, the level of cognate tRNA can be elevated in the host cell. This elevation can be achieved by increasing the copy number of the respective tRNA gene, for example by inserting into the host cell the relevant tRNA gene on a compatible multiple copy plasmid, or alternatively inserting the tRNA gene into the expression vector itself. When using an *E. coli* expression system, *E. coli* host cells having enhanced expression of argU expression (for recognition of AGG/AGA) may be employed. In addition, host cells comprising tRNA genes for ilex (for recognition of AUA), leuW (for recognition of CUA), proL (for recognition of CCC) or glyT (for recognition of GGA) may also be employed, Brinkmann et al. *Genes,* 85, 109-114, (1989), Kane F J. *Curr. Opin. Biotechnol.* 6:494-500 (1995), Rosenburg et al, *J. Bacteriol.* 175, 716-722, (1993), Siedel et al, *Biochemistry,* 31, 2598-2608, (1992).

Molecular techniques are well known for the preparation of expression vectors.

The nucleic acid molecule for incorporation into the expression vector of the invention, as described above, can be prepared by synthesizing nucleic acid molecules using mutually priming oligonucleotides and the nucleic acid sequences described herein.

A number of molecular techniques have been developed to operably link DNA to vectors via complementary cohesive termini. In one embodiment, complementary homopolymer tracts can be added to the nucleic acid molecule to be inserted into the vector DNA. The vector and nucleic acid molecule are then joined by hydrogen bonding between the complementary homopolymeric tails to form recombinant DNA molecules.

In an alternative embodiment, synthetic linkers containing one or more restriction sites provide are used to operably link the nucleic acid molecule to the expression vector. In one embodiment, the nucleic acid molecule is generated by restriction endonuclease digestion as described earlier.

Alternatively, a vector comprising ligation-independent cloning (LIC) sites can be employed. The required PCR amplified nucleic acid molecule can then be cloned into the LIC vector without restriction digest or ligation (Aslanidis and de Jong, *Nucl. Acid. Res.* 18, 6069-6074, (1990), Haun, et al, *Biotechniques* 13, 515-518 (1992).

In order to isolate and/or modify the nucleic acid molecule of interest for insertion into the chosen plasmid, it is preferable to use PCR. Appropriate primers for use in PCR preparation of the sequence can be designed to isolate the required coding region of the nucleic acid molecule, add restriction endonuclease or LIC sites, place the coding region in the desired reading frame.

In a preferred embodiment a nucleic acid molecule for incorporation into an expression vector of the invention is prepared by the use of the polymerase chain reaction as disclosed by Saiki et al (1988) *Science* 239, 487-491, using appropriate oligonucleotide primers. The coding region is amplified, whilst the primers themselves become incorporated into the amplified sequence product. In a preferred embodiment the amplification primers contain restriction endonuclease recognition sites which allow the amplified sequence product to be cloned into an appropriate vector.

The expression vectors of the invention can contain a single copy of the nucleic acid molecule described previously, or multiple copies of the nucleic acid molecule described previously.

Host Cells

In one aspect the invention provides a host cell transformed or transfected with an expression vector of the invention.

"Host cell" as used herein, refers to the particular subject cell and also to the progeny or potential progeny of such a cell. Because certain modifications may occur in succeeding generations due to either mutation or environmental influences, such progeny may not, in fact, be identical to the parent cell, but are still included within the scope of the term as used herein.

The host cell for use in the expression system of the present invention may be an aerobic cell or alternatively a facultative anaerobic cell. Preferably, the cell is a bacterial cell. Alternatively, the cell may be a yeast cell (e.g. *Saccharomyces, Pichia*), an algae cell, an insect cell, or a plant cell.

Bacterial host cells include Gram-positive and Gram-negative bacteria. Suitable bacterial host cells include, but are not limited to the Gram-negative bacteria, for example a bacterium of the family Enterobacteria, most preferably *Escherichia coli. E. Coli* is the most preferred bacterial host cells for the present invention. Expression in *E. Coli* offers numerous advantages over other expression systems, particularly low development costs and high production yields. Cells suitable for high protein expression include, for example, *E. coli* W3110, the B strains of *E. coli. E. coli* BL21, BL21 (DE3), and BL21 (DE3) pLysS, pLysE, DH1, DH41, DH5, DH5I, DH5IF', DH5IMCR, DH10B, DhIOB/p3, DH1 IS, C600, HB101, JM101, JM105, JM109, JM110, K38, RR1, Y1088, Y1089, CSH18, ER1451, ER1647 are particularly suitable for expression. *E. Coli* K12 strains are also preferred as such strains are standard laboratory strains, which are non-pathogenic, and include NovaBlue, JM109 and DH5α (Novogen®), *E. Coli* K12 RV308, *E. Coli* K12 C600, *E. Coli* HB101, see, for example, Brown, Molecular Biology Labfax (Academic Press (1991)).

Standard techniques for propagating vectors in prokaryotic hosts are well-known to those of skill in the art (see, for example, Ausubel et al. Short Protocols in Molecular Biology 3$^{rd}$ Edition (John Wiley & Sons 1995)).

To maximize recombinant protein expression in *E. coli*, the expression vectors of the invention may express the nucleic acid molecule incorporated therein in a host bacteria with an impaired capacity to proteolytically cleave the recombinant protein (Gottesman, S., (1990) Gene Expression Technology: Methods in Enzymology 185, Academic Press, San Diego, Calif., 119-128). Alternatively, the nucleic acid molecule incorporated into an expression vector of the invention, can be attenuated so that the individual codons for each amino acid are those preferentially utilized in *E. coli* (Wada et al., (1992) Nucleic Acids Res. 20:2111-2118). Such alteration of nucleic acid sequences of the invention can be carried out by standard DNA synthesis techniques.

A host cell of the invention may be used in an expression system for producing a chaperone/usher family polymer.

The expression vector of the present invention can be introduced into host cells by conventional transformation or transfection techniques.

"Transformation" and "transfection", as used herein, refer to a variety of techniques known in the art for introducing foreign nucleic acids into a host cell. Transformation of appropriate host cells with an expression vector of the present invention is accomplished by methods known in the art and typically depends on both the type of vector and host cell. Said techniques include, but are not limited to calcium phosphate or calcium chloride co-precipitation, DEAE-dextran-mediated transfection, lipofection, chemoporation or electroporation.

Techniques known in the art for the transformation of bacterial host cells are disclosed in for example, Sambrook et al (1989) Molecular Cloning, A Laboratory Manual, Cold Spring Harbor Laboratory, Cold Spring Harbor, N.Y.; Ausubel et al (1987) Current Protocols in Molecular Biology, John Wiley and Sons, Inc., NY; Cohen et al (1972) Proc. Natl. Acad. Sci. USA 69, 2110; Luchansky et al (1988) Mol. Microbiol. 2, 637-646. All such methods are incorporated herein by reference.

Successfully transformed cells, that is, those cells containing the expression vector of the present invention, can be identified by techniques well known in the art. For example, cells transfected with the expression vector of the present invention can be cultured to produce a chaperone/usher family member. Cells can be examined for the presence of the expression vector DNA by techniques well known in the art. Alternatively, the presence of a chaperone/usher family member, or portion and fragments thereof can be detected using antibodies which hybridize thereto.

In a preferred embodiment the invention comprises a culture of transformed host cells. Preferably the culture is clonally homogeneous.

The host cell can contain a single copy of expression vectors of the invention described previously, or alternatively, multiple copies of expression vectors, i.e multiple copies of identical or non-identical expression vectors.

Polymer Production

A host cell transformed with an expression vector, comprising a nucleic acid molecule as hereinbefore described, can be used to produce (i.e., express) a chaperone/usher family polymer.

In one aspect the invention provides a method for producing a chaperone/usher family polymer comprising at least one chaperone/usher family polypeptide monomer comprising an exogenous bioactive sequence, said method comprising: i) incorporating a nucleic acid molecule that encodes a chaperone/usher family polypeptide monomer comprising an exogenous bioactive sequence into an expression vector for expression in a host cell; and ii) transfecting a host cell with the expression vector; wherein said host cell is provided with a nucleic acid molecule that encodes a periplasmic chaperone specific for the chaperone/usher family polypeptide monomer and a nucleic acid molecule that encodes an outer membrane usher protein specific for the chaperone/usher family polypeptide monomer and wherein the resulting transfected host cell produces a chaperone/usher family polymer.

Preferably, the chaperone/usher family polymer is a fraction 1 antigen polymer, a SAF1 polymer or an Afa/Dr polymer, as hereinbefore described.

Preferably, the nucleic acid molecule that encodes a recombinant chaperone/usher family polypeptide monomer comprising an exogenous bioactive sequence encodes a CAF1 polypeptide monomer, comprising an exogenous bioactive sequence, a SAF1 polypeptide monomer comprising an exogenous bioactive sequence or an Afa/Dr polypeptide monomer comprising an exogenous bioactive sequence, as hereinbefore described.

Preferably, said bioactive sequence is a cell adhesion recognition motif, a growth factor sequence motif or a protease site, as hereinbefore described.

Preferably, said periplasmic chaperone specific for the recombinant chaperone/usher family polypeptide monomer is a periplasmic chaperone specific for CAF1, SAF1 or Afa/Dr, as hereinbefore described.

Preferably, said outer membrane usher protein specific for the recombinant chaperone/usher family polypeptide monomer is an outer membrane usher protein specific for CAF1, SAF1 or Afa/Dr, as hereinbefore described.

Preferably the host cell is provided with the nucleic acid molecule that encodes a periplasmic chaperone specific for the chaperone/usher family polypeptide monomer by incorporating the nucleic acid molecule that encodes the periplasmic chaperone specific for the chaperone/usher family polypeptide monomer into an expression vector for expression in the host cell; and transfecting the host cell with the expression vector. The expression vector can be the same vector incorporating a nucleic acid molecule that encodes a chaperone/usher family polypeptide monomer or a different expression vector.

Preferably the host cell is provided with the nucleic acid molecule that encodes an outer membrane usher protein specific for the chaperone/usher family polypeptide monomer by incorporating the nucleic acid molecule that encodes the outer membrane usher protein specific for the chaperone/usher family polypeptide monomer into an expression vector for expression in the host cell; and transfecting the host cell with the expression vector. The expression vector can be the same vector incorporating the nucleic acid molecule that encodes a chaperone/usher family polypeptide monomer and/or the nucleic acid molecule that encodes a periplasmic chaperone specific for the chaperone/usher family polypeptide monomer, or a different expression vector.

Preferably, the host cell is further provided with a nucleic acid molecule that encodes an expression regulator specific for the chaperone/usher family polypeptide monomer. Preferably, said expression regulator specific for the recombinant chaperone/usher family polypeptide monomer is a periplasmic chaperone specific for CAF1, SAF1 or Afa/Dr, as hereinbefore described.

Preferably the host cell is provided with the nucleic acid molecule that encodes an expression regulator specific for the chaperone/usher family polypeptide monomer by incorporating the nucleic acid molecule that encodes the expression regulator specific for the chaperone/usher family polypeptide monomer into an expression vector for expression in the host cell; and transfecting the host cell with the expression vector. The expression vector can be the same vector incorporating the nucleic acid molecule that encodes a chaperone/usher family polypeptide monomer and/or the nucleic acid molecule that encodes a periplasmic chaperone specific for the chaperone/usher family polypeptide monomer and/or the nucleic acid molecule that encodes an outer membrane usher protein specific for the chaperone/usher family polypeptide monomer, or a different expression vector.

The host cell can be any host cell. Preferably the host cell is a gram negative bacteria, as hereinbefore described.

The present invention comprises an expression system for the large scale production of chaperone/usher family polymer, utilizing expression vectors of the invention as hereinbefore described. Preferably the expression system is an *E. coli* expression system.

Transformed host cells of the invention or transformed host cells comprising the expression vectors of the invention are grown or cultured in the manner with which the skilled worker is familiar, depending on the host organism. As a rule, host cells are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen.

The pH of the liquid medium can either be kept constant, that is to say regulated during the culturing period, or not. The cultures can be grown batchwise, semi-batchwise or continuously. Nutrients can be provided at the beginning of the fermentation or fed in semi-continuously or continuously. The products produced can be isolated from the organisms by processes known to the skilled worker, for example by extraction, distillation, crystallization, if appropriate precipitation with salt, and/or chromatography.

An overview of known cultivation methods can be found in the textbook by Chmiel (Bioprozeβtechnik 1. Einführung in die Bioverfahrenstechnik [Bioprocess technology 1. Introduction to Bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Brunswick/Wiesbaden, 1994)).

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Transformed host cells can be cultured in aerobic or anaerobic conditions. In aerobic conditions, preferably, oxygen is continuously removed from the culture medium, by for example, the addition of reductants or oxygen scavengers, or, by purging the reaction medium with neutral gases.

Techniques known in the art for the large scale culture of host cells are disclosed in for example, Bailey and Ollis (1986) Biochemical Engineering Fundamentals, McGraw-Hill, Singapore; or Shuler (2001) Bioprocess Engineering: Basic Concepts, Prentice Hall. All such techniques are incorporated herein by reference.

The host cells of the invention can be cultured in a vessel, for example a bioreactor. Bioreactors, for example fermentors, are vessels that comprise cells or enzymes and typically are used for the production of molecules on an industrial scale. The molecules can be recombinant proteins (e.g. a chaperone/usher family polymer of the invention). Typically, cell based bioreactors comprise the cells of interest and include all the nutrients and/or co-factors necessary to carry out the reactions.

Accordingly, the invention provides a method for producing a chaperone/usher family polymer comprising at least one chaperone/usher family polypeptide monomer comprising an exogenous bioactive sequence comprising: i) providing a vessel comprising a host cell of the invention; as hereinbefore described; and ii) providing cell culture conditions which facilitate recombinant chaperone/usher family polypeptide monomer expression by a cell culture contained in the vessel; and optionally iii) collecting chaperone/usher family polymer from the vessel.

Examples

1. Experimental Overview 1.1 Subcloning of Caf1, Expression and Purification.

The caf operon (about 5.2 Kb in size) was amplified by PCR (30 amplification cycles; 95° C. for 20 s, 55° C. for 10 s, 70° C. for 5 min) (PCR Express, Hybaid, UK) using oligonucleotide primer pair F1 Forward (5'-ATA AAT CGG TTC AGT GGC CTC AAC GCT GTG-3') (SEQ ID NO:49) and F1 Reverse (5'-GGT TAG GCT CAA AGT AGG ATA ATT C-3') (SEQ ID NO:50), the plasmid pAH34L (9) encoding caf operon ((GenBank, accession number AY450847) as a template and the KOD HOT START DNA polymerase (Novagen, UK) which generates blunt-ended fragments. The PCR product obtained was loaded on a 0.7% agarose gel stained with ethidium bromide (0.5 ug/Ml). DNA was visualised on the trans-illuminator (UV light of wavelength 254 nm) (Gel-Doc Bio-RAD, UK). The PCR product of oligonucleotides which corresponds to the caf operon was excised from the agarose gel using a sterile scalpel blade. The extracted DNA band was purified with QIAquick gel extraction kit and QIAquick PCR purification kit (Qiagen, UK). After that DNA purified was loaded on a 0.7% agarose gel containing ethidium bromide (0.5 µg/Ml), visualised on the trans-illuminator and quantified using Quantity one software (Gel-Doc Bio-RAD, UK). Before subcloning the PCR product into a new vector, restriction analyses were performed to confirm the identity of the PCR product. Then, the purified PCR product was subcloned into a new vector. Initially, the inventors attempted to subclone caf operon into Psmart-HC-Amp and Psmart-LC-Kan vectors (Lucigen, USA). The copy number of Psmart-HC is similar to Puc19, about 300-500 copies per cell. The copy number of Psmart-LC is similar to Pbr322, about 15-30 copies per cell. The Psmart vectors are pre-digested, with blunt, dephosphorylated ends. The small size of the Psmart vectors (1.7-2.0 Kb) could facilitate subcloning and mutagenesis experiments of the large insert DNA. After DNA purification the PCR product must be treated with T4 polynucleotide kinase (10 U) (NEB, UK) to add 5'-phosphates to oligonucleotides in order to allow subsequent ligation. In the cloneSmart ligation reaction, the pre-processed Psmart vector is ligated with blunt, phosphorylated insert (200 ng of insert). The positive control used was the lambda/HcII insert (500 ng) and the negative control without insert was also performed following the manufacturer's instructions and recommendations for the ligation (Lucigen, US). Transformants of $E.$ $coli$ 10 G chemically competent cells [F-mcrA D(mrr-hsdRMS-mcrBC) φ80dlacZΔM15 ΔlacX74 endA1 recA1araD139 Δ(ara, leu)7697 galU galK rpsL nupGλ– tonA] (Lucigen, USA) containing the new recombinant plasmid, were selected on LB agar plates containing the appropriate antibiotic for either Psmart HC-Amp and LC-Kan. The plates were incubated overnight at 37° C. Afterwards, improvements to subclone the caf operon were made such as increasing the incubation time to 24 hours at 4° C. A second attempt to subclone caf operon was conducted using pGem-T Easy (Promega, UK). The high copy number pGem-T Easy Vectors were prepared by cutting it with EcoR V and adding a 3' terminal thymidine to both ends. These single 3'-T overhangs at the insertion site greatly improve the efficiency of ligation of a PCR product into the small size plasmids (3 Kb) by preventing recircularization of the vector and providing a compatible overhang for PCR products (Promega, UK). The purified PCR product was modified using the A-tailing procedure, which adds a 3' terminal 'A' overhang onto the PCR product that was amplified using a blunt-ended enzyme following the manufacturer's instructions and recommendations for A-tailing procedure (pGem-T EASY kit from Promega, UK). The ligations reactions were prepared including standard reaction, positive control (control insert DNA) and background control (no insert DNA) following the manufacturer's instructions and recommendations for the ligation reaction (pGem-T EASY kit from Promega, UK) with the exception of the incubation time and temperature for the reactions, which was 24 hours at 4° C. After that, the ligation reactions were heat-denatured at 65° C. for 10 minutes. Transformants of $E.$ $coli$ DH5α cells [F-φ80lacZΔM15 Δ(lacZYA-argF)U169 deoR recA1 endA1 hsdR17(rk–, mk+) phoA supE44 thi-1 gyrA96 relA1λ⁻] (Invitrogen, UK) containing the new recombinant plasmid, designated $E.$ $Coli$ (pGem-TF1) were selected on LB agar plates containing 100 µL of ampicillin and 20 µL of X-Gal (50 mg/Ml) was spread on the LB agar plates. The plates were incubated overnight at 37° C. On the following day, a single colony was picked from each successful transformation and introduced into a tube containing agar in order to be sent for sequencing (Beckman Coulter Genomics—Formerly Agencourt Bioscience and Cogenics, UK). In parallel restriction analysis of pGem-TF1 plasmid from plasmid miniprep were performed.

For protein expression and purification, $E.$ $Coli$ BL21 (DE3) cells (Invitrogen, UK) were transformed with pGem-TF1. Cells were prepared and harvested, and protein isolation was performed as described previously (8). Briefly, cells were grown at 37° C. for 19 hours with shaking (170 rpm). The cells were centrifuged at 14 000×g for 45 min at 4° C. and the cell pellet and flocculant layer (mainly Caf1) resuspended in 100 Ml phosphate-buffered saline (PBS) pH 7.6. After 30 minutes incubation, the resuspension was centrifuged at 14 000×g for 30 min and the supernatant was adjusted to 40% ammonium sulphate saturation. After centrifuged at 14 000×g for 30 min at 4° C., the ammonium sulphate pellet was resuspended in PBS was centrifuged at 27 000×g to remove insoluble material, followed by filter sterilisation using 0.22 µm disposable filter (Millex, Millipore, UK). Aliquots of 100 µL of the caf1 sample were applied to an FPLC Superdex 200 column (GE Healthcare) that had been previously equilibrated with PBS. The caf1 was eluted with the same buffer at a flow rate of 0.5 Ml/min. Peak fractions were collected and analysed for caf1 by 12% SDS-PAGE gel and western blotting (using a monoclonal antibody raised to F1). Protein samples were sent to Pinnacle—Proteomics and Biological Mass spectrometry service at Newcastle University to confirm the identity of the protein studied using Peptide Mass Fingerprinting (PMF) procedure.

1.2 Construction of Caf1-RGDS Mutants by Site Directed Mutagenesis, Expression and Purification.

Mutations within the caf1 gene were created in pGem-TF1 by PCR using Pfu polymerase (Stratagene), (18 amplification cycles; 95° C. for 1 min, 95° C. for 50 sec, 60° C. for 50 s, 68° C. for 8.5 min) (PCR Express, Hybaid, UK) as described (XL Quickchange kit, Stratagene) used for large plasmids. Coding primers (mutations in lower case) were as shown in table 1:

TABLE 1 coding primers used to create mutations in the caf1 gene.

| Oligonucleotide | 5'-3' | Sequence |
|---|---|---|
| Caf1G94insD; S95insF (SEQ ID NO: 51) | forward | 5'-ATTGGCAAGGATTCTAGAggtGATttcTTTGATATCTCTCCTAAG-3' |
| Caf1G94insD; S95insF (SEQ ID NO: 52) | reverse | 5'-CTTAGGAGAGATATCAAAggaATCaccTCTAGAATCCTTGCCAAT-3' |

TABLE 1-continued coding primers used to create mutations in the caf1 gene.

| Oligonucleotide | 5'-3' | Sequence |
|---|---|---|
| Caf1A66R; S69P (SEQ ID NO: 53) | forward | 5'-TAACTTTACAGATGCCaggGGTGATagcCCCATGTACTTAACAT-3' |
| Caf1A66R; S69P (SEQ ID NO: 54) | reverse | 5'-ATGTTAAGTACATGGGgctATCACCcctGGCATCTGTAAAGTTA-3' |
| Caf1V106R; D109S (SEQ ID NO: 55) | forward | 5'-ACGGTGAGAACCTTcgtGGGGAttcCGTCGTCTTGGCTAC-3' |
| Caf1V106R; D109S (SEQ ID NO: 56) | reverse | 5'-GTAGCCAAGACGAcggAATCCCCacgAAGGTTCTCACCGT-3' |
| Caf1MDN31GRG; DS34GN (SEQ ID NO: 57) | forward | 5'-CTCCAATTACAATTggtagaggagactctGGAAACATCGATAC-3' |
| Caf1MDN31GRG; DS34GN (SEQ ID NO: 58) | reverse | 5'-GTATCGATGTTTCCagagtctcctctaccAATTGTAATTGGAG-3' |
| Caf1QDGN76RGDS (SEQ ID NO: 59) | forward | 5'-ACTTAACATTTACTTCTcgaggagattcaAACCACCAATTCACTAC-3' |
| Caf1QDGN76RGDS (SEQ ID NO: 60) | reverse | 5'-GTAGTGAATTGGTGGTTtgaatctcctcgAGAAGTAAATGTTAAGT-3' |

The 8.2 Kb amplified product was treated with DpnI. E. Coli DH5α was transformed with the DpnI-treated 8.2 Kb amplified product. For one transformant from each construct, the complete sequence of the mutated caf1 was confirmed ((Beckman Coulter Genomics—Formerly Agencourt Bioscience and Cogenics, UK).

1.3 Transmission Electron Microscopy (TEM).

Protein samples and the negatively stained specimens were prepared as described previously (10). Briefly caf1 WT and caf1 RGDS mutant protein samples were prepared in distilled water to a final concentration of 50 µg/ml. An electron microscope grid with thin carbon support film was applied to a 10 µl sample droplet, held for 10-20 s and drained using a filter paper. Buffer and salts were then washed away using three 20 µl droplets of water and the remaining carbon-adsorbed protein/adjuvant was negatively stained by adding a 20 µl droplet of 2% uranyl acetate solution. The negative stain was drained with a filter paper and the grid was allowed to air dry. Negatively stained specimens were studied in a Philips CM100 transmission electron microscope operated at 100 Kv. Electron micrographs were recorded in a tagged image file format (TIFF), routinely at image magnifications of ×130 000.

1.4 Cell Adhesion Assay.

3T3 fibroblasts and PC12 were purchased from American Type Culture Collection (ATCC; http://www.lgcpromochematcc.com) and maintained as previously described (4). For Caf1 Protein coating 100 µL of proteins of interest (caf1 WT and caf1 RGDS mutant) and controls were added into a 96-well plate. BSA, OmpA-RGDS, were used as controls. Non-coating wells were also used as control. Proteins were diluted in 10 mM PBS, pH 7.6 to obtain the desired concentration, 100 µg/Ml. All the protein solutions were filtered using a 0.2 µm filter. Each solution was pipetted into a culture plate using a multi-channel pipette for a 96-well plate. The plate was sealed with parafilm and incubated overnight at 4° C. The proteins solutions were aspirated from the plate wells and wash once the wells with 10 Mm PBS pH 7.6. The PBS was removed from the wells and the plate reserved for cell culture. Then, 3T3 Fibroblasts cells were harvested at 1000×g for 5 min. The cell pellet was resuspended in 10 Mm PBS pH7.4 with calcium and magnesium at a concentration of $2.5×10^6$ cells/Ml. The cells were washed twice in 10 mM PBS pH 7.4 with calcium and magnesium at a concentration of $1×10^6$ cell/Ml. 100 µL of prepared cells suspension was added to each well. The plate was placed in the incubator at 37° C. for 2 hours. After 2 hours of incubation the cells which did not attach were removed inverting the plate. Cells were washed twice with 10 mM PBS pH 7.4 with calcium and magnesium for 5 minutes and fixed with 4% paraformaldehyde in PBS pH 7.4 (Sigma-Aldrich, UK) for 30 minutes. The paraformaldehyde solution was removed and the cells were washed three times with PBS pH 7.4 for 5 minutes each wash and then stained with 10 µg/Ml of DAPI (Sigma-Aldrich, UK) in PBS pH 7.4 for 25 minutes. The DAPI solution was removed and the cells were washed three times with PBS pH 7.4 for 5 minutes each wash. After that the cells were stained with rhodamine-phalloidin conjugated (200 ng/Ml) (Sigma-aldrich) for 15 minutes. Then the phalloidin solution was removed and the cells were washed three times with PBS pH 7.4 for 5 minutes each wash. The wells were filled in with PBS pH 7.4 and measurements were effectuated using Fluorimeter. For cell adhesion assay using the fluorescence microscope, glass coverslips were coated with caf1 WT and caf1 RGDS mutant following the same protocol mentioned above. After that $1×10^5$ of PC12 cells were added in RPMI 1640 medium without serum per well of a 6-well culture plate containing the glass coverslips coated with proteins. The cells were maintained at 37° C., 5% $CO_2$ in an incubator for 3 hours. After 3 hours cultures were washed once with 2 Ml sterile phosphate buffered saline (PBS) (Cambrex), fixed and staining as mentioned above.

2. Results 2.1. Subcloning Caf Operon 2.1.1. PCR Amplification of Caf Operon Using Pah34L Vector as a Template and Restriction Digest of PCR Product The amplification of E. Coli plasmid pAH34L (12) (about 11 Kbp in size), which includes the Yersinia pestis caf operon, by PCR using the F1 pair of primers and PCR cycle conditions has shown a band of 5.2 Kb (FIG. 3a). The resulting PCR product was digested with HindIII and BamHI restriction enzymes which cut the caf operon and EcoRI which does not cut caf operon (FIG. 3b).

The PCR product obtained was confirmed by restriction analysis to be the caf operon.

2.1.2. Caf Operon Purification and Quantification and Restriction Digest

After confirming that the PCR product obtained was the caf operon, a DNA fragment of the expected size (5.2 Kb) was purified using QIAGEN Gel Extraction kit and quantified using Quantity One® software (Bio-Rad) (FIG. 4a). Then, the identity and integrity of the DNA fragment was confirmed by restriction analysis with HindIII and BamHI restriction enzymes which cut the caf operon and EcoRI which does not cut caf operon (FIG. 4b).

The PCR product was purified, a single band of 5.2 Kb was shown on the electrophoresis gel and restriction analyses have shown that band was the caf operon. From this purification 64 ng/µL of purified PCR product was obtained.

2.1.3. Sequencing of pGem-TF1

Figure 5:
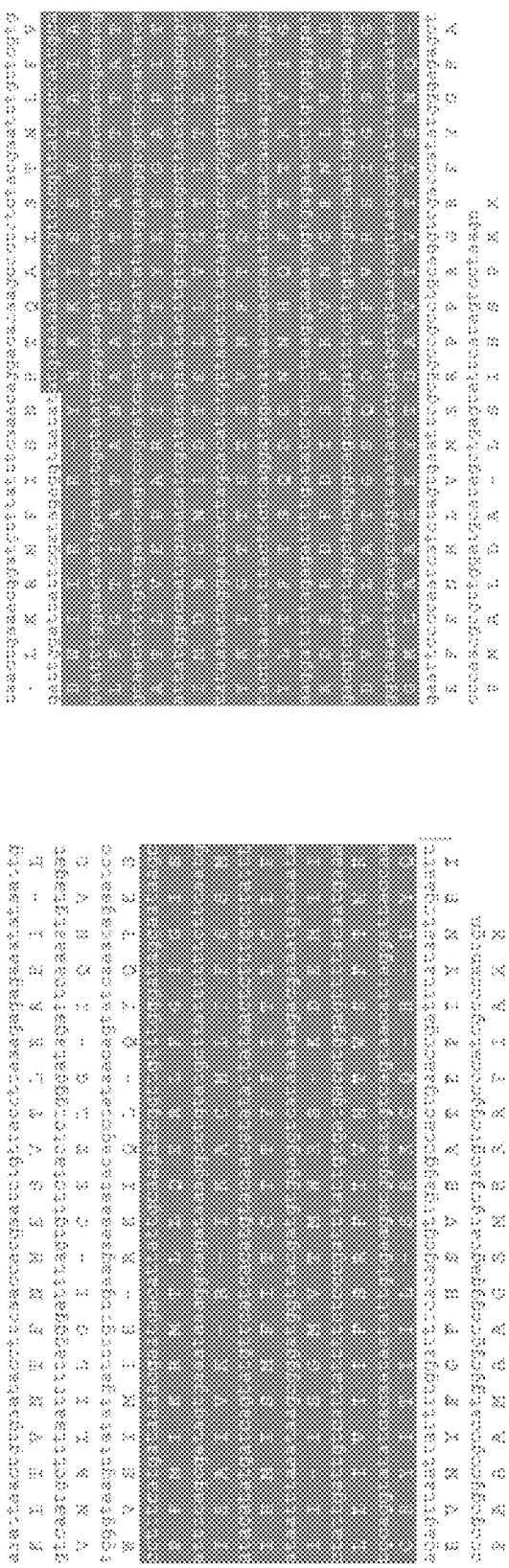
Figure 6:
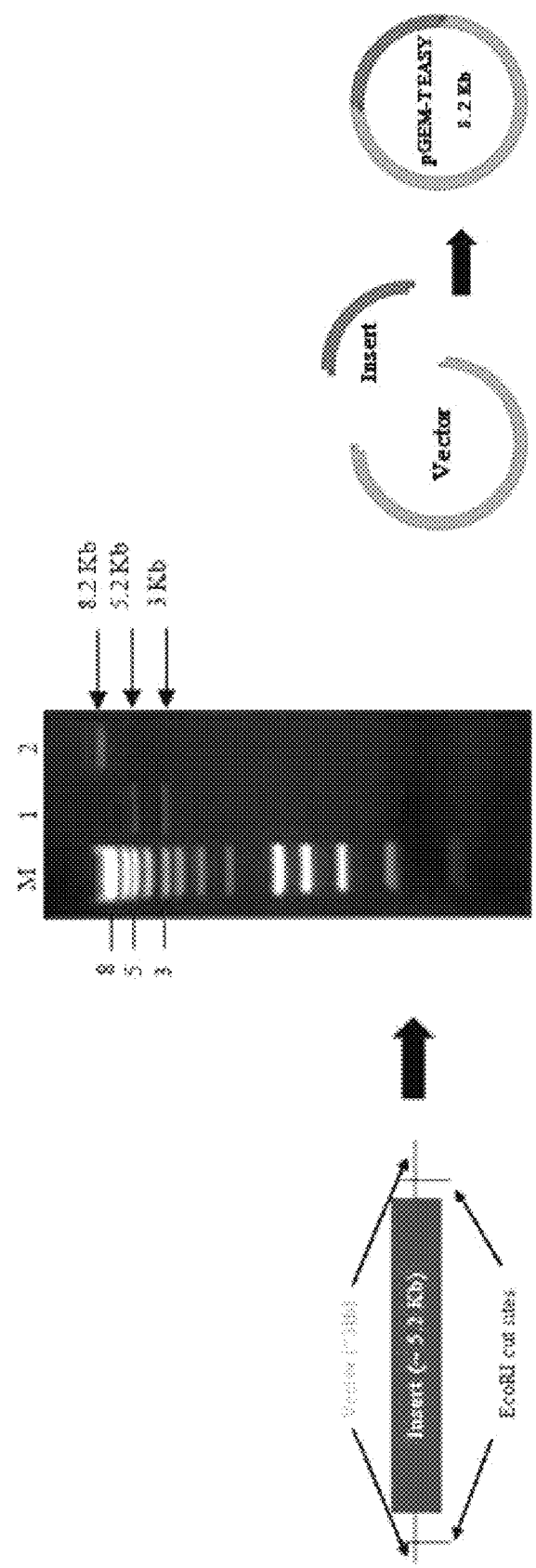
Figure 7:
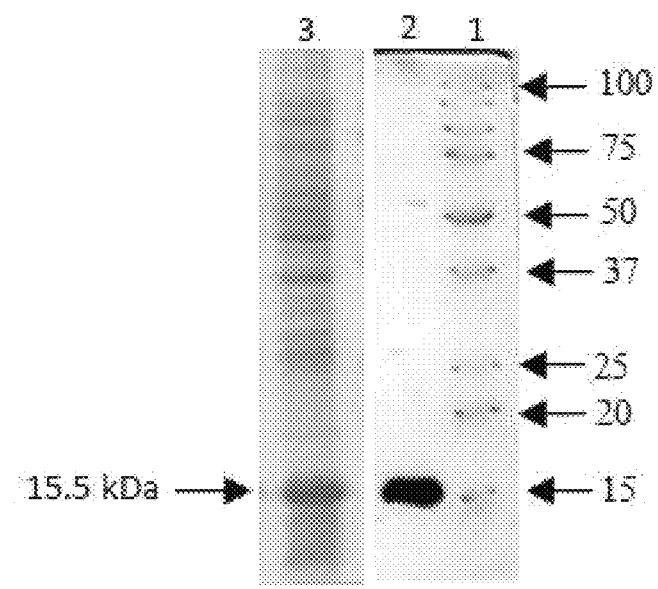
Figure 8:
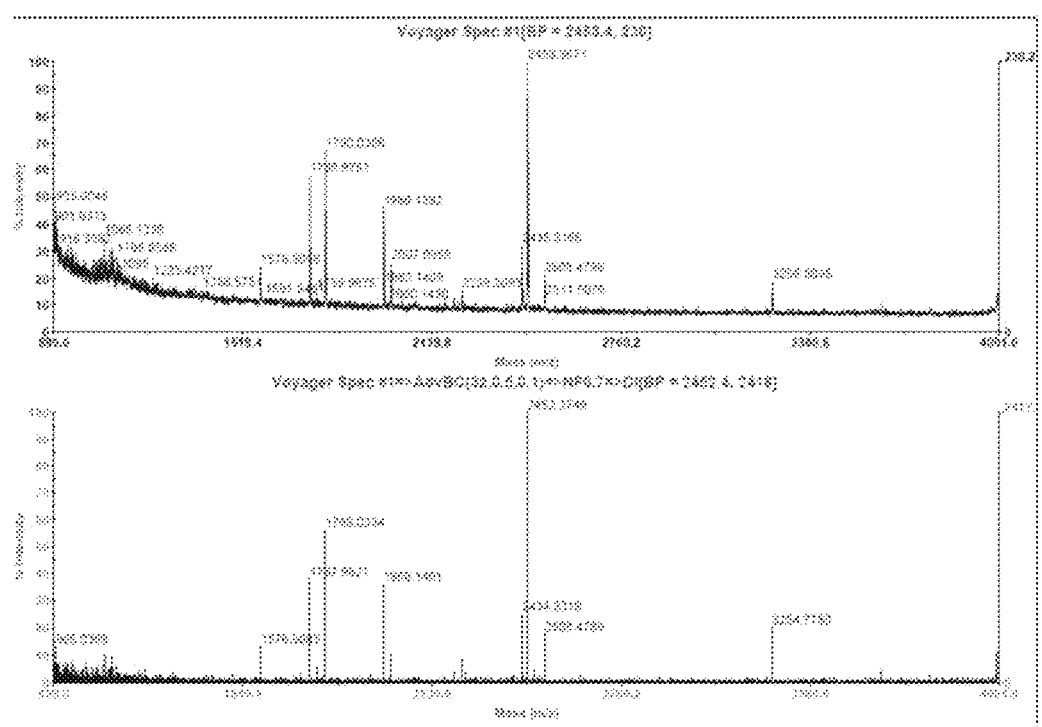
Figure 10:
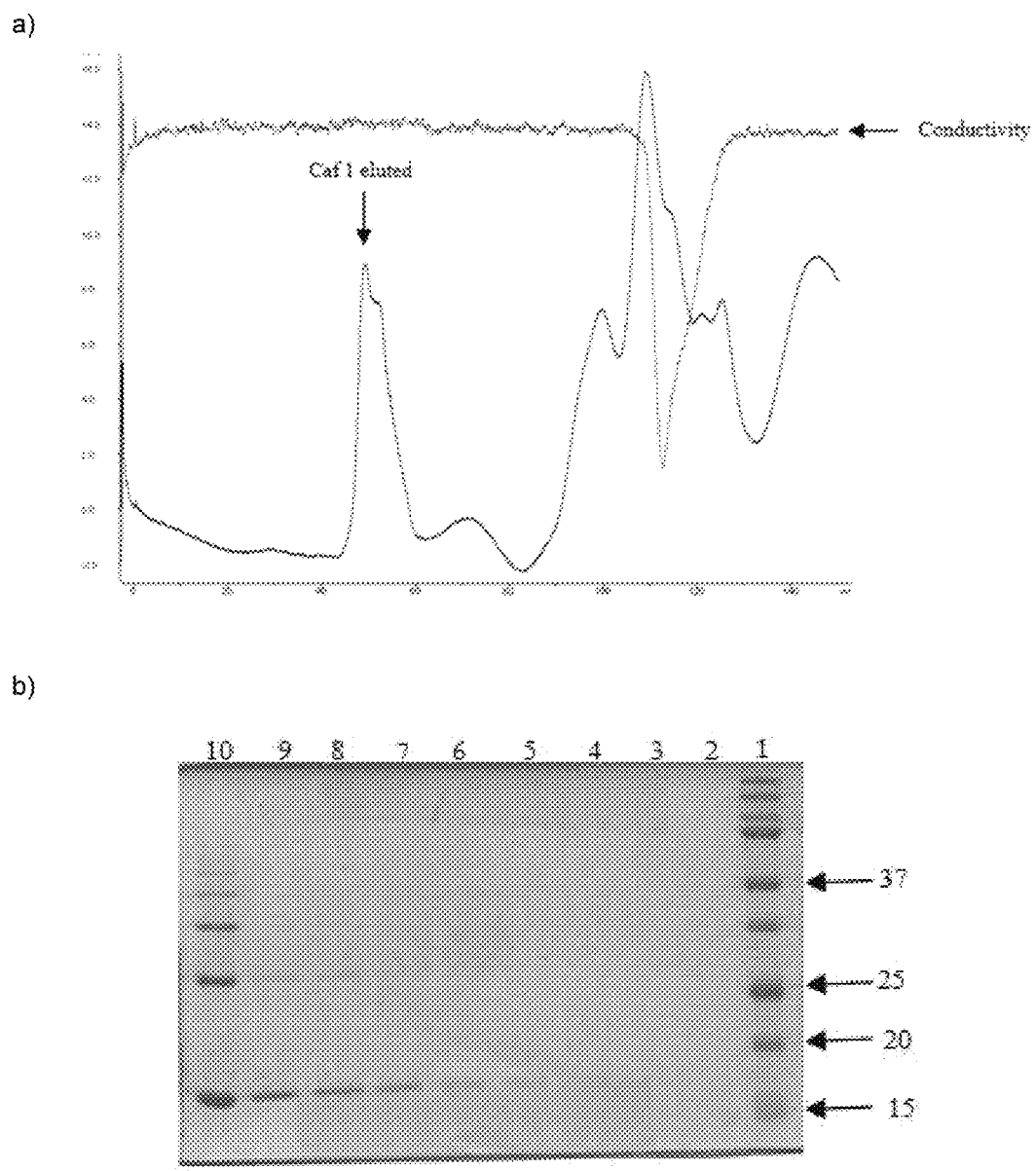
Figure 11:
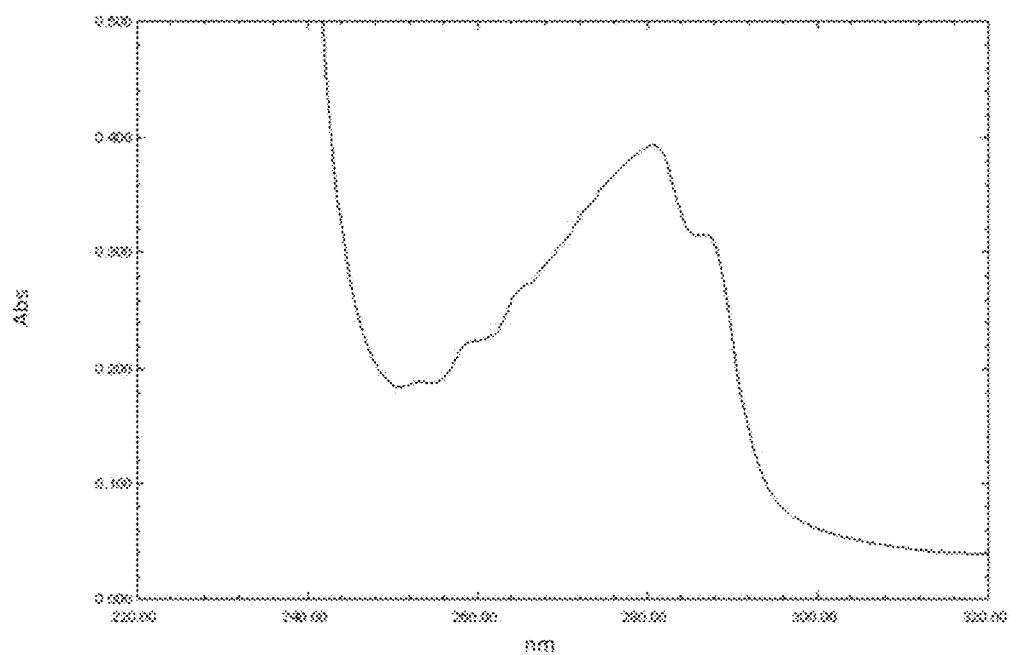
Figure 12:
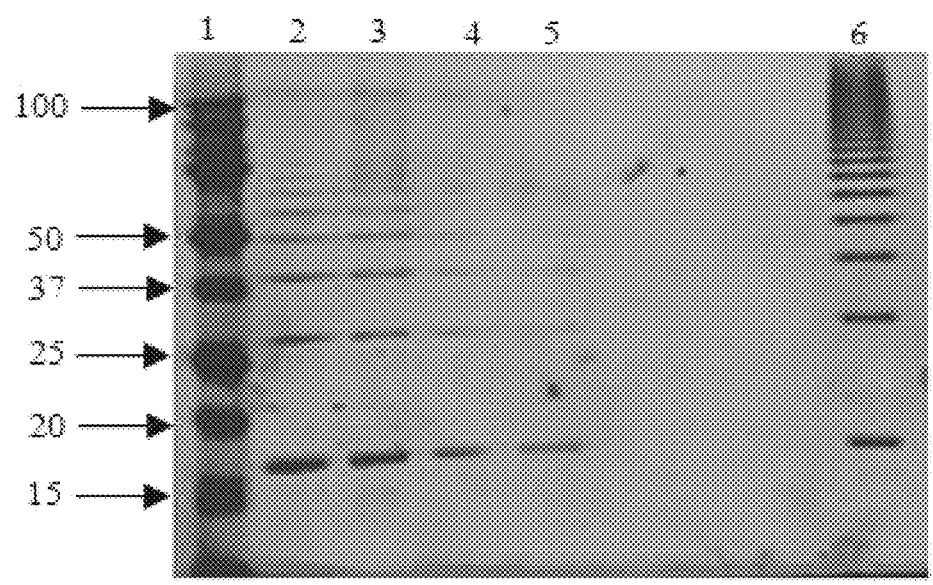
Figure 13:
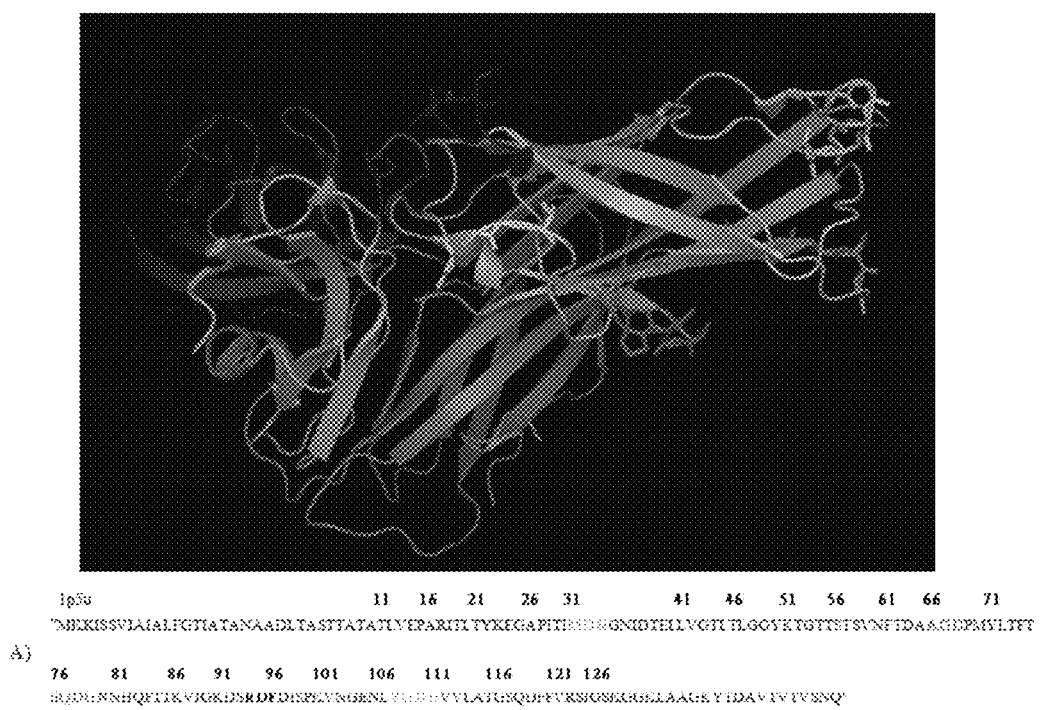
Figure 15:
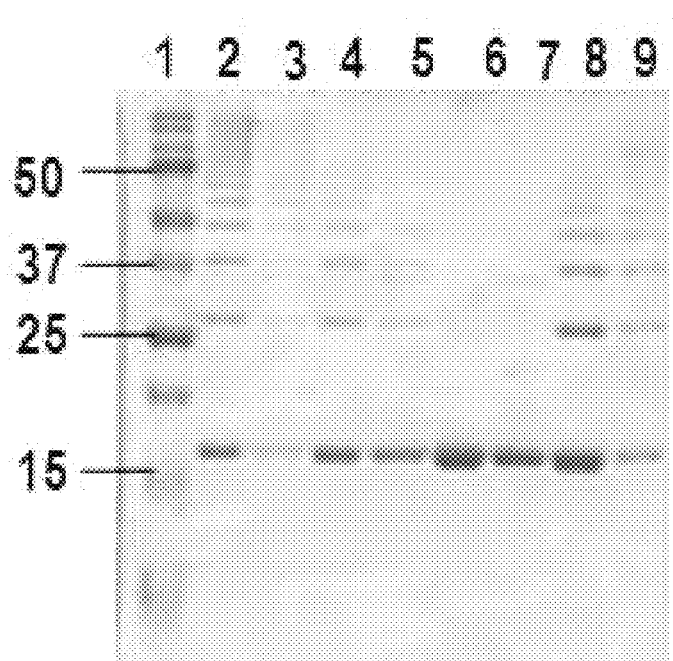

Subcloning experiments from pAH34L plasmid allowed the inventors to construct plasmid pGem-T Easy carrying the caf operon. Results provided by gene sequencing has shown that the amino acid sequence of the caf operon cloned into pGem-T Easy (FIG. 5) was identical to the previously reported sequence from *Yersinia pestis* strain 482 plasmid Pmt1 caf1 operon, complete sequence (GenBank: AY450847.1).

Sequencing results showed the complete and correct sequence for Caf1 and caf1R genes from the caf operon.

2.1.4. Restriction Digests of pGem-TF1

The restrictions analysis gel using EcoRI restriction enzyme, which has two restriction sites in the pGem-T EASY plasmid and is able to release the insert, has shown two bands: one band with 3 Kb which might correspond to the vector and the second band above 5 Kb which might correspond to the insert (FIG. 6).

Restrictions analysis using EcoRI which releases the insert has also confirmed that the insert cloned has the right size (expected size of 5.2 Kb).

2.1.5. SDS PAGE Gel and Western Blotting

Results from SDS page and western blotting using anti-F1 antibody (Avecia, UK) (FIG. 7) have shown the reported molecular mass of the F1 antigen which is 15.5 Kda (2), and in the western blot a band with an $M_r$ of 16,000, which is reacted with an F1 polyclonal antibody was identified in solution of *Escherichia coli*/Pah34L and also *Escherichia coli*/pGem-T Easy, both plasmids containing caf operon, grown for 19 h at 37° C. in L broth containing kanamycin (50 μg/Ml) and ampicillin (100 μg/Ml), respectively.

Expression of caf1 was shown by SDS PAGE and Western blotting using anti-F1 antibody.

2.1.6. Mass Spectrometry of Caf1 Protein

In order to confirm the identity of the band of 15.5 kDa on the 12% SDS-page gel, the band was sent to mass spectrometry. Results obtained confirmed that the band of 15.5 kDa is caf1 (FIG. 8).

2.2. Caf1 Protein Expression and Purification

The centrifugation of *E. Coli* BL21(DE3) (pGem-TF1) cultures resulted in the sedimentation of bacterial cells above which a layer of flocculated material was visible. In preliminary experiments, this flocculated material was shown to be mainly Caf1. Additional caf1 could be removed from the surface of the bacterial cells by gentle washing in PBS. The caf1 was purified by ammonium sulphate fractionation followed by FPLC Superdex 200 gel filtration chromatography, yielding approximately 10 mg of Caf1 per liter of culture.

2.2.1. Size Exclusion Chromatography Using Superdex 200 and Calibration Curve

FPLC Superdex 200 gel filtration chromatography column (maximum pressure: 3 Mpa; flow rate: 2 Ml/min; mobile phase: PBS buffer pH 7.6; volume of sample injected: up to 5 Ml) were used in this study to purify caf1. Caf1 eluted in the void volume ($V_0$) (50.5 ml) of the gel filtration column and total volume ($V_T$) was 18 ml. The standard protein markers for the gel filtration chromatography are presented in the table 2. The results are shown in FIG. 9.

TABLE 2

The standard protein markers for the gel filtration chromatography

| Protein | Molecular weight (MW) (kDa) | $Log_{10}$ MW | $V_e$ (Ml) | Distribution coefficient ($K_D$) $K_D = (V_e - V_0)/(V_T - V_0)$ |
|---|---|---|---|---|
| Carbonic Anhydrase | 29 | 1.46 | 105 | 0.872 |
| Albumin | 66 | 1.82 | 98 | 0.760 |
| Alchol Dehydrogenase | 150 | 2.18 | 94 | 0.696 |
| Beta Amylase | 200 | 2.30 | 92 | 0.664 |
| Apoferritin | 443 | 2.65 | 88 | 0.600 |
| Thryroglobulin | 669 | 2.82 | 82 | 0.504 |

2.2.2. Chromatogram and SDS PAGE Gel

Samples were injected in the Superdex 200 gel filtration column at 2 ml/min using PBS buffer pH 7.6 as mobile phase. Each fraction was collected in a Falcon tube. Chromatogram (FIG. 10*a*) shows protein elution and each fraction collected was loaded on 12% SDS-PAGE (FIG. 10*b*).

2.2.3. Determination of the Protein Concentration by UV Spectrophotometer

Purified protein was quantified using a spectrophotometer, as illustrated in FIG. 11.

2.3. Formation of Caf1 Oligomers

After protein purification, the inventors prepared caf1 oligomers. Caf1 samples were incubated at 95° C. for 45 seconds (FIG. 12).

2.4. Construction of Caf1-RGDS Mutants Using Site Directed Mutagenesis. Expression and Purification 2.4.1. CafM:Caf1 Complex and Caf1-RGDS Mutants Construction Using PyMOL and the access number (GenBank, accession number AY450847) RGDS peptides were inserted into the loops of the F1 fibre model structure (FIG. 13). The mutagenic primers were designed using OligoAnalyser 3.1 software.

2.4.2. Sequencing

After site directed mutagenesis, colonies of each successful transformation were sent for sequencing. Results obtained from gene sequencing of Caf1MDN31GRG; DS34GN are shown below (FIGS. 14A and 14B).

2.4.3. SDS PAGE Gel

Fractions of purified Caf1QDGN76RGDS mutant protein were loaded on 12% SDS-PAGE (FIG. 15).

2.5. Transmission Electron Microscopy

Images from pGem-TF1 and pGem-TF1 Caf1QDGN76RGDS were captured using a transmission electron microscope (FIG. 16).

3. Cell Biology

3.1. Measurement of Cell Adhesion on 96-Well Plates Coated with caf1 WT or RGDS Mutant Using Fluorimeter.

TABLE 3

Preliminary results using caf1 as a scaffold for cell culture presenting RGDS peptides has shown some effects on 3T3 Fibroblasts cells. Orla 1 is a control protein conisting of the transmembrane domain of *E coli* protein OmpA without cell attachment motifs inserted Cooke, M. J., Zahir, T., Phillips, S. R., Shah, D. S. H., Athey, D., Lakey, J. H., Shoichet, M. S. and Przyborski, S. A. (2010) 'Neural differentiation regulated by biomimetic surfaces presenting motifs of extracellular matrix proteins', Journal of Biomedical Materials Research Part A, 93A(3), pp. 824-832.

| | Caf1 WT | Caf1 RGDS | Orla 1 | Non coating | BSA |
|---|---|---|---|---|---|
| | 0.168 | 1.314 | 1.319 | 0.737 | 0.338 |
| | 0.296 | 1.013 | 1.523 | 0.489 | 1.653 |
| | 0.282 | 0.386 | 1.344 | 1.091 | 0.197 |
| | 0.169 | 0.361 | 0.383 | 0.471 | 1.006 |
| | 0.196 | 1.577 | 1.525 | 1.162 | 0.841 |
| | 0.205 | 0.365 | 1.448 | 1.02 | 0.734 |
| | 0.326 | 0.358 | 1.379 | 1.201 | 1.944 |
| | 0.216 | 0.811 | 1.667 | 1.028 | 1.534 |
| | 0.322 | 0.432 | 1.431 | 1.059 | 0.322 |
| | 0.488 | 1.449 | 0.94 | 1.306 | 0.322 |
| | 0.216 | 2.772 | 0.747 | 1.444 | 1.499 |
| | 0.416 | 3.174 | 0.397 | 1.293 | 1.395 |
| SUM | 3.3 | 14.012 | 14.103 | 12.301 | 11.785 |
| AVERAGE | 0.507692 | 2.155692 | 2.169692 | 1.892461538 | 1.813077 |

Figure 17:
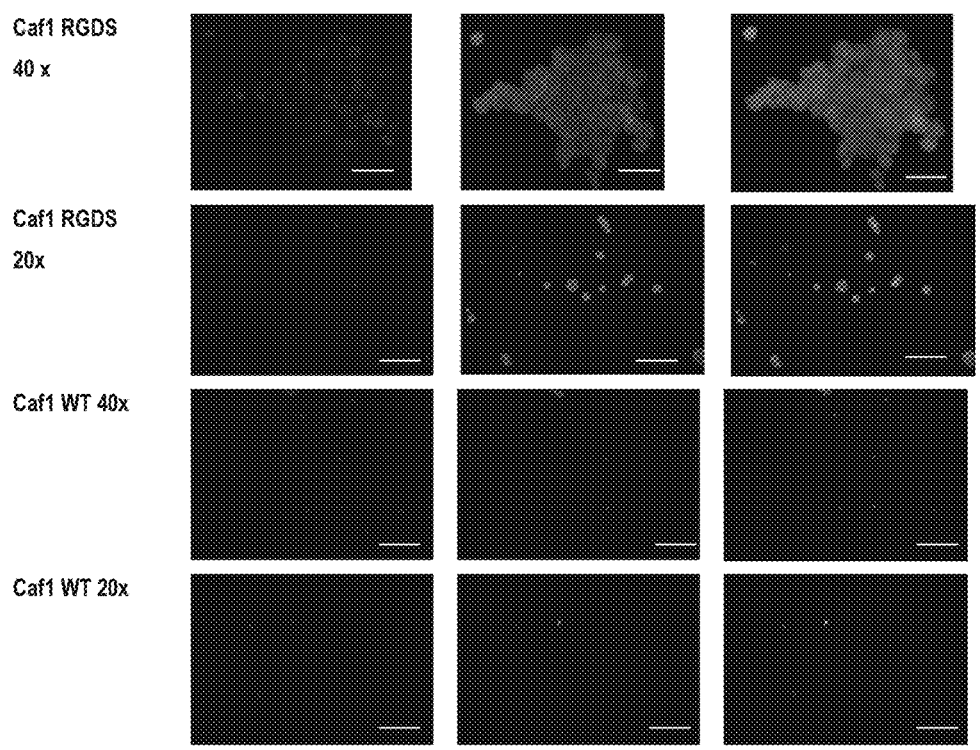

3.2 PC12 Cell Adhesion Assay on Glass Coverslips Coated with caf1 WT or RGDS Mutant by Fluorescence Microscopy FIG. 17 shows the results of a PC12 cell adhesion assay.

4. Formation of Mixed Caf1 Polymers from Different Types of Monomer

The following data demonstrates that by adding an additional plasmid expressing mutant Caf1 it is possible incorporate two different monomer types into the resultant caf1 polymer. Thus complex mixed polymers (i.e. heterogenous polymers) are possible.

4.1 Co-Expression of Caf1 WT Using Two Compatible Plasmids, the pAH34L and pBAD33

The design and synthesis of a second generation of scaffolds for cell culture is described, in which the same scaffold contains several different ECM motifs to enhance cell adhesion, (for example the PHSRN from fibronectin (and not only one cell adhesive motif as in Caf1-RGDS)) or to promote other biological processes such as differentiation with the inclusion of growth factors. Specific protease cleavable sites which can be recognised and cleaved by, for example, metalloproteinases secreted by the cells at specific time points of the cellular development including migration may also be incorporated.

Generation of a scaffold comprising a mixed polymer may have a number of advantages. Scaffolds will often only require a low density of active motifs, which can be diluted by inactive monomers. This can improve expression levels of the polymer if the motif bearing monomer is slow to assemble in the secretion pathway.

The inventors have demonstrated that it is possible to successfully secrete Caf1 mutants (e.g. with additional motifs or bioactive sequences) interspersed with the Caf1 wild type through the chaperone/usher system. The simultaneous expression of two different genes is designated co-expression and is generally achieved with two or more plasmids, each carrying the gene of one subunit (e.g. mutant caf1 or wildtype caf1) and a different selection marker. The plasmids should have different compatible replicons (19).

The two plasmids used in this study are pAH34L and pBAD33, however, any suitable plasmids may be used. The pAH34L plasmid (8) encodes the caf operon and the compatible pBAD33 plasmid encodes only the caf1 gene. The pAH34L caf1 gene expression is temperature-regulated which is maximally expressed at 37° C. Below this temperature the levels of caf1 gene expression decrease. The plasmid pBAD33 (20) is a low copy plasmid, coding for chloramphenicol resistance, containing the $P_{BAD}$ promoter of the araBAD (arabinose) operon and the gene encoding the positive and negative regulator of this promoter (araC).

The cloning of the caf1 gene into the pBAD33 plasmid was conducted by GeneArt. The inventors then introduced the ribosomal binding site—Shine-Dalgarno sequence (AGGAGG), 8 basepairs upstream of the start codon AUG. The plasmid pAH34L contains the ColE 1 origin of replication and the plasmid pBAD33 contains the pACYC184 origin of replication.

This system has several advantages; including (1) the modulation of caf1 gene expression and protein production by controlling either the temperature or the concentration of arabinose. The expression of caf1 encoded by pAH34L can be induced by performing the cell culture growth at 37° C. or above and repressed by decreasing the temperature to below 37° C. At 23° C. the expression levels of the caf1 gene are very low. The expression levels of caf1 encoded by pBAD33 can be modulated over a varied range of L-arabinose concentrations, usually from 0.002-2% and reduced to extremely low levels by the presence of glucose, which represses the gene expression. A further advantage of the system is that (2) it results in the production of hybrid Caf1 polymers (Caf1 mutants+Caf1 WT).

Two groups of three glass test tubes, each containing 5 mL of LB broth media supplemented with 20 μg/mL of chloramphenicol, 0.2% L-arabinose, 100 μg/mL of ampicillin and both 100 μg/mL of ampicillin and 20 μg/mL of chloramphenicol antibiotics were inoculated with a single colony of *E. coli* TOP10 transformed with either pBAD33_SD_Caf1, pAH34L or both pBAD33_SD_Caf1+pAH34L, respectively. 0.2% of glucose was added to one group of tubes whereas no glucose was added to the other group of tubes. All the glass test tubes were incubated at 37° C. in a rotation wheel at 180 rpm. When cultures reached the mid-log phase of growth (optical density of 0.5-0.6 at 600 nm), three different concentrations of L-arabinose were added to separate glass test tubes within each group: 0.02, 0.2 and 2%. After 16 h of incubation the bacterial cell culture was transferred to a 15 ml Falcon tube and these were centrifuged at 3000 rpm for 15 minutes at 4° C. Photographs of all Falcon tubes were taken. The sizes of the pellet and flocculent layer were immediately measured on the Falcon tube using a ruler (FIG. 60).

FIG. 60 shows some examples of the measurements of the flocculent layer and the cell pellet of the cultures in the study. Although the presence of a flocculent layer was observed in all tubes containing either *E. coli* TOP10/pAH34L or *E. coli* TOP10/pBAD33_SD_Caf1+pAH34L, in the tubes containing 0.2% of D-glucose the flocculent layer was thicker than in the tubes where no D-glucose was added.

In the tubes containing *E. coli* TOP10/pBAD33_SD_Caf1 only no flocculent layer was observed either in the presence or absence of D-glucose.

Equivalent experiments were carried out using different concentrations (0, 0.02, 0.2 and 2%) of L-arabinose in the presence or absence of D-glucose. Excess LB media, approximately 4 ml was carefully taken out of each Falcon tube using a pipette. The flocculent layer, with the remaining LB, was carefully separated from the cell pellet using the pipette. Samples of this layer were added to SDS-sample buffer and heated at 100° C. for 5 minutes and loaded onto 12% SDS-PAGE gels. One of the gels was stained with Coomassie Brilliant Blue and the other gel was used to perform a western blot. The blot was probed for Caf1 using an anti-Caf1 antibody followed by detection of bound antibody using goat anti-mouse IgA-horse-radish peroxidise conjugate. Bound antibody was detected using 4CN (4-chloro-1-naphthol) substrate.

Figure 61:
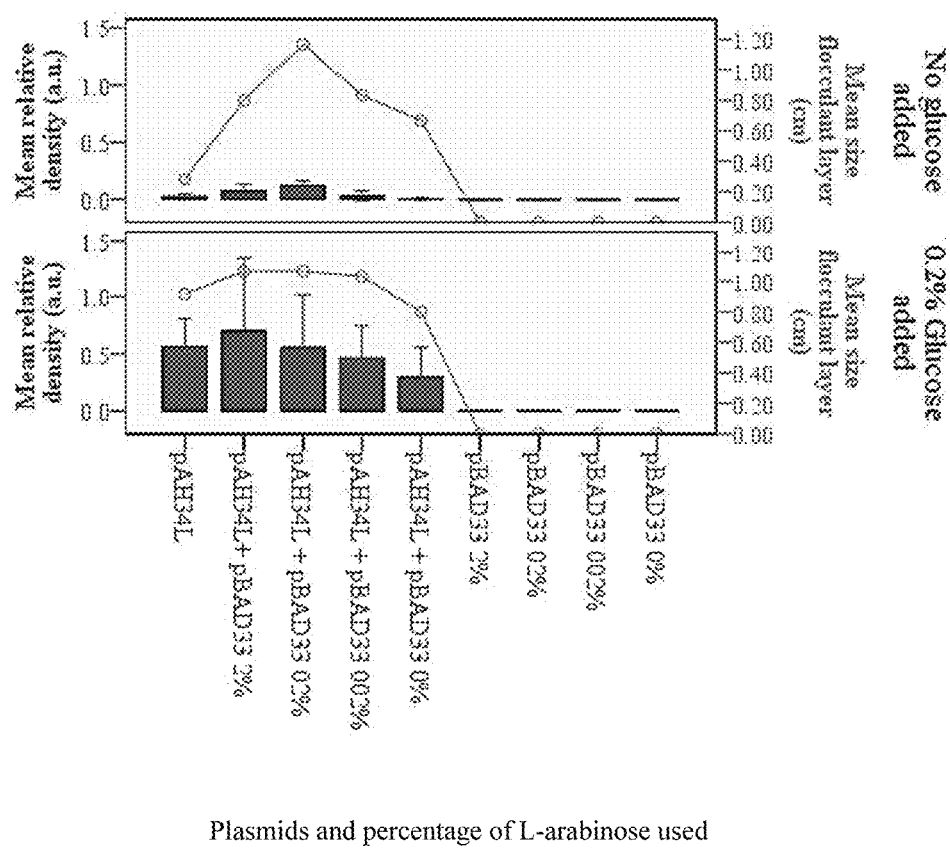

The western blot membrane was scanned and analysed by the ImageJ software to compare the density of the bands on the western blot. The mean of the relative density of the bands and the standard error of the mean were determined. The results obtained for the quantification of the Caf1 present in the flocculent layer and the size of the flocculent layer measured can be seen in FIG. 61. FIG. 61 shows the relation between the size of flocculent layer and the quantity of Caf1 protein present in the flocculent layer.

4.2. Expression of Heterologous Proteins Fused to the Caf1 Subunit in *Escherichia coli*

The caf1 gene in pBAD33 was mutated by the insertion of: (1) 6-Histidine near its N-terminus (Caf1-6HisNT); (2) PHSRN motif which is the RGD synergy sequence in fibronectin (Caf1-PHSRN) in the loop 1 of Caf1 (Caf1-PHSRN Loop1); (3) FLAG epitope (DYKDDDDK) (SEQ ID NO:61) in the N-terminus of Caf1 (caf1-FLAG epitope NT); (4) Cysteine in the NT-terminus of Caf1 (Caf1-Cys-NT); (5) Cysteine in the loop 4 of Caf1 (Caf1-G35C Loop4); Cysteine in the loop 2 of Caf1 (Caf1-Q106C Loop 2); (6) PENFF (SEQ ID NO:62) cleavage site for Metalloproteinase 13 (MMP13) in the N-terminus of Caf1 (Caf1-PENFF-NT); (7) 6-Histidine in the N-terminus of Caf1 followed by a spacer linking peptide (GGGGSGGGGS) (SEQ ID NO:63, Caf1-6His-NT spacer); (8) 6-Histidine in the C-terminus of Caf1 (Caf1-6His-CT); (9) PHSRN motif in the loop 3 of Caf1 (Caf1-PHSRN Loop3). These mutations in the caf1 gene were designed as variants of the caf1 gene. The variants were synthesised and cloned into pBAD33 vector by GeneArt (Invitrogen Life Technologies).

4.2.1. Co-Expression of Caf1 Mutants Using the Vector pBAD33 and pAH34L

The caf1 gene (528 bp in size; GenBank, accession number AY450847) mutants were synthesised by GeneArt (Table 4) and cloned into pBAD33 vector between KpnI and XbaI restriction sites; followed by two stop codons.

4.2.2 Small-Scale Caf1 Mutant Co-Expression

LB broth supplemented with 100 μg/ml of ampicillin or 20 μg/ml of chloramphenicol antibiotics and with both 100 μg/ml of ampicillin and 20 μg/ml of chloramphenicol antibiotics were used for culturing *E. coli* TOP10/pBAD33_SD_Caf1mutants, *E. coli* TOP10/pAH34L and *E. coli* TO P10/pBAD33_SD_Caf1mutants+pAH34L, respectively.

Two groups with three glass test tubes each containing 10 ml of LB broth media with the required antibiotics were incubated at 37° C. with 180 rpm shaking until their optical density had reached 0.5-0.6 at 600 nm. After measuring the optical density, 0.2% of L-arabinose was added in the respective tubes. The following day, the bacterial cell culture was transferred to a 15 ml Falcon tube in aseptic conditions. The cultures were centrifuged and prepared to be analysed by SDS-PAGE and western blot as described before. This experiment was performed in triplicate.

TABLE 4

The Caf1 amino acid sequences of genes synthesised in pBAD33

| Caf1 | Amino acid sequence |
| --- | --- |
| Caf1-6His NT (SEQ ID NO: 64) | MKKISSVIAIALFGTIATANAASSHHHHHHDLTASTTATATLVEP ARITLTYKEGAPITIMDNGNIDTELLVGTLTLGGYKTGTTSTSVN FTDAAGDPMYLTFTSQDGNNHQFTTKVIGKDSRDFDISPKVN GENLVGDDVVLATGSQDFFVRSIGSKGGKLAAGKYTDAVTVT VSNQ |
| Caf1-6His NT + Spacer linking peptide (SEQ ID NO: 65) | MKKISSVIAIALFGTIATANAASSHHHHHHGGGGSGGGGSDLT ASTTATATLVEPARITLTYKEGAPITIMDNGNIDTELLVGTLTLG GYKTGTTSTSVNFTDAAGDPMYLTFTSQDGNNHQFTTKVIGK DSRDFDISPKVNGENLVGDDVVLATGSQDFFVRSIGSKGGKL AAGKYTDAVTVTVSNQ |
| Caf1-PHSRN (DSRN) Loop1 (SEQ ID NO: 66) | MKKISSVIAIALFGTIATANAADLTASTTATATLVEPARITLTYKE GAPITIMDNGNIDTELLVGTLTLGGYKTGTTSTSVNFTDAAGDP MYLTFTSQDGNNHQFTTKVIGKPHSRNGGDISPKVNGENLVG DDVVLATGSQDFFVRSIGSKGGKLAAGKYTDAVTVTVSNQ |
| Caf1_PHSRN (NLVGD) Loop 3 (SEQ ID NO: 67) | MKKISSVIAIALFGTIATANAADLTASTTATATLVEPARITLTYKE GAPITIMDNGNIDTELLVGTLTLGGYKTGTTSTSVNFTDAAGDP MYLTFTSQDGNNHQFTTKVIGKDSRDFDISPKVNGEPHSRND VVLATGSQDFFVRSIGSKGGKLAAGKYTDAVTVTVSNQ |
| Caf1_FLAG epitope NT (SEQ ID NO: 68) | MKKISSVIAIALFGTIATANAADYKDDDDKDLTASTTATATLVEP ARITLTYKEGAPITIMDNGNIDTELLVGTLTLGGYKTGTTSTSVN FTDAAGDPMYLTFTSQDGNNHQFTTKVIGKDSRDFDISPKVN GENLVGDDVVLATGSQDFFVRSIGSKGGKLAAGKYTDAVTVT VSNQ |

TABLE 4-continued

The Caf1 amino acid sequences of genes synthesised in pBAD33

| Caf1 | Amino acid sequence |
|---|---|
| Caf1_Cys NT (SEQ ID NO: 69) | MKKISSVIAIALFGTIATANAA<u>C</u>DLTASTTATATLVEPARITLTYK EGAPITIMDNGNIDTELLVGTLTLGGYKTGTTSTSVNFTDAAGD PMYLTFTSQDGNNHQFTTKVIGKDSRDFDISPKVNGENLVGD DVVLATGSQDFFVRSIGSKGGKLAAGKYTDAVTVTVSNQ |
| Caf1_G35C Loop 4 (SEQ ID NO: 70) | MKKISSVIAIALFGTIATANAADLTASTTATATLVEPARITLTYKE GAPITIMDN<u>C</u>NIDTELLVGTLTLGGYKTGTTSTSVNFTDAAGDP MYLTFTSQDGNNHQFTTKVIGKDSRDFDISPKVNGENLVGDD VVLATGSQDFFVRSIGSKGGKLAAGKYTDAVTVTVSNQ |
| Caf1_Q106C Loop 2 (SEQ ID NO: 71) | MKKISSVIAIALFGTIATANAADLTASTTATATLVEPARITLTYKE GAPITIMDNGNIDTELLVGTLTLGGYKTGTTSTSVNFTDAAGDP MYLTFTS<u>C</u>DGNNHQFTTKVIGKDSRDFDISPKVNGENLVGDD VVLATGSQDFFVRSIGSKGGKLAAGKYTDAVTVTVSNQ |
| Caf1_PENFF-NT (SEQ ID NO: 72) | MKKISSVIAIALFGTIATANAA<u>PENFF</u>DLTASTTATATLVEPARIT LTYKEGAPITIMDNGNIDTELLVGTLTLGGYKTGTTSTSVNFTD AAGDPMYLTFTSQDGNNHQFTTKVIGKDSRDFDISPKVNGEN LVGDDVVLATGSQDFFVRSIGSKGGKLAAGKYTDAVTVTVSN Q |

Pl

TABLE 5-continued

Measurements of the flocculent layer thickness in *E. coli* TOP10 cells transformed with plasmid pBAD33_SD_caf1 mutants jointly with pAH34L encoding for Caf1 WT. The same measurements were performed in *E. coli* TOP10 transformed with plasmid pAH34L and with plasmid pBAD33_SD_caf1 mutants in separately. All data are reported as mean of three independent experiments ± standard error of the mean (S.E.M).

| Plasmids | Flocculent layer (cm) (Mean ± S.E.M) n = 3 | |
|---|---|---|
| | No L-arabinose | 0.2% L-arabinose |
| pBAD33_SD_caf1-G35C Loop 4 | — | — |
| pBAD33_SD_caf1-Q106C Loop2 | — | — |
| pBAD33_SD_caf1-PENFF-NT | — | — |
| pBAD33_SD_caf1-6His-NT spacer | — | — |
| pBAD33_SD_caf1-6His-CT + pAH34L | — | — |
| pBAD33_SD_caf1-PHSRN Loop 3 | — | — |
| pAH34L | 0.1 ± 0.003 | 0.1 ± 0.005 |

Figure 62:
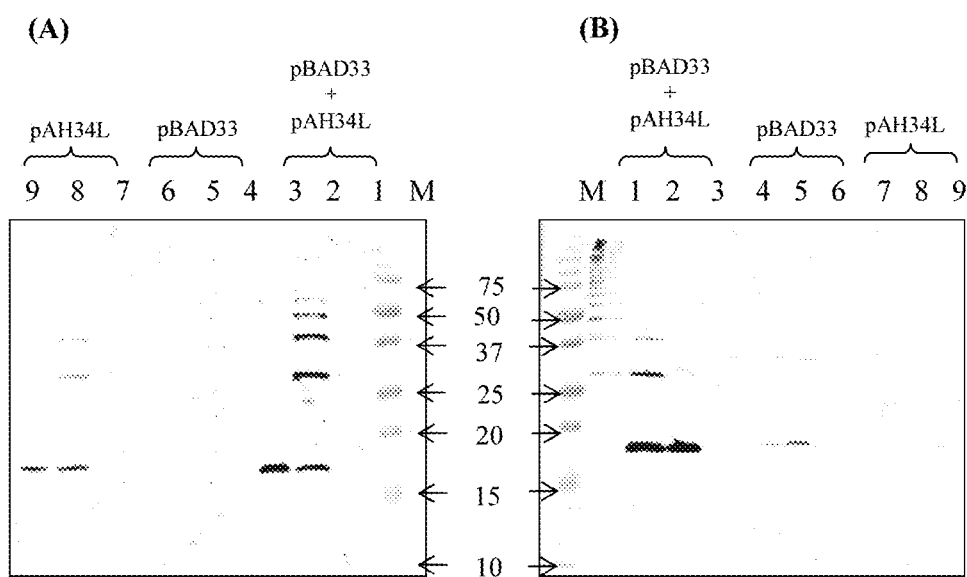

FIG. 62 shows that the pBAD33_SD_ caf1-FLAG epitope NT+pAH34L sample contains Caf1 protein detected by the anti-Caf1 antibody (FIG. 62-A) and it is in the polymeric form. Caf1 polymers were observed after heating the sample for 45 seconds at 100° C. (western blot A—lane 2). A different result was obtained for the pBAD33_SD_ caf1-FLAG epitope NT only sample in which no Caf1 was detected. In the pAH34L samples Caf1 in a polymeric form was detected (western blot A—lane 8). The western blot performed for the same samples but using the anti-FLAG epitope revealed the presence of Caf1-FLAG epitope NT in a polymeric form (western blot B—lane 2). The pAH34L samples which did not encode for Caf1-FLAG epitope NT did not stain with the anti-FLAG epitope antibody (western blot B—lanes 7-9). In the sample containing pBAD33_SD_ caf1-FLAG epitope NT some weak bands were detected corresponding to the FLAG epitope in the monomer form only (western blot B—lanes 5 and 6).

Figure 63:
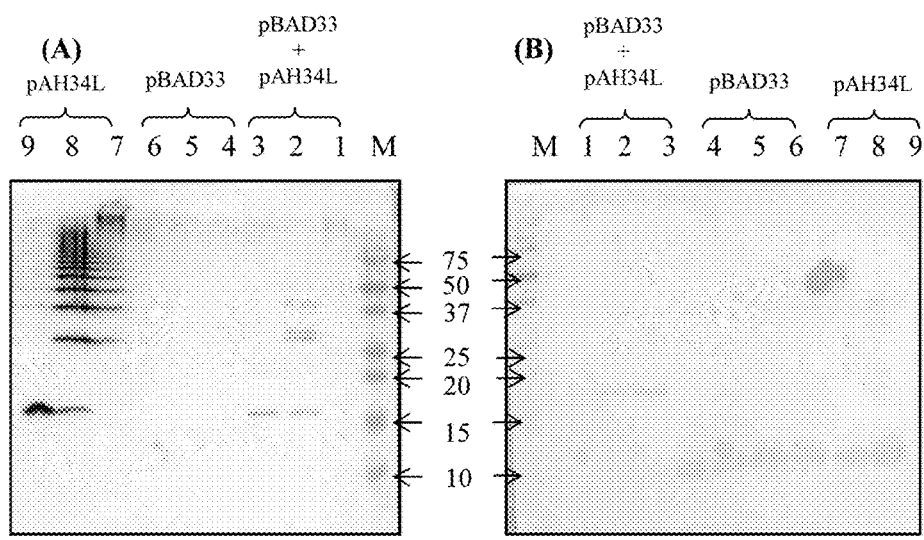

FIG. 63 shows that the pBAD33_SD_Caf1-6His-NT+ pAH34L sample contains Caf1 protein detected by the anti-Caf1 antibody (FIG. 63-A) and it is in the polymeric form. Caf1 polymers were observed after heating the sample for 45 seconds at 100° C. (western blot A—lane 2). No Caf1 was detected in the pBAD33_SD_Caf1-6His-NT sample. The pAH34L samples contained Caf1 in a polymeric form (western blot A—lane 8). The western blot performed for the same samples but using the anti-poly-histidine revealed the presence of a very small quantity of Caf1-6His-NT and in a monomeric form (western blot B—lane 1-3). The pAH34L did not encode for Caf1-6His-NT and no band was detected (western blot B—lanes 7-9). In the sample containing pBAD33_SD_caf1-6His-NT some non-specific bands were detected only (western blot B—lanes 4-6).

Figure 64:
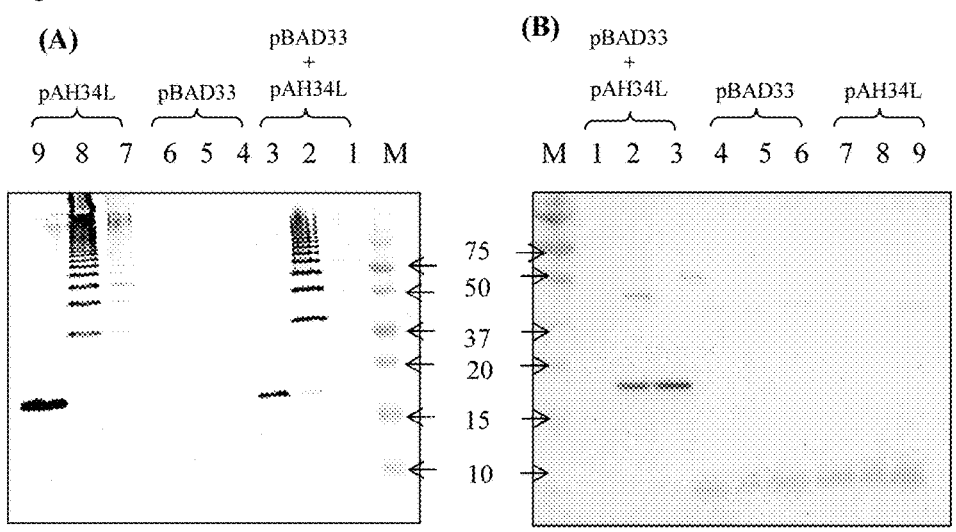

FIG. 64 shows that the pBAD33_SD_caf1-6His-NT spacer+pAH34L sample contains Caf1 protein detected by the anti-Caf1 antibody (FIG. 64-A) and it is in the polymeric form. Caf1 polymers were observed after heating the sample for 45 seconds at 100° C. (western blot A—lane 2). No Caf1 was detected in pBAD33_SD_ caf1-6His-NT spacer sample. In the pAH34L samples were detected Caf1 in a polymeric form (western blot A—lane 8). The western blot performed for the same samples but using anti-poly-histidine revealed the presence of Caf1-6His-NT spacer in a dimeric and monomeric form (western blot B—lane 1-3). The pAH34L did not encode for caf1-6His-NT spacer and thus no band was detected in the western blot B—lanes 7-9.

In the sample containing pBAD33_SD_ caf1-6His-NT spacer some non-specific bands were detected (western blot B—lanes 4-6).

Figure 65:
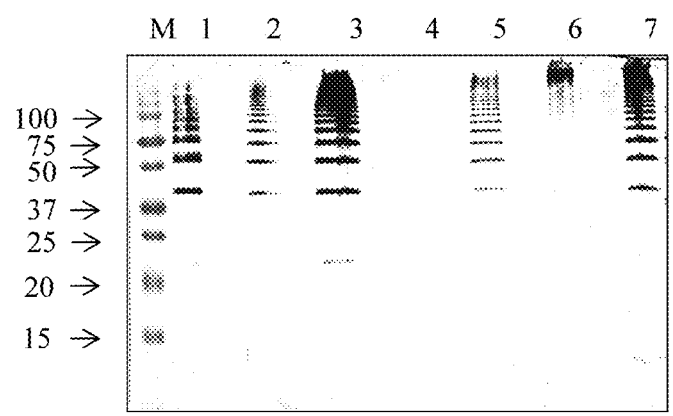
Figure 67:
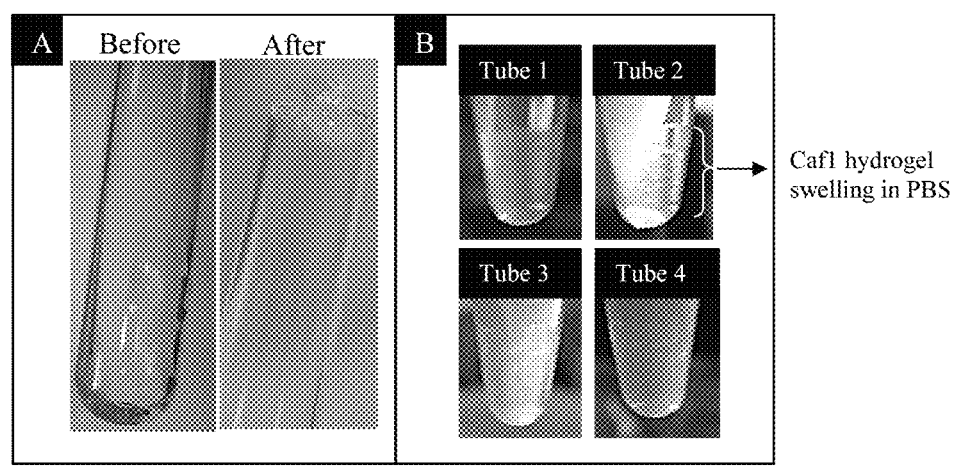
Figure 68:
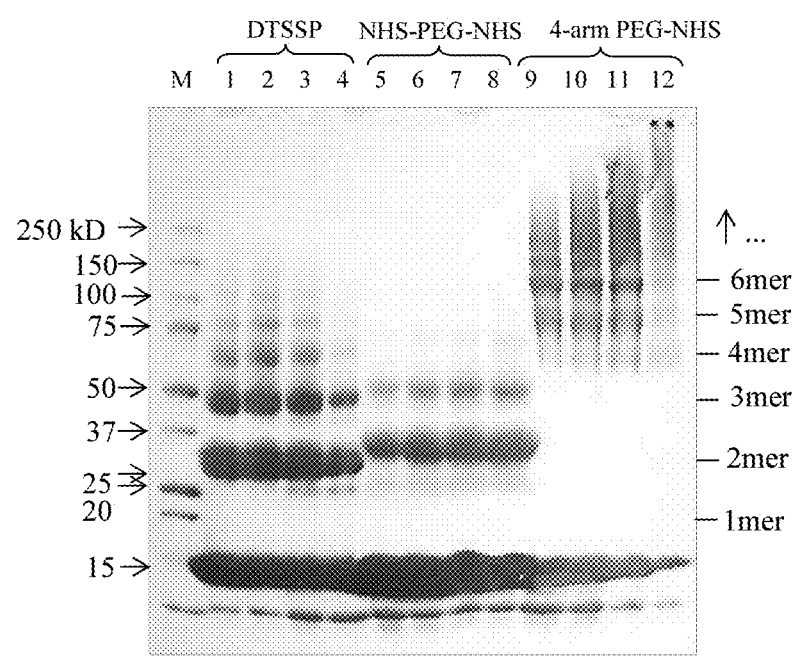

FIG. 65 shows that the pBAD33_SD_caf1-PHSRN Loop1+pAH34L, pBAD33_SD_caf1-Cys-NT+pAH34L, pBAD33_SD_caf1-G350 Loop 4+pAH34L, pBAD33_SD_caf1-PENFF-NT+pAH34L samples contains polymeric Caf1 protein detected by the anti-Caf1 antibody. The purified Caf1 in a polymeric form was detected by the monoclonal anti-Caf1 antibody. The pBAD33_SD_caf1-Q1060 Loop2+pAH34L sample was not detected by the monoclonal anti-Caf1 antibody and the pBAD33_SD_caf1-PHSRN Loop 3+pAH34L sample did not produce a ladder.

4.3 Discussion 4.3.1. Co-Expression of Caf1 WT was Mediated by the Two Compatible Plasmids, pAH34L and pBAD33

This study demonstrates a system for co-expression of copies of the caf1 gene using the plasmid pBAD33 which contains: (1) the pBR322-compatible p15A origin of replication from the pACYC184 vector and (2) resistance to chloramphenicol antibiotic, and the caf operon using the plasmid pAH34L which has a different origin of replication (ColE1) and antibiotic resistance (kanamycin) and thus cells can maintain both plasmids if grown on kanamycin/chloramphenicol L-agar plates. Based on the size of the flocculent layer, TOP10 *E. coli* cells transformed by two compatible plasmids and grown in media containing L-arabinose expressed higher levels of caf1 gene. This was confirmed by western blot using the monoclonal anti-Caf1 antibody.

In other studies Båga and co-workers (16) investigated the overproduction of PapA (the major pilin subunit) by electron microscopy and immunoblot analysis of PapA antigen. For that, they constructed a plasmid pPAP267, which overproduces just the PapA pilin subunit and it was introduced into HB101 cells harbouring the pPAP5, which contain the wild-type pap operon (composed of 11 genes responsible for the expression of papA pilin) and found that the expression of PapA was 10-fold higher in comparison with pPap5 alone and also the pili were longer than the wild-type. This showed the possibility of co expression but the polymers produced were homogenous and there was no direct evidence that the pPAP5 products were in the polymer.

In this study, it was possible to modulate the Caf1 expression over a range of L-arabinose concentrations, from 0.02 to 2%. The levels of caf1 expression increased with the increase of L-arabinose concentration (FIG. 61). In the absence of L-arabinose very low levels of caf1 expression were achieved. The TOP10 strain (ara⁻) can transport L-arabinose but does not metabolise it, which is important for expression studies since the level of L-arabinose is constant inside the cell and does not decrease over time.

However, an efficient repression of caf1 expression was not achieved in the presence of 0.2% D-glucose. In fact, cells grow better and expressed more protein in some cases with glucose.

4.3.2 Caf1-Flag and Caf1-6his-NT+Spacer were Co-Inserted into Polymers with Caf1 WT The inventors have developed an approach to co-express Caf1 mutants with Caf1 WT (caf wildtype) using the expression system mentioned above. Analysis of co-expression of Caf1 mutants was performed by western blot using antibodies against the proteins in the study.

Caf1-FLAG co-expressed with Caf1 WT proteins, resulting in the generation of mixed polymers. To the inventors knowledge this is the first demonstration of mixed polymers of this type. Zavialov et al. (21) have presented an approach for heterologous expression of recombinant proteins in *E. coli*. For that, they created genes encoding chimeric proteins in which for example, the human Interleukine-1β was introduced between the Caf1 signal peptide and the mature Caf1 subunit leaving the C-terminus of the Caf1 subunit available to interact with the chaperone, Caf1M. This system did not however produce polymers.

In this study the Caf1-FLAG and Caf1-6His-NT spacer were detected in Caf1 polymers secreted on the surface of *E. coli* (see western blot for FLAG epitope using the monoclonal anti-FLAG epitope antibody, FIG. 62) mediated by the chaperone-usher system. The western blot performed did not reveal the presence of Caf1-6His-NT without a spacer in the polymer. Successful polymer formation was observed when Caf1 WT was expressed with the other Caf1 mutants: Caf1-PHSRN, Caf1-Cys (except Q106C) and Caf1-PENFF.

5. Cross-Linking Caf1 Hydrogels

Caf1 WT was covalently cross-linked with three cross-linkers containing different spacer arm length (i.e. the distances between conjugated molecules) and different numbers of the same functional group, N-hydroxysuccinimide (NHS) at the end.

The NHS-ester reacts with primary amines to form covalent amide bonds. The reaction is usually performed in phosphate buffer at pH 7.2-8.0 for 0.5 h at room temperature. Primary amine buffers such as Tris-buffered saline are not compatible because they compete for reaction; however, in some procedures, it is useful to add Tris or glycine buffer at the end of a conjugation procedure to quench (stop) the reaction. The reaction releases N-hydroxysuccinimide (M.W. 115), which can be removed easily by dialysis or desalting.

In this study, the inventors analysed Caf1WT hydrogels by the traditional scanning electron microscopy SEM, after gelation, after gelation followed by freeze drying, and also by Environmental scanning electron microscopy (ESEM). The ESEM methodology is a variant of SEM which works in a low vacuum and has the ability to keep the sample in a hydrated state due to the control of the water vapour pressure within the chamber by maintaining the sample temperature constant using the Peltier stage. Moreover, the sample can be prepared without coating with carbon or gold unlike high-vacuum SEM applications that require the coating of the sample to avoid charge build-up.

5.1 Experimental Results

5.1.1 Cross-Linking of CAF1 WT with Different Spacer Arm Lengths

Caf1 protein at a final concentration of 30 mg/ml was cross-linked with DTSSP (Pierce), NHS-PEG-NHS (Creative PAGWorks) and 4-arm NHS-PEG (Creative PEGWorks) solutions at final concentrations of 3, 6, 9 and 15 mg/ml which correspond to ratio of cross-linking (w/w, cross-linkers:Caf1) of 1:10, 1:5, 1:3, 1:2, respectively. The methods used for crosslinking were in accordance with the manufacturer's instructions. The Caf1 hydrogels at these ratios were characterised regarding their gelation time, swelling, degree of cross-linking analysed by SDS-PAGE gel, Transmission Electron microscopy (TEM), biocompatibility of the Caf1 hydrogels with mammalian cells performing viability/cytotoxicity assay and morphology studied by Scanning Electron microscopy (SEM).

5.1.2 Gelation Time

The gelation rate of the Caf1 hydrogels was monitored under sealed conditions at room temperature for 30 minutes, stirring every minute. Table 6 shows that increasing the concentration of DTSSP cross-linker did not change the gelation time. After 30 minutes the reaction did not lose its fluidity, e.g. when the tubes were slightly inverted the solution in the tube slid along the walls of the glass test tubes and did not result in a gel, thus the gelation time was not determined ("N.D"). However, increasing the concentration of NHS-PEG-NHS (also called "2-arm-PEG-NHS" herein) decreased slightly the gelation time. A more visible decrease in the gelation time was observed by the addition of 4-arm PEG-NHS. The gelation rate of the 4-arm PEG-NHS was quicker than the 2-arm PEG-NHS. For example the quickest gelation time for 4-arm-PEG-NHS and NHS-PEG-NHS was 2 seconds and 24 min, respectively. Nevertheless, based only in these simple observations we noticed that all Caf1 hydrogels cross-linked with the different cross-linkers resulted in a sample viscosity comparable with the viscosity of the corresponding solution of the Caf1.

5.1.3 Swelling

The swelling of Caf1 hydrogels cross-linked with DTSSP, NHS-PEG-NHS and 4-arm PEG-NHS at different concentrations were determined based on analysis of changes in diameter (differences between the initial diameter before swelling and final diameter after swelling by the addition of PBS) which increased with the decrease of cross-linker concentration. This trend was more pronounced for the Caf1 hydrogel cross-linked with DTSSP (w/w ratio of cross-linking of 1:10).

TABLE 6

Analysis of the gelation time of Caf1 cross-linked with DTSSP, NHS-PEG-NHS and 4-arm PEG-NHS hydrogels at room temperature (≤30 min) and the percentage of change between the initial diameter of the hydrogels drops on the plastic surface and their final diameter after addition of PBS and incubation at 37° C. All data are reported as mean percentage of three independent experiments ± standard error of the mean (S.E.M).

| Protein | Cross-linker | Ratio (crosslinker:protein) (w/w) | Gelation time(min) | Swelling % Mean ± S.E.M |
|---|---|---|---|---|
| Caf1 | DTSSP | 1:10 | N.D | 61.2 ± 0.17 |
| | | 1:5 | N.D | 58.1 ± 0.12 |
| | | 1:3 | N.D | 54.3 ± 0.11 |
| | | 1:2 | N.D | 44.4 ± 0.11 |
| | NHS-PEG-NHS | 1:10 | N.D | 40.3 ± 0.17 |
| | | 1:5 | 27 ± 0.58 | 40.2 ± 0.42 |
| | | 1:3 | 26 ± 0.33 | 35.2 ± 0.33 |
| | | 1:2 | 24 ± 0.33 | 32.9 ± 0.49 |
| | 4-arm PEG-NHS | 1:10 | 22 ± 0.33 | 24.2 ± 0.60 |
| | | 1:5 | 5 ± 0.17 | 24.7 ± 0.33 |
| | | 1:3 | 4 ± 0.33 | 14.2 ± 0.05 |
| | | 1:2 | 2 ± 0.17 | 14.2 ± 0.03 |

FIG. 67 shows transparent Caf1 hydrogels cross-linked with 4-arm PEG-NHS after 2 min (FIG. 67-A) and the swelling properties of the Caf1 hydrogels depending on the ratio of cross-linking, higher for the 1:10 and 1:5 than for 1:3 and 1:2 (FIG. 67-B).

5.1.4 Degree of Cross-Linking

Caf1 polymers were treated with three different cross-linkers each presenting a NHS reactive group on each end of the cross-linker. The NHS group reacts with primary amine groups of lysines at pH 7-8.5 to form stable amide bonds. The reactions were terminated after 30 min. After cross-linking, the samples were incubated in SDS sample buffer at 100° C. for 5 min and the loaded onto a 4-20% gradient polyacrylamide gel for electrophoresis. FIG. 68 shows the denatured Caf1 protein samples and revealed the degree of cross-linking. At the bottom of the gel bands of approximately 15 kDa were observed, corresponding to non-cross-linked monomers. In the case of Caf1 cross-linked with DTSSP, the dimer bands are resolved between 25 and 37 kDa protein standard markers (lanes 1-4). In the case of Caf1 cross-linked with NHS-PEG-NHS the dimer bands ran approximately with the 37 kDa protein standard markers (lanes 5-8). The Caf1 cross-linking with 4-arm PEG-NHS presents a second band which is resolved between 50 and 75 kDa protein standard markers (lanes 9 to 12). The remaining high molecular weight bands cannot be defined only by SDS-PAGE gel analysis. Increasing the ratio of cross-linking using different cross-linkers decreased the Caf1 monomeric fraction.

Table 7 shows the values of relative density obtained by densitometry using the image J software. Analysis of the cross-linked fraction and non-cross-linked fraction were performed. The theoretic values for the cross-linked fractions were determined by subtracting the amount of Caf1 protein sample (in the absence of cross-linkers) to the Caf1 protein sample (in the presence of one of the cross-linkers) non-cross-linked fraction. Increasing the concentration of the cross-linkers increased the Caf1 cross-linked fraction, according to the theoretical values and decreased the Caf1 non-cross-linked fraction. The exception was for the Caf1 cross-linking with 4-arm PEG-NHS sample at a mass ratio of 1:2 which showed a decrease in the non-cross-linked and in the cross-linked fraction. The theoretical value was higher than that obtained for the cross-linked fraction.

TABLE 7

Relative densitometry for Caf1 non-cross-linked and cross-linked fractions was determined by ImageJ software. All data are reported as mean of three independent experiments ± standard error of the mean (S.E.M).

| Cross-linker | Caf1:Cross-linker (w/w) | Non-cross-linked fraction (Mean ± S.E.M) | Cross-linked fraction (Mean ± S.E.M) | * Theoretical values for the cross-linked fraction |
|---|---|---|---|---|
| DTSSP | 1:10 | 0.34 ± 0.016 | 0.55 ± 0.033 | 0.66 |
|  | 1:5 | 0.33 ± 0.0015 | 0.58 ± 0.08 | 0.67 |
|  | 1:3 | 0.30 ± 0.010 | 0.63 ± 0.05 | 0.70 |
|  | 1:2 | 0.28 ± 0.0018 | 0.82 ± 0.06 | 0.72 |
| NHS-PEG-NHS | 1:10 | 0.87 ± 0.0095 | 0.11 ± 0.015 | 0.13 |
|  | 1:5 | 0.86 ± 0.068 | 0.17 ± 0.026 | 0.14 |
|  | 1:3 | 0.72 ± 0.0039 | 0.20 ± 0.07 | 0.28 |
|  | 1:2 | 0.61 ± 0.0008 | 0.30 ± 0.04 | 0.39 |
| 4-armNHS-PEG | 1:10 | 0.71 ± 0.013 | 0.33 ± 0.022 | 0.30 |
|  | 1:5 | 0.33 ± 0.014 | 0.57 ± 0.04 | 0.67 |
|  | 1:3 | 0.21 ± 0.014 | 0.62 ± 0.023 | 0.79 |
|  | 1:2 | 0.16 ± 0.0036 | 0.28 ± 0.02 | 0.84 |

* $Caf1_{cross-linked\ fraction} = Caf1_{free-molecules} - Caf1 \times Cross-linker\ X_{remained\ non-cross-linked\ fraction}$ FIG. 69 shows examples of TEM images of Caf1 cross-linking using the short-spacer DTSSP (12.0 Å), the long-spacer NHS-PEG-NHS (~197 Å) and the long-spacer with 4-arm PEG-NHS (~394 Å) at the same molecular ratio 1:10 (Caf1:cross-linker). The Caf1 hydrogels were prepared as described before, after gelation and swelling in PBS pH 7.4, the Caf1 hydrogels were diluted in nanopure water. The size of hydrogels formed was determined by Jmicrovision version 1.2.5 (Roduit, 2007). Lines along the perimeter of the hydrogel meshes (pieces of hydrogel) were drawn. Graphs were constructed using the SPSS version 19.

TEM images show small pieces of Caf1 hydrogels cross-linked with DTSSP with average sizes of 76 nm and a uniform size distribution ranging from 10 to 300 nm. Caf1 hydrogels cross-linked with NHS-PEG-NHS presented an average size of 393 nm and a more disperse size distribution with mesh sizes ranging from 10 to 600 nm. The Caf1 hydrogels cross-linked with 4-arm PEG-NHS showed an average size of 254 nm and extreme size distribution from around 20 nm to 1500 nm.

6 Viability and Cytotoxicity Assay

The viability/cytotoxicity assay (Promega) is used to assess cell viability and cytotoxicity of the materials used. The first part of the assay simultaneously measures two protease activities; one is a marker of cell viability, and the other is a marker of cytotoxicity. The live-cell protease activity is restricted to intact viable cells and is measured using a fluorogenic, cell-permeant, peptide substrate (glycylphenyl-alanyl-aminofluorocoumarin; GF-AFC). The substrate enters intact cells and is cleaved by the live-cell protease activity to generate a fluorescent signal proportional to the number of living cells. This live-cell protease becomes inactive upon loss of cell membrane integrity and leakage into the surrounding culture medium. A second, fluorogenic cell-impermeant peptide substrate (bis-alanylalanyl-phenyl-alanyl-rhodamine 110; bis-AAF-R110) is used to measure dead-cell protease activity, which is released from cells that have lost membrane integrity. Because bis-AAF-R110 is not cell-permeant, essentially no signal from this substrate is generated by intact, viable cells.

Rat primary osteoblasts were cultured using standard culturing techniques on the surface of Caf1 hydrogels (made in accordance with the invention). After 24 h, viability and membrane integrity were determined by the viability/cytotoxicity assay (Promega), in which intact viable cells protease activity is measured using a fluorogenic, cell-permeant, peptide substrate (glycylphenylalanyl-aminofluorocoumarin; GF-AFC) and dead-cell protease activity is measured by the cell-impermeant peptide substrate (bis-alanylalanyl-phenylalanyl-rhodamine 110; bis-AAF-R110). Table 8 shows the percentage of viability and cytotoxicity for rat primary osteoblasts attached on Caf1 hydrogels. Cells tolerated 2D culture on the Caf1 hydrogels shown by 70-80% viability and low percentages for cytoxicity.

TABLE 8

Percentage of cell viability and cytotoxicity when attached on Caf1 hydrogels cross-linked with different cross-linkers at various ratios.

| Hydrogels | Ratio (crosslinker:protein) | Cell viability (%) | Cell cytotoxicity (%) |
|---|---|---|---|
| Caf1: DTSSP | 1:10 | 80% | 20% |
|  | 1:5 | 76% | 24% |
|  | 1:3 | 78% | 22% |
|  | 1:2 | 80% | 20% |
| Caf1: NHS-PEG-NHS | 1:10 | 77% | 23% |
|  | 1:5 | 77% | 23% |
|  | 1:3 | 76% | 24% |
|  | 1:2 | 73% | 27% |
| Caf1: 4-arm PEG-NHS | 1:10 | 71% | 29% |
|  | 1:5 | 77% | 23% |
|  | 1:3 | 75% | 25% |
|  | 1:2 | 74% | 26% |
| Only Caf1 | — | 61% | 39% |
| DME Medium | — | 84% | 16% |
| 15% ethanol | — | 7% | 93% |

7. Hydrogels Comprising Caf1 Polymers Crosslinked with 4-Arm PEG-NHS

Figure 70:
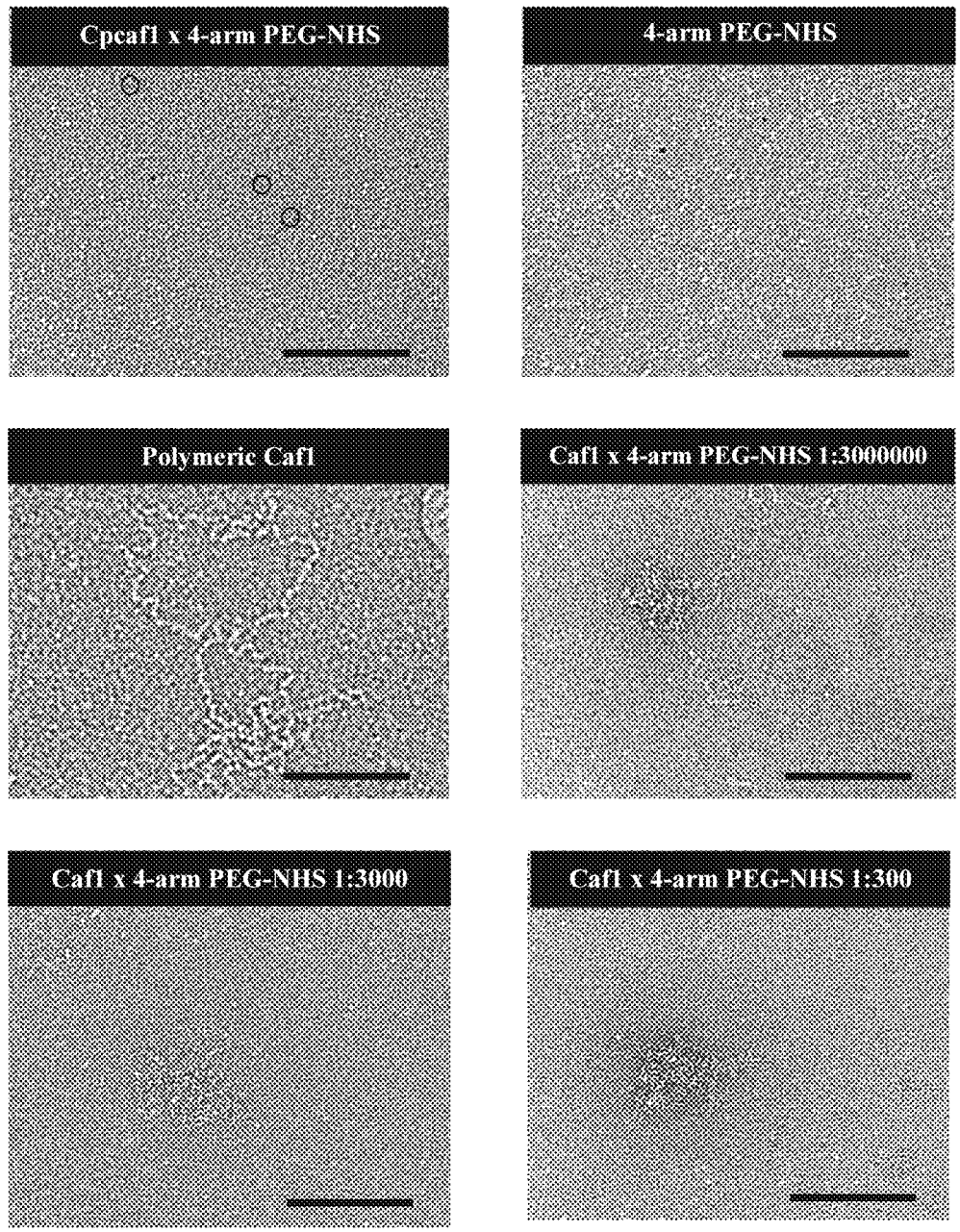

The ability of Caf1 polymers cross-linked with 4-arm PEG-NHS to form a hydrogel was explored. FIG. 70 shows TEM images of both the monomeric circularly permuted variation of Caf1 (cpCaf1) (22) and Caf1 polymers cross-linked with 4-arm PEG-NHS, only 4-arm PEG-NHS and Caf1 alone.

The TEM images (FIG. 70) revealed that monomeric circularly permuted variation of Caf1 (cpCaf1) (22) cross-linked with 4-arm PEG-NHS did not form visible gel-like structures. Only very small structures indicated by the circles were observed. In addition, both the 4-arm PEG-NHS and Caf1 alone did not form large hydrogel networks. Some examples of these hydrogels networks begin to be visible using Caf1 polymers cross-linked with 4-arm PEG-NHS at various ratios of cross-linking (w/w).

The Caf1 polymer cross-linked with 4-arm PEG-NHS at various ratios of cross-linking (Caf1:cross-linker, w/w) samples at 1:3000000, 1:300000, 1:30000, 1:3000, 1:300, 1:60 and 1:30 after gelation as mentioned before were heated at 100° C. for 5 min in SDS-sample buffer and loaded onto a SDS-PAGE. The gel was scanned and analysed as described above by ImageJ version 1.46. The values corresponding to Caf1 cross-linked fraction either determined by ImageJ the Caf1 non-cross-linked fraction are presented in Table 9. The Caf1 cross-linked fraction increased with the increase of cross-linker concentration.

TABLE 9

Relative densitometry for Caf1 non-cross-linked and cross-linked fractions was determined by ImageJ software. All data are reported as mean of three independent experiments ± standard error of the mean (S.E.M).

| Caf1:4-arm PEG-NHS | Non-cross-linked fraction (Mean ± S.E.M) | Cross-linked fraction (Mean ± S.E.M) | *Theoretical values for cross-linked fraction |
|---|---|---|---|
| 1:3000000 | 0.99 ± 0.0034 | 0.006 ± 0.0014 | 0.01 |
| 1:300000 | 0.99 ± 0.0024 | 0.0079 ± 0.0015 | 0.01 |
| 1:30000 | 0.98 ± 0.0023 | 0.043 ± 0.033 | 0.02 |
| 1:3000 | 0.97 ± 0.0022 | 0.051 ± 0.028 | 0.03 |
| 1:300 | 0.89 ± 0.0017 | 0.14 ± 0.066 | 0.11 |
| 1:60 | 0.85 ± 0.0016 | 0.18 ± 0.05 | 0.15 |
| 1:30 | 0.73 ± 0.0026 | 0.22 ± 0.07 | 0.27 |

Figure 71:
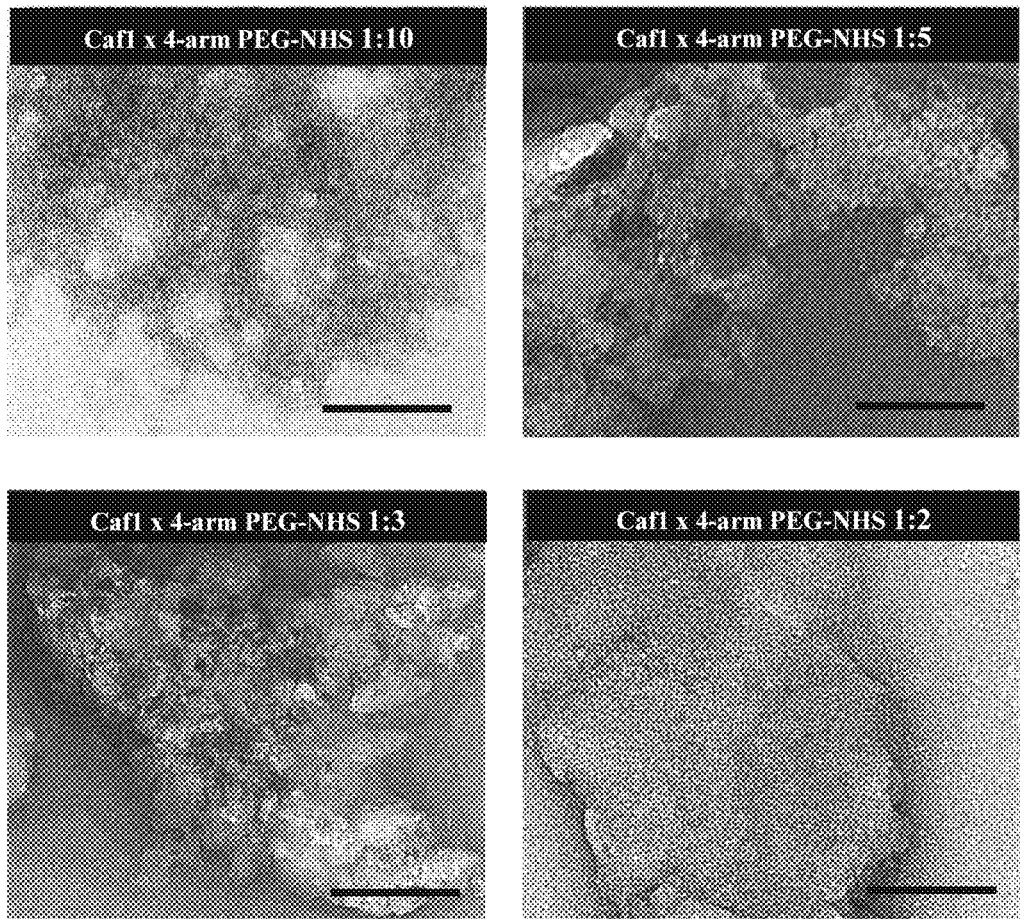

*$Caf1_{cross-linked\,fraction} = Caf1_{free-molecules} - Caf1 \times Cross-linker\,X_{remained\,non-cross-linked\,fraction}$ The TEM images (FIG. 71) revealed that Caf1 polymers cross-linked with 4-arm PEG-NHS at 1:10 (w/w, Caf1: cross-linker) form a more dense hydrogel structure than in FIG. 70 however the hydrogels formed have a wide distribution of pores with dimensions much smaller than 100 nm. The hydrogel structure becomes more compact with the increase of cross-linker. At a ratio of 1:2, the hydrogel presents as an amorphous structure with no visible pores.

7.1 Morphology of Caf1 Hydrogel by Scanning Electron Microscopy (SEM)

Figure 72:
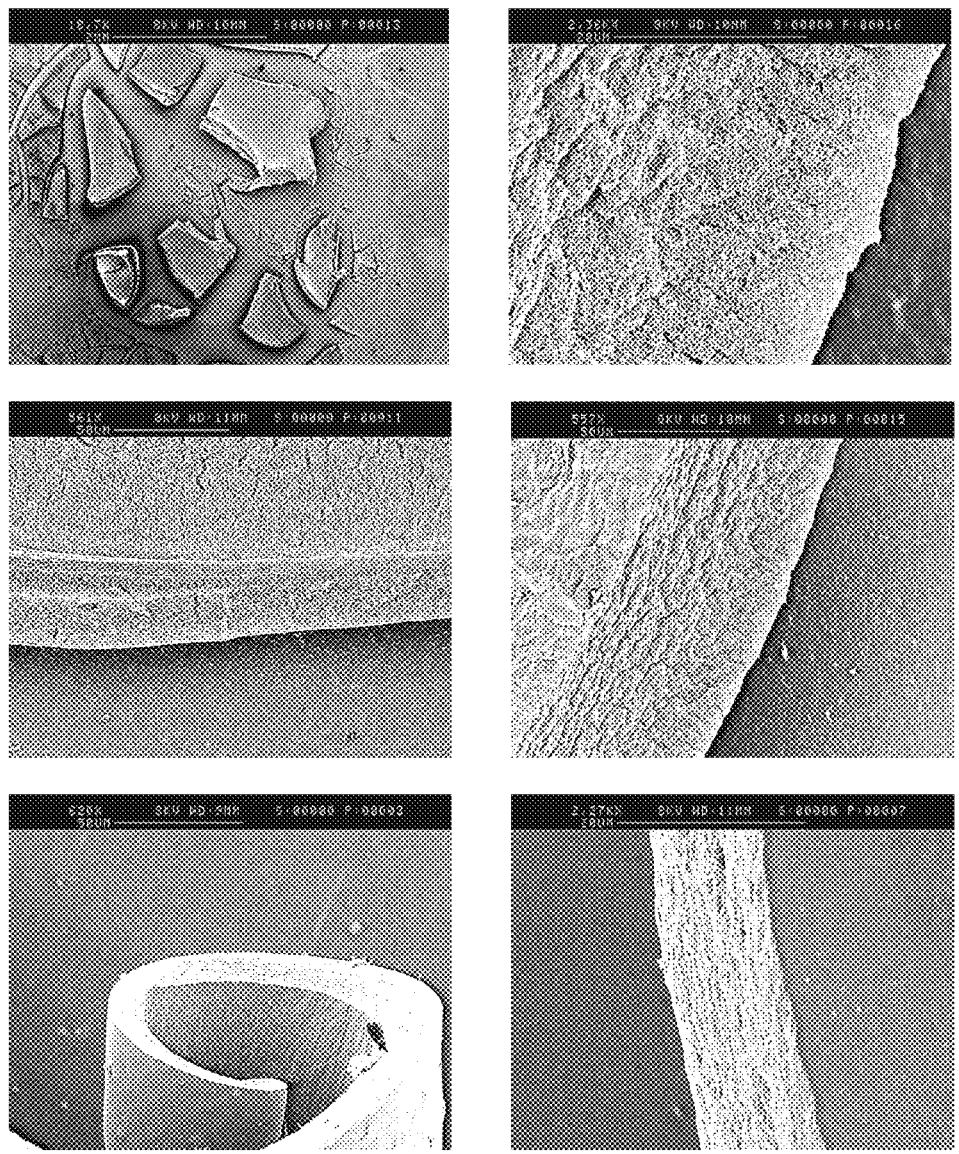

FIG. 72 shows Caf1 hydrogel cross-linked with 4-arm PEG-NHS at a ratio of 1:3 with a very compact structure and thus the diameter of the pores was not determined. However, they seem to be in the order of nanometers. The first SEM image shows the Caf1 hydrogel broken into several pieces. The next SEM images reveal the interior of these Caf1 hydrogel pieces.

Figure 73:
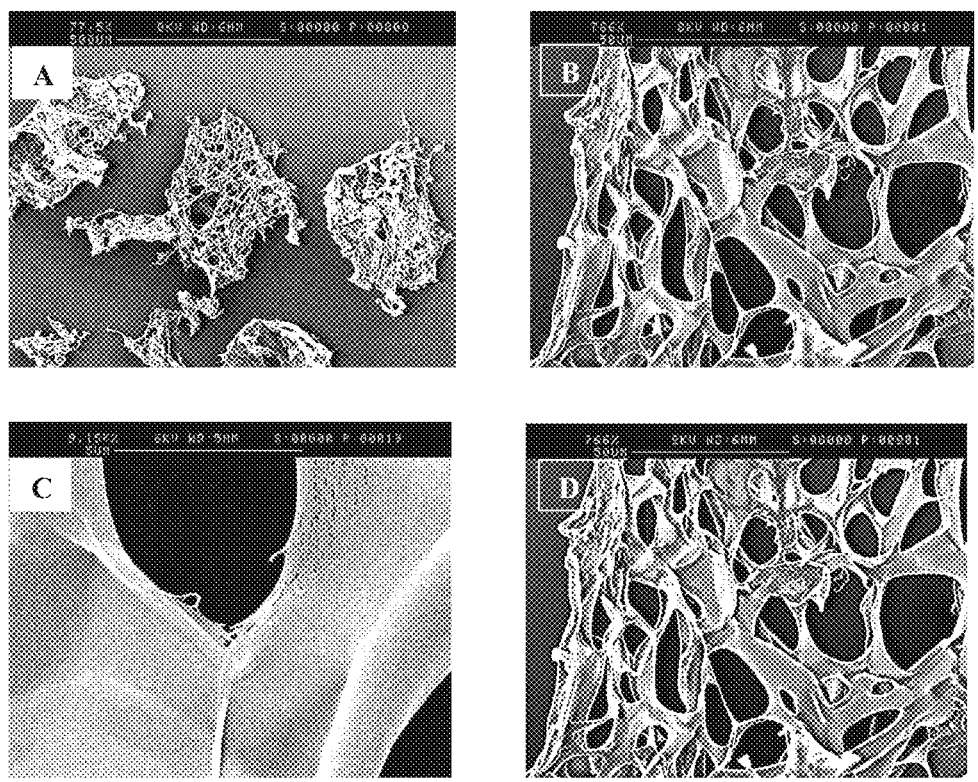

FIG. 73 shows Caf1 freeze-dried hydrogels which display a mesh-like architecture presenting a pore diameter ranging from 3 µm to 22 µm with an mean pore diameter of 8±0.003 µm.

Unprocessed hydrated Caf1 hydrogels were visualised by ESEM. In ESEM, the hydrogels are exposed to a saturated water vapour environment with minimal drying which allows the study of the pore structure of the hydrogels in the natural hydrated state. The hydrated Caf1 hydrogel exhibited nanopores ranging from 100 nm to 600 nm. The mean size of the pores was approximately 300±0.005 nm but the size distribution observed seems relatively wide. The void spaces of Caf1 protein hydrogel are larger than dehydrated Caf1 hydrogel (FIG. 72).

8 Morphology of Mammalian Cells on the Caf1 Hydrogel by SEM

Figure 75:
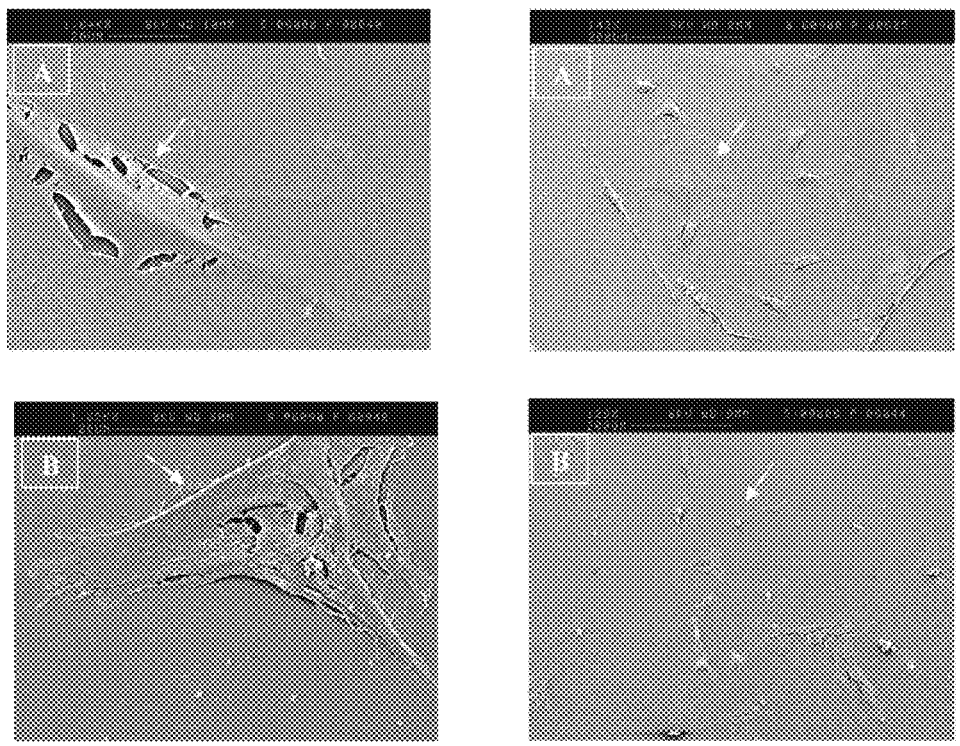

Mouse 3T3 fibroblasts and rat primary osteoblasts were cultured using standard culture conditions on the surface of Caf1 WT hydrogels made in accordance with the invention. After 24 h, cells were fixed in 2% of glutaraldehyde, dehydrated and gold coating to be visualised by traditional SEM. In 2D cultures, more fibroblasts presented elongated morphology than osteoblasts. (FIG. 75). The majority of the osteoblasts displayed a rounded morphology and only a few cells show a visible spreading on surfaces coated with Caf1 hydrogels. The Caf1 used to generate the hydrogels was WT caf1 which has non adhesive properties (as discussed herein). From the data shown herein, it can be concluded that introduction of an RGD type motif into the WT caf1 would increase the fibroblast interaction. Importantly at this stage the inventors have shown that the gels are not cytotoxic.

9 General Discussion of Examples 5 to 8

9.1 Caf1 Protein Cross-Linked with 4-Arm PEG-NHS Formed a Gel-Like Material.

Caf1 hydrogels were prepared at room temperature using the tube-inversion method. The gelation time was visually estimated to be within 24 to 27 min for NHS-PEG-NHS and 2 to 22 min for 4-arm PEG-NHS, depending on the concentration of the cross-linker. The higher the concentration of these two cross-linkers the quicker the gelation time. The reaction of Caf1 with different concentrations of DTSSP did not allow the visual estimation of the gelation time since a solid gel was not observed (Table 6).

Thus, the gelation rate was significantly quicker with 4-arm PEG-NHS than the NHS-PEG-NHS and the DTSSP. The increase in gelation rate of 4-arm PEG-NHS could be due to the structure of 4-arm PEG which influences its ability to react with the primary amine groups of Caf1.

The data provided herein showed that the structure of 4-arm PEG-NHS was important for the formation of a gel within a few minutes. The Caf1 protein cross-linked with 4-arm PEG-NHS in ratios (w/w) of 1:5, 1:3 and 1:2 formed hydrogels in 5, 4 and 2 min, respectively (Table 6). Nevertheless, Caf1 protein cross-linked with DTSSP was not gel-like material even after 30 min using the same protein: cross-linker ratios and under sealed conditions (Table 9). The cross-linking reaction time of 30 min was determined based on the available literature and as described in the product instructions. The cross-linkers contain N-hydroxy-succinimide (NHS) ester at the end of the chain which reacts immediately with the primary amines (—NH2) of the proteins, and can be rapidly hydrolysed in aqueous solution.

Caf1 hydrogels cross-linked with linear PEG-NHS (NHS-PEG-NHS) was less efficient at forming hydrogels in the same ratios and preparation conditions. In this case the gelation time was slower than with 4-arm PEG-NHS (Table 6). Possibly the reaction between Caf1 and either DTSSP or NHS-PEG requires additional time to form a more compact structure during gelation.

The gelation time reported here is on the order of minutes, which is comparable with other studies using PEG hydrogels.

9.2 Swelling

The diameter of drops of Caf1 hydrogel cross-linked with DTSSP, NHS-PEG-NHS and 4-arm PEG-NHS changed little with increasing cross-linker added to the reaction. This means that if the concentration of cross-linker is increased, the difference between the initial diameter of the drop measured and the final diameter of the same drop after 16 h in PBS at 37° C. is less and then the ratio between the difference of the two diameters and the initial diameter is lesser than if we added less cross-linker to the reaction with Caf1 polymers, i.e. the Caf1 hydrogel with less cross-linker concentration will spread lesser than the one with more concentration of cross-linker.

Comparing, for example, the diameter change of Caf1 hydrogel cross-linked with DTSSP at ratio of cross-linking of 1:10 is higher (61.2%) than both the diameter change of Caf1 hydrogel cross-linked with NHS-PEG-NHS (40.3%) and 4-arm PEG-NHS (24.2%) using the same ratio of cross-linking (Table 6). Without being limited to this theory, this result could indicate that the hydrogel swelling is a function of network structure of the cross-linker which is consistent with previous research.

9.3 Caf1 Hydrogel Cross-Linked with 4-Arm PEG-NHS Shows a Higher Degree of Cross-Linking (FIG. 68)

After Caf1 hydrogel cross-linking for 30 min at room temperature, 10 μl of each hydrogel were heated at 100° C. for 5 min in the presence of SDS-sample buffer and loaded onto a 4-20% gradient gel as well as the control Caf1 protein without any cross-linker at the same concentration used for the formation of Caf1 hydrogel. The gel was stained with Coomassie Brilliant Blue, scanned and analysed by ImageJ version 1.46 software. The band of approximately 15 kDa corresponding to the Caf1 monomer in the non-cross linked Caf1 sample (control) was used as reference for the subsequent analysis. The relative density of the Caf1 monomer band in Caf1 samples cross-linked with the different cross-linkers at various concentrations was determined. The ratio between the values obtained for each sample and the value obtained for the reference sample allowed the determination of the relative density for each band to be calculated. The calculation using the monomers was more accurate than using relative amounts of dimer, trimer, etc due to the presence of a single band with about 15 kDa corresponding to the Caf1 monomer. Since the calculations of the relative density for the high molecular weight bands were more complex. These were considered a single band and designed as "Caf1 cross-linked fraction".

At the bottom of the gel the bands with approximately 15 kDa should correspond to the monomers of Caf1 which were not cross-linked. In the case of Caf1 cross-linked with DTSSP, the bands which are resolved between the 25 and 37 kDa protein standard markers could correspond to the Caf1 dimers (35 kDa) linked by one molecule of DTSSP (608.51 Da) (lanes 1-4). In the case of Caf1 cross-linked with NHS-PEG-NHS the bands with approximately 37 kDa protein standard markers might correspond to a Caf1 dimer linked by one molecule of NHS-PEG-NHS (10 kDa) (lanes 5-8). The Caf1 cross-linking with 4-arm PEG-NHS presents a second band which is resolved between 50 and 75 kDa protein standard markers that could correspond to the Caf1 dimer (35 kDa) linked by one molecule of 4-arm PEG-NHS (20 kDa) (lanes 9 to 12). The remaining high molecular weight bands are not possible to define them only by SDS-PAGE gel analysis. Increasing the ratio of cross-linking using different cross-linkers decreased the Caf1 monomeric fraction. A more accurate technique to determine the mass of the complexes formed by Caf1 and cross-linkers could be mass spectrometry, but varying levels of cross-linker attached to monomers would make this difficult.

The theoretical values for the cross-linked fraction were calculated by subtracting the value of the Caf1 non-cross-linked fraction of each sample analysed from the Caf1 reference. As the concentration of the cross-linkers increased the Caf1 cross-linked fraction also increased. In the case of the highest concentration of 4 arm PEG-NHS (20000 Da) the high molecular weight of Caf1 cross-linked fraction did not allow it to totally pass through the gradient gel and thus the value for Caf1 cross-linked fraction calculated (0.28) was higher than the theoretical values calculated (0.84).

9.4 Caf1 Hydrogel Cross-Linked with DTSSP Revealed a Highly Compact Structure However NHS-PEG-NHS and 4-Arm PEG-NHS Formed Porous Scaffold. High Concentrations of 4-Arm PEG-NHS Resulted in a More Compact Structure (FIGS. 69 to 71)

Caf1 polymers cross-linked with a short arm length cross-linker such as DTSSP (12.0 Å) promote a closer contact between the Caf1 fibres and increase the probability of Caf1 self-assembling. Thus, the images obtained by TEM revealed a compact Caf1 hydrogel which reflects this Caf1 fibres proximity (FIG. 69-A).

A different result was obtained for Caf1 polymers cross-linked with a long spacer NHS-PEG-NHS (197 Å), which can better separate the Caf1 fibres. Large Caf1 hydrogel meshes were observed by TEM (FIG. 69-B).

When the even longer spacers (394 Å) with four arms containing a functional group (NHS) each were used, the interactions between Caf1 and the 4-arm PEG-NHS were frequent due to the number of NHS groups and lysines residues on the Caf1 available for the reaction. The structure was more condensed that on NHS-PEG-NHS (FIG. 69-C).

TEM observations revealed hydrogel meshes (pieces of hydrogel). Without being limited to this theory, this could be due to (1) the preparation of hydrogel for TEM analysis; (2) differences in Caf1 polymer length; (3) number of cross-linking sites obtained by the Caf1 and cross-linker reaction (FIG. 69). Possibly large meshes of hydrogel are the result of high stability in the chemical interactions formed between Caf1 polymer and cross-linkers. It seems that Caf1 hydrogel cross-linked with NHS-PEG-NHS are slightly more stable and flexible than the Caf1 hydrogels cross-linked with 4-arm PEG-NHS which form a stiffer network with more cross-linking sites.

The 4-arm PEG-NHS was further characterised due to the fact that it formed a gel-like network.

The Caf1 hydrogels were only obtained with the Caf1 in a polymeric form approximately up to 1.5 μm long seen by Soliakov and colleagues (10) which is composed of many monomers each of them containing 8 lysines that can interact with NHS functional groups presented in the cross-linkers ends. In the Caf1 monomeric form this large networks were not seen just as in the other control, 4-arm PEG-NHS only (FIG. 70). The small dots indicated by circles might correspond to bead-like structures analysed by Soliakov and colleagues (10) as Caf1 monomers.

Without being limited to this theory, a highly porous hydrogel (FIG. 71) could be advantageous to the swelling and water uptake and also as a scaffold for cell culture can allow the passage of nutrients, oxygen through the pores. The TEM images confirmed that the formation of the Caf1 hydrogels depends on the cross-linker concentration and structure.

Figure 74:
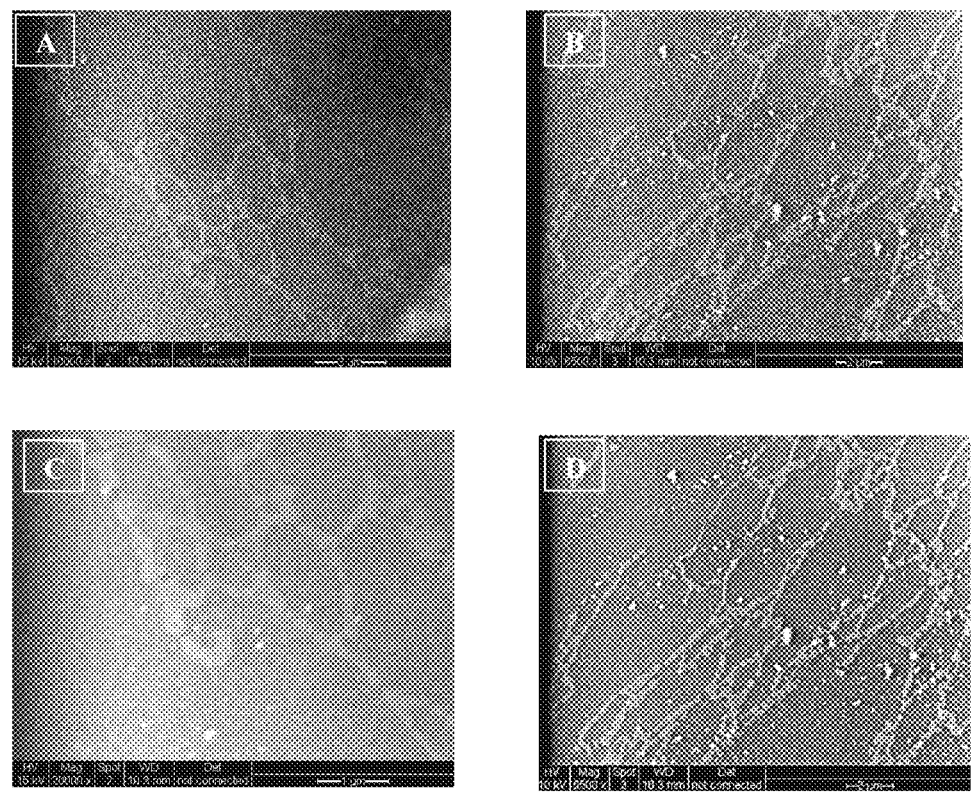

9.5 Caf1 Hydrogels Presented Varying Pore Diameters Depending on the Technique Used (FIGS. 73 and 74)

The pore diameter of Caf1 hydrogels were assessed by SEM and ESEM. The samples analysed by SEM were prepared by critical point drying and dehydrated using differential ethanol concentrations which might cause some collapse of the network. The pores diameters obtained were on the order of nanometers, while freeze-dried hydrogels presented larger pore with a mean pore diameter of 8±0.003 µm (can be seen in FIG. 73).

Caf1 hydrogels were then analysed by ESEM to avoid the dehydration process. The images revealed a mesh-like network structure with a mean pore diameter of 300 nm (can be seen in FIG. 74).

9.6 Caf1 WT Hydrogels are Non-Toxic for Cells However Promote Low Cell Adhesion

Cell hydrogel interaction was examined by measuring the cell viability and spreading on glass coverslips surfaces coated with Caf1 hydrogel cross-linked with 4-arm PEG-NHS (w/w ratio of cross-linking of 1:2). Viable primary osteoblasts seeded onto Caf1 hydrogel displayed few elongated expansion and most of the cells were in a rounded-shape. The mouse 3T3 fibroblasts were not tested for viability. Nevertheless, it was visible that more fibroblasts displayed an elongated morphology when seeded onto Caf1 hydrogels. The cell adhesion and spreading could be improved by the addition of cell adhesive peptides (e.g. RGDS) and also incorporation of proteolytic degradation sites such as metalloproteinases cleavage sites.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCES

1—Abramov, V. M., Vasiliev, A. M., Khlebnikov, V. S., Vasilenko, R. N., Kulikova, N. L., Kosarev, I. V., Ishchenko, A. T., Gillespie, J. R., Millett, I. S., Fink, A. L. and Uversky, V. N. (2002) Structural and functional properties of *Yersinia pestis* Caf1 capsular antigen and their possible role in fulminant development of primary pneumonic plague. J Proteome Res. 1(4):307-15

2—Galyov, E. E., Smirnov, Oyu, Karlishev, A. V., Volkovoy, K. I., Denesyuk, A. I., Nazimov, I. V., Rubtsov, K. S., Abramov, V. M., Dalvadyanz, S. M. and Zav'yalov, V. P. (1990) Nucleotide sequence of the *Yersinia pestis* gene encoding F1 antigen and the primary structure of the protein. Putative T and B cell epitopes. FEBS Lett. 277(1-2):230-2

3—Garmory, H. S., Leckenby, M. W., Griffin, K. F., Elvin, S. J., Taylor, R. R., Hartley, M. G., Hanak, J. A. J., Williamson, E. D. And Cranenburgh, R. M. (2005) Antibiotic-Free Plasmid Stabilization by Operator-Repressor Titration for Vaccine Delivery by Using Live *Salmonella* nteric Serovar *Typhimurium*. Infection and Immunity. 73(4): 2005-2011

4—Greene, L. A. And Tischler, A. S. (1976) Establishment of a Noradrenergic Clonal Line of Rat Adrenal Pheochromocytoma Cells Which Respond to Nerve Growth Factor. Proc Natl Acad Sci USA. 73(7): 2424-8.

5—Hung, D. L., Knight, S. D., Woods, R. M., Pinkner, J. S. and Hultgren, S. J. (1996) Molecular basis of two subfamilies of immunoglobulin-like chaperones. EMBO Journal. 15(15) 3792-3805.

6—Lindler, L. E., and Tall, B. D. (1993) *Yersinia pestis* Ph 6 antigen forms fimbriae and is induced by intracellular association with macrophages. Molecular Microbiology 8(2). 311-324.

7—Lutolf, M. P. (2009) Integration column: Artificial ECM: expanding the cell biology toolbox in 3D. Integrative Biology. 1(3): 235-241

8—Miller J., Williamson E. D., Lakey J. H., Pearce M. J., Jones S. M., Titball R. W. Macromolecular organisation of recombinant *Yersinia pestis* F1 antigen and the effect of structure on immunogenicity. (1998) FEMS Immunol Med Microbiol. 21(3):213-21

9—Morton M., Garmory H. S., Perkins S. D., O'Dowd A. M., Griffin K. F., Turner A. K., Bennett A. M., Titball R. W. (2004) A *Salmonella* nteric serovar *Typhi* vaccine expressing *Yersinia pestis* F1 antigen on its surface provides protection against plague in mice. Vaccine. 22(20): 2524-32.

10—Soliakov A., Harris J. R., Watkinson A., Lakey J. H. (2010) The structure of *Yersinia pestis* Caf1 polymer in free and adjuvant bound states. Vaccine. 28(35):5746-54.

11—Tibbitt, M., Anseth, K. S. (2009) Hydrogels as Extracellular Matrix mimics for 3D cell culture. Biotechnology and Bioengineering. 103(4): 655-663

12—Titball R. W., Howells A. M., Oyston P. C., Williamson E. D. (1997) Expression of the *Yersinia pestis* capsular antigen (F1 antigen) on the surface of an aroA mutant of *Salmonella typhimurium* induces high levels of protection against plague. Infectious Immunology. 65(5):1926-30

13—Williams, R. C., Gewurz, H. And Quie, P. G. (1972) Effects of fraction 1 from *Yersinia pestis* on phagocytosis in vitro. Journal of infectious diseases. 126(3): 235-241.

14—Zaviolov, A. V., Kersley, J., Korpela, T., Zavýalov, V. P., MacIntyre, S. and Knight, S. D (2002) Donor strand complementation mechanism in the biogenesis of non-pilus systems. Molecular Microbiology. 45(4): 983-995.

15—Zavialov, A. V. and Knight, S. D. (2007) A novel self-capping mechanism controls aggregation of periplasmic chaperone Caf1M. Molecular Microbiology. 64(1): 153-164.

16—Baga, M., Norgren, M. & Normark, S. (1987). BIOGENESIS OF *ESCHERICHIA-COLI* PAP PILI-PAPH, A MINOR PILIN SUBUNIT INVOLVED IN CELL ANCHORING AND LENGTH MODULATION. Cell 49, 241-251.

17—Zavialov, A. V., Batchikova, N. V., Korpela, T., Petrovskaya, L. E., Korobko, V. G., Kersley, J., MacIntyre, S. & Zav'yalov, V. P. (2001). Secretion of recombinant proteins via the chaperone/usher pathway in *Escherichia coli*. Applied and Environmental Microbiology 67, 1805-1814.

18—Piatek, R., Zalewska, B., Bury, K. and Kur, J. (2005) 'The chaperone-usher pathway of bacterial adhesin biogenesis—from molecular mechanism to strategies of antibacterial prevention and modern vaccine design', Acta Biochimica Polonica, 52(3), pp. 639-646.

19—Scheich, Christoph; Kummel, Daniel; Soumailakakis, Dimitri; Heinemann, Udo; Bussow, Konrad (2007) "Vectors for co-expression of an unrestricted number of proteins." Nucleic acids research, vol 35, issue 6

20—Guzman, Lm; Belin, D; Carson, Mj; et al. (1995) "Tight regulation, modulation, and high-level expression by vectors containing the arabinose p-bad promoter" journal of bacteriology Volume: 177 Issue: 14 Pages: 4121-4130

21—Zavialov, A V; Batchikova, N V; Korpela, T; et al. (2001)—"Secretion of recombinant proteins via the chaperone/usher pathway in *Escherichia coli*", Applied And Environmental Microbiology, Volume: 67 Issue: 4 Pages: 1805-1814.

22—Chalton, D. A., Musson, J. A., Flick-Smith, H., Walker, N., McGregor, A., Lamb, H. K., Williamson, E. D., Miller, J., Robinson, J. H. and Lakey, J. H. (2006) 'Immunogenicity of a *Yersinia pestis* vaccine antigen monomerized by circular permutation', Infection and Immunity, 74(12), pp. 6624-6631.

Further embodiments of the invention are described in the following numbered paragraphs:

Paragraph 1. A chaperone/usher family polypeptide monomer comprising a exogenous bioactive sequence.

Paragraph 2. The polypeptide according to paragraph 1 wherein said polypeptide is a FG loop long family polypeptide monomer.

Paragraph 3. The polypeptide according to paragraph 2, wherein said polypeptide is selected from the group consisting of Caf1, Saf1 and Afa/Dr.

Paragraph 4. The polypeptide according to paragraph 3, wherein said polypeptide is a Caf1 polypeptide.

Paragraph 5. The polypeptide according to paragraph 4, wherein said polypeptide is at least 70% identical to the polypeptide of SEQ ID NO:5. Alternatively, said polypeptide is at least 70% identical to the polypeptide of SEQ ID NO: 5 lacking the first 21 amino acid residues.

Paragraph 6. The polypeptide according to paragraph 1 wherein said polypeptide is a FG loop short family polypeptide monomer.

Paragraph 7. The polypeptide according to paragraph 6, wherein said polypeptide is selected from the group consisting of Fim and Pap.

Paragraph 8. The polypeptide according to any one of paragraphs 1 to 7, wherein said bioactive sequence is selected from the group consisting of a cell adhesion recognition motif, a growth factor sequence motif and a protease site.

Paragraph 9. The polypeptide according to paragraph 8, wherein said bioactive sequence is a cell adhesion recognition motif.

Paragraph 10. The polypeptide according to paragraph 9, wherein said cell adhesion recognition motif is an extracellular matrix cell adhesion recognition motif.

Paragraph 11. The polypeptide according to paragraph 10, wherein said cell adhesion recognition motif is from collagen, elastin, fibronectin, laminin, osteopontin, vitronectin or tenascin.

Paragraph 12. The polypeptide according to paragraph 11, wherein said cell adhesion recognition motif comprises the amino acid sequence RGD.

Paragraph 13. The polypeptide according to paragraph 11, wherein said cell adhesion recognition motif comprises the amino acid sequence PHSRN.

Paragraph 14. The polypeptide according to any one of paragraphs 1 to 13, wherein said bioactive sequence is comprised within said polypeptide at a site which is comprised within a loop structure upon folding of said polypeptide.

Paragraph 15. A chaperone/usher family polymer comprising at least one chaperone/usher family polypeptide monomer according to any one of paragraph 1 to 14.

Paragraph 16. The chaperone/usher family polymer according to paragraph 15, wherein said polymer is a fraction 1 antigen polymer, and said at least one chaperone/usher family polypeptide monomer is a CAF1 polypeptide monomer.

Paragraph 17. The chaperone/usher family polymer according to paragraph 15 or paragraph 16, wherein said exogenous bioactive sequence is a cell adhesion recognition motif comprising the amino acid sequence RGD.

Paragraph 18. The chaperone/usher family polymer according to any one of paragraphs 15 to 17, further comprising at least one naturally occurring CAF1 polypeptide monomer.

Paragraph 19. The chaperone/usher family polymer according to paragraph 18, wherein said at least one naturally occurring CAF1 polypeptide monomer is a *Yersinia pestis* CAF1 polypeptide.

Paragraph 20. The chaperone/usher family polymer according to paragraph 19, wherein said *Yersinia pestis* CAF1 polypeptide has the polypeptide sequence of SEQ ID NO:5. Alternatively, said *Yersinia pestis* CAF1 polypeptide has the polypeptide sequence of SEQ ID NO:5 lacking the first 21 amino acid residues.

Paragraph 21. The chaperone/usher family polymer according to any one of paragraphs 15 to 20, further comprising at least one further polypeptide monomer according to any one of paragraphs 1 to 14, wherein said exogenous bioactive sequence of said at least one further polypeptide monomer is distinct from said exogenous bioactive sequence of said at least one chaperone/usher family polypeptide monomer.

Paragraph 22. The chaperone/usher family polymer according to paragraph 21, wherein said exogenous bioactive sequence of said at least one chaperone/usher family polypeptide monomer is a cell adhesion recognition motif comprising the amino acid sequence RGD and wherein said exogenous bioactive sequence of said at least one further polypeptide monomer is a cell adhesion recognition motif comprising the amino acid sequence PHSRN.

Paragraph 23. A hydrogel comprising the polypeptide according to any one of paragraphs 1 to 14 or the chaperone/usher family polymer according to any one of paragraphs 15 to 22.

Paragraph 24. The hydrogel according to paragraph 23, further comprising a cross linking agent.

Paragraph 25. The hydrogel according to paragraph 24, wherein said cross linking agent is a biodegradable cross linking agent.

Paragraph 26. The hydrogel according to paragraph 24, wherein said cross linking agent is a non-degradable cross linking agent.

Paragraph 27. The hydrogel according to paragraph 24, wherein said cross linking agent comprises polyethylene glycol.

Paragraph 28. Use of a hydrogel according to any one of paragraphs 24 to 27 as a cell support scaffold.

Paragraph 29. The use according to paragraph 28, wherein said scaffold is a 2D cell support scaffold. Alternatively, said scaffold is a 1D cell support scaffold.

Paragraph 30. The use according to paragraph 28, wherein said scaffold is a 3D cell support scaffold.

Paragraph 31. A wound dressing comprising the hydrogel according to any one of paragraphs 23 to 27.

Paragraph 32. A hydrogel according to any one of paragraphs 23 to 27 for use in the treatment of a wound.

Paragraph 33. The hydrogel for use according to paragraph 32, wherein said wound is a chronic wound or wherein said wound is an acute wound.

Paragraph 34. An ocular implant comprising the hydrogel according to any one of paragraphs 23 to 27.

Paragraph 35. A hydrogel according to any one of paragraphs 23 to 27 for use in the treatment of an ocular injury.

Paragraph 36. An expression vector for producing a chaperone/usher family polypeptide monomer, comprising the operably linked elements of:
   a) a transcription promoter element;
   b) a nucleic acid molecule that encodes a chaperone/usher family polypeptide monomer comprising a exogenous bioactive sequence; and
   c) a transcriptional terminator.

Paragraph 37. The expression vector according to paragraph 36, wherein said nucleic acid molecule that encodes a chaperone/usher family polypeptide monomer comprising an exogenous bioactive sequence encodes a CAF1 polypeptide monomer.

Paragraph 38. The expression vector according to paragraph 37, wherein said exogenous bioactive sequence is a cell adhesion recognition motif.

Paragraph 39. The expression vector according to paragraph 37 or paragraph 38, wherein said nucleic acid molecule has at least 70% identity to the nucleotide sequence of SEQ ID NO: 1.

Paragraph 40. The expression vector according to any one of paragraphs 36 to 39, further comprising a nucleic acid molecule that encodes a periplasmic chaperone specific for the chaperone/usher family polypeptide monomer.

Paragraph 41. The expression vector according to paragraph 40, wherein said nucleic acid molecule that encodes a periplasmic chaperone specific for the chaperone/usher family polypeptide monomer encodes a periplasmic chaperone specific for CAF1.

Paragraph 42. The expression vector according to paragraph 41, wherein said nucleic acid molecule that encodes the periplasmic chaperone specific for CAF1 has at least 70% identity to the nucleotide sequence of SEQ ID NO: 2.

Paragraph 43. The expression vector according to anyone of paragraphs 36 to 42, further comprising a nucleic acid molecule that encodes an outer membrane usher protein specific for the chaperone/usher family polypeptide monomer.

Paragraph 44. The expression vector according to paragraph 43, wherein said nucleic acid molecule that encodes an outer membrane usher protein specific for the chaperone/usher family polypeptide monomer encodes an outer membrane usher protein specific for CAF1.

Paragraph 45. The expression vector according to paragraph 44, wherein said nucleic acid molecule that encodes the outer membrane usher protein specific for CAF1 has at least 70% identity to the nucleotide sequence of SEQ ID NO: 3.

Paragraph 46. The expression vector according to anyone of paragraphs 36 to 45, further comprising a nucleic acid molecule that encodes an expression regulator protein specific for the chaperone/usher family polypeptide monomer.

Paragraph 47. The expression vector according to paragraph 46, wherein said nucleic acid molecule that encodes an expression regulator protein specific for the chaperone/usher family polypeptide monomer encodes an expression regulator protein specific for CAF1.

Paragraph 48. The expression vector according to paragraph 47, wherein said nucleic acid molecule that encodes the expression regulator protein specific for CAF1 has at least 70% identity to the nucleotide sequence of SEQ ID NO: 4.

Paragraph 49. A host cell transformed with the expression vector according to any one of paragraphs 36 to 48.

Paragraph 50. The host cell according to paragraph 49, wherein said cell is a bacterial cell.

Paragraph 51. The host cell according to paragraph 50, wherein said bacterial cell is a gram negative bacterial cell.

Paragraph 52. The host cell according to paragraph 51, wherein said bacterial cell is *Escherichia coli*.

Paragraph 53. A method for producing a chaperone/usher family polymer comprising at least one chaperone/usher family polypeptide monomer comprising an exogenous bioactive sequence, said method comprising:
   i) incorporating a nucleic acid molecule that encodes a chaperone/usher family polypeptide monomer comprising an exogenous bioactive sequence into an expression vector for expression in a host cell; and
   ii) transfecting a host cell with the expression vector;
wherein said host cell is provided with a nucleic acid molecule that encodes a periplasmic chaperone specific for the chaperone/usher family polypeptide monomer and a nucleic acid molecule that encodes an outer membrane usher protein specific for the chaperone/usher family polypeptide monomer and wherein the resulting transfected host cell produces a chaperone/usher family polymer.

Paragraph 54. The method according to paragraph 53, wherein said chaperone/usher family polymer is a fraction 1 antigen polymer and said at least one chaperone/usher family polypeptide monomer comprising an exogenous bioactive sequence is a CAF1 polypeptide monomer.

Paragraph 55. The method according to paragraph 54, wherein said nucleic acid molecule that encodes the CAF1 polypeptide monomer comprising an exogenous bioactive sequence has at least 70% identity to the nucleotide sequence of SEQ ID NO: 1.

Paragraph 56. The method according to paragraph 54 or paragraph 55, wherein said nucleic acid molecule that encodes a periplasmic chaperone specific for the chaperone/usher family polypeptide monomer encodes a periplasmic chaperone specific for CAF1 and wherein said nucleic acid molecule that encodes an outer membrane usher protein specific for the chaperone/usher family polypeptide monomer encodes an outer membrane usher protein specific for CAF1.

Paragraph 57. The method according to paragraph 56, wherein said nucleic acid molecule that encodes the periplasmic chaperone specific for CAF1 has at least 70% identity to the nucleotide sequence of SEQ ID NO: 2.

Paragraph 58. The method according to paragraph 56 or paragraph 57, wherein said nucleic acid molecule that encodes the outer membrane usher protein specific for CAF1 has at least 70% identity to the nucleotide sequence of SEQ ID NO: 3.

Paragraph 59. The method according to any one of paragraphs 56 to 58, wherein said host cell is provided with the nucleic acid molecule that encodes a periplasmic chaperone specific for CAF1 by:
  i) incorporating the nucleic acid molecule that encodes a periplasmic chaperone specific for CAF1 into an expression vector for expression in the host cell; and
  ii) transfecting the host cell with the expression vector.

Paragraph 60. The method according to paragraph 59, wherein said expression vector further comprises the nucleic acid molecule that encodes a CAF1 polypeptide monomer comprising a cell adhesion recognition motif.

Paragraph 61. The method according to any one of paragraphs 56 to 60, wherein said host cell is provided with the nucleic acid molecule that encodes the outer membrane usher protein specific for CAF1 by:
  i) incorporating the nucleic acid molecule that encodes the outer membrane usher protein specific for CAF1 into an expression vector for expression in the host cell; and
  ii) transfecting the host cell with the expression vector.

Paragraph 62. The method according to paragraph 61, wherein said expression vector further comprises the nucleic acid molecule that encodes a CAF1 polypeptide monomer comprising a cell adhesion recognition motif and/or the nucleic acid molecule that encodes a periplasmic chaperone specific for CAF1.

Paragraph 63. The method according to paragraph 53 to 62, wherein said host cell is further provided with a nucleic acid molecule that encodes an expression regulator specific for the chaperone/usher family polypeptide monomer.

Paragraph 64. The method according to paragraph 63, wherein said nucleic acid molecule that encodes an expression regulator specific for the chaperone/usher family polypeptide monomer encodes an expression regulator specific for CAF1.

Paragraph 65. The method according to paragraph 63 or paragraph 64, wherein said nucleic acid molecule that encodes the expression regulator specific for CAF1 has at least 70% identity to the nucleotide sequence of SEQ ID NO: 4.

Paragraph 66. The method according to any one of paragraphs 53 to 65, wherein said bioactive sequence is a cell adhesion recognition motif.

Paragraph 67. The method according to any one of paragraphs 53 to 66, wherein said host cell is a bacterial cell.

Paragraph 68. The method according to paragraph 67, wherein said bacterial cell is a gram negative bacterial cell.

Paragraph 69. The method according to paragraph 68, wherein said bacterial cell is *Escherichia coli*.

Paragraph 70. A method for producing a chaperone/usher family polymer comprising at least one chaperone/usher family polypeptide monomer comprising an exogenous bioactive sequence comprising:
  i) providing a vessel comprising a host cell according to any one of paragraphs 49 to 52;
  ii) providing cell culture conditions which facilitate chaperone/usher family polypeptide monomer expression by a cell culture contained in the vessel; and optionally
  iii) collecting chaperone/usher family polymer from the vessel.

Paragraph 71. Use of a fraction 1 antigen polymer as an antifouling agent.

Paragraph 72. An antifouling composition comprising a fraction 1 antigen polymer.

Paragraph 73. A chaperone/usher family polypeptide monomer as described herein with reference to the accompanying drawings.

Paragraph 74. A chaperone/usher family polymer as described herein with reference to the accompanying drawings.

Paragraph 75. A hydrogel as described herein with reference to the accompanying drawings.

Paragraph 76. A wound dressing as described herein with reference to the accompanying drawings.

Paragraph 77. A wound dressing as described herein with reference to the accompanying drawings.

Paragraph 78. An ocular implant as described herein with reference to the accompanying drawings.

Paragraph 79. An expression vector as described herein with reference to the accompanying drawings.

Paragraph 80. A host cell transformed as described herein with reference to the accompanying drawings.

Paragraph 81. A method for producing a chaperone/usher family polymer as described herein with reference to the accompanying drawings.

The invention claimed is:

1. A chaperone/usher family polymer comprising at least one chaperone/usher family polypeptide monomer, wherein said at least one chaperone/usher family polypeptide monomer comprises an exogenous bioactive sequence, and wherein said chaperone/usher family polymer is a polymeric pilus.

2. The chaperone/usher family polymer according to claim 1, wherein the bioactive sequence is:

(a) substantially non-immunogenic;
(b) selected from the group consisting of a cell adhesion recognition motif, a growth factor sequence motif and a protease site; or
(c) comprised within said monomer at a site which is comprised within a loop structure upon folding of said polypeptide.

3. The chaperone/usher family polymer according to claim 1, wherein the monomer is:

(a) a FG loop long family polypeptide monomer; or
(b) a FG loop short family polypeptide monomer.

4. The chaperone/usher family polymer according to claim 1, wherein said polymer is a fraction 1 antigen polymer, and said at least one chaperone/usher family polypeptide monomer is a CAF1 polypeptide monomer.

5. The chaperone/usher family polymer according to claim 1, wherein the polymer comprises at least one further chaperone/usher family polypeptide monomer, wherein said further chaperone/usher family polypeptide monomer differs from said at least one chaperone/usher family polypeptide monomer comprising an exogenous bioactive sequence by at least one amino acid.

6. The chaperone/usher family polymer according to claim 5, wherein the further chaperone/usher family polypeptide monomer:
   (a) is a chaperone/usher family polypeptide monomer without said exogenous bioactive sequence;
   (b) comprises an exogenous bioactive sequence that is distinct from said exogenous bioactive sequence of said at least one chaperone/usher family polypeptide monomer; or
   (c) comprises an exogenous bioactive sequence that is a cell adhesion recognition motif comprising the amino acid sequence PHSRN, wherein said exogenous bioactive sequence of said at least one chaperone/usher family polypeptide monomer is a cell adhesion recognition motif comprising the amino acid sequence RGD.

7. A hydrogel comprising the chaperone/usher family polymer according to claim 1.

8. The hydrogel according to claim 7, further comprising a cross linking agent.

9. A cell support scaffold comprising a hydrogel according to claim 7.

10. The cell support scaffold according to claim 9, wherein said scaffold is a 2D cell support scaffold or a 3D cell support scaffold.

11. A wound dressing or ocular implant comprising the hydrogel according to claim 7.

12. A method of treating damaged tissue in a subject in need thereof, comprising administering a hydrogel according to claim 7 to the subject, wherein the damaged tissue is a wound or an ocular injury.

13. The method according to claim 12, wherein said wound is a chronic wound or wherein said wound is an acute wound.

14. A method for producing a chaperone/usher family polymeric pilus comprising at least one chaperone/usher family polypeptide monomer comprising an exogenous bioactive sequence, said method comprising:
   i) incorporating a nucleic acid molecule that encodes a chaperone/usher family polypeptide monomer comprising an exogenous bioactive sequence into an expression vector for expression in a host cell; and
   ii) transfecting a host cell with the expression vector;
   wherein said host cell is provided with a nucleic acid molecule that encodes a periplasmic chaperone specific for the chaperone/usher family polypeptide monomer and a nucleic acid molecule that encodes an outer membrane usher protein specific for the chaperone/usher family polypeptide monomer, and wherein the resulting transfected host cell produces a chaperone/usher family polymeric pilus including the monomer.

15. The method according to claim 14, wherein the bioactive sequence is:

(a) substantially non-immunogenic; or
(b) a cell adhesion recognition motif.

16. The method according to claim 14, wherein said chaperone/usher family polymeric pilus is a fraction 1 antigen polymer and said at least one chaperone/usher family polypeptide monomer comprising an exogenous bioactive sequence is a CAF1 polypeptide monomer.

17. The method according to claim 16, wherein said nucleic acid molecule that encodes the CAF1 polypeptide monomer comprising an exogenous bioactive sequence has at least 70% identity to the nucleotide sequence of SEQ ID NO: 1.

18. The method according to claim 16, wherein said nucleic acid molecule that encodes a periplasmic chaperone specific for the chaperone/usher family polypeptide monomer encodes a periplasmic chaperone specific for CAF1 and wherein said nucleic acid molecule that encodes an outer membrane usher protein specific for the chaperone/usher family polypeptide monomer encodes an outer membrane usher protein specific for CAF1.

19. The method according to claim 18, wherein said nucleic acid molecule that encodes the periplasmic chaperone specific for CAF1 has at least 70% identity to the nucleotide sequence of SEQ ID NO: 2.

20. The method according to claim 18, wherein said nucleic acid molecule that encodes the outer membrane usher protein specific for CAF1 has at least 70% identity to the nucleotide sequence of SEQ ID NO: 3.

21. The method according to claim 18, wherein said host cell is provided with the nucleic acid molecule that encodes a periplasmic chaperone specific for CAF1 by:
   i) incorporating the nucleic acid molecule that encodes a periplasmic chaperone specific for CAF1 into an expression vector for expression in the host cell; and
   ii) transfecting the host cell with the expression vector.

22. The method according to claim 21, wherein said expression vector further comprises the nucleic acid molecule that encodes a CAF1 polypeptide monomer comprising a cell adhesion recognition motif.

23. The method according to claim 18, wherein said host cell is provided with the nucleic acid molecule that encodes the outer membrane usher protein specific for CAF1 by:
   i) incorporating the nucleic acid molecule that encodes the outer membrane usher protein specific for CAF1 into an expression vector for expression in the host cell; and
   ii) transfecting the host cell with the expression vector.

24. The method according to claim 23, wherein said expression vector further comprises the nucleic acid molecule that encodes a CAF1 polypeptide monomer comprising a cell adhesion recognition motif and/or the nucleic acid molecule that encodes a periplasmic chaperone specific for CAF1.

25. The method according to claim 14, wherein said host cell is further provided with a nucleic acid molecule that encodes an expression regulator specific for the chaperone/usher family polypeptide monomer.

26. The method according to claim 25, wherein said nucleic acid molecule that encodes an expression regulator specific for the chaperone/usher family polypeptide monomer encodes an expression regulator specific for CAF1.

27. The method according to claim 14, wherein said host cell is a bacterial cell.

28. An antifouling composition comprising a hydrogel including a fraction 1 antigen polymeric pilus.

* * * * *

SEQUENCE LISTING

<160> NUMBER OF SEQ ID NOS: 108

<210> SEQ ID NO 1
<211> LENGTH: 513
<212> TYPE: DNA
<213> ORGANISM: Yersinia pestis

<400> SEQUENCE: 1

```
atgaaaaaaa tcagttccgt tatcgccatt gcattatttg gaactattgc aactgctaat      60
gcggcagatt taactgcaag caccactgca acggcaactc ttgttgaacc agcccgcatc     120
actcttacat ataaggaagg cgctccaatt acaattatgg acaatggaaa catcgataca     180
```

```
gaattacttg ttggtacgct tactcttggc ggctataaaa caggaaccac tagcacatct      240
gttaacttta cagatgccgc gggtgatccc atgtacttaa catttacttc tcaggatgga      300
aataaccacc aattcactac aaaagtgatt ggcaaggatt ctagagattt tgatatctct      360
cctaaggtaa acggtgagaa ccttgtgggg gatgacgtcg tcttggctac gggcagccag      420
gatttctttg ttcgctcaat tggttccaaa ggcggtaaac ttgcagcagg taaatacact      480
gatgctgtaa ccgtaaccgt atctaaccaa taa                                   513

<210> SEQ ID NO 2
<211> LENGTH: 777
<212> TYPE: DNA
<213> ORGANISM: Yersinia pestis

<400> SEQUENCE: 2
atgattttaa atagattaag tacgttagga attattactt tcggcatgct tagttttgct       60
gcgaactctg ctcaaccaga tatcaaattc gcaagcaaag agtatggcgt gactataggt      120
gagagtagga tcatataccc gttagatgct gctggcgtta tggtctcggt gaaaaacacc      180
caagattatc cggttctcat tcagtctagg atctacgacg agaataaaga aaagaatca       240 gaggatcctt tcgtggtcac tccgccattg tttcgattgg atgctaagca acaaaattct      300
ttgcgtatag ctcaggctgg aggtgttttc ccgcgagata agagagcct aaagtggtta      360 tgcgtaaaag ggattccacc aaaggatgaa gatatatggg ttgatgatgc gacaaataag      420
caaaaattca atccagacaa agatgtggga gtgttcgtgc aattcgcaat taataattgc      480
attaagcttt tggttcgacc gaatgaatta aaaggaaccc ctatacagtt tgctgaaaag      540
ttaagctgga agttgatgg ggggaagcta attgctgaaa acccctcacc tttctacatg      600
aacataggtg aattaacatt tggagggaaa agtattcctt ctcactatat tccacctaaa      660
tcgacgtggg cttttgattt gccaaaagga ctagcgggag cacgtaatgt ttcgtggaga      720
ataattaatg atcagggagg gttggatcgt ttgtattcca aaaatgtgac tttatga        777

<210> SEQ ID NO 3
<211> LENGTH: 1000
<212> TYPE: DNA
<213> ORGANISM: Yersinia pestis

<400> SEQUENCE: 3
atgaggtatt caaagctgtt cctgtgtgca gggttaactt tggcaacatt gccttgttgg       60
ggacgcgcat atacttttga ctctactatg cttgatacga atagtggaga gagtatagat      120
gtatctcttt ttaatcaagg acttcaactt ccaggtaatt attttgttaa tgtttttgta      180
aatggtcgaa aggtagactc tggaaatatc gacttccgtc tagaaaaaca taatggaaaa      240
gaacttcttt ggccatgcct atcatcctta caattgacaa agtatggcat tgatatagat      300
aaatatcctg attaataaa atctggtaca gagcaatgtg ttgatttatt agcaatacca      360
cattcagatg tgcagtttta ttttaatcag cagaaattat cgttaattgt gccaccacag      420
gcacttttac ctagatttga tggcattatg ccaatgcaat tgtgggatga cggcattcct      480
gctctgttca tgaattataa tacgaacatg cagacaagaa aattcagaga aggaggcaag      540
tctctggact cttattatgc tcagttgcaa ccgggattaa acatagggc ttggcgcttt       600 cgtagttcaa cctcatggtg gaaacaacaa ggatggcagc gttcgtatat ttatgccgag      660
cgaggattga atacaattaa gagccgtttg acattggggg aaacctattc tgatagcagt      720
atctttgaca gtatcccgat taaggggata aaaattgctt cagatgaatc gatggttcct      780
```

```
tattaccaat ggaattttgc tccagttgtt cgcggtatcg cacgtacaca agccagggta      840
gaggttttaa gagatggcta cactgtaagt aatgagttgg tgccctcggg accatttgag      900
ttagcaaatc ttcctctggg tgggggagt ggtgagctga aagtcatcat tcatgaaagt       960
gatggaacaa agcaagtttt tacagttcca tatgacacac                          1000

<210> SEQ ID NO 4
<211> LENGTH: 906
<212> TYPE: DNA
<213> ORGANISM: Yersinia pestis

<400> SEQUENCE: 4
atgctaaaac agatgactgt aaattcaatt attcaatata tagaagagaa tctcgagtcg       60
aaattcatta acattgactg tttggttttg tattcaggat tcagcagaag gtatttgcaa      120
atttccttta aggaatatgt cggaatgcct attggaacat atattagagt tagaagggct      180
agtagagctg ctgcactatt acggcttaca aggctgacaa taatagagat atcagcaaag      240
cttttttatg attcgcaaca gacattcacc agagaattta agaaaatatt tggttatacc      300
ccacggcagt ataggatgat ccctttttgg tcctttaaag gtttgttggg tagaagggaa      360
attaactgtg aataccttca accacgaatc tgttacctta agagagaaa tataattggt       420 caatgcttta attttaggga tttagtgttc tactctggga tagattcaaa atgtagattg      480
ggtaagttat atgattcgtt gaagaaaaat acagctataa cagtatcaaa cagaatcccc      540
tttcatgata aaacgaatga cattattgca agaacggttg tttgggatag gaataagcat      600
ttcagcgata gtgaaataaa ggtagataaa ggcctgtatg cttattttt cttcaatgat       660 acatatgatc agtatgttca tcacatgtac aacatatatt ataactcttt gcctatttat      720
aatttaaata gcgggatgg ttacgatgtg gaggtcataa aaagacgaaa tgacaatact       780
attgattgtc attattttct cccgatttat tgtgatgaca tggagttta caatgaaatg       840 caggtatatc acaataatat tgtgaagccg gaaatgtcag taacattagg attaccaaag      900
agttaa                                                                906

<210> SEQ ID NO 5
<211> LENGTH: 170
<212> TYPE: PRT
<213> ORGANISM: Yersinia pestis

<400> SEQUENCE: 5

Met Lys Lys Ile Ser Ser Val Ile Ala Ile Ala Leu Phe Gly Thr Ile
1               5                   10                  15

Ala Thr Ala Asn Ala Ala Asp Leu Thr Ala Ser Thr Thr Ala Thr Ala
                20                  25                  30

Thr Leu Val Glu Pro Ala Arg Ile Thr Leu Thr Tyr Lys Glu Gly Ala
        35                  40                  45

Pro Ile Thr Ile Met Asp Asn Gly Asn Ile Asp Thr Glu Leu Leu Val
    50                  55                  60

Gly Thr Leu Thr Leu Gly Gly Tyr Lys Thr Gly Thr Thr Ser Thr Ser
65                  70                  75                  80

Val Asn Phe Thr Asp Ala Ala Gly Asp Pro Met Tyr Leu Thr Phe Thr
                85                  90                  95

Ser Gln Asp Gly Asn Asn His Gln Phe Thr Thr Lys Val Ile Gly Lys
                100                 105                 110

Asp Ser Arg Asp Phe Asp Ile Ser Pro Lys Val Asn Gly Glu Asn Leu
```

```
                115                 120                 125
Val Gly Asp Asp Val Val Leu Ala Thr Gly Ser Gln Asp Phe Phe Val
            130                 135                 140

Arg Ser Ile Gly Ser Lys Gly Gly Lys Leu Ala Ala Gly Lys Tyr Thr
145                 150                 155                 160

Asp Ala Val Thr Val Thr Val Ser Asn Gln
                165                 170

<210> SEQ ID NO 6
<211> LENGTH: 258
<212> TYPE: PRT
<213> ORGANISM: Yersinia pestis

<400> SEQUENCE: 6

Met Ile Leu Asn Arg Leu Ser Thr Leu Gly Ile Ile Thr Phe Gly Met
1               5                   10                  15

Leu Ser Phe Ala Ala Asn Ser Ala Gln Pro Asp Ile Lys Phe Ala Ser
            20                  25                  30

Lys Glu Tyr Gly Val Thr Ile Gly Glu Ser Arg Ile Tyr Pro Leu
        35                  40                  45

Asp Ala Ala Gly Val Met Val Ser Val Lys Asn Thr Gln Asp Tyr Pro
    50                  55                  60

Val Leu Ile Gln Ser Arg Ile Tyr Asp Glu Asn Lys Glu Lys Glu Ser
65                  70                  75                  80

Glu Asp Pro Phe Val Val Thr Pro Pro Leu Phe Arg Leu Asp Ala Lys
                85                  90                  95

Gln Gln Asn Ser Leu Arg Ile Ala Gln Ala Gly Gly Val Phe Pro Arg
            100                 105                 110

Asp Lys Glu Ser Leu Lys Trp Leu Cys Val Lys Gly Ile Pro Pro Lys
        115                 120                 125

Asp Glu Asp Ile Trp Val Asp Asp Ala Thr Asn Lys Gln Lys Phe Asn
    130                 135                 140

Pro Asp Lys Asp Val Gly Val Phe Val Gln Phe Ala Ile Asn Asn Cys
145                 150                 155                 160

Ile Lys Leu Leu Val Arg Pro Asn Glu Leu Lys Gly Thr Pro Ile Gln
                165                 170                 175

Phe Ala Glu Asn Leu Ser Trp Lys Val Asp Gly Gly Lys Leu Ile Ala
            180                 185                 190

Glu Asn Pro Ser Pro Phe Tyr Met Asn Ile Gly Glu Leu Thr Phe Gly
        195                 200                 205

Gly Lys Ser Ile Pro Ser His Tyr Ile Pro Pro Lys Ser Thr Trp Ala
    210                 215                 220

Phe Asp Leu Pro Lys Gly Leu Ala Gly Ala Arg Asn Val Ser Trp Arg
225                 230                 235                 240

Ile Ile Asn Asp Gln Gly Gly Leu Asp Arg Leu Tyr Ser Lys Asn Val
                245                 250                 255

Thr Leu

<210> SEQ ID NO 7
<211> LENGTH: 833
<212> TYPE: PRT
<213> ORGANISM: Artificial Sequence
<220> FEATURE:
<223> OTHER INFORMATION: Caf1A

<400> SEQUENCE: 7
```

```
Met Arg Tyr Ser Lys Leu Phe Leu Cys Ala Gly Leu Thr Leu Ala Thr
1               5                   10                  15

Leu Pro Cys Trp Gly Arg Ala Tyr Thr Phe Asp Ser Thr Met Leu Asp
            20                  25                  30

Thr Asn Ser Gly Glu Ser Ile Asp Val Ser Leu Phe Asn Gln Gly Leu
        35                  40                  45

Gln Leu Pro Gly Asn Tyr Phe Val Asn Val Phe Val Asn Gly Arg Lys
    50                  55                  60

Val Asp Ser Gly Asn Ile Asp Phe Arg Leu Glu Lys His Asn Gly Lys
65                  70                  75                  80

Glu Leu Leu Trp Pro Cys Leu Ser Ser Leu Gln Leu Thr Lys Tyr Gly
                85                  90                  95

Ile Asp Ile Asp Lys Tyr Pro Asp Leu Ile Lys Ser Gly Thr Glu Gln
                100                 105                 110

Cys Val Asp Leu Leu Ala Ile Pro His Ser Asp Val Gln Phe Tyr Phe
            115                 120                 125

Asn Gln Gln Lys Leu Ser Leu Ile Val Pro Pro Gln Ala Leu Leu Pro
        130                 135                 140

Arg Phe Asp Gly Ile Met Pro Met Gln Leu Trp Asp Asp Gly Ile Pro
145                 150                 155                 160

Ala Leu Phe Met Asn Tyr Asn Thr Asn Met Gln Thr Arg Lys Phe Arg
                165                 170                 175

Glu Gly Gly Lys Ser Leu Asp Ser Tyr Tyr Ala Gln Leu Gln Pro Gly
            180                 185                 190

Leu Asn Ile Gly Ala Trp Arg Phe Arg Ser Ser Thr Ser Trp Trp Lys
        195                 200                 205

Gln Gln Gly Trp Gln Arg Ser Tyr Ile Tyr Ala Glu Arg Gly Leu Asn
    210                 215                 220

Thr Ile Lys Ser Arg Leu Thr Leu Gly Glu Thr Tyr Ser Asp Ser Ser
225                 230                 235                 240

Ile Phe Asp Ser Ile Pro Ile Lys Gly Ile Lys Ile Ala Ser Asp Glu
                245                 250                 255

Ser Met Val Pro Tyr Tyr Gln Trp Asn Phe Ala Pro Val Val Arg Gly
            260                 265                 270

Ile Ala Arg Thr Gln Ala Arg Val Glu Val Leu Arg Asp Gly Tyr Thr
        275                 280                 285

Val Ser Asn Glu Leu Val Pro Ser Gly Pro Phe Glu Leu Ala Asn Leu
    290                 295                 300

Pro Leu Gly Gly Ser Gly Glu Leu Lys Val Ile Ile His Glu Ser
305                 310                 315                 320

Asp Gly Thr Lys Gln Val Phe Thr Val Pro Tyr Asp Thr Pro Ala Val
            325                 330                 335

Ala Leu Arg Lys Gly Tyr Phe Glu Tyr Ser Met Met Gly Gly Glu Tyr
            340                 345                 350

Arg Pro Ala Asn Asp Leu Thr Gln Thr Ser Tyr Val Gly Ala Leu Gly
        355                 360                 365

Met Lys Tyr Gly Leu Pro Arg Asn Leu Thr Leu Tyr Gly Gly Leu Gln
    370                 375                 380

Gly Ser Gln Asn Tyr His Ala Ala Leu Gly Ile Gly Ala Met Leu
385                 390                 395                 400

Gly Asp Phe Gly Ala Ile Ser Thr Asp Val Thr Gln Ala Asp Ser Gln
                405                 410                 415

Lys Asn Lys Gln Lys Lys Glu Ser Gly Gln Arg Trp Arg Val Arg Tyr
```

```
                420             425             430
Asn Lys Tyr Leu Gln Ser Gly Thr Ser Leu Asn Ile Ala Ser Glu Glu
            435             440             445

Tyr Ala Thr Glu Gly Phe Asn Lys Leu Ala Asp Thr Leu Asn Thr Tyr
450             455             460

Cys Lys Pro Asn Thr Arg Asn Asp Cys Arg Phe Asp Tyr Ala Lys Pro
465             470             475             480

Lys Asn Lys Val Gln Phe Asn Leu Ser Gln Ser Ile Pro Gly Ser Gly
            485             490             495

Thr Leu Asn Phe Ser Gly Tyr Arg Lys Asn Tyr Trp Arg Asp Ser Arg
            500             505             510

Ser Thr Thr Ser Phe Ser Val Gly Tyr Asn His Phe Phe Arg Asn Gly
            515             520             525

Met Ser Leu Thr Leu Asn Leu Ser Lys Thr Gln Asn Ile Asn Lys Tyr
            530             535             540

Gly Glu Lys Thr Ser Glu Leu Leu Ser Asn Ile Trp Leu Ser Phe Pro
545             550             555             560

Leu Ser Arg Trp Leu Gly Asn Asn Ser Ile Asn Ser Asn Tyr Gln Met
            565             570             575

Thr Ser Asp Ser His Gly Asn Thr Thr His Glu Val Gly Val Tyr Gly
            580             585             590

Glu Ala Phe Asp Arg Gln Leu Tyr Trp Asp Val Arg Glu Arg Phe Asn
            595             600             605

Glu Lys Gly Arg Lys Tyr Thr Ser Asn Ala Leu Asn Leu Asn Tyr Arg
            610             615             620

Gly Thr Tyr Gly Glu Ile Ser Gly Asn Tyr Ser Tyr Asp Gln Thr Gln
625             630             635             640

Ser Gln Leu Gly Ile Gly Val Asn Gly Asn Met Val Ile Thr Gln Tyr
            645             650             655

Gly Ile Thr Ala Gly Gln Lys Thr Gly Asp Thr Ile Ala Leu Val Gln
            660             665             670

Ala Pro Asp Ile Ser Gly Ala Ser Val Gly Tyr Trp Pro Gly Met Lys
            675             680             685

Thr Asp Phe Arg Gly Tyr Thr Asn Tyr Gly Tyr Leu Thr Pro Tyr Arg
690             695             700

Glu Asn Lys Val Glu Ile Asn Pro Val Thr Leu Pro Asn Asp Ala Glu
705             710             715             720

Ile Thr Asn Asn Ile Val Ser Val Ile Pro Thr Lys Gly Ala Val Val
            725             730             735

Leu Ala Lys Phe Asn Ala Arg Ile Gly Gly Arg Leu Phe Leu His Leu
            740             745             750

Lys Arg Ser Asp Asn Lys Pro Val Pro Phe Gly Ser Ile Val Thr Ile
            755             760             765

Glu Gly Gln Ser Ser Ser Gly Ile Val Gly Asp Asn Ser Gly Val
            770             775             780

Tyr Leu Thr Gly Leu Pro Lys Lys Ser Lys Ile Leu Val Lys Trp Gly
785             790             795             800

Arg Asp Lys Asn Gln Ser Cys Ser Ser Asn Val Val Leu Pro Glu Lys
            805             810             815

Thr Asp Ile Ser Gly Ala Tyr Arg Leu Ser Thr Thr Cys Ile Leu Asn
            820             825             830

Asn
```

```
<210> SEQ ID NO 8
<211> LENGTH: 301
<212> TYPE: PRT
<213> ORGANISM: Artificial Sequence
<220> FEATURE:
<223> OTHER INFORMATION: Caf1R

<400> SEQUENCE: 8

Met Leu Lys Gln Met Thr Val Asn Ser Ile Ile Gln Tyr Ile Glu Glu
1               5                   10                  15

Asn Leu Glu Ser Lys Phe Ile Asn Ile Asp Cys Leu Val Leu Tyr Ser
                20                  25                  30

Gly Phe Ser Arg Arg Tyr Leu Gln Ile Ser Phe Lys Glu Tyr Val Gly
            35                  40                  45

Met Pro Ile Gly Thr Tyr Ile Arg Val Arg Arg Ala Ser Arg Ala Ala
        50                  55                  60

Ala Leu Leu Arg Leu Thr Arg Leu Thr Ile Ile Glu Ile Ser Ala Lys
65                  70                  75                  80

Leu Phe Tyr Asp Ser Gln Gln Thr Phe Thr Arg Glu Phe Lys Lys Ile
                85                  90                  95

Phe Gly Tyr Thr Pro Arg Gln Tyr Arg Met Ile Pro Phe Trp Ser Phe
            100                 105                 110

Lys Gly Leu Leu Gly Arg Arg Glu Ile Asn Cys Glu Tyr Leu Gln Pro
        115                 120                 125

Arg Ile Cys Tyr Leu Lys Glu Arg Asn Ile Ile Gly Gln Cys Phe Asn
130                 135                 140

Phe Arg Asp Leu Val Phe Tyr Ser Gly Ile Asp Ser Lys Cys Arg Leu
145                 150                 155                 160

Gly Lys Leu Tyr Asp Ser Leu Lys Lys Asn Thr Ala Ile Thr Val Ser
                165                 170                 175

Asn Arg Ile Pro Phe His Asp Lys Thr Asn Asp Ile Ile Ala Arg Thr
            180                 185                 190

Val Val Trp Asp Arg Asn Lys His Phe Ser Asp Ser Glu Ile Lys Val
        195                 200                 205

Asp Lys Gly Leu Tyr Ala Tyr Phe Phe Phe Asn Asp Thr Tyr Asp Gln
210                 215                 220

Tyr Val His His Met Tyr Asn Ile Tyr Tyr Asn Ser Leu Pro Ile Tyr
225                 230                 235                 240

Asn Leu Asn Lys Arg Asp Gly Tyr Asp Val Glu Val Ile Lys Arg Arg
                245                 250                 255

Asn Asp Asn Thr Ile Asp Cys His Tyr Phe Leu Pro Ile Tyr Cys Asp
            260                 265                 270

Asp Met Glu Phe Tyr Asn Glu Met Gln Val Tyr His Asn Asn Ile Val
        275                 280                 285

Lys Pro Glu Met Ser Val Thr Leu Gly Leu Pro Lys Ser
290                 295                 300

<210> SEQ ID NO 9
<211> LENGTH: 166
<212> TYPE: PRT
<213> ORGANISM: Salmonella enterica

<400> SEQUENCE: 9

Met Lys Ser Ile Lys Lys Leu Ile Ile Ala Ser Ala Leu Ser Met Met
1               5                   10                  15

Ala Ala Ser Cys Tyr Ala Gly Ser Phe Leu Pro Asn Ser Glu Gln Gln
```

```
                    20                  25                  30

Lys Ser Val Asp Ile Val Phe Ser Ser Pro Gln Asp Leu Thr Val Ser
            35                  40                  45

Leu Ile Pro Val Ser Gly Leu Lys Ala Gly Lys Asn Ala Pro Ser Ala
        50                  55                  60

Lys Ile Ala Lys Leu Val Val Asn Ser Thr Thr Leu Lys Glu Phe Gly
65                  70                  75                  80

Val Arg Gly Ile Ser Asn Asn Val Val Asp Ser Thr Gly Thr Ala Trp
                85                  90                  95

Arg Val Ala Gly Lys Asn Thr Gly Lys Glu Ile Gly Val Gly Leu Ser
            100                 105                 110

Ser Asp Ser Leu Arg Arg Ser Asp Ser Thr Glu Lys Trp Asn Gly Val
        115                 120                 125

Asn Trp Met Thr Phe Asn Ser Asn Asp Thr Leu Asp Ile Val Leu Thr
    130                 135                 140

Gly Pro Ala Gln Asn Val Thr Ala Asp Thr Tyr Pro Ile Thr Leu Asp
145                 150                 155                 160

Val Val Gly Tyr Gln Pro
                165

<210> SEQ ID NO 10
<211> LENGTH: 501
<212> TYPE: DNA
<213> ORGANISM: Salmonella enterica

<400> SEQUENCE: 10
atgaaaagca taaaaaatt gattatcgca agtgcgttga gcatgatggc tgctagttgt      60
tatgctggct cattttttgcc gaactcagag caacaaaaat cagtggatat tgtgttttcc    120
tctccccaag atttaaccgt atcgcttatt ccagtgtcgg gcttaaaggc tgggaaaaat    180
gctcctagcg cgaaaattgc gaagcttgta gttaattcta ctactcttaa agaattcggg    240 gtcagggga tttctaacaa cgtggtagac agtactggca ctgcatggcg tgtagctggt     300
aaaaatactg gtaaagagat cggtgtgggc ttatcaagtg acagtcttag aagatctgat    360
agcacggaaa aatggaatgg ggtgaactgg atgacctta atagcaatga cacacttgat    420
attgtcctga caggaccggc gcagaatgtc acagctgaca cgtacccaat aactttagac    480
gtagtgggat atcaacctta a                                              501

<210> SEQ ID NO 11
<211> LENGTH: 161
<212> TYPE: PRT
<213> ORGANISM: Escherichia coli

<400> SEQUENCE: 11

Met Lys Lys Leu Ala Ile Ile Gly Ala Thr Ser Val Met Met Met Thr
1               5                   10                  15

Gly Thr Ala Gln Ala Asn Phe Ser Ser Gly Thr Asn Gly Lys Val
                20                  25                  30

Asp Leu Thr Ile Thr Glu Glu Cys Arg Val Thr Val Glu Ser Lys Ser
            35                  40                  45

Glu Ser Phe Leu Arg Ser Gly Leu Val Ala Asn Arg His Ile Thr Asn
        50                  55                  60

Leu Gly Ile Gln Ser Thr Gly Cys Gly Thr Gly Gln Arg Val Ala Leu
65                  70                  75                  80

Lys Leu Gly Ala Gly Ser Tyr Asp Asp Thr Asn Gly Ala His Met Thr
```

His Glu Asn Gly Thr Asp Lys Leu Leu Val Ser Met Gly Ser Ala Thr
            100                 105                 110

Gly Asp Gly Thr Gln Asp Gly Gly Val Tyr Tyr Ile Asn Arg Asp Gly
        115                 120                 125

Asn Trp Asn Gly Gln Met Val Phe Ile Val Arg Asn Asp Gln Gln His
    130                 135                 140

Leu Pro Thr Gly Lys Tyr Thr Leu Asn Leu Glu Gly Gly Phe Trp Thr
145                 150                 155                 160

Lys

<210> SEQ ID NO 12
<211> LENGTH: 456
<212> TYPE: DNA
<213> ORGANISM: Escherichia coli

<400> SEQUENCE: 12
atgaaaaaat tagcgatcat aggcgcaacc agcgtaatga tgatgaccgg caccgctcaa      60
gccaatttta ccagcagcgg caccaacggg aaggtcgacc tgactataac cgaagaatgc     120
cgcgtgacag tcgagagcaa aagcgagtcg ttcttgcgaa gcggcctggt cgccaacagg     180
cacatcacta acctcgggat ccaatccacg gggtgtggga caggacaacg tgtcgcgctc     240
aagcttggcg cgggctcgta cgacgacacg aacgggcgc acatgacgca cgaaaacggc     300
actgacaagc ttctggtgag tatgggctct gcgacgggcg atgggaccca agacggcggt     360
gtatattata tcaaccggga cggaactgga acgggcagat ggtgttcatc gtacgaaatg     420
accaacagca cctaccaacc ggcaagtaca ccctga                              456

<210> SEQ ID NO 13
<211> LENGTH: 182
<212> TYPE: PRT
<213> ORGANISM: Escherichia coli

<400> SEQUENCE: 13

Met Lys Ile Lys Thr Leu Ala Ile Val Val Leu Ser Ala Leu Ser Leu
1               5                   10                  15

Ser Ser Thr Ala Ala Leu Ala Ala Thr Thr Val Asn Gly Gly Thr
                20                  25                  30

Val His Phe Lys Gly Glu Val Asn Ala Ala Cys Ala Val Asp Ala
            35                  40                  45

Gly Ser Val Asp Gln Thr Val Gln Leu Gly Gln Val Arg Thr Ala Ser
    50                  55                  60

Leu Ala Gln Glu Gly Ala Thr Ser Ser Ala Val Gly Phe Asn Ile Gln
65                  70                  75                  80

Leu Asn Asp Cys Asp Thr Asn Val Ala Ser Lys Ala Ala Val Ala Phe
                85                  90                  95

Leu Gly Thr Ala Ile Asp Ala Gly His Thr Asn Val Leu Ala Leu Gln
            100                 105                 110

Ser Ser Ala Ala Gly Ser Ala Thr Asn Val Gly Val Gln Ile Leu Asp
        115                 120                 125

Arg Thr Gly Ala Ala Leu Ala Leu Asp Gly Ala Thr Phe Ser Ser Glu
    130                 135                 140

Thr Thr Leu Asn Asn Gly Thr Asn Thr Ile Pro Phe Gln Ala Arg Tyr
145                 150                 155                 160

Phe Ala Thr Gly Ala Ala Thr Ser Gly Ala Ala Asn Ala Asp Ala Thr

Phe Lys Val Gln Tyr Gln
        180

<210> SEQ ID NO 14
<211> LENGTH: 549
<212> TYPE: DNA
<213> ORGANISM: Escherichia coli

<400> SEQUENCE: 14

```
atgaaaatta aaactctggc aatcgttgtt ctgtcggctc tgtccctcag ttctacagcg     60
gctctggccg ctgccacgac ggtaaatggt gggaccgttc actttaaagg ggaagttgtt    120
aacgccgctt gcgcagttga tgcaggctct gttgatcaaa ccgttcagtt aggacaggtt    180
cgtaccgcat cgctggcaca ggaaggagcg accagttctg ctgtcggttt taacattcag    240
ctgaatgatt gcgataccaa tgttgcatct aaagccgctg ttgccttttt aggtacggcg    300
attgatgcgg tcataccaa cgttctggct ctgcagagtt cagctgcggg tagcgcaaca    360
aacgttggtg tgcagatcct ggacagaacg ggtgctgcgc tggcgctgga cggtgcgaca    420
tttagttcag aaacaaccct gaataacgga accaacacca ttccgttcca ggcgcgttat    480
tttgcaaccg gtgccgcaac ctcgggtgct gctaatgcgg atgcgacctt caaggttcag    540
tatcaataa                                                             549
```

<210> SEQ ID NO 15
<211> LENGTH: 185
<212> TYPE: PRT
<213> ORGANISM: Escherichia coli

<400> SEQUENCE: 15

Met Ile Lys Ser Val Ile Ala Gly Ala Val Ala Met Ala Val Val Ser
1               5                   10                  15

Phe Gly Val Asn Asn Ala Ala Pro Thr Ile Pro Gln Gly Gln Gly Lys
            20                  25                  30

Val Thr Phe Asn Gly Thr Val Val Asp Ala Pro Cys Ser Ile Ser Gln
        35                  40                  45

Lys Ser Ala Asp Gln Ser Ile Asp Phe Gly Gln Leu Ser Lys Ser Phe
    50                  55                  60

Leu Glu Ala Gly Gly Val Ser Lys Pro Met Asp Leu Asp Ile Glu Leu
65                  70                  75                  80

Val Asn Cys Asp Ile Thr Ala Phe Lys Gly Gly Asn Gly Ala Lys Lys
                85                  90                  95

Gly Thr Val Lys Leu Ala Phe Thr Gly Pro Ile Val Asn Gly His Ser
            100                 105                 110

Asp Glu Leu Asp Thr Asn Gly Gly Thr Gly Thr Ala Ile Val Val Gln
        115                 120                 125

Gly Ala Gly Lys Asn Val Val Phe Asp Gly Ser Glu Gly Asp Ala Asn
    130                 135                 140

Thr Leu Lys Asp Gly Glu Asn Val Leu His Tyr Thr Ala Val Val Lys
145                 150                 155                 160

Lys Ser Ser Ala Val Gly Ala Ala Val Thr Glu Gly Ala Phe Ser Ala
                165                 170                 175

Val Ala Asn Phe Asn Leu Thr Tyr Gln
            180                 185

<210> SEQ ID NO 16

<211> LENGTH: 550
<212> TYPE: DNA
<213> ORGANISM: Escherichia coli

<400> SEQUENCE: 16

```
tgccggtgcg gtagctatgg cagtggtgtc ttttggtgta aataatgctg ctccaactat    60
tccacagggg cagggtaaag taacttttaa cggaactgtt gttgatgctc catgcagcat   120
ttctcagaaa tcagctgatc agtctattga ttttggacag ctttcaaaaa gcttccttga   180
ggcaggaggt gtatccaaac caatggactt agatattgaa ttggttaatt gtgatattac   240
tgcctttaaa ggtggtaatg gcgccaaaaa agggactgtt aagctggctt ttactggccc   300
gatagttaat ggacattctg atgagctaga tacaaatggt ggtacgggca cagctatcgt   360
agttcagggg gcaggtaaaa acgttgtctt cgatggctcc gaaggtgatg ctaataccct   420
gaaagatggt gaaaacgtgc tgcattatac tgctgttgtt aagaagtcgt cagccgttgg   480
tgccgctgtt actgaaggtg ccttctcagc agttgcgaat tcaacctga cttatcagta   540
atactgataa                                                          550
```

<210> SEQ ID NO 17
<211> LENGTH: 246
<212> TYPE: PRT
<213> ORGANISM: Artificial Sequence
<220> FEATURE:
<223> OTHER INFORMATION: SafB

<400> SEQUENCE: 17

```
Met Lys Ile Ile Ser Phe Gly Val Met Ala Ala Val Leu Phe Val Ser
1               5                   10                  15

Asn Ser Ile Thr Pro Pro Val Tyr Ala Ala Glu Gln Lys Leu Ser Leu
            20                  25                  30

Asn Thr Lys Ser Phe Ser Val Lys Leu Gly Ala Thr Arg Val Ile Tyr
        35                  40                  45

His Ala Gly Thr Val Gly Ala Thr Leu Ser Val Ser Asn Pro Gln Asn
    50                  55                  60

Tyr Pro Ile Leu Val Gln Ser Ser Val Lys Ala Asp Lys Ser Ser
65                  70                  75                  80

Pro Ala Pro Phe Leu Val Met Pro Pro Leu Phe Arg Leu Glu Ala Asn
                85                  90                  95

Gln Gln Ser Gln Leu Arg Ile Val Arg Thr Gly Gly Asp Met Pro Thr
            100                 105                 110

Asp Arg Glu Thr Leu Gln Trp Val Cys Val Lys Ala Val Pro Pro Glu
        115                 120                 125

Asn Glu Pro Ser Asp Thr Gln Ala Lys Gly Ala Thr Leu Asp Leu Asn
    130                 135                 140

Leu Ser Ile Asn Val Cys Asp Lys Leu Ile Phe Arg Pro Asp Ala Val
145                 150                 155                 160

Lys Gly Thr Pro Glu Asp Val Ala Gly Asn Leu Arg Trp Val Glu Ala
                165                 170                 175

Gly Asn Lys Leu Lys Val Glu Asn Pro Thr Pro Phe Tyr Met Asn Leu
            180                 185                 190

Ala Ser Val Thr Val Gly Gly Lys Pro Ile Thr Gly Leu Glu Tyr Ile
        195                 200                 205

Pro Pro Phe Ala Asp Lys Thr Leu Asn Met Pro Gly Ser Ala His Gly
    210                 215                 220

Asp Val Glu Trp Arg Val Ile Thr Asp Phe Gly Gly Glu Ser His Pro
```

Phe His Tyr Val Leu Lys
                245

<210> SEQ ID NO 18
<211> LENGTH: 741
<212> TYPE: DNA
<213> ORGANISM: Artificial Sequence
<220> FEATURE:
<223> OTHER INFORMATION: SafB

<400> SEQUENCE: 18

```
atgaaaatta ttagttttgg tgtaatggcg gctgttttat tcgtctctaa ttctataact    60
cctccagtgt atgccgctga gcagaaatta agtttaaaca ctaaatcatt cagcgtgaag   120
ctgggggcta cacgggtgat ttatcacgct ggtacagttg agccacgct  tcggtgagc   180
aacccgcaga attaccctat tttggttcag tcttcagtca aagcagcaga caaaagttcg   240
cctgctcctt ttttggtgat gccgcctcta tttcgtttag aagcgaacca gcagagtcaa   300
ctgcgtattg tccgtactgg tggtgacatg ccaacggatc gtgagacttt acagtgggtc   360
tgtgtaaagg cggtaccacc cgaaaatgaa ccgtcggata cacaggctaa gggcgcgacc   420
cttgacctca atttgtccat caacgtctgt gataagctga ttttccgccc ggatgccgtg   480
aaggggacgc cggaagatgt tgcaggaaat ttaagatggg tggaggcggg caacaaactt   540
aaggtggaga accccacccc gttttacatg aatttagcct ccgtcacagt agggggaaag   600
cccattacag ggcttgagta tatccccccct tttgctgaca aaacactaaa tatgccaggt   660
agtgcccatg gtgatgtcga gtggagagtt attactgact ttggtggtga aagtcatccg   720
ttccactacg tccttaaata a                                             741
```

<210> SEQ ID NO 19
<211> LENGTH: 247
<212> TYPE: PRT
<213> ORGANISM: Artificial Sequence
<220> FEATURE:
<223> OTHER INFORMATION: DraB

<400> SEQUENCE: 19

Met Lys Met Arg Ala Val Ala Val Phe Thr Gly Met Leu Thr Gly Val
1               5                   10                  15

Leu Ser Val Ala Gly Leu Leu Ser Ala Gly Ala Tyr Ala Ala Gly Gly
            20                  25                  30

Glu Gly Asn Met Ser Ala Ser Ala Thr Glu Thr Asn Ala Arg Val Phe
        35                  40                  45

Ser Leu His Leu Gly Ala Thr Arg Val Val Tyr Asn Pro Ala Ser Ser
    50                  55                  60

Gly Glu Thr Leu Thr Val Ile Asn Asp Gln Asp Tyr Pro Met Leu Val
65                  70                  75                  80

Gln Ser Glu Val Leu Ser Glu Asp Gln Lys Ser Pro Ala Pro Phe Val
                85                  90                  95

Val Thr Pro Pro Leu Phe Arg Leu Asp Gly Gln Gln Ser Ser Arg Leu
            100                 105                 110

Arg Ile Val Arg Thr Gly Gly Glu Phe Pro Pro Asp Arg Glu Ser Leu
        115                 120                 125

Gln Trp Ile Cys Val Lys Gly Ile Pro Pro Lys Glu Gly Asp Arg Trp
    130                 135                 140

Ala Glu Gly Lys Asp Gly Glu Lys Lys Ala Asp Lys Val Ser Leu Asn 145                 150                 155                 160
Val Gln Leu Ser Val Ser Ser Cys Ile Lys Leu Phe Val Arg Pro Pro
                    165                 170                 175
Ala Val Lys Gly Arg Pro Asp Asp Val Ala Gly Lys Val Glu Trp Gln
                    180                 185                 190
Arg Ala Gly Asn Arg Leu Lys Gly Val Asn Pro Thr Pro Phe Tyr Ile
                    195                 200                 205
Asn Leu Ser Thr Leu Thr Val Gly Gly Lys Glu Val Lys Glu Arg Glu
            210                 215                 220
Tyr Ile Ala Pro Phe Ser Ser Arg Glu Tyr Pro Leu Pro Ala Gly His
225                 230                 235                 240
Arg Val Arg Phe Ser Gly Arg
                245

<210> SEQ ID NO 20
<211> LENGTH: 744
<212> TYPE: DNA
<213> ORGANISM: Artificial Sequence
<220> FEATURE:
<223> OTHER INFORMATION: DraB

<400> SEQUENCE: 20
atgaaaatgc gggctgtggc tgtgttcacc ggcatgctga cgggagtgtt atcagtggca     60
ggtttgctgt cagcggggc atatgccgcc ggggagaag gaatatgtc tgcatccgcg      120
acggagacaa cgccagagt attctcgctg catctggggg ccacgcgggt ggtttacaac     180
ccggcctcgt cggggagac gctgacggtg attaatgacc aggactatcc gatgctggtg    240
cagtcggagg tgctgagtga ggaccagaag agtccggcgc cttttgtggt gacaccgccg    300
ttgttccgtc ttgatggtca gcagtcgagt cgtctgcgta ttgtcaggac gggcggggag    360
tttccgccag accgtgagag tctgcagtgg atttgcgtga aaggcattcc gccgaaggaa    420
ggtgacaggt gggcggaagg gaaggacggg gagaagaagg ctgacaaagt ctccctgaat    480
gtacagcttt cagtgagcag ctgcatcaag ctgtttgttc gtccgccggc ggtgaagggg    540
cgaccggatg atgtggccgg caaggtggag tggcagaggg ccggcaacag gctgaagggg    600
gttaacccga cgccgtttta catcaacctg tccacgctga cggtgggggg taaggaagtg    660
aaggagcgtg aatatattgc gccgttttcc tcccgtgaat atccgctgcc tgcggggcat    720
cgggtaaggt tcagtggaag gtga                                            744

<210> SEQ ID NO 21
<211> LENGTH: 836
<212> TYPE: PRT
<213> ORGANISM: Artificial Sequence
<220> FEATURE:
<223> OTHER INFORMATION: SafC

<400> SEQUENCE: 21

Met Lys Phe Lys Gln Pro Ala Leu Leu Leu Phe Ile Ala Gly Val Val
1               5                   10                  15
His Cys Ala Asn Ala His Thr Tyr Thr Phe Asp Ala Ser Met Leu Gly
                20                  25                  30
Asp Ala Ala Lys Gly Val Asp Met Ser Leu Phe Asn Gln Gly Leu Gln
            35                  40                  45
Gln Pro Gly Thr Tyr Arg Val Asp Val Met Val Asn Gly Lys Arg Val
        50                  55                  60
Asp Thr Arg Asp Val Val Phe Lys Leu Glu Lys Asp Gly Gln Gly Thr

-continued

```
               65                  70                  75                  80
Pro Val Leu Ala Pro Cys Leu Thr Val Ser Gln Leu Ser Arg Tyr Gly
                    85                  90                  95

Val Lys Thr Glu Asp Tyr Pro Gln Leu Trp Lys Ala Ala Lys Pro Pro
                100                 105                 110

Asp Glu Cys Ala Asp Leu Thr Ala Ile Pro Gln Ala Lys Ala Val Leu
                115                 120                 125

Asp Ile Asn Asn Gln Gln Leu Gln Leu Ser Ile Pro Gln Leu Ala Leu
            130                 135                 140

Arg Pro Glu Phe Lys Gly Ile Ala Pro Glu Asp Leu Trp Asp Asp Gly
145                 150                 155                 160

Ile Pro Ala Phe Leu Met Asn Tyr Ser Ala Arg Thr Gln Thr Asp
                165                 170                 175

Tyr Lys Met Asp Met Val Gly Arg Asp Asn Ser Ser Trp Val Gln Leu
                180                 185                 190

Gln Pro Gly Ile Asn Ile Gly Ala Trp Arg Val Arg Asn Ala Thr Ser
                195                 200                 205

Trp Gln Arg Ser Ser Gln Leu Ser Gly Lys Trp Gln Ala Ala Tyr Thr
            210                 215                 220

Tyr Ala Glu Arg Gly Leu Tyr Ser Leu Lys Ser Arg Leu Thr Leu Gly
225                 230                 235                 240

Gln Lys Thr Ser Gln Gly Glu Ile Phe Asp Ser Val Pro Phe Thr Gly
                245                 250                 255

Val Met Leu Ala Ser Asp Asp Asn Met Val Pro Tyr Ser Glu Arg Gln
                260                 265                 270

Phe Ala Pro Val Val Arg Gly Ile Ala Arg Thr Gln Ala Arg Val Glu
            275                 280                 285

Val Lys Gln Asn Gly Tyr Thr Ile Tyr Asn Thr Thr Val Ala Pro Gly
            290                 295                 300

Pro Phe Ala Leu Arg Asp Leu Ser Val Thr Asp Ser Ser Gly Asp Leu
305                 310                 315                 320

His Val Thr Val Trp Glu Ala Asp Gly Ser Thr Gln Met Phe Val Val
                325                 330                 335

Pro Tyr Gln Thr Pro Ala Ile Ala Leu His Gln Gly Tyr Leu Lys Tyr
                340                 345                 350

Ser Leu Leu Ala Gly Arg Tyr Arg Ser Ser Asp Ser Ala Thr Asp Lys
            355                 360                 365

Arg Gln Ile Ala Gln Ala Thr Leu Met Tyr Gly Leu Pro Trp Asn Leu
370                 375                 380

Thr Ala Tyr Gly Gly Ile Gln Ser Ala Thr His Asn Gln Ala Ala Leu
385                 390                 395                 400

Leu Gly Leu Gly Gly Ser Leu Gly Arg Trp Gly Ser Leu Ser Val Asp
                405                 410                 415

Gly Ser Asp Thr His Ser Gln Arg Gln Gly Glu Ala Val Gln Gln Gly
                420                 425                 430

Ala Ser Trp Arg Leu Arg Tyr Ser Asn Gln Leu Thr Ala Thr Gly Thr
            435                 440                 445

Asn Phe Phe Leu Thr Arg Trp Gln Tyr Ala Ser Gln Gly Tyr Asn Thr
450                 455                 460

Leu Ser Asp Val Leu Asp Ser Tyr Arg His Asn Gly Asn Arg Leu Trp
465                 470                 475                 480

Ser Trp Arg Glu Asn Leu Gln Pro Ser Ser Arg Thr Thr Leu Met Leu
                485                 490                 495
```

Ser Gln Ser Trp Gly Arg His Leu Gly Asn Leu Ser Leu Thr Gly Ser
            500                 505                 510

Arg Thr Asp Trp Arg Asn Arg Pro Gly His Asp Ser Tyr Gly Leu
        515                 520                 525

Ser Trp Gly Thr Ser Ile Gly Gly Ser Leu Ser Leu Asn Trp Asn
    530                 535                 540

Gln Asn Arg Thr Leu Trp Arg Asn Gly Ala His Arg Lys Glu Asn Ile
545                 550                 555                 560

Thr Ser Leu Trp Phe Ser Met Pro Leu Ser Arg Trp Thr Gly Asn Asn
                565                 570                 575

Val Ser Ala Ser Trp Gln Met Thr Ser Pro Ser His Gly Gly Gln Thr
            580                 585                 590

Gln Gln Val Gly Val Asn Gly Glu Ala Phe Ser Gln Gln Leu Asp Trp
        595                 600                 605

Glu Val Arg Gln Ser Tyr Arg Ala Asp Ala Pro Pro Gly Gly Gly Asn
    610                 615                 620

Asn Ser Ala Leu His Leu Ala Trp Asn Gly Asp Tyr Gly Leu Leu Gly
625                 630                 635                 640

Gly Asp Tyr Ser Tyr Ser Arg Ala Met Arg Gln Met Gly Val Asn Ile
                645                 650                 655

Ala Gly Gly Ile Val Ile His His His Gly Val Thr Leu Gly Gln Pro
            660                 665                 670

Leu Gln Gly Ser Val Ala Leu Val Glu Ala Pro Gly Ala Ser Gly Val
        675                 680                 685

Pro Val Gly Gly Trp Pro Gly Val Lys Thr Asp Phe Arg Gly Asp Thr
    690                 695                 700

Thr Val Gly Asn Leu Asn Val Tyr Gln Glu Asn Thr Val Ser Leu Asp
705                 710                 715                 720

Pro Ser Arg Leu Pro Asp Asp Ala Glu Val Thr Gln Thr Asp Val Arg
                725                 730                 735

Val Val Pro Thr Glu Gly Ala Val Val Glu Ala Lys Phe His Thr Arg
            740                 745                 750

Ile Gly Ala Arg Ala Leu Met Thr Leu Lys Arg Glu Asp Gly Ser Ala
        755                 760                 765

Ile Pro Phe Gly Ala Gln Val Thr Val Asn Gly Gln Asp Gly Ser Ala
    770                 775                 780

Ala Leu Val Asp Thr Asp Ser Gln Val Tyr Leu Thr Gly Leu Ala Asp
785                 790                 795                 800

Lys Gly Glu Leu Thr Val Lys Trp Gly Ala Gln Gln Cys Arg Val Asn
                805                 810                 815

Tyr Arg Leu Pro Ala His Lys Gly Ile Ala Gly Leu Tyr Gln Met Ser
            820                 825                 830

Gly Leu Cys Arg
        835

<210> SEQ ID NO 22
<211> LENGTH: 2511
<212> TYPE: DNA
<213> ORGANISM: Artificial Sequence
<220> FEATURE:
<223> OTHER INFORMATION: SafC

<400> SEQUENCE: 22
atgaagttca aacaacctgc cttgctactg ttcatcgcgg gagtggttca ttgcgcaaat        60

-continued

```
gcgcacactt acacattcga tgcatcaatg ttgggcgatg cagcgaaagg ggttgatatg      120 tcgctctttta accaggggtt acaacagcca gggacttatc gcgtggacgt gatggtgaat      180
ggtaaacgtg tcgacacccg tgatgtggtg ttcaaattgg aaaaggatgg gcaaggaacg      240
cctgttctgg ctccttgttt gacggtcagt cagctttcac gctacggcgt aaaaacggaa      300
gattaccctc agttgtggaa agcagcaaag cccccagatg agtgtgcgga tctgaccgcc      360
attccacagg ctaaagcggt actggatatc aataatcagc aactgcaact gagtattccg      420
cagttggcgt tgcgtccgga atttaagggg atcgctccag aagatctttg ggatgatggt      480
attccggcgt ttctgatgaa ctacagtgcg aggacaacgc agacggatta caaaatggat      540
atggtggggc gtgacaactc ttcctgggta caactgcaac cgggaatcaa tataggtgcg      600
tggcgtgtcc gcaatgcgac cagctggcag cggagtagtc aactgtcggg aagtggcag      660 gcagcatata cctatgctga cgtggactg tactcactaa aaagtcgtct gactctgggg      720
caaaagactt cgcaggggga gatatttgat agtgtgccat ttaccggtgt gatgttggca      780
tcggatgaca acatggtgcc ctacagtgag cggcagtttg ctccggtagt gcgtgggatt      840
gcccgcacgc aggctcgggt ggaggtcaaa cagaatggtt acaccattta caacaccact      900
gtggcgcccg gaccgtttgc actgcgggat ctgtcggtaa cagacagtag tggtgatctg      960
catgtcaccg tgtgggaggc cgatggcagt acacaaatgt tgtggtgcc gtatcagacc     1020 ccggcgatag cactgcacca gggatatttg aagtacagcc tgttggcggg ccgataccga     1080
tcgtcagact ctgcaacgga taagcggcag atcgcgcagg ctacgttgat gtatggtctg     1140
ccgtggaatc tcactgcata cggcggtata cagagtgcaa cgcataatca agctgcattg     1200 cttggttttgg gggatctct cgggcggtgg gggagtttat ctgtcgatgg aagcgacaca     1260
cacagtcagc gtcaggggga ggcggtacag caaggagcct cctggcgact gcgttacagc     1320
aaccagctga ctgcgacggg gacaaatttt tttctgacga gatggcagta tgcctcgcag     1380
ggctataaca ccctatccga tgtgctcgac agttatcgac ataatggcaa ccgtctatgg     1440
tcgtggcggg aaaatttgca gccgagctcg cgtactaccc tgatgttgag tcagtcatgg     1500
gggaggcatt tgggcaatct gagtttaacc ggttcccgta ccgactggcg taatcgcccc     1560
ggtcatgatg acagctacgg actgagttgg ggaacctcta tcggaggggg ctcgctgtca     1620
ttgaactgga atcaaaacag aacgctgtgg cgcaatggcg cgcaccgtaa agagaacata     1680
accagcctgt ggttcagtat gccattaagc cgctggacgg ggaataatgt aagtgctagt     1740
tggcagatga cttcaccatc acacggtggt cagacgcaac aagtgggggt caacggagag     1800
gcattcagtc agcaactgga ttgggaggtg cgtcagagtt accgtgccga tgccccgcca     1860
ggtggtggta ataacagcgc attgcacttg gcatggaatg gggattacgg cctgttaggt     1920
ggtgactata gctacagccg ggcgatgcgc cagatgggag tcaatatcgc gggaggtata     1980
gttatccacc atcatggtgt gacgctgggg caacctttgc aaggctcagt ggcgctggtt     2040
gaagcgccag gggcctcggg ggtgccagtt ggcggctggc ctggcgttaa gacggatttt     2100
cgtggcgaca ccacagtggg caacctgaac gtctatcagg agaatacagt cagcctcgat     2160
ccgtcgcgac taccgatga cgcagagagtc acacaaaccg atgtgcgcgt ggtgccaacc     2220 gaagggggcgg tggtggaagc gaagtttcac actcgcatcg gggccagggc actgatgacg     2280
ctgaaacggg aagatggtag cgccattcct ttcggggcgc aggttacagt caatgggcag     2340
gatggcagtg ctgctctggt ggatactgat agccaggttt atctcactgg tttggcggat     2400
aagggcgaac tgacggtgaa atggggagca cagcaatgtc gggttaacta ccgcctacct     2460
```
gcccacaagg gaatcgcggg cttgtatcaa atgagcggtc tctgcagata g            2511

<210> SEQ ID NO 23
<211> LENGTH: 859
<212> TYPE: PRT
<213> ORGANISM: Artificial Sequence
<220> FEATURE:
<223> OTHER INFORMATION: DraC

<400> SEQUENCE: 23

Met Arg Asp Thr Ser Ser Gly Arg Met Arg Thr Gly Val Thr Gly Leu
1               5                   10                  15

Ala Leu Ala Val Met Val Ala Cys Val Met Phe Arg Ala Glu Ser Gly
            20                  25                  30

Ile Ala Arg Thr Tyr Ser Phe Asp Ala Ala Met Leu Lys Gly Gly Gly
        35                  40                  45

Lys Gly Val Asp Leu Thr Leu Phe Glu Glu Gly Gly Gln Leu Pro Gly
    50                  55                  60

Ile Tyr Pro Val Asp Ile Ile Leu Asn Gly Ser Arg Val Asp Ser Gln
65                  70                  75                  80

Glu Met Ala Phe His Ala Glu Arg Asp Ala Glu Gly Arg Pro Tyr Leu
                85                  90                  95

Lys Thr Cys Leu Thr Arg Glu Met Leu Ala Arg Tyr Gly Val Arg Ile
            100                 105                 110

Glu Glu Tyr Pro Ala Leu Phe Arg Ala Ser Gly Glu Gly Arg Gly Ala
        115                 120                 125

Ser Val Ala Glu Glu Ala Cys Ala Asp Leu Thr Ala Ile Pro Gln Ala
    130                 135                 140

Thr Glu Ser Tyr Gln Phe Ala Ala Gln Gln Leu Val Leu Gly Ile Pro
145                 150                 155                 160

Gln Val Ala Pro Ser Ala Ala Glu Gly Asp Trp Pro Glu Ala Leu Trp
                165                 170                 175

Asp Asp Gly Ile Pro Ala Phe Leu Leu Asn Trp Gln Ala Asn Ala Gly
            180                 185                 190

Arg Ser Glu Tyr Arg Gly Tyr Gly Lys Arg Val Thr Asp Ser Tyr Trp
        195                 200                 205

Val Ser Leu Gln Pro Gly Ile Asn Ile Gly Pro Trp Arg Val Arg Asn
    210                 215                 220

Leu Thr Thr Trp Asn Arg Ser Ser Gly Gln Ser Gly Lys Trp Glu Ser
225                 230                 235                 240

Ser Tyr Ile Arg Ala Glu Arg Gly Leu Asn Gly Ile Lys Ser Arg Leu
                245                 250                 255

Thr Leu Gly Glu Asp Tyr Thr Pro Ser Asp Ile Phe Ser Val Pro
            260                 265                 270

Phe Arg Gly Ala Met Met Ser Ser Asp Glu Ser Met Val Pro Tyr Asn
        275                 280                 285

Leu Arg Glu Phe Ala Pro Val Val Arg Gly Ile Ala Arg Thr Gln Ala
    290                 295                 300

Arg Ile Glu Val Arg Gln Asn Gly Tyr Leu Ile Gln Ser Gln Thr Val
305                 310                 315                 320

Ala Pro Gly Ala Phe Ala Leu Thr Asp Leu Pro Val Thr Gly Ser Gly
                325                 330                 335

Ser Asp Leu Gln Val Thr Val Leu Glu Ser Asp Gly Thr Ala Gln Val
            340                 345                 350

```
Phe Thr Val Pro Phe Thr Thr Pro Ala Ile Ala Leu Arg Glu Gly Tyr
            355                 360                 365

Leu Lys Tyr Asn Val Thr Ala Gly Gln Tyr Arg Ser Ser Asp Asp Ala
    370                 375                 380

Val Glu His Thr Ser Leu Gly Gln Val Thr Ala Met Tyr Gly Leu Pro
385                 390                 395                 400

Trp Gly Leu Thr Val Tyr Gly Gly Leu Gln Gly Ala Asp Asp Tyr Gln
                405                 410                 415

Ser Ala Ala Leu Gly Leu Gly Trp Ser Leu Gly Arg Leu Gly Ala Val
                420                 425                 430

Ser Leu Asp Thr Thr His Ser Arg Gly Gln Gln Lys Gly His Asp Tyr
            435                 440                 445

Glu Thr Gly Asp Thr Trp Arg Ile Arg Tyr Asn Lys Ser Phe Glu Leu
    450                 455                 460

Thr Gly Thr Ser Phe Thr Ala Ala Ser Tyr Gln Tyr Ser Ser Asp Gly
465                 470                 475                 480

Tyr His Thr Leu Pro Asp Val Leu Asp Thr Trp Arg Asp Asp Arg Tyr
                485                 490                 495

Ala Tyr Arg His Thr Glu Asn Arg Ser Arg Arg Thr Thr Leu Ser Leu
            500                 505                 510

Ser Gln Ser Leu Gly Gln Trp Gly Tyr Val Gly Leu Asn Gly Ser Arg
    515                 520                 525

Asp Glu Tyr Arg Asp Arg Pro His Arg Asp Tyr Phe Gly Ala Ser Tyr
                535                 540
        530

Ser Thr Ser Trp Asn Asn Ile Ser Leu Ser Val Asn Trp Ser Arg Asn
545                 550                 555                 560

Arg Asn Ser Gly Gly Tyr Tyr Gly Gly Trp Ser Arg Thr Glu Asp Ser
                565                 570                 575

Val Ser Met Trp Met Ser Val Pro Leu Gly Arg Trp Phe Gly Gly Ala
                580                 585                 590

Asp Asn Asp Ile Ser Thr Thr Ala Gln Met Gln Arg Ser Thr Gly Gln
            595                 600                 605

Asp Thr Arg Tyr Glu Ala Gly Leu Asn Gly Arg Ala Phe Asp Arg Arg
    610                 615                 620

Leu Tyr Trp Asp Val Arg Glu Gln Met Val Pro Gly Ser Glu Ser His
625                 630                 635                 640

Ala Asp Thr Ser Arg Leu Asn Leu Thr Trp Tyr Gly Thr Tyr Gly Glu
                645                 650                 655

Leu Thr Gly Met Tyr Ser Tyr Ser Ser Thr Met Arg Gln Leu Asn Ala
                660                 665                 670

Gly Met Ser Gly Ser Met Val Ala His Ser Glu Gly Val Thr Phe Gly
            675                 680                 685

Gln Arg Thr Gly Asp Thr Val Ala Leu Ile Ala Ala Pro Gly Val Ser
    690                 695                 700

Gly Ala Ser Val Gly Gly Trp Pro Gly Val Arg Thr Asp Phe Arg Gly
705                 710                 715                 720

Tyr Thr Leu Ala Gly Tyr Ala Ser Pro Tyr Gln Glu Asn Val Leu Thr
                725                 730                 735

Leu Asp Pro Thr Thr Phe Pro Glu Asp Ala Glu Val Pro Gln Thr Asp
                740                 745                 750

Ser Arg Val Val Pro Thr Lys Gly Ala Val Val Arg Ala Gly Phe Arg
            755                 760                 765

Thr Arg Val Gly Gly Arg Ala Leu Val Ser Leu Ala Arg Gln Asp Gly
```

```
                   770                 775                 780
Thr Pro Leu Pro Phe Gly Ala Val Val Thr Val Glu Gly Glu Ala Gly
785                 790                 795                 800

Gln Ala Ala Gly Ser Ala Gly Val Val Gly Asp Arg Gly Glu Val Tyr
            805                 810                 815

Leu Ser Gly Leu Lys Glu Ser Gly Lys Leu Lys Ala Gln Trp Gly Glu
        820                 825                 830

Asn Ser Leu Cys His Ala Asp Tyr Arg Leu Pro Glu Glu Lys Gly Pro
        835                 840                 845

Ala Gly Ile Phe Leu Thr Arg Thr Val Cys Met
    850                 855

<210> SEQ ID NO 24
<211> LENGTH: 2580
<212> TYPE: DNA
<213> ORGANISM: Artificial Sequence
<220> FEATURE:
<223> OTHER INFORMATION: DraC

<400> SEQUENCE: 24
```

| | | | | | |
|---|---|---|---|---|---|
| atgcgtgata | cttcttcagg | gcggatgaga | acgggggtga | cagggctggc | gctggctgtg | 60 |
| atggtggcct | gtgtgatgtt | cgtgcggag | agtggtattg | cgcgcaccta | ctcctttgat | 120 |
| gcggccatgc | tgaaaggtgg | cgggaagggg | gtggacctga | ccctgtttga | ggaaggtggg | 180 |
| cagttacccg | gcatttatcc | ggttgacatt | atcctgaatg | gttcccgtgt | ggattcacag | 240 |
| gagatggcct | tcacgcgga | gagggacgcg | gagggcaggc | cttatctgaa | gacctgtctg | 300 |
| acccgtgaga | tgctggcgcg | ttacggggtc | aggattgagg | aatatccggc | gttgttccgt | 360 |
| gcatccggag | agggtcgtgg | tgcctccgtg | gcggaggagg | cctgtgctga | cctgacggcg | 420 |
| ataccgcagg | ccacggagag | ttatcagttt | gctgcccagc | aactggttct | gggtatccct | 480 |
| caggtggcac | cgtccgcagc | tgaggggat | tggccgagg | cgttatggga | tgatggcatt | 540 |
| ccggcttttc | tgctgaactg | gcaggcgaat | gcggggcgca | gtgagtaccg | gggttacggg | 600 |
| aagcgtgtca | cggacagtta | ctgggtcagt | ctgcagccgg | aatcaacat | tggaccctgg | 660 |
| cgtgtgagga | acctgaccac | ctggaacagg | tcatccggtc | agtcgggaaa | tgggagagt | 720 |
| tcatacatac | gtgctgagcg | ggggctgaac | gggataaaga | gtcgcctgac | gctgggtgag | 780 |
| gattacacgc | cgtcagacat | ttttgacagt | gtgccttcc | gggggcgat | gatgagttct | 840 |
| gatgagagta | tggtgcctta | taacctgcgt | gaatttgcgc | cggttgtacg | tggcattgcc | 900 |
| cgcacgcagg | ccaggataga | ggtgcgtcag | aacggctatc | tgatacaaag | tcagacggtg | 960 |
| gcgccggggg | catttgccct | gacggacctg | ccggtgacgg | ggtccggcag | tgacctgcag | 1020 |
| gtgacggtgc | tggaatcaga | cgggacggcg | caggttttca | cggtgccgtt | caccacgccg | 1080 |
| gccattgcgc | tgcgtgaggg | gtacctgaag | tacaacgtca | cggcgggtca | gtaccgttca | 1140 |
| tcggatgatg | cggttgagca | cacgtcgctg | gacaggtga | cggccatgta | cggtctgccg | 1200 |
| tgggggctga | cggtgtacgg | ggggcttcag | ggagcggacg | attaccagtc | tgcggctctg | 1260 |
| gggcttggct | ggtcactggg | gcgtctgggg | gcggtgtcgc | tggacacgac | gcactcccgg | 1320 |
| gggcagcaga | agggacatga | ttatgagacc | ggtgacacct | ggcgtatccg | ttataacaag | 1380 |
| tcgtttgagc | tgacggggac | gagttttacg | gcagcgagtt | atcagtactc | atcggatggt | 1440 |
| taccatacgc | tgccggacgt | gctggacacc | tggcgtgatg | accggtacgc | ataccgtcac | 1500 |
| acggagaacc | ggagtcgccg | taccacgctg | agtctgagtc | agtccctggg | tcagtggggc | 1560 |

```
tatgtgggac tgaacggcag ccgggatgag taccgtgaca gaccgcaccg tgattatttt    1620
ggcgcgtcat acagtacgtc ctggaacaat atctcgctgt cggttaactg gtcacgcaac    1680
cgcaacagcg gcggctatta cggtggctgg tcgcgtacgg aagacagtgt cagtatgtgg    1740
atgagtgtgc cgctgggacg ctggtttggg ggggcggata acgatatcag taccacggcg    1800
cagatgcagc gttccacggg acaggatacc cggtatgagg ccgggctgaa cggacgggca    1860
tttgaccgcc ggctgtactg ggatgtccgt gagcagatgg tgccgggcag tgagagccat    1920
gctgacacca gtcgtctgaa cctgacgtgg tacgggacat atggtgaact gacggggatg    1980
tacagttaca gcagcacgat gcgccagctg aacgccggga tgtccggcag catggttgcc    2040
cacagtgagg gggtcacctt tggtcagcgg accggggata cggtggcact gattgcggca    2100
ccgggcgtga gtggtgcgtc tgtgggtggc tggccgggtg tgagaacgga tttccggggg    2160
tatacgctgg ccggttatgc gtcaccgtac caggagaacg tgctgacact ggacccgacg    2220
acgtttccgg aggatgcgga agtgccgcag acggacagtc gtgtggtgcc gacgaagggg    2280
gcagtggtcc gggccggatt caggacccgt gtgggtggtc gtgcgctggt gagtctggcc    2340
cgtcaggacg gaacgccgct gccgtttggt gcggtggtga cagttgaggg cgaagcgggt    2400
caggctgcgg gatcagccgg tgtggtggga ccgtggtg aggtgtacct gagcgggctg      2460
aaggaaagcg gtaagctgaa ggcgcagtgg ggagagaaca gtctgtgcca tgcggattac    2520
cgtcttccgg aagagaaggg tcctgcgggg atatttctga cccgtacggt gtgtatgtga    2580
```

<210> SEQ ID NO 25
<211> LENGTH: 300
<212> TYPE: PRT
<213> ORGANISM: Escherichia coli

<400> SEQUENCE: 25

```
Met Lys Arg Val Ile Thr Leu Phe Ala Val Leu Leu Met Gly Trp Ser
1               5                   10                  15

Val Asn Asp Trp Ser Phe Ala Cys Lys Thr Ala Asn Gly Thr Ala Ile
            20                  25                  30

Pro Ile Gly Gly Gly Ser Ala Asn Val Tyr Val Asn Leu Ala Pro Val
        35                  40                  45

Val Asn Val Gly Gln Asn Leu Val Asp Leu Ser Thr Gln Ile Phe
    50                  55                  60

Cys His Asn Asp Tyr Pro Glu Thr Ile Thr Asp Tyr Val Thr Leu Gln
65                  70                  75                  80

Arg Gly Ser Ala Tyr Gly Gly Val Leu Ser Asn Phe Ser Gly Thr Val
                85                  90                  95

Lys Tyr Ser Gly Ser Ser Tyr Pro Phe Pro Thr Thr Ser Glu Thr Pro
            100                 105                 110

Arg Val Val Tyr Asn Ser Arg Thr Asp Lys Pro Trp Pro Val Ala Leu
        115                 120                 125

Tyr Leu Thr Pro Val Ser Ala Gly Gly Val Ala Ile Lys Ala Gly
        130                 135                 140

Ser Leu Ile Ala Val Leu Ile Leu Arg Gln Thr Asn Asn Tyr Asn Ser
145                 150                 155                 160

Asp Asp Phe Gln Phe Val Trp Asn Ile Tyr Ala Asn Asn Asp Val Val
                165                 170                 175

Val Pro Thr Gly Gly Cys Asp Val Ser Ala Arg Asp Val Thr Val Thr
            180                 185                 190

Leu Pro Asp Tyr Pro Gly Ser Val Pro Ile Pro Leu Thr Val Tyr Cys
```

Ala Lys Ser Gln Asn Leu Gly Tyr Tyr Leu Ser Gly Thr Thr Ala Asp
         195                 200                 205
    210                 215                 220

Ala Gly Asn Ser Ile Phe Thr Asn Thr Ala Ser Phe Ser Pro Ala Gln
225                 230                 235                 240

Gly Val Gly Val Gln Leu Thr Arg Asn Gly Thr Ile Ile Pro Ala Asn
                    245                 250                 255

Asn Thr Val Ser Leu Gly Ala Val Gly Thr Ser Ala Val Ser Leu Gly
                260                 265                 270

Leu Thr Ala Asn Tyr Ala Arg Thr Gly Gly Gln Val Thr Ala Gly Asn
                275                 280                 285

Val Gln Ser Ile Ile Gly Val Thr Phe Val Tyr Gln
290                 295                 300

<210> SEQ ID NO 26
<211> LENGTH: 1040
<212> TYPE: DNA
<213> ORGANISM: Escherichia coli

<400> SEQUENCE: 26
taagagtcag cctataccta cagctgaacc cgaagagatg attgtaatga aacgagttat      60
taccctgttt gctgtactgc tgatgggctg gtcggtaaat gactggtcat tcgcctgtaa     120
aaccgccaat ggtaccgcta tccctattgg cggtggcagc gccaatgttt atgtaaacct     180
tgcgcccgtc gtgaatgtgg ggcaaaacct ggtcgtggat ctttcgacgc aaatcttttg     240
ccataacgat tatccggaaa ccattacaga ctatgtcaca ctgcaacgag gctcggctta     300
tggcggcgtg ttatctaatt tttccgggac cgtaaaatat agtggcagta gctatccatt     360
tcctaccacc agcgaaacgc cgcgcgttgt ttataattcg agaacggata gccgtggcc      420 ggtggcgctt tatttgacgc ctgtgagcag tgcgggcggg gtggcgatta agctggctc      480 attaattgcc gtgcttatttt tgcgacagac caacaactat aacagcgatg atttccagtt    540
tgtgtggaat atttacgcca ataatgatgt ggtggtgcct actggcggct gcgatgtttc     600
tgctcgtgat gtcaccgtta ctctgccgga ctaccctggt tcagtgccaa ttcctcttac     660
cgtttattgt gcgaaaagcc aaaacctggg gtattacctc tccggcacaa ccgcagatgc     720
gggcaactcg attttcacca ataccgcgtc gttttcacct gcacagggcg tcggcgtaca     780
gttgacgcgc aacggtacga ttattccagc gaataacacg gtatcgttag gagcagtagg     840
gacttcggcg gtgagtctgg gattaacggc aaattatgca cgtaccggag ggcaggtgac     900
tgcagggaat gtgcaatcga ttattggcgt gacttttgtt tatcaataaa gaaatcacag     960
gacattgcta atgctggtac gcaatattac ctgaagctaa aaacctgcac gttagccctt    1020
tgtaggccag ataagacgcg                                                1040

<210> SEQ ID NO 27
<211> LENGTH: 167
<212> TYPE: PRT
<213> ORGANISM: Escherichia coli

<400> SEQUENCE: 27

Met Lys Trp Cys Lys Arg Gly Tyr Val Leu Ala Ala Ile Leu Ala Leu
1               5                   10                  15

Ala Ser Ala Thr Ile Gln Ala Ala Asp Val Thr Ile Thr Val Asn Gly
                20                  25                  30

Lys Val Val Ala Lys Pro Cys Thr Val Ser Thr Thr Asn Ala Thr Val

```
                 35                  40                  45
Asp Leu Gly Asp Leu Tyr Ser Phe Ser Leu Met Ser Ala Gly Ala Ala
             50                  55                  60

Ser Ala Trp His Asp Val Ala Leu Glu Leu Thr Asn Cys Pro Val Gly
 65                  70                  75                  80

Thr Ser Arg Val Thr Ala Ser Phe Ser Gly Ala Ala Asp Ser Thr Gly
                 85                  90                  95

Tyr Tyr Lys Asn Gln Gly Thr Ala Gln Asn Ile Gln Leu Glu Leu Gln
            100                 105                 110

Asp Asp Ser Gly Asn Thr Leu Asn Thr Gly Ala Thr Lys Thr Val Gln
            115                 120                 125

Val Asp Asp Ser Gln Ser Ala His Phe Pro Leu Gln Val Arg Ala
            130                 135                 140

Leu Thr Val Asn Gly Gly Ala Thr Gln Gly Thr Ile Gln Ala Val Ile
145                 150                 155                 160

Ser Ile Thr Tyr Thr Tyr Ser
                165
```

<210> SEQ ID NO 28
<211> LENGTH: 504
<212> TYPE: DNA
<213> ORGANISM: Escherichia coli

<400> SEQUENCE: 28

```
atgaaatggt gcaaacgtgg gtatgtattg gcggcaatat tggcgctcgc aagtgcgacg      60
atacaggcag ccgatgtcac catcacggtg aacggtaagg tcgtcgccaa accgtgtacg     120
gtttccacca ccaatgccac ggttgatctc ggcgatcttt attctttcag tcttatgtct     180
gccggggcgg catcggcctg gcatgatgtt gcgcttgagt tgactaattg tccggtggga     240
acgtcgaggg tcactgccag cttcagcggg gcagccgaca gtaccggata ttataaaaac     300
caggggaccg cgcaaaacat ccagttagag ctacaggatg acagtggcaa cacattgaat     360
actggcgcaa ccaaaacagt tcaggtggat gattcctcac aatcagcgca cttcccgtta     420
caggtcagag cattgacagt aaatggcgga gccactcagg gaaccattca ggcagtgatt     480
agcatcacct atacctacag ctga                                            504
```

<210> SEQ ID NO 29
<211> LENGTH: 176
<212> TYPE: PRT
<213> ORGANISM: Escherichia coli

<400> SEQUENCE: 29

```
Met Arg Asn Lys Pro Phe Tyr Leu Leu Cys Ala Phe Leu Trp Leu Ala
  1               5                  10                  15

Val Ser His Ala Leu Ala Ala Asp Ser Thr Ile Thr Ile Arg Gly Tyr
             20                  25                  30

Val Arg Asp Asn Gly Cys Ser Val Ala Ala Glu Ser Thr Asn Phe Thr
             35                  40                  45

Val Asp Leu Met Glu Asn Ala Ala Lys Gln Phe Asn Asn Ile Gly Ala
         50                  55                  60

Thr Thr Pro Val Val Pro Phe Arg Ile Leu Leu Ser Pro Cys Gly Asn
 65                  70                  75                  80

Ala Val Ser Ala Val Lys Val Gly Phe Thr Gly Val Ala Asp Ser His
                 85                  90                  95

Asn Ala Asn Leu Leu Ala Leu Glu Asn Thr Val Ser Ala Ala Ser Gly
```

```
                100                 105                 110
Leu Gly Ile Gln Leu Leu Asn Glu Gln Gln Asn Gln Ile Pro Leu Asn
            115                 120                 125

Ala Pro Ser Ser Ala Leu Ser Trp Thr Thr Leu Thr Pro Gly Lys Pro
    130                 135                 140

Asn Thr Leu Asn Phe Tyr Ala Arg Leu Met Ala Thr Gln Val Pro Val
145                 150                 155                 160

Thr Ala Gly His Ile Asn Ala Thr Ala Thr Phe Thr Leu Glu Tyr Gln
                165                 170                 175

<210> SEQ ID NO 30
<211> LENGTH: 531
<212> TYPE: DNA
<213> ORGANISM: Escherichia coli

<400> SEQUENCE: 30
atgagaaaca aaccttttta tcttctgtgc gctttttgt ggctggcggt gagtcacgct      60
ttggctgcgg atagcacgat tactatccgc ggctatgtca gggataacgg ctgtagtgtg    120
gccgctgaat caaccaattt tactgttgat ctgatggaaa acgcggcgaa gcaatttaac    180
aacattggcg cgacgactcc tgttgttcca tttcgtattt tgctgtcacc ctgtggtaat    240
gccgtttctg ccgtaaaggt tgggtttact ggcgttgcag atagccacaa tgccaacctg    300
cttgcacttg aaaatacggt gtcagcggct cgggactgg aatacagct tctgaatgag      360 cagcaaaatc aaatacccct taatgctcca tcgtccgcgc tttcgtggac gaccctgacg    420
ccgggtaaac caaatacgct gaatttttac gcccggctaa tggcgacaca ggtgcctgtc    480
actgcggggc atatcaatgc cacggctacc ttcactcttg aatatcagta a              531

<210> SEQ ID NO 31
<211> LENGTH: 335
<212> TYPE: PRT
<213> ORGANISM: Escherichia coli

<400> SEQUENCE: 31

Met Lys Lys Trp Phe Pro Ala Phe Leu Phe Leu Ser Leu Ser Gly Gly
1               5                   10                  15

Asn Asp Ala Leu Ala Gly Trp His Asn Val Met Phe Tyr Ala Phe Asn
            20                  25                  30

Asp Tyr Leu Thr Thr Asn Ala Gly Asn Val Lys Val Ile Asp Gln Pro
        35                  40                  45

Gln Leu Tyr Ile Pro Trp Asn Thr Gly Ser Ala Thr Ala Thr Tyr Tyr
    50                  55                  60

Ser Cys Ser Gly Pro Glu Phe Ala Ser Gly Val Tyr Phe Gln Glu Tyr
65                  70                  75                  80

Leu Ala Trp Met Val Val Pro Lys His Val Tyr Thr Asn Glu Gly Phe
                85                  90                  95

Asn Ile Phe Leu Asp Val Gln Ser Lys Tyr Gly Trp Ser Met Glu Asn
            100                 105                 110

Glu Asn Asp Lys Asp Phe Tyr Phe Val Asn Gly Tyr Glu Trp Asp
        115                 120                 125

Thr Trp Thr Asn Asn Gly Ala Arg Ile Cys Phe Tyr Pro Gly Asn Met
    130                 135                 140

Lys Gln Leu Asn Asn Lys Phe Asn Asp Leu Val Phe Arg Val Leu Leu
145                 150                 155                 160

Pro Val Asp Leu Pro Lys Gly His Tyr Asn Phe Pro Val Arg Tyr Ile
```

```
                    165                 170                 175
Arg Gly Ile Gln His His Tyr Tyr Asp Leu Trp Gln Asp His Tyr Lys
            180                 185                 190

Met Pro Tyr Asp Gln Ile Lys Gln Leu Pro Ala Thr Asn Thr Leu Met
            195                 200                 205

Leu Ser Phe Asp Asn Val Gly Gly Cys Gln Pro Ser Thr Gln Val Leu
            210                 215                 220

Asn Ile Asp His Gly Ser Ile Val Ile Asp Arg Ala Asn Gly Asn Ile
225                 230                 235                 240

Ala Ser Gln Thr Leu Ser Ile Tyr Cys Asp Val Pro Val Ser Val Lys
            245                 250                 255

Ile Ser Leu Leu Arg Asn Thr Pro Pro Ile Tyr Asn Asn Asn Lys Phe
            260                 265                 270

Ser Val Gly Leu Gly Asn Gly Trp Asp Ser Ile Ile Ser Leu Asp Gly
            275                 280                 285

Val Glu Gln Ser Glu Glu Ile Leu Arg Trp Tyr Thr Ala Gly Ser Lys
            290                 295                 300

Thr Val Lys Ile Glu Ser Arg Leu Tyr Gly Glu Gly Lys Arg Lys
305                 310                 315                 320

Pro Gly Glu Leu Ser Gly Ser Met Thr Met Val Leu Ser Phe Pro
            325                 330                 335

<210> SEQ ID NO 32
<211> LENGTH: 1169
<212> TYPE: DNA
<213> ORGANISM: Escherichia coli

<400> SEQUENCE: 32
ggccagtatg agcatgattt ataactgagt catacctaaa tgaataactg taattacgga      60
agtgatttct gatgaaaaaa tggttccctg cttttttatt tttatccctg tcaggcggta    120
atgatgcttt agctggatgg cacaatgtca tgttttatgc ttttaacgac tatttaacta    180
caaatgctgg taatgttaag gttattgacc aacctcagct atatatacccc tggaatacag   240
gctctgctac agcaacttat tattcgtgct caggtccgga atttgcgagt ggagtgtatt    300
ttcaggagta tctggcctgg atggttgttc ctaaacatgt ctatactaat gaggggttta    360
atatatttct tgatgttcag agcaaatatg gttggtctat ggagaatgaa atgacaaag    420
atttttactt ctttgttaat ggttatgaat gggatacatg gacaaataat ggtgcccgta    480
tatgttccta tcctggaaat atgaagcagt tgaacaataa atttaatgat ttagtattca    540
gggttctttt gccagtagat ctccccaagg gacattataa ttttcctgtg agatatatac    600
gtggaataca gcaccattac tatgatctct ggcaggatca ttataaaatg ccttacgatc    660
agattaagca gctacctgcc actaatacat tgatgttatc attcgataat gttgggggat    720
gccagccgtc aacacaagta cttaatatag accatgggag tattgtgatt gatcgtgcta    780
acggaaatat tgcaagtcag acgctttcaa tttattgcga tgtaccagtt agtgtaaaaa    840
tatctctgct cagaaataca ccaccaatat acaataataa taaattttcg gttgggttag    900
gtaatggctg ggattcgata atatctcttg atggggttga acagagtgag gaaatattac    960
gctggtacac agccggctca aaaacagtaa agattgagag caggttgtat ggtgaagagg   1020
gaaagagaaa acccggggag ctatctggtt ctatgactat ggttctgagt ttcccctgaa   1080
taagatgatg gattatctga ctggctgttc atcagtcgga taatgatgaa aactgatgag   1140
caacaggttg tcgggcaatg tcaggatcc                                      1169
```

<210> SEQ ID NO 33
<211> LENGTH: 167
<212> TYPE: PRT
<213> ORGANISM: Escherichia coli

<400> SEQUENCE: 33

Met Ile Arg Leu Ser Leu Phe Ile Ser Leu Leu Thr Ser Val Ala
1               5                   10                  15

Val Leu Ala Asp Val Gln Ile Asn Ile Arg Gly Asn Val Tyr Ile Pro
            20                  25                  30

Pro Cys Thr Ile Asn Asn Gly Gln Asn Ile Val Val Asp Phe Gly Asn
            35                  40                  45

Ile Asn Pro Glu His Val Asp Asn Ser Arg Gly Glu Val Thr Lys Thr
50                  55                  60

Ile Ser Ile Ser Cys Pro Tyr Lys Ser Gly Ser Leu Trp Ile Lys Val
65                  70                  75                  80

Thr Gly Asn Thr Met Gly Gly Gln Asn Asn Val Leu Ala Thr Asn
                85                  90                  95

Ile Thr His Phe Gly Ile Ala Leu Tyr Gln Gly Lys Gly Met Ser Thr
            100                 105                 110

Pro Leu Ile Leu Gly Asn Gly Ser Gly Asn Gly Tyr Gly Val Thr Ala
            115                 120                 125

Gly Leu Asp Thr Ala Arg Ser Thr Phe Thr Phe Thr Ser Val Pro Phe
        130                 135                 140

Arg Asn Gly Ser Gly Ile Leu Asn Gly Gly Asp Phe Gln Thr Thr Ala
145                 150                 155                 160

Ser Met Ser Met Ile Tyr Asn
                165

<210> SEQ ID NO 34
<211> LENGTH: 504
<212> TYPE: DNA
<213> ORGANISM: Escherichia coli

<400> SEQUENCE: 34
atgattcgtt tatcattatt tatatcgttg cttctgacat cggtcgctgt actggctgat      60
gtgcagatta acatcagggg gaatgtttat atcccccccat gcaccattaa taacgggcag    120
aatattgttg ttgattttgg gaatattaat cctgagcacg tggacaactc acgtggtgaa    180
gtcacaaaaa ccataagcat atcctgtccg tataagagtg gctctctctg gataaaagtt    240
acgggaaata ctatgggagg aggtcagaat aatgtactgg caacaaatat aactcatttt    300
ggtatagcgc tgtatcaggg aaaaggaatg tcaacacctc ttatattagg taatggttca    360
ggaaatggtt acggagtgac agcaggtctg gacacagcac gttcaacgtt caccttttact  420 tcagtgccct ttcgtaatgg cagcgggata ctgaatggcg gggatttcca gaccacggcc    480
agtatgagca tgatttataa ctga                                          504

<210> SEQ ID NO 35
<211> LENGTH: 173
<212> TYPE: PRT
<213> ORGANISM: Escherichia coli

<400> SEQUENCE: 35

Met Lys Lys Ile Arg Gly Leu Cys Leu Pro Val Met Leu Gly Ala Val
1               5                   10                  15

Leu Met Ser Gln His Val His Ala Val Asp Asn Leu Thr Phe Arg Gly
            20                  25                  30

Lys Leu Ile Ile Pro Ala Cys Thr Val Ser Asn Thr Thr Val Asp Trp
            35                  40                  45

Gln Asp Val Glu Ile Gln Thr Leu Ser Gln Asn Gly Asn His Glu Lys
50                  55                  60

Glu Phe Thr Val Asn Met Arg Cys Pro Tyr Asn Leu Gly Thr Met Lys
65                  70                  75                  80

Val Thr Ile Thr Ala Thr Asn Thr Tyr Asn Asn Ala Ile Leu Val Gln
                85                  90                  95

Asn Thr Ser Asn Thr Ser Ser Asp Gly Leu Leu Val Tyr Leu Tyr Asn
            100                 105                 110

Ser Asn Ala Gly Asn Ile Gly Thr Ala Ile Thr Leu Gly Thr Pro Phe
            115                 120                 125

Thr Pro Gly Lys Ile Thr Gly Asn Asn Ala Asp Lys Thr Ile Ser Leu
        130                 135                 140

His Ala Lys Leu Gly Tyr Lys Gly Asn Met Gln Asn Leu Ile Ala Gly
145                 150                 155                 160

Pro Phe Ser Ala Thr Ala Thr Leu Val Ala Ser Tyr Ser
                165                 170

<210> SEQ ID NO 36
<211> LENGTH: 492
<212> TYPE: DNA
<213> ORGANISM: Escherichia coli

<400> SEQUENCE: 36
atgaaaaaga taagaggttt gtgtcttccg gtaatgctgg gggcagtgtt aatgtctcag    60
catgtacatg cagttgataa tctgaccttc agaggaaaac tgattattcc tgcctgtact   120
gtaagcaaca caactgttga ctggcaggat gtagagattc agaccctgag tcaaaatgga   180
aatcacgaaa aagagtttac tgtgaatatg cggtgtccct ataatctggg aacaatgaag   240
gttacgataa cggcaacaaa cacttataac aatgctattt tagttcagaa tacatcaaac   300
acatcttctg atgggttact cgtttatctt tataacagta atgcaggaaa tattgggact   360
gcgataactt tagggactcc atttacgccc ggaaaaatca caggtaataa tgcagataaa   420
actatatcac ttcatgccaa acttggatat aaagggaata tgcagaattt gatagccggt   480
cctttctctg ca                                                      492

<210> SEQ ID NO 37
<211> LENGTH: 178
<212> TYPE: PRT
<213> ORGANISM: Escherichia coli

<400> SEQUENCE: 37

Met Ile Lys Ser Thr Gly Ala Leu Leu Leu Phe Ala Ala Leu Ser Ala
1               5                   10                  15

Gly Gln Ala Ile Ala Ser Asp Val Ala Phe Arg Gly Asn Leu Leu Asp
            20                  25                  30

Arg Pro Cys His Val Ser Gly Asp Ser Leu Asn Lys His Val Val Phe
            35                  40                  45

Lys Thr Arg Ala Ser Arg Asp Phe Trp Tyr Pro Pro Gly Arg Ser Pro
        50                  55                  60

Thr Glu Ser Phe Val Ile Arg Leu Glu Asn Cys His Ala Thr Ala Val
65                  70                  75                  80

```
Gly Lys Ile Val Thr Leu Thr Phe Lys Gly Thr Glu Glu Ala Ala Leu
                85                  90                  95

Pro Gly His Leu Lys Val Thr Gly Val Asn Ala Gly Arg Leu Gly Ile
            100                 105                 110

Ala Leu Leu Asp Thr Asp Gly Ser Ser Leu Leu Lys Pro Gly Thr Ser
        115                 120                 125

His Asn Lys Gly Gln Gly Glu Lys Val Thr Gly Asn Ser Leu Glu Leu
    130                 135                 140

Pro Phe Gly Ala Tyr Val Val Ala Thr Pro Glu Ala Leu Arg Thr Lys
145                 150                 155                 160

Ser Val Val Pro Gly Asp Tyr Glu Ala Thr Ala Thr Phe Glu Leu Thr
                165                 170                 175

Tyr Arg

<210> SEQ ID NO 38
<211> LENGTH: 537
<212> TYPE: DNA
<213> ORGANISM: Escherichia coli

<400> SEQUENCE: 38
atgataaaaa gcacaggcgc tcttttactg tttgccgcac tgtctgccgg acaggcaata      60
gcctcagatg tggcattcag gggtaatctg cttgacagac cctgccatgt gtccggtgac     120
agtctgaata acatgtcgt cttcaaaacc cgggcgtcca gggatttctg gtatccgccc      180
ggacgttcgc cgacagagtc gtttgtcatc aggctggaaa actgccatgc aacagcagtt     240
ggcaaaattg tgaccctgac ctttaagggg acggaagagg cggccctccc gggccatctg     300
aaggtaaccg gagtgaatgc tggccggtta ggcattgcac tgctggacac cgatggcagc     360
agtctgctga aacccggcac ctcccataac aaaggccagg gggaaaaggt taccggaaac     420
agtcttgagc ttcctttcgg cgcgtatgtt gtggcaacgc cggaagccct gcggacgaag     480
agtgtggtac ccggtgatta tgaagcaaca gccacgtttg aattgacata tcgttag       537

<210> SEQ ID NO 39
<211> LENGTH: 4
<212> TYPE: PRT
<213> ORGANISM: Artificial Sequence
<220> FEATURE:
<223> OTHER INFORMATION: Cell adhesion recognition motif derived from
      fibronenctin

<400> SEQUENCE: 39

Arg Gly Asp Ser
1

<210> SEQ ID NO 40
<211> LENGTH: 5
<212> TYPE: PRT
<213> ORGANISM: Artificial Sequence
<220> FEATURE:
<223> OTHER INFORMATION: Cell adhesion recognition motif derived from
      fibronenctin

<400> SEQUENCE: 40

Pro His Ser Arg Asn
1               5

<210> SEQ ID NO 41
<211> LENGTH: 15
<212> TYPE: PRT
<213> ORGANISM: Artificial Sequence
```

```
<220> FEATURE:
<223> OTHER INFORMATION: Cell adhesion recognition motif derived from
      Collagen I

<400> SEQUENCE: 41

Gly Thr Pro Gly Pro Gln Gly Ile Ala Gly Gln Arg Gly Val Val
1               5                   10                  15

<210> SEQ ID NO 42
<211> LENGTH: 7
<212> TYPE: PRT
<213> ORGANISM: Artificial Sequence
<220> FEATURE:
<223> OTHER INFORMATION: Cell adhesion recognition motif derived from
      Collagen IV

<400> SEQUENCE: 42

Met Asn Tyr Tyr Ser Asn Ser
1               5

<210> SEQ ID NO 43
<211> LENGTH: 5
<212> TYPE: PRT
<213> ORGANISM: Artificial Sequence
<220> FEATURE:
<223> OTHER INFORMATION: Cell adhesion recognition motif derived from
      Laminin

<400> SEQUENCE: 43

Tyr Ile Gly Ser Arg
1               5

<210> SEQ ID NO 44
<211> LENGTH: 5
<212> TYPE: PRT
<213> ORGANISM: Artificial Sequence
<220> FEATURE:
<223> OTHER INFORMATION: Cell adhesion recognition motif derived from
      Laminin

<400> SEQUENCE: 44

Ile Lys Val Ala Val
1               5

<210> SEQ ID NO 45
<211> LENGTH: 7
<212> TYPE: PRT
<213> ORGANISM: Artificial Sequence
<220> FEATURE:
<223> OTHER INFORMATION: Cell adhesion recognition motif derived from
      Fibronectin

<400> SEQUENCE: 45

Phe His Arg Arg Ile Lys Ala
1               5

<210> SEQ ID NO 46
<211> LENGTH: 4
<212> TYPE: PRT
<213> ORGANISM: Artificial Sequence
<220> FEATURE:
<223> OTHER INFORMATION: Cell adhesion recognition motif derived from
      Fibronectin

<400> SEQUENCE: 46

Leu Asp Val Pro
1
```

```
<210> SEQ ID NO 47
<211> LENGTH: 4
<212> TYPE: PRT
<213> ORGANISM: Artificial Sequence
<220> FEATURE:
<223> OTHER INFORMATION: Cell adhesion recognition motif derived from
      Fibronectin

<400> SEQUENCE: 47

Ile Asp Ala Pro
1

<210> SEQ ID NO 48
<211> LENGTH: 20
<212> TYPE: PRT
<213> ORGANISM: Artificial Sequence
<220> FEATURE:
<223> OTHER INFORMATION: Bioactive growth factor sequence motif

<400> SEQUENCE: 48

Lys Ile Pro Lys Ala Ser Ser Val Pro Thr Glu Leu Ser Ala Ile Ser
1               5                   10                  15

Thr Leu Tyr Leu
            20

<210> SEQ ID NO 49
<211> LENGTH: 30
<212> TYPE: DNA
<213> ORGANISM: Artificial Sequence
<220> FEATURE:
<223> OTHER INFORMATION: F1 Forward primer for caf amplification

<400> SEQUENCE: 49
ataaatcggt tcagtggcct caacgctgtg                                      30

<210> SEQ ID NO 50
<211> LENGTH: 25
<212> TYPE: DNA
<213> ORGANISM: Artificial Sequence
<220> FEATURE:
<223> OTHER INFORMATION: F1 Reverse primer for caf amplification

<400> SEQUENCE: 50
ggttaggctc aaagtaggat aattc                                           25

<210> SEQ ID NO 51
<211> LENGTH: 45
<212> TYPE: DNA
<213> ORGANISM: Artificial Sequence
<220> FEATURE:
<223> OTHER INFORMATION: Caf1G94insD; S95insF. Forward primer.

<400> SEQUENCE: 51
attggcaagg attctagagg tgatttcttt gatatctctc ctaag                     45

<210> SEQ ID NO 52
<211> LENGTH: 45
<212> TYPE: DNA
<213> ORGANISM: Artificial Sequence
<220> FEATURE:
<223> OTHER INFORMATION: Caf1G94insD; S95insF. Reverse primer.

<400> SEQUENCE: 52
cttaggagag atatcaaagg aatcacctct agaatccttg ccaat                     45
```

<210> SEQ ID NO 53
<211> LENGTH: 44
<212> TYPE: DNA
<213> ORGANISM: Artificial Sequence
<220> FEATURE:
<223> OTHER INFORMATION: Caf1A66R; S69P. Forward primer.

<400> SEQUENCE: 53
taactttaca gatgccaggg gtgatagccc catgtactta acat            44

<210> SEQ ID NO 54
<211> LENGTH: 44
<212> TYPE: DNA
<213> ORGANISM: Artificial Sequence
<220> FEATURE:
<223> OTHER INFORMATION: Caf1A66R; S69P. Reverse primer.

<400> SEQUENCE: 54
atgttaagta catgggcta tcacccctgg catctgtaaa gtta            44

<210> SEQ ID NO 55
<211> LENGTH: 40
<212> TYPE: DNA
<213> ORGANISM: Artificial Sequence
<220> FEATURE:
<223> OTHER INFORMATION: Caf1V106R; D109S. Forward primer.

<400> SEQUENCE: 55
acggtgagaa ccttcgtggg gattccgtcg tcttggctac            40

<210> SEQ ID NO 56
<211> LENGTH: 40
<212> TYPE: DNA
<213> ORGANISM: Artificial Sequence
<220> FEATURE:
<223> OTHER INFORMATION: Caf1V106R; D109S. Reverse primer.

<400> SEQUENCE: 56
gtagccaaga cgacggaatc cccacgaagg ttctcaccgt            40

<210> SEQ ID NO 57
<211> LENGTH: 43
<212> TYPE: DNA
<213> ORGANISM: Artificial Sequence
<220> FEATURE:
<223> OTHER INFORMATION: Caf1MDN31GRG; DS34GN. Forward primer.

<400> SEQUENCE: 57
ctccaattac aattggtaga ggagactctg gaaacatcga tac 43

<210> SEQ ID NO 58
<211> LENGTH: 43
<212> TYPE: DNA
<213> ORGANISM: Artificial Sequence
<220> FEATURE:
<223> OTHER INFORMATION: Caf1MDN31GRG; DS34GN. Reverse primer.

<400> SEQUENCE: 58
gtatcgatgt ttccagagtc tcctctacca attgtaattg gag 43

<210> SEQ ID NO 59
<211> LENGTH: 46
<212> TYPE: DNA
<213> ORGANISM: Artificial Sequence
<220> FEATURE:
<223> OTHER INFORMATION: Caf1QDGN76RGDS. Forward primer.

<400> SEQUENCE: 59
acttaacatt tacttctcga ggagattcaa accaccaatt cactac                              46

<210> SEQ ID NO 60
<211> LENGTH: 46
<212> TYPE: DNA
<213> ORGANISM: Artificial Sequence
<220> FEATURE:
<223> OTHER INFORMATION: Caf1QDGN76RGDS. Reverse primer.

<400> SEQUENCE: 60
gtagtgaatt ggtggtttga atctcctcga gaagtaaatg ttaagt                              46

<210> SEQ ID NO 61
<211> LENGTH: 8
<212> TYPE: PRT
<213> ORGANISM: Artificial Sequence
<220> FEATURE:
<223> OTHER INFORMATION: N-terminal Caf1-FLAG epitope

<400> SEQUENCE: 61

Asp Tyr Lys Asp Asp Asp Asp Lys
1               5

<210> SEQ ID NO 62
<211> LENGTH: 5
<212> TYPE: PRT
<213> ORGANISM: Artificial Sequence
<220> FEATURE:
<223> OTHER INFORMATION: N-terminal Caf1-PENFF cleavage site for
      Metalloproteinase 13 (MMP13)

<400> SEQUENCE: 62

Pro Glu Asn Phe Phe
1               5

<210> SEQ ID NO 63
<211> LENGTH: 10
<212> TYPE: PRT
<213> ORGANISM: Artificial Sequence
<220> FEATURE:
<223> OTHER INFORMATION: Caf1-6His-NT spacer

<400> SEQUENCE: 63

Gly Gly Gly Gly Ser Gly Gly Gly Gly Ser
1               5                   10

<210> SEQ ID NO 64
<211> LENGTH: 178
<212> TYPE: PRT
<213> ORGANISM: Artificial Sequence
<220> FEATURE:
<223> OTHER INFORMATION: Caf1-6His NT

<400> SEQUENCE: 64

Met Lys Lys Ile Ser Ser Val Ile Ala Ile Ala Leu Phe Gly Thr Ile
1               5                   10                  15

Ala Thr Ala Asn Ala Ala Ser Ser His His His His His His Asp Leu
            20                  25                  30

Thr Ala Ser Thr Thr Ala Thr Ala Thr Leu Val Glu Pro Ala Arg Ile
        35                  40                  45

Thr Leu Thr Tyr Lys Glu Gly Ala Pro Ile Thr Ile Met Asp Asn Gly
    50                  55                  60

Asn Ile Asp Thr Glu Leu Leu Val Gly Thr Leu Thr Leu Gly Gly Tyr

```
                65                  70                  75                  80
Lys Thr Gly Thr Thr Ser Thr Ser Val Asn Phe Thr Asp Ala Ala Gly
                    85                  90                  95

Asp Pro Met Tyr Leu Thr Phe Thr Ser Gln Asp Gly Asn Asn His Gln
                100                 105                 110

Phe Thr Thr Lys Val Ile Gly Lys Asp Ser Arg Asp Phe Asp Ile Ser
                115                 120                 125

Pro Lys Val Asn Gly Glu Asn Leu Val Gly Asp Val Val Leu Ala
            130                 135                 140

Thr Gly Ser Gln Asp Phe Phe Val Arg Ser Ile Gly Ser Lys Gly Gly
145                 150                 155                 160

Lys Leu Ala Ala Gly Lys Tyr Thr Asp Ala Val Thr Val Thr Val Ser
                    165                 170                 175

Asn Gln

<210> SEQ ID NO 65
<211> LENGTH: 188
<212> TYPE: PRT
<213> ORGANISM: Artificial Sequence
<220> FEATURE:
<223> OTHER INFORMATION: Caf1-6His NT + Spacer linking peptide

<400> SEQUENCE: 65

Met Lys Lys Ile Ser Ser Val Ile Ala Ile Ala Leu Phe Gly Thr Ile
1               5                   10                  15

Ala Thr Ala Asn Ala Ala Ser Ser His His His His His Gly Gly
                20                  25                  30

Gly Gly Ser Gly Gly Gly Gly Ser Asp Leu Thr Ala Ser Thr Thr Ala
            35                  40                  45

Thr Ala Thr Leu Val Glu Pro Ala Arg Ile Thr Leu Thr Tyr Lys Glu
        50                  55                  60

Gly Ala Pro Ile Thr Ile Met Asp Asn Gly Asn Ile Asp Thr Glu Leu
65                  70                  75                  80

Leu Val Gly Thr Leu Thr Leu Gly Gly Tyr Lys Thr Gly Thr Thr Ser
                85                  90                  95

Thr Ser Val Asn Phe Thr Asp Ala Ala Gly Asp Pro Met Tyr Leu Thr
                100                 105                 110

Phe Thr Ser Gln Asp Gly Asn Asn His Gln Phe Thr Thr Lys Val Ile
                115                 120                 125

Gly Lys Asp Ser Arg Asp Phe Asp Ile Ser Pro Lys Val Asn Gly Glu
            130                 135                 140

Asn Leu Val Gly Asp Val Val Leu Ala Thr Gly Ser Gln Asp Phe
145                 150                 155                 160

Phe Val Arg Ser Ile Gly Ser Lys Gly Lys Leu Ala Ala Gly Lys
                165                 170                 175

Tyr Thr Asp Ala Val Thr Val Thr Val Ser Asn Gln
            180                 185

<210> SEQ ID NO 66
<211> LENGTH: 172
<212> TYPE: PRT
<213> ORGANISM: Artificial Sequence
<220> FEATURE:
<223> OTHER INFORMATION: Caf1-PHSRN (DSRN) Loop1

<400> SEQUENCE: 66

Met Lys Lys Ile Ser Ser Val Ile Ala Ile Ala Leu Phe Gly Thr Ile
```

```
            1               5                  10                 15
Ala Thr Ala Asn Ala Ala Asp Leu Thr Ala Ser Thr Thr Ala Thr Ala
                    20                  25                 30

Thr Leu Val Glu Pro Ala Arg Ile Thr Leu Thr Tyr Lys Glu Gly Ala
            35                  40                 45

Pro Ile Thr Ile Met Asp Asn Gly Asn Ile Asp Thr Glu Leu Leu Val
     50                  55                 60

Gly Thr Leu Thr Leu Gly Gly Tyr Lys Thr Gly Thr Thr Ser Thr Ser
 65                  70                  75                 80

Val Asn Phe Thr Asp Ala Ala Gly Asp Pro Met Tyr Leu Thr Phe Thr
                    85                  90                 95

Ser Gln Asp Gly Asn Asn His Gln Phe Thr Thr Lys Val Ile Gly Lys
                    100                 105                110

Pro His Ser Arg Asn Gly Gly Asp Ile Ser Pro Lys Val Asn Gly Glu
                    115                 120                125

Asn Leu Val Gly Asp Asp Val Val Leu Ala Thr Gly Ser Gln Asp Phe
                    130                 135                140

Phe Val Arg Ser Ile Gly Ser Lys Gly Gly Lys Leu Ala Ala Gly Lys
145                 150                 155                160

Tyr Thr Asp Ala Val Thr Val Thr Val Ser Asn Gln
                    165                 170
```

<210> SEQ ID NO 67
<211> LENGTH: 170
<212> TYPE: PRT
<213> ORGANISM: Artificial Sequence
<220> FEATURE:
<223> OTHER INFORMATION: Caf1_PHSRN (NLVGD) Loop 3

<400> SEQUENCE: 67

```
Met Lys Lys Ile Ser Ser Val Ile Ala Ile Ala Leu Phe Gly Thr Ile
 1               5                  10                 15

Ala Thr Ala Asn Ala Ala Asp Leu Thr Ala Ser Thr Thr Ala Thr Ala
                    20                  25                 30

Thr Leu Val Glu Pro Ala Arg

<213> ORGANISM: Artificial Sequence
<220> FEATURE:
<223> OTHER INFORMATION: Caf1_FLAG epitope NT

<400> SEQUENCE: 68

```
Met Lys Lys Ile Ser Ser Val Ile Ala Ile Ala Leu Phe Gly Thr Ile
1               5                   10                  15

Ala Thr Ala Asn Ala Ala Asp Tyr Lys Asp Asp Asp Lys Asp Leu
            20                  25                  30

Thr Ala Ser Thr Thr Ala Thr Ala Thr Leu Val Glu Pro Ala Arg Ile
            35                  40                  45

Thr Leu Thr Tyr Lys Glu Gly Ala Pro Ile Thr Ile Met Asp Asn Gly
        50                  55                  60

Asn Ile Asp Thr Glu Leu Leu Val Gly Thr Leu Thr Leu Gly Gly Tyr
65                  70                  75                  80

Lys Thr Gly Thr Thr Ser Thr Ser Val Asn Phe Thr Asp Ala Ala Gly
                85                  90                  95

Asp Pro Met Tyr Leu Thr Phe Thr Ser Gln Asp Gly Asn Asn His Gln
            100                 105                 110

Phe Thr Thr Lys Val Ile Gly Lys Asp Ser Arg Asp Phe Asp Ile Ser
        115                 120                 125

Pro Lys Val Asn Gly Glu Asn Leu Val Gly Asp Val Val Leu Ala
130                 135                 140

Thr Gly Ser Gln Asp Phe Phe Val Arg Ser Ile Gly Ser Lys Gly Gly
145                 150                 155                 160

Lys Leu Ala Ala Gly Lys Tyr Thr Asp Ala Val Thr Val Thr Val Ser
                165                 170                 175

Asn Gln
```

<210> SEQ ID NO 69
<211> LENGTH: 171
<212> TYPE: PRT
<213> ORGANISM: Artificial Sequence
<220> FEATURE:
<223> OTHER INFORMATION: Caf1_Cys NT

<400> SEQUENCE: 69

```
Met Lys Lys Ile Ser Ser Val Ile Ala Ile Ala Leu Phe Gly Thr Ile
1               5                   10                  15

Ala Thr Ala Asn Ala Ala Cys Asp Leu Thr Ala Ser Thr Thr Ala Thr
            20                  25                  30

Ala Thr Leu Val Glu Pro Ala Arg Ile Thr Leu Thr Tyr Lys Glu Gly
            35                  40                  45

Ala Pro Ile Thr Ile Met Asp Asn Gly Asn Ile Asp Thr Glu Leu Leu
        50                  55                  60

Val Gly Thr Leu Thr Leu Gly Gly Tyr Lys Thr Gly Thr Thr Ser Thr
65                  70                  75                  80

Ser Val Asn Phe Thr Asp Ala Ala Gly Asp Pro Met Tyr Leu Thr Phe
                85                  90                  95

Thr Ser Gln Asp Gly Asn Asn His Gln Phe Thr Thr Lys Val Ile Gly
            100                 105                 110

Lys Asp Ser Arg Asp Phe Asp Ile Ser Pro Lys Val Asn Gly Glu Asn
        115                 120                 125

Leu Val Gly Asp Val Val Leu Ala Thr Gly Ser Gln Asp Phe Phe
130                 135                 140

Val Arg Ser Ile Gly Ser Lys Gly Gly Lys Leu Ala Ala Gly Lys Tyr
```

```
145                 150                 155                 160
Thr Asp Ala Val Thr Val Thr Val Ser Asn Gln
                165                 170

<210> SEQ ID NO 70
<211> LENGTH: 170
<212> TYPE: PRT
<213> ORGANISM: Artificial Sequence
<220> FEATURE:
<223> OTHER INFORMATION: Caf1_G35C Loop 4

<400> SEQUENCE: 70

Met Lys Lys Ile Ser Ser Val Ile Ala Ile Ala Leu Phe Gly Thr Ile
1               5                   10                  15

Ala Thr Ala Asn Ala Ala Asp Leu Thr Ala Ser Thr Thr Ala Thr Ala
                20                  25                  30

Thr Leu Val Glu Pro Ala Arg Ile Thr Leu Thr Tyr Lys Glu Gly Ala
            35                  40                  45

Pro Ile Thr Ile Met Asp Asn Cys Asn Ile Asp Thr Glu Leu Leu Val
        50                  55                  60

Gly Thr Leu Thr Leu Gly Gly Tyr Lys Thr Gly Thr Thr Ser Thr Ser
65                  70                  75                  80

Val Asn Phe Thr Asp Ala Ala Gly Asp Pro Met Tyr Leu Thr Phe Thr
                85                  90                  95

Ser Gln Asp Gly Asn Asn His Gln Phe Thr Thr Lys Val Ile Gly Lys
            100                 105                 110

Asp Ser Arg Asp Phe Asp Ile Ser Pro Lys Val Asn Gly Glu Asn Leu
        115                 120                 125

Val Gly Asp Asp Val Val Leu Ala Thr Gly Ser Gln Asp Phe Phe Val
130                 135                 140

Arg Ser Ile Gly Ser Lys Gly Gly Lys Leu Ala Ala Gly Lys Tyr Thr
145                 150                 155                 160

Asp Ala Val Thr Val Thr Val Ser Asn Gln
                165                 170

<210> SEQ ID NO 71
<211> LENGTH: 170
<212> TYPE: PRT
<213> ORGANISM: Artificial Sequence
<220> FEATURE:
<223> OTHER INFORMATION: Caf1_Q106C Loop 2

<400> SEQUENCE: 71

Met Lys Lys Ile Ser Ser Val Ile Ala Ile Ala Leu Phe Gly Thr Ile
1               5                   10                  15

Ala Thr Ala Asn Ala Ala Asp Leu Thr Ala Ser

Asp Ser Arg Asp Phe Asp Ile Ser Pro Lys Val Asn Gly Glu Asn Leu
            115                 120                 125

Val Gly Asp Asp Val Val Leu Ala Thr Gly Ser Gln Asp Phe Phe Val
    130                 135                 140

Arg Ser Ile Gly Ser Lys Gly Gly Lys Leu Ala Ala Gly Lys Tyr Thr
145                 150                 155                 160

Asp Ala Val Thr Val Thr Val Ser Asn Gln
                165                 170

<210> SEQ ID NO 72
<211> LENGTH: 175
<212> TYPE: PRT
<213> ORGANISM: Artificial Sequence
<220> FEATURE:
<223> OTHER INFORMATION: Caf1_PENFF-NT

<400> SEQUENCE: 72

Met Lys Lys Ile Ser Ser Val Ile Ala Ile Ala Leu Phe Gly Thr Ile
1               5                   10                  15

Ala Thr Ala Asn Ala Ala Pro Glu Asn Phe Phe Asp Leu Thr Ala Ser
                20                  25                  30

Thr Thr Ala Thr Ala Thr Leu Val Glu Pro Ala Arg Ile Thr Leu Thr
            35                  40                  45

Tyr Lys Glu Gly Ala Pro Ile Thr Ile Met Asp Asn Gly Asn Ile Asp
    50                  55                  60

Thr Glu Leu Leu Val Gly Thr Leu Thr Leu Gly Gly Tyr Lys Thr Gly
65                  70                  75                  80

Thr Thr Ser Thr Ser Val Asn Phe Thr Asp Ala Ala Gly Asp Pro Met
                85                  90                  95

Tyr Leu Thr Phe Thr Ser Gln Asp Gly Asn Asn His Gln Phe Thr Thr
            100                 105                 110

Lys Val Ile Gly Lys Asp Ser Arg Asp Phe Asp Ile Ser Pro Lys Val
    115                 120                 125

Asn Gly Glu Asn Leu Val Gly Asp Asp Val Val Leu Ala Thr Gly Ser
130                 135                 140

Gln Asp Phe Phe Val Arg Ser Ile Gly Ser Lys Gly Gly Lys Leu Ala
145                 150                 155                 160

Ala Gly Lys Tyr Thr Asp Ala Val Thr Val Thr Val Ser Asn Gln
                165                 170                 175

<210> SEQ ID NO 73
<211> LENGTH: 24
<212> TYPE: DNA
<213> ORGANISM: Artificial Sequence
<220> FEATURE:
<223> OTHER INFORMATION: T7 promoter primer

<400> SEQUENCE: 73
aattctaata cgactcacta tagg                                        24

<210> SEQ ID NO 74
<211> LENGTH: 18
<212> TYPE: DNA
<213> ORGANISM: Artificial Sequence
<220> FEATURE:
<223> OTHER INFORMATION: pUC/M13 forward primer

<400> SEQUENCE: 74
gtaaaacgac ggccagtg                                               18

<210> SEQ ID NO 75
<211> LENGTH: 654
<212> TYPE: DNA
<213> ORGANISM: Yersinia pestis
<220> FEATURE:
<221> NAME/KEY: misc_feature
<222> LOCATION: (650)..(651)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t

<400> SEQUENCE: 75

```
aaattaactg tgaatacctt caaccacgaa tctgttacct taaagagaga aatataattg      60
gtcaatgctt taattttagg gatttagtgt tctactctgg gatagattca aaatgtagat     120
tgggtaagtt atatgattcg ttgaagaaaa atacagctat aacagtatca aacagaatcc     180
cctttcatga taaaacgaat gacattattg caagaacggt tgtttgggat aggaataagc     240
atttcagcga tagtgaaata aaggtagata aaggcctgta tgcttatttt ttcttcaatg     300
atacatatga tcagtatgtt catcacatgt acaacatata ttataactct ttgcctattt     360
ataatttaaa taagcgggat ggttacgatg tggaggtcat aaaaagacga aatgacaata     420
ctattgattg tcattatttt ctcccgattt attgtgatga catggagttt tacaatgaaa     480
tgcaggtata tcacaataat attgtgaagc cggaaatgtc agtaacatta ggattaccaa     540
agagttaatt attttggatt tcacagcgtt gaggccactg aaccgattta taatcgaatt     600
cccgcggccg ccatggcggc cgggagcatg cgacgtcggc ccatcgcccn ntgn           654
```

<210> SEQ ID NO 76
<211> LENGTH: 18
<212> TYPE: PRT
<213> ORGANISM: Yersinia pestis

<400> SEQUENCE: 76

Lys Leu Thr Val Asn Thr Phe Asn His Glu Ser Val Thr Leu Lys Arg
1               5                   10                  15

Glu Ile

<210> SEQ ID NO 77
<211> LENGTH: 9
<212> TYPE: PRT
<213> ORGANISM: Yersinia pestis

<400> SEQUENCE: 77

Leu Val Asn Ala Leu Ile Leu Gly Ile
1               5

<210> SEQ ID NO 78
<211> LENGTH: 5
<212> TYPE: PRT
<213> ORGANISM: Yersinia pestis

<400> SEQUENCE: 78

Cys Ser Thr Leu Gly
1               5

<210> SEQ ID NO 79
<211> LENGTH: 12
<212> TYPE: PRT
<213> ORGANISM: Yersinia pestis

```
<400> SEQUENCE: 79

Ile Gln Asn Val Asp Trp Val Ser Tyr Met Ile Arg
1               5                   10

<210> SEQ ID NO 80
<211> LENGTH: 5
<212> TYPE: PRT
<213> ORGANISM: Yersinia pestis

<400> SEQUENCE: 80

Arg Lys Ile Gln Leu
1               5

<210> SEQ ID NO 81
<211> LENGTH: 32
<212> TYPE: PRT
<213> ORGANISM: Yersinia pestis

<400> SEQUENCE: 81

Gln Tyr Gln Thr Glu Ser Pro Phe Met Ile Lys Arg Met Thr Leu Leu
1               5                   10                  15

Gln Glu Arg Leu Phe Gly Ile Gly Ile Ser Ile Ser Ala Ile Val Lys
            20                  25                  30

<210> SEQ ID NO 82
<211> LENGTH: 33
<212> TYPE: PRT
<213> ORGANISM: Yersinia pestis

<400> SEQUENCE: 82

Ile Lys Ala Cys Met Leu Ile Phe Ser Ser Met Ile His Met Ile Ser
1               5                   10                  15

Met Phe Ile Thr Cys Thr Thr Tyr Ile Ile Thr Leu Cys Leu Phe Ile
            20                  25                  30

Ile

<210> SEQ ID NO 83
<211> LENGTH: 10
<212> TYPE: PRT
<213> ORGANISM: Yersinia pestis

<400> SEQUENCE: 83

Ile Ser Gly Met Val Thr Met Trp Arg Ser
1               5                   10

<210> SEQ ID NO 84
<211> LENGTH: 34
<212> TYPE: PRT
<213> ORGANISM: Yersinia pestis

<400> SEQUENCE: 84

Lys Asp Glu Met Thr Ile Leu Leu Ile Val Ile Ile Phe Ser Arg Phe
1               5                   10                  15

Ile Val Met Thr Trp Ser Phe Thr Met Lys Cys Arg Tyr Ile Thr Ile
            20                  25                  30

Ile Leu

<210> SEQ ID NO 85
<211> LENGTH: 5
<212> TYPE: PRT
<213> ORGANISM: Yersinia pestis
```

<400> SEQUENCE: 85

Ser Arg Lys Cys Gln
1               5

<210> SEQ ID NO 86
<211> LENGTH: 41
<212> TYPE: PRT
<213> ORGANISM: Yersinia pestis
<220> FEATURE:
<221> NAME/KEY: misc_feature
<222> LOCATION: (40)..(41)
<223> OTHER INFORMATION: Xaa can be any naturally occurring amino acid

<400> SEQUENCE: 86

Asp Tyr Gln Arg Val Asn Tyr Phe Gly Phe His Ser Val Glu Ala Thr
1               5                   10                  15

Glu Pro Ile Tyr Asn Arg Ile Pro Ala Ala Ala Met Ala Ala Gly Ser
            20                  25                  30

Met Arg Arg Arg Pro Ile Ala Xaa Xaa
        35                  40

<210> SEQ ID NO 87
<211> LENGTH: 703
<212> TYPE: DNA
<213> ORGANISM: Yersinia pestis
<220> FEATURE:
<221> NAME/KEY: misc_feature
<222> LOCATION: (703)..(703)
<223> OTHER INFORMATION: n is a, c, g, or t

<400> SEQUENCE: 87

```
taactgaaac ggatgtttat ttcaaacagg acacaagccc tctctacgaa tttgttcgtg    60
gattggatta ttcgatagag gtaatatatg aaaaaaatca gttccgttat cgccattgca   120
ttatttggaa ctattgcaac tgctaatgcg gcagatttaa ctgcaagcac cactgcaacg   180
gcaactcttg ttgaaccagc ccgcatcact cttacatata aggaaggcgc tccaattaca   240
attatggaca atggaaacat cgatacagaa ttacttgtcg gtacgcttac tcttggcggc   300
tataaaacag gaaccactag cacatctgtt aactttacag atgccgcggg tgatcccatg   360
tacttaacat ttacttctca ggatggaaat aaccaccaat tcactacaaa agtgattggc   420
aaggattcta gagattttga tatctctcct aaggtaaacg gtgagaacct tgtgggggat   480
gacgtcgtct tggctacggg cagccaggat ttctttgttc gctcaattgg ttccaaaggc   540
ggtaaacttg cagcaggtaa atacactgat gctgtaaccg taccgtatc taaccaataa   600
gaattcccca atcatctagt gaattcgcgg ccgcctgcag gtcgaccata tgggagagct   660
cccaacgcgt tggatgcata gctgagtatt catagtccta agn                     703
```

<210> SEQ ID NO 88
<211> LENGTH: 24
<212> TYPE: PRT
<213> ORGANISM: Yersinia pestis

<400> SEQUENCE: 88

Leu Lys Arg Met Phe Ile Ser Asn Arg Thr Gln Ala Leu Ser Thr Asn
1               5                   10                  15

Leu Phe Val Asp Trp Ile Ile Arg
            20

<210> SEQ ID NO 89
<211> LENGTH: 171

<212> TYPE: PRT
<213> ORGANISM: Yersinia pestis

<400> SEQUENCE: 89

Tyr Met Lys Lys Ile Ser Ser Val Ile Ala Ile Ala Leu Phe Gly Thr
1               5                   10                  15

Ile Ala Thr Ala Asn Ala Ala Asp Leu Thr Ala Ser Thr Thr Ala Thr
                20                  25                  30

Ala Thr Leu Val Glu Pro Ala Arg Ile Thr Leu Thr Tyr Lys Glu Gly
            35                  40                  45

Ala Pro Ile Thr Ile Met Asp Asn Gly Asn Ile Asp Thr Glu Leu Leu
        50                  55                  60

Val Gly Thr Leu Thr Leu Gly Gly Tyr Lys Thr Gly Thr Thr Ser Thr
65                  70                  75                  80

Ser Val Asn Phe Thr Asp Ala Ala Gly Asp Pro Met Tyr Leu Thr Phe
                85                  90                  95

Thr Ser Gln Asp Gly Asn Asn His Gln Phe Thr Thr Lys Val Ile Gly
            100                 105                 110

Lys Asp Ser Arg Asp Phe Asp Ile Ser Pro Lys Val Asn Gly Glu Asn
        115                 120                 125

Leu Val Gly Asp Asp Val Val Leu Ala Thr Gly Ser Gln Asp Phe Phe
    130                 135                 140

Val Arg Ser Ile Gly Ser Lys Gly Gly Lys Leu Ala Ala Gly Lys Tyr
145                 150                 155                 160

Thr Asp Ala Val Thr Val Thr Val Ser Asn Gln
                165                 170

<210> SEQ ID NO 90
<211> LENGTH: 26
<212> TYPE: PRT
<213> ORGANISM: Yersinia pestis

<400> SEQUENCE: 90

Glu Phe Pro Asn His Leu Val Asn Ser Arg Pro Pro Ala Gly Arg Pro
1               5                   10                  15

Tyr Gly Arg Ala Pro Asn Ala Leu Asp Ala
                20                  25

<210> SEQ ID NO 91
<211> LENGTH: 8
<212> TYPE: PRT
<213> ORGANISM: Yersinia pestis
<220> FEATURE:
<221> NAME/KEY: misc_feature
<222> LOCATION: (8)..(8)
<223> OTHER INFORMATION: Xaa can be any naturally occurring amino acid

<400> SEQUENCE: 91

Leu Ser Ile His Ser Pro Lys Xaa
1               5

<210> SEQ ID NO 92
<211> LENGTH: 639
<212> TYPE: DNA
<213> ORGANISM: Artificial Sequence
<220> FEATURE:
<223> OTHER INFORMATION: Mutant Caf1G94insD; S95insF
<220> FEATURE:
<221> NAME/KEY: misc_feature
<222> LOCATION: (620)..(620)
<223> OTHER INFORMATION: n is a, c, g, or t
<220> FEATURE:

```
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (636)..(638)
<223> OTHER INFORMATION: n is a, c, g, or t

<400> SEQUENCE: 92
tagaggtaat atatgaaaaa aatcagttcc gttatcgcca ttgcattatt tggaactatt      60
gcaactgcta atgcggcaga tttaactgca agcaccactg caacggcaac tcttgttgaa     120
ccagcccgca tcactcttac atataaggaa ggcgctccaa ttacaattat ggacaatgga     180
aacatcgata cagaattact tgtcggtacg cttactcttg gcggctataa aacaggaacc     240
actagcacat ctgttaactt tacagatgcc gcgggtgatc ccatgtactt aacatttact     300
tctcaggatg gaaataacca ccaattcact acaaaagtga ttggcaagga ttctagaggt     360
gattcctttg atatctctcc taaggtaaac ggtgagaacc ttgtggggga tgacgtcgtc     420
ttggctacgg gcagccagga tttctttgtt cgctcaattg gttccaaagg cggtaaactt     480
gcagcaggta aatacactga tgctgtaacc gtaaccgtat ctaaccaata gaattcccc     540 aatcactagt gaattcgcgg ccgcctgcag gtcgaccata tgggagagct cccaacgcgt     600
tggatgcata gcttgagtan tctatantnc actaannnc                            639

<210> SEQ ID NO 93
<211> LENGTH: 173
<212> TYPE: PRT
<213> ORGANISM: Artificial Sequence
<220> FEATURE:
<223> OTHER INFORMATION: Mutant Caf1G94insD; S95insF

<400> SEQUENCE: 93

Tyr Met Lys Lys Ile Ser Ser Val Ile Ala Ile Ala Leu Phe Gly Thr
1               5                   10                  15

Ile Ala Thr Ala Asn Ala Ala Asp Leu Thr Ala Ser Thr Thr Ala Thr
            20                  25                  30

Ala Thr Leu Val Glu Pro Ala Arg Ile Thr Leu Thr Tyr Lys Glu Gly
        35                  40                  45

Ala Pro Ile Thr Ile Met Asp Asn Gly Asn Ile Asp Thr Glu Leu Leu
    50                  55                  60

Val Gly Thr Leu Thr Leu Gly Gly Tyr Lys Thr Gly Thr Thr Ser Thr
65                  70                  75                  80

Ser Val Asn Phe Thr Asp Ala Ala Gly Asp Pro Met Tyr Leu Thr Phe
                85                  90                  95

Thr Ser Gln Asp Gly Asn Asn His Gln Phe Thr Thr Lys Val Ile Gly
            100                 105                 110

Lys Asp Ser Arg Gly Asp Ser Phe Asp Ile Ser Pro Lys Val Asn Gly
        115                 120                 125

Glu Asn Leu Val Gly Asp Asp Val Val Leu Ala Thr Gly Ser Gln Asp
    130                 135                 140

Phe Phe Val Arg Ser Ile Gly Ser Lys Gly Gly Lys Leu Ala Ala Gly
145                 150                 155                 160

Lys Tyr Thr Asp Ala Val Thr Val Thr Val Ser Asn Gln
                165                 170
```

```
<210> SEQ ID NO 94
<211> LENGTH: 5
<212> TYPE: PRT
<213> ORGANISM: Artificial Sequence
<220> FEATURE:
<223> OTHER INFORMATION: Mutant Caf1G94insD; S95insF

<400> SEQUENCE: 94

Glu Phe Pro Asn His
1               5

<210> SEQ ID NO 95
<211> LENGTH: 29
<212> TYPE: PRT
<213> ORGANISM: Artificial Sequence
<220> FEATURE:
<223> OTHER INFORMATION: Mutant Caf1G94insD; S95insF
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (28)..(29)
<223> OTHER INFORMATION: Xaa can be any naturally occurring amino acid

<400> SEQUENCE: 95

Ile Arg Gly Arg Leu Gln Val Asp His Met Gly Glu Leu Pro Thr Arg
1               5                   10                  15

Trp Met His Ser Leu Ser Xaa Leu Xaa Xaa Thr Xaa Xaa
            20                  25

<210> SEQ ID NO 96
<211> LENGTH: 593
<212> TYPE: DNA
<213> ORGANISM: Artificial Sequence
<220> FEATURE:
<223> OTHER INFORMATION: Mutant Caf1A66R; S69P
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (586)..(586)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t
<220> FEATURE:
<221> NAME/KEY: misc_feature
<222> LOCATION: (593)..(593)
<223> OTHER INFORMATION: n is a, c, g, or t

<400> SEQUENCE: 96
tatatgaaaa aaatcagttc cgttatcgcc attgcattat ttggaactat tgcaactgct      60
aatgcggcag atttaactgc aagcaccact gcaacggcaa ctcttgttga accagcccgc     120
atcactctta catataagga aggcgctcca attacaatta tggacaatgg aaacatcgat     180
acagaattac ttgtcggtac gcttactctt ggcggctata aacaggaac cactagcaca      240 tctgttaact ttacagatgc caggggtgat agcccatgt acttaacatt tcactacaaa      300
agtgattggc aaggattcta gagatttga tatctctcct aaggtaaacg gtgagaacct      360
```

```
tgtgggggat gacgtcgtct tggctacggg cagccaggat ttctttgttc gctcaattgg    420
ttccaaaggc ggtaaacttg cagcaggtaa atacactgat gctgtaaccg taaccgtatc    480
taaccaataa gaattcccca atcactagtg aattcgcggc cgcctgcagg tcgaccatat    540
gggagagctc ccaacgcgtt ggatgcatag cttgagtant ctatantccn ttn           593
```

```
<210> SEQ ID NO 97
<211> LENGTH: 106
<212> TYPE: PRT
<213> ORGANISM: Artificial Sequence
<220> FEATURE:
<223> OTHER INFORMATION: Mutant Caf1A66R; S69P

<400> SEQUENCE: 97
```

Tyr Met Lys Lys Ile Ser Ser Val Ile Ala Ile Ala Leu Phe Gly Thr
1               5                   10                  15

Ile Ala Thr Ala Asn Ala Ala Asp Leu Thr Ala Ser Thr Thr Ala Thr
            20                  25                  30

Ala Thr Leu Val Glu Pro Ala Arg Ile Thr Leu Thr Tyr Lys Glu Gly
        35                  40                  45

Ala Pro Ile Thr Ile Met Asp Asn Gly Asn Ile Asp Thr Glu Leu Leu
    50                  55                  60

Val Gly Thr Leu Thr Leu Gly Gly Tyr Lys Thr Gly Thr Thr Ser Thr
65                  70                  75                  80

Ser Val Asn Phe Thr Asp Ala Arg Gly Asp Ser Pro Met Tyr Leu Thr
                85                  90                  95

Phe His Tyr Lys Ser Asp Trp Gln Gly Phe
            100                 105

```
<210> SEQ ID NO 98
<211> LENGTH: 5
<212> TYPE: PRT
<213> ORGANISM: Artificial Sequence
<220> FEATURE:
<223> OTHER INFORMATION: Mutant Caf1A66R; S69P

<400> SEQUENCE: 98
```

Glu Pro Cys Gly Gly
1               5

```
<210> SEQ ID NO 99
<211> LENGTH: 20
<212> TYPE: PRT
<213> ORGANISM: Artificial Sequence
<220> FEATURE:
<223> OTHER INFORMATION: Mutant Caf1A66R; S69P

<400> SEQUENCE: 99
```

Arg Arg Leu Gly Tyr Gly Gln Pro Gly Phe Leu Cys Ser Leu Asn Trp
1               5                   10                  15

Phe Gln Arg Arg
            20

```
<210> SEQ ID NO 100
<211> LENGTH: 4
<212> TYPE: PRT
<213> ORGANISM: Artificial Sequence
<220> FEATURE:
<223> OTHER INFORMATION: Mutant Caf1A66R; S69

<400> SEQUENCE: 100
```

Thr Cys Ser Arg

<210> SEQ ID NO 101
<211> LENGTH: 7
<212> TYPE: PRT
<213> ORGANISM: Artificial Sequence
<220> FEATURE:
<223> OTHER INFORMATION: Mutant Caf1A66R; S69P

<400> SEQUENCE: 101

Cys Cys Asn Arg Asn Arg Ile
1               5

<210> SEQ ID NO 102
<211> LENGTH: 28
<212> TYPE: PRT
<213> ORGANISM: Artificial Sequence
<220> FEATURE:
<223> OTHER INFORMATION: Mutant Caf1A66R; S69P

<400> SEQUENCE: 102

Pro Ile Arg Ile Pro Gln Ser Leu Val Asn Ser Arg Pro Pro Ala Gly
1               5                   10                  15

Arg Pro Tyr Gly Arg Ala Pro Asn Ala Leu Asp Ala
            20                  25

<210> SEQ ID NO 103
<211> LENGTH: 8
<212> TYPE: PRT
<213> ORGANISM: Artificial Sequence
<220> FEATURE:
<223> OTHER INFORMATION: Mutant Caf1A66R; S69P
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 103

Leu Glu Xaa Ser Ile Xaa Xaa Xaa
1               5

<210> SEQ ID NO 104
<211> LENGTH: 510
<212> TYPE: DNA
<213> ORGANISM: Artificial Sequence
<220> FEATURE:
<223> OTHER INFORMATION: Mutant Caf1V106R; D109S

<400> SEQUENCE: 104
atgaaaaaaa tcagttccgt tatcgccatt gcattatttg aactattgc aactgctaat      60 gcggcagatt taactgcaag caccactgca acggcaactc ttgttgaacc agcccgcatc    120
actcttacat ataaggaagg cgctccaatt acaattatgg acaatggaaa catcgataca    180
gaattacttg tcggtacgct tactcttggc ggctataaaa caggaaccac tagcacatct    240
gttaacttta cagatgccgc gggtgatccc atgtacttaa catttacttc tcaggatgga    300
aataaccacc aattcactac aaaagtgatt ggcaaggatt ctagagattt tgatatctct    360
cctaaggtaa acggtgagaa ccttcgtggg gattccgtcg tcttggctac gggcagccag    420
gatttctttg ttcgctcaat tggttccaaa ggcggtaaac ttgcagcagg taaatacact    480
gatgctgtaa ccgtaaccgt atctaaccaa                                     510

<210> SEQ ID NO 105
<211> LENGTH: 170
<212> TYPE: PRT
<213> ORGANISM: Artificial Sequence
<220> FEATURE:
<223> OTHER INFORMATION: Mutant Caf1V106R; D109S

<400> SEQUENCE: 105

```
Met Lys Lys Ile Ser Ser Val Ile Ala Ile Ala Leu Phe Gly Thr Ile
1               5                   10                  15

Ala Thr Ala Asn Ala Ala Asp Leu Thr Ala Ser Thr Thr Ala Thr Ala
            20                  25                  30

Thr Leu Val Glu Pro Ala Arg Ile Thr Leu Thr Tyr Lys Glu Gly Ala
        35                  40                  45

Pro Ile Thr Ile Met Asp Asn Gly Asn Ile Asp Thr Glu Leu Leu Val
    50                  55                  60

Gly Thr Leu Thr Leu Gly Gly Tyr Lys Thr Gly Thr Thr Ser Thr Ser
65                  70                  75                  80

Val Asn Phe Thr Asp Ala Ala Gly Asp Pro Met Tyr Leu Thr Phe Thr
                85                  90                  95

Ser Gln Asp Gly Asn Asn His Gln Phe Thr Thr Lys Val Ile Gly Lys
            100                 105                 110

Asp Ser Arg Asp Phe Asp Ile Ser Pro Lys Val Asn Gly Glu Asn Leu
        115                 120                 125

Arg Gly Asp Ser Val Val Leu Ala Thr Gly Ser Gln Asp Phe Phe Val
    130                 135                 140

Arg Ser Ile Gly Ser Lys Gly Gly Lys Leu Ala Ala Gly Lys Tyr Thr
145                 150                 155                 160

Asp Ala Val Thr Val Thr Val Ser Asn Gln
                165                 170
```

<210> SEQ ID NO 106
<211> LENGTH: 622
<212> TYPE: DNA
<213> ORGANISM: Artificial Sequence
<220> FEATURE:
<223> OTHER INFORMATION: Mutant Caf1QDGN76RGDS
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (619)..(619)
<223> OTHER INFORMATION: n is a, c, g, or t

<400> SEQUENCE: 106

```
atgaaaaaaa tcagttccgt tatcgccatt gcattatttg gaactattgc aactgctaat      60
gcggcagatt taactgcaag caccactgca acggcaactc ttgttgaacc agcccgcatc     120
actcttacat ataaggaagg cgctccaatt acaattatgg acaatggaaa catcgataca     180
gaattacttg tcggtacgct tactcttggc ggctataaaa caggaaccac tagcacatct     240
gttaacttta cagatgccgc gggtgatccc atgtacttaa catttacttc tcaggagat     300
tcaaaccacc aattcactac aaaagtgatt ggcaaggatt ctagagattt tgatatctct     360
cctaaggtaa acggtgagaa ccttgtgggg gatgacgtcg tcttggctac gggcagccag     420
gatttctttg ttcgctcaat tggttccaaa ggcggtaaac ttgcagcagg taaatacact     480
gatgctgtaa ccgtaaccgt atctaaccaa taagaattcc ccaatcacta gtgaattcgc     540
```

```
ggccgcctgc aggtcgacca tatgggagag ctcccaacgc gttggatgca tagcttgagt    600
antctatagt gtcactaanc tc                                             622
```

```
<210> SEQ ID NO 107
<211> LENGTH: 170
<212> TYPE: PRT
<213> ORGANISM: Artificial Sequence
<220> FEATURE:
<223> OTHER INFORMATION: Mutant Caf1QDGN76RGDS

<400> SEQUENCE: 107

Met Lys Lys Ile Ser Ser Val Ile Ala Ile Ala Leu Phe Gly Thr Ile
1               5                   10                  15

Ala Thr Ala Asn Ala Ala Asp Leu Thr Ala Ser Thr Thr Ala Thr Ala
            20                  25                  30

Thr Leu Val Glu Pro Ala Arg Ile Thr Leu Thr Tyr Lys Glu Gly Ala
        35                  40                  45

Pro Ile Thr Ile Met Asp Asn Gly Asn Ile Asp Thr Glu Leu Leu Val
    50                  55                  60

Gly Thr Leu Thr Leu Gly Gly Tyr Lys Thr Gly Thr Thr Ser Thr Ser
65                  70                  75                  80

Val Asn Phe Thr Asp Ala Ala Gly Asp Pro Met Tyr Leu Thr Phe Thr
                85                  90                  95

Ser Arg Gly Asp Ser Asn His Gln Phe Thr Thr Lys Val Ile Gly Lys
            100                 105                 110

Asp Ser Arg Asp Phe Asp Ile Ser Pro Lys Val Asn Gly Glu Asn Leu
        115                 120                 125

Val Gly Asp Asp Val Val Leu Ala Thr Gly Ser Gln Asp Phe Phe Val
    130                 135                 140

Arg Ser Ile Gly Ser Lys Gly Gly Lys Leu Ala Ala Gly Lys Tyr Thr
145                 150                 155                 160

Asp Ala Val Thr Val Thr Val Ser Asn Gln
                165                 170

<210> SEQ ID NO 108
<211> LENGTH: 24
<212> TYPE: PRT
<213> ORGANISM: Artificial Sequence
<220> FEATURE:
<223> OTHER INFORMATION: Mutant Caf1QDGN76RGDS
<220> FEATURE:
<221> NAME/KEY: misc_feature
<222> LOCATION: (23)..(23)
<223> OTHER INFORMATION: Xaa can be any naturally occurring amino acid

<400> SEQUENCE: 108

Ile Arg Gly Arg Leu Gln Val Asp His Met Gly Glu Leu Pro Thr Arg
1               5                   10                  15

Trp Met His Ser Leu Ser Xaa Leu
            20
```